US011617770B2

(12) United States Patent
Dos Reis Serra et al.

(10) Patent No.: US 11,617,770 B2
(45) Date of Patent: Apr. 4, 2023

(54) SPOREFORMING PROBIOTIC STRAINS, METHODS AND USES THEREOF

(71) Applicants: CIIMAR—CENTRO INTERDISCIPLINAR DE INVESTIGAçÂO MARINHA E AMBIENTAL, Matosinhos (PT); UNIVERSIDADE DO PORTO, Oporto (PT)

(72) Inventors: Claudia Alexandra Dos Reis Serra, Matosinhos (PT); Paula Cristina Enes Oliveira Da Silva, Matosinhos (PT); Aires Oliva Teles, Oporto (PT); Fernando Tavares, Oporto (PT)

(73) Assignees: CIIMAR—CENTRO INTERDISCIPLINAR DE INVESTIGAÇÃO MARINHA E AMBIENTAL, Matosinhos (PT); UNIVERSIDADE DO PORTO, Oporto (PT)

( * ) Notice: Subject to any disclaimer, the term of this patent is extended or adjusted under 35 U.S.C. 154(b) by 0 days.

(21) Appl. No.: 17/288,383

(22) PCT Filed: Oct. 24, 2019

(86) PCT No.: PCT/IB2019/059131
§ 371 (c)(1),
(2) Date: Apr. 23, 2021

(87) PCT Pub. No.: WO2020/084565
PCT Pub. Date: Apr. 30, 2020

(65) Prior Publication Data
US 2021/0379122 A1 Dec. 9, 2021

(30) Foreign Application Priority Data
Oct. 24, 2018 (PT) .......................... 115101

(51) Int. Cl.
A61K 35/742 (2015.01)
A23K 50/80 (2016.01)
A23K 10/18 (2016.01)
C12N 1/20 (2006.01)
C12R 1/125 (2006.01)
C12R 1/07 (2006.01)
A61K 35/00 (2006.01)

(52) U.S. Cl.
CPC ............ A61K 35/742 (2013.01); A23K 10/18 (2016.05); A23K 50/80 (2016.05); C12N 1/205 (2021.05); A61K 2035/115 (2013.01); C12R 2001/07 (2021.05); C12R 2001/125 (2021.05)

(58) Field of Classification Search
None
See application file for complete search history.

(56) References Cited

U.S. PATENT DOCUMENTS 9,247,757 B2 * 2/2016 Schmidt .................. A23K 10/18

OTHER PUBLICATIONS

Newaj-Fyzul et al. Journal of Microbiology, 2007, 103, 1699-1706.*
Fetissov SO. Role of the gut microbiota in host appetite control: bacterial growth to animal feeding behaviour. Nat Rev Endocrinol. 2016. DOI: 10.1038/nrendo.2016.150. PubMed PMID: 27616451.
Bäumler AJ, Sperandio V. Interactions between the microbiota and pathogenic bacteria in the gut. Nature. 2016;535. DOI: 10.1038/nature18849.
Ganguly S, Prasad, A. Microflora in fish digestive tract plays significant role in digestion and metabolism. Reviews in Fish Biology and Fisheries. 2012; 22:11-6.
Ray AK, Ghosh, K., Ringo, E. Enzyme-producing bacteria isolated from fish gut: a review. Aquaculture Nutrition. 2012; 18:465-92. doi: 10.1111/j.1365-2095.2012.00943.x.
FAO. The state of world fisheries and aquaculture: Opportunities and challenges. Food and agriculture Organization of the United Nations. Rome, Italy. 2014. 243 p.
Krogdahl A, Penn, M., Thorsen, J., Refstie, S., Bakke, A.M. Important antinutrients in plant feedstuffs for aquaculture: an update on recent findings regarding responses in salmonids. Aquaculture Research. 2010; 41:333-44.
Sinha AK, Kumar, V., Makkar, H.P.S., De Boeck, G., Becker, K. Non-starch polysaccharides and their role in fish nutrition—A review. Food Chemistry. 2011; 127:1409-26.
Joint FAO/WHO Working Group Report on Guidelines for the Evaluation of Probiotics in Food, (2002).
Setlow P. Spore Resistance Properties. Microbiol Spectr. 2014; 2(5). DOI: 10.1128/microbiolspec.TBS-0003-2012. PubMed PMID: 26104355.
Tam NK, Uyen NQ, Hong HA, Duc le H, Hoa TT, Serra CR, et al. The intestinal life cycle of Bacillus subtilis and close relatives. J Bacteriol. 2006; 188(7):2692-700. DOI: 10.1128/JB.188.7.2692-2700.2006. PubMed PMID: 16547057; PubMed Central PMCID: PMCPMC1428398.
EFSA-BIOHAZ. Scientific Opinion on the update of the list of QPS-recommended biological agents intentionally added to food and feed as notified to EFSA, European Food Safety Authority Panel on Biological Hazards (EFSA-BIOHAZ). EFSA Journal 2017; 15(3):4664. DOI: 10.2903/j.efsa.2017.4664.
Cutting SM. Bacillus probiotics. Food Microbiol. 2011; 28(2):214-20. DOI: 10.1016/j.fm.2010.03.007. PubMed PMID: 21315976.
Bader J, Albin A, Stahl U. Spore-forming bacteria and their utilisation as probiotics. Benef Microbes. 2012; 3(1):67-75. DOI: 10.3920/BM2011.0039. PubMed PMID: 22348911.

(Continued)

*Primary Examiner* — Vera Afremova
(74) *Attorney, Agent, or Firm* — Leason Ellis LLP

(57) ABSTRACT

The present disclosure relates to the isolation, identification and characterization of novel sporeforming probiotic strain(s) with NSPase (Non-Starch Polysaccharides-active hydrolases) activity isolated from fish gut microbiota, methods and uses thereof. The sporeforming probiotic strain(s) with NSPase activity now disclosed are able of producing carbohydrate-active enzymes (CAZymes) that hydrolyse non-starch polysaccharides (NSPs) and accesses their potential as probiotics (PRO) for use in particular in aquafeeds.

3 Claims, 6 Drawing Sheets

Specification includes a Sequence Listing.

(56) References Cited

OTHER PUBLICATIONS

Kunst F, Ogasawara N, Moszer I, Albertini AM, Alloni G, Azevedo V, et al. The complete genome sequence of the gram-positive bacterium Bacillus subtilis. Nature. 1997; 390(6657):249-56. DOI: 10.1038/36786. PubMed PMID: 9384377.

Harwood CR, Cutting SM. Chemically defined growth media and supplements. In: Harwood CR, Cutting SM, editors. Molecular biological methods for Bacillus. Chichester, UK: John Wiley & Sons Ltd; 1990. p. 548.

EFSA-FEEDAP. Guidance on the assessment of bacterial susceptibility to antimicrobials of human and veterinary importance, European Food Safety Authority Panel on Additives and Products or Substances used in Animal Feed (EFSA-FEEDAP). EFSA Journal. 2012; 10(6):2740.

Serra CR, Earl AM, Barbosa TM, Kolter R, Henriques AO. Sporulation during growth in a gut isolate of Bacillus subtilis. J Bacteriol. 2014; 196(23):4184-96. DOI: 10.1128/JB.01993-14. PubMed PMID: 25225273; PubMed Central PMCID: PMCPMC4248874.

Casula G, Cutting SM. Bacillus probiotics: spore germination in the gastrointestinal tract. Appl Environ Microbiol. 2002; 68(5):2344-52. PubMed PMID: 11976107; PubMed Central PMCID: PMCPMC127533.

Xue Z, Zhang W, Wang L, Hou R, Zhang M, Fei L, et al. The bamboo-eating giant panda harbors a carnivore-like gut microbiota, with excessive seasonal variations. MBio. 2015; 6(3):e00022-15. DOI: 10.1128/mBio.00022-15. PubMed PMID: 25991678; PubMed Central PMCID: PMCPMC4442137.

Zhou Z, Zhou X, Li J, Zhong Z, Li W, Liu X, et al. Transcriptional regulation and adaptation to a highfiber environment in Bacillus subtilis HH2 isolated from feces of the giant panda. PLoS One. 2015; 10(2):e0116935. DOI: 10.1371/journal.pone.0116935. PubMed PMID: 25658435; PubMed Central PMCID: PMCPMC4319723.

EFSA-FEEDAP. Guidance for the preparation of dossiers for technological additives, European Food Safety Authority Panel on Additives and Products or Substances used in Animal Feed (EFSA-FEEDAP). EFSA Journal. 2012; 10(1).

EFSA-FEEDAP. Guidance on the assessment of the toxigenic potential of *Bacillus* species used in animal nutrition, European Food Safety Authority Panel on Additives and Products or Substances used in Animal Feed (EFSA-FEEDAP). EFSA Journal 2014; 12(5).

Cabello FC, Godfrey HP, Buschmann AH, Dolz HJ. Aquaculture as yet another environmental gateway to the development and globalisation of antimicrobial resistance. Lancet Infect Dis. 2016. DOI: 10.1016/S1473-3099(16)00100-6. PubMed PMID: 27083976.

A.K. Ray et al, "Enzyme-producing bacteria isolated from fish gut: a review", Aquaculture Nutrition, vol. 18, No. 5, Apr. 20, 2012, p. 465-492, XP055665975, DOI: 10.1111/j.1365-2095.2012.00943.x, ISSN:1353-5773; Abstract; p. 481, right-hand column—p. 483, right-hand column; Figure 1; Relevant to claim No. 1-10.

Adorian Taida Juliana et al, "Effects of Probiotic BacteriaBacilluson Growth Performance, Digestive Enzyme Activity, and Hematological Parameters of Asian Sea Bass, *Lates calcarifer* (Bloch)", Feb. 9, 2018, vol. 11, No. 1, p. 248-255, XP036751251, DOI: 10.1007/S12602-018-9393-Z, ISSN:1867-1306; Abstract; p. 250, right-hand column—p. 251, left-hand column; Relevant to claim No. 1-10.

Bidhan C. De et al, "Probiotics in fish and shellfish culture: immunomodulatory and ecophysiological responses", Fish Physiology and Biochemistry., vol. 40, Jan. 14, 2014, p. 921-971, XP055665406, DOI: 10.1007/s10695-013-9897-0, ISSN:0920-1742; The whole document; Relevant to claim No. 1-10.

Xiao-Yan You et al, "Complete genome sequence of the molybdenum-resistant bacterium Bacillus subtilis strain LM 4-2", Standards in Genomic Sciences, vol. 10, No. 1, Dec. 1, 2015, XP055665539, DOI: 10.1186/s40793-015-0118-6; Figure 2.

& You et al, "myo-inositol transporter IoIT [*Bacillus* sp. LM 4-2].", Genbank17 Dec. 2015; XP002797431; The whole document; Relevant to claim No. 1-10.

Cláudia R. Serra et al., "Selection of carbohydrate-active probiotics from the gut of carnivorous fish fed plant-based diets", Scientific Reports, vol. 9, No. 1, Apr. 23, 2019, XP055665402, DOI: 10.1038/s41598-019-42716-7; The whole document; Relevant to claim No. 1-10.

Magalhães R. et al, "Carbohydrases supplementation increased nutrient utilization in white seabream (*Diplodus sargus*) juveniles fed high soybean meal diets", Aquaculture, Oct. 2016, vol. 463, pp. 43-50; The whole document; Relevant to claim No. 1-18.

Batista S. et al, "Changes in intestinal microbiota, immune- and stress-related transcript levels in Senegalese sole (*Solea senegalensis*) fed plant ingredient diets intercropped with probiotics or immunostimulants", Aquaculture, May 2016, vol. 458, pp. 149-157; The whole document; Relevant to claim No. 1-18.

Adeoye A.A et al, "Supplementation of formulated diets for tilapia (*Oreochromis niloticus*) with selected exogenous enzymes: Overall performance and effects on intestinal histology and microbiota", Animal feed science and technology, May 2016, vol. 215, pp. 133-143; The whole document; Relevant to claim No. 1-18.

Denstadli V. et al, "Enzyme pretreatment of fibrous ingredients for carnivorous fish: Effects on nutrient utilisation and technical feed quality in rainbow trout (*Oncurhynchus mykiss*)", Aquaculture, Oct. 2011, vol. 319, No. 3-4, pp. 391-397; The whole document; Relevant to claim No. 1-18.

Mannose-6-phosphate isomerase, class I [Bacillus subtilis], https://www.ncbi.nlm.nih.gov/protein/WP_070547898.1?report=genbank&log$=prottop&blast_ rank=1&RID=AW0WXGSC015 [Retrieved from the Internet on Apr. 9, 2019]; The whole document; Relevant to claim No. 14-19.

MULTISPECIES: sugar porter family MFS transporter [Bacillus], https://www.ncbi.nlm.nih.gov/protein/WP_080481020.1?report=genbank&log$=prottop&blast_ rank=1&RID=AW1FCXJ9015 [Retrieved from the Internet on Apr. 9, 2019]; The whole document; Relevant to claim No. 14-19.

* cited by examiner

```
                       SEQUENCE LISTING

<160> NUMBER OF SEQ ID NOS: 207

<210> SEQ ID NO 1
<211> LENGTH: 202
<212> TYPE: PRT
<213> ORGANISM: Bacillus subtilis
<220> FEATURE:
<223> OTHER INFORMATION: >ABP10118

<400> SEQUENCE: 1

Met Asn Leu Thr Gly Glu Ser Lys Asn Phe Asp Asp Tyr Leu Leu Glu
1               5                   10                  15

Leu Asn Glu Val Asp Tyr Ser Asn Pro Ile Ile Cys Ala Leu Ala Asn
            20                  25                  30

Glu Leu Phe Asn Pro Leu Gln Thr Glu Ile Glu Lys Val Lys Ile Ala
        35                  40                  45

Tyr Glu Phe Val Arg Asp Glu Ile Ser His Thr Trp Asp Thr Gln Ser
    50                  55                  60

Lys Arg Val Thr Cys Asn Ala Ser Glu Val Leu Ser Phe Lys Glu Gly
65                  70                  75                  80

Ile Cys Tyr Ala Lys Ser Asn Leu Leu Ala Ala Leu Leu Arg Ser Glu
                85                  90                  95

Gly Ile Pro Thr Gly Phe Cys Tyr Gln Arg Leu Met Leu Phe Asn Thr
            100                 105                 110
```

```
Pro Asp Lys Gly Tyr Cys Ile His Ala Leu Asn Ala Val Phe Phe His
        115                 120                 125

Ser Leu Asn Lys Trp Ile Arg Leu Asp Ser Arg Gly Asn Lys Ile Gly
130                 135                 140

Ile Asp Ala Gln Phe Ser Leu Asp Lys Glu Arg Leu Ala Phe Pro Ile
145                 150                 155                 160

Arg Gln Glu Phe Asp Glu Ile Asp Tyr Pro Leu Ile Tyr Val Arg Pro
                165                 170                 175

His Pro Lys Thr Ile Ala Val Leu Lys Glu His Lys Asp Ala Ile Glu
            180                 185                 190

Met Tyr Lys Tyr His Leu Pro Glu Arg Ile
        195                 200

<210> SEQ ID NO 2
<211> LENGTH: 215
<212> TYPE: PRT
<213> ORGANISM: Bacillus subtilis
<220> FEATURE:
<223> OTHER INFORMATION: >ABP10119

<400> SEQUENCE: 2

Met Ile Trp Leu Val Gly Leu Asp Trp Ser Ile Gln Trp Gly Thr Val
1               5                   10                  15

Phe Thr Val Ala Gly Thr Leu Thr Ala Ala Phe Leu Gly Gln Val Phe
            20                  25                  30

Ser His Arg Tyr Ser Gln Lys Arg Glu Glu Ile Lys Gln Lys Lys Glu
        35                  40                  45

Ser Phe Gln Asn Leu Tyr Ser Pro Val Val Phe Lys Ile Leu Asn Tyr
    50                  55                  60

Leu Glu Leu Glu Arg Glu Lys Gln Asn Ile Met Phe Ile Lys Gly Leu
65                  70                  75                  80

Asp Glu Thr Glu Phe Thr Glu Arg Tyr Gln Asp Asp Glu Leu Tyr Asn
                85                  90                  95

Pro Ser Ile Glu Phe Lys Glu Ile Leu Glu Ile Val Gly Leu Asn Leu
            100                 105                 110

Lys Tyr Gly Ser Leu Glu Leu Ile Arg Glu Tyr Gln Glu Thr Leu Ser
        115                 120                 125

Ile Ala Lys Arg Met Glu Ala Phe Glu Gly His Cys Gly Thr His Leu
130                 135                 140

Tyr Phe Cys Gly Val Phe Ile Ser Asp Tyr Ile Asn Leu Ser Lys Asp
145                 150                 155                 160

Leu Gly Val Tyr Ser Gln Thr Met Glu Thr Ser Thr Glu Gly Ser Leu
                165                 170                 175

Leu Leu Ser Arg Leu Glu Thr Leu Ile Pro Gln Leu Val Leu Glu
            180                 185                 190

Cys Leu Trp Asn Phe Tyr Leu Gly Phe Phe Met Gln Tyr Leu Val Leu
        195                 200                 205

Ile Lys Lys Ile Asn Ile Leu
        210                 215

<210> SEQ ID NO 3
<211> LENGTH: 286
<212> TYPE: PRT
<213> ORGANISM: Bacillus subtilis
<220> FEATURE:
<223> OTHER INFORMATION: >ABP10120

<400> SEQUENCE: 3
```

```
Met Glu Leu Lys Asn Lys Ile Lys Arg Val Ala Ile Tyr Leu Arg Lys
1               5                   10                  15

Ser Arg Asn Lys Glu Gly Glu Thr Glu Thr Leu Ala Lys His
            20                  25                  30

Arg Lys Arg Leu Leu Asp Ile Ala His Lys Asn Asn Trp Gln Tyr Glu
            35                  40                  45

Ile Phe Gln Glu Val Gly Ser Ser Met Asp Glu Met Arg Pro Glu Cys
50                      55                  60

Gln Arg Met Ile Asn Lys Leu Thr Asp Gly Ile Phe Asp Ala Val Leu
65                  70                  75                  80

Ser Val Asn Leu Ala Arg Val Thr Arg Asp Ala Glu Thr Pro Lys
                85                  90                  95

Phe Met Asn Leu Leu Arg Gln Asp Asp Ile Leu Phe Val Thr Asp Ser
                    100                 105                 110

Glu Arg Val Tyr Asp Leu Glu Val Gln Glu Asp Trp Gln Ala Leu Lys
            115                 120                 125

Phe Thr Gly Phe Val Asn Asn Trp Glu Tyr Glu Asn Ile Lys Ala Gln
130                 135                 140

Leu Arg Lys Gly Lys Lys Asp Ser Ala Lys Met Gly Arg Trp Ser Asn
145                 150                 155                 160

Gly Lys Pro Asn Tyr Gly Tyr Ile Tyr Asn Arg Leu Glu Arg Lys Leu
                165                 170                 175

Glu Ile Asp Glu Glu Lys Ala Lys Ala Val Lys Leu Ala Phe Gln Met
            180                 185                 190

Thr Ile Asp Gly Ile Gly Ala Asp Asn Ile Ala Val Lys Leu Asn Lys
            195                 200                 205

Leu Gly Tyr Arg Thr Asn Lys Gly Lys Phe Phe His Gly Gln Ser Ile
210                 215                 220

Val Arg Met Ile Arg Ser Glu Ile Tyr Lys Gly Trp Ile Val Ala Asn
225                 230                 235                 240

Arg Leu Lys Gly Arg Asn Lys Thr Asn Gly Lys Ile Arg Pro Gln Asp
                245                 250                 255

Gln Trp Ile Val Val Lys Asp Ala Val Lys Pro Cys Ile Ile Asp Glu
            260                 265                 270

Asp Thr Trp Asp Lys Ala Asn Lys Ala Gly His Leu Ile Lys
            275                 280                 285

<210> SEQ ID NO 4
<211> LENGTH: 153
<212> TYPE: PRT
<213> ORGANISM: Bacillus subtilis
<220> FEATURE:
<223> OTHER INFORMATION: ABP10121

<400> SEQUENCE: 4

Met Tyr Ser Tyr Lys Leu Ile Asp Asn Glu Lys Val Arg Glu Lys Leu
1               5                   10                  15

Glu Glu Leu Ile Asp Glu Lys Arg Glu Ile His Leu Lys Leu Thr Asp
            20                  25                  30

Asn His Leu Asp Lys His Leu Gly Ile Thr Tyr Asp Leu Leu Asp Val
            35                  40                  45

Asn Asp Asp Gly Ser Tyr Ser Gly Phe Phe Arg Thr Thr Pro Tyr Ile
50                      55                  60

Arg Arg Ser Asp Leu Ile Leu Pro Gly Glu Ser Ile Gly Ile Lys Leu
65                  70                  75                  80
```

```
Pro Ser Tyr Phe Leu Ile Met Ile Asn Tyr Leu Ser Arg Leu Glu Glu
                85                  90                  95

Gln Asp Cys Phe Pro Glu Leu Glu Leu Lys Ile Thr Tyr Asn Asp Thr
            100                 105                 110

Asn Phe Lys Thr Trp Glu Thr Lys Phe Ile Ile Lys Val Asp Gln Ile
        115                 120                 125

Ser Lys Ile Glu Ile Ser Ser Phe Tyr Lys Leu Gln Thr Ser Leu Val
    130                 135                 140

Tyr Glu Phe Ile Ser Lys Asn Lys Lys
145                 150

<210> SEQ ID NO 5
<211> LENGTH: 604
<212> TYPE: PRT
<213> ORGANISM: Bacillus subtilis
<220> FEATURE:
<223> OTHER INFORMATION: >ABP10181

<400> SEQUENCE: 5

Met Ala Val Val Thr Thr Ile Lys His Pro Met Ile Ser Gly Tyr Val
1               5                   10                  15

Lys Gly Phe Val Asp Lys Tyr Glu Ile Ser Arg Arg Lys Ala Lys Asn
                20                  25                  30

Glu His Asn Ile Phe Glu Met Phe Ile Asn Asp Leu Ile Leu Ser Ser
            35                  40                  45

Tyr Asn Asn Asp Pro Asn Ala Ser Tyr Glu Asp Met Glu Thr Gly Thr
        50                  55                  60

Ala Phe Gly Ile Asp Gly Val Ala Ile Phe Ile Asn Asp Lys Leu Val
65                  70                  75                  80

Glu Gly Val Glu Asp Val Asp Tyr Ile Cys Asn Ser Thr Arg Lys Ile
                85                  90                  95

Glu Val Lys Phe Leu Phe Thr Gln Thr Lys Thr Ser Glu Lys Phe Asp
            100                 105                 110

Arg Ser Glu Val Arg Asp Phe Leu Gln Gly Val Asn Arg Phe Phe Asn
        115                 120                 125

Phe Glu Phe Cys Glu Ile Thr Glu Leu Lys Asn Ser Trp Glu Thr Ala
130                 135                 140

Lys Tyr Ile Tyr Asp Leu Ser Thr Lys Phe Lys Asn Asp Pro Ala Leu
145                 150                 155                 160

Lys Met Tyr Tyr Thr Ala Leu Ala Pro Lys Lys Ile Ser Val Lys Asp
                165                 170                 175

Glu Asp Ile Asp Leu His Leu Lys Ser Glu Ile Leu Thr Gly Leu Glu
            180                 185                 190

Val Leu Lys Gln Arg Tyr Ile Phe Asp Glu Asp Asn Ile Ser Leu Asn
        195                 200                 205

Phe Ile Gly Leu Lys Glu Ile Arg Glu Leu His Gln Lys Glu Asn Asn
    210                 215                 220

Leu Thr Glu Ile Lys Phe Asn Leu Asp Lys Gln Pro Val Pro Tyr Pro
225                 230                 235                 240

Lys Asp Ser Thr Gly Ile Ile Lys Ser Ala Tyr Phe Gly Leu Ile Lys
                245                 250                 255

Leu Glu Asp Leu Leu Asp Ile Leu Ser Glu Ala Val Asp Gly Glu Arg
            260                 265                 270

Ile Leu Arg Lys Gly Ile Phe Glu Asp Asn Ile Arg Asp Tyr Leu Gly
        275                 280                 285
```

```
Ala Asn Glu Lys Phe Asp Val Asn Leu Asp Met Lys Asn Gly Leu Thr
    290                 295                 300
Gly Thr Asn Ala His Leu Phe Gly Leu Leu Asn Asn Gly Ile Thr Ile
305                 310                 315                 320
Ile Ala Asp Gln Val His Ile Ile Ser Thr Glu Ala Ser Leu Val Asn
                325                 330                 335
Tyr Gln Ile Val Asn Gly Cys Gln Thr Ser Asn Val Ile Phe Glu Ser
                340                 345                 350
Leu Lys Asp Ile Ile Glu Lys Asn Ile Tyr Ile Pro Ile Arg Leu Ile
            355                 360                 365
Gly Thr Glu Asp Glu Asp Thr Lys Asn Ala Ile Ile Lys Ala Thr Asn
370                 375                 380
Ser Gln Thr Ala Leu Lys Pro Glu Gln Leu Leu Ala Leu Arg Asp Glu
385                 390                 395                 400
Gln Lys Ser Leu Glu Glu Tyr Tyr Arg Ala Lys Arg Asn Gln Asn Lys
                405                 410                 415
Phe Leu Leu Tyr Tyr Glu Arg Arg Thr Glu Gln Tyr Arg Asn Glu Asp
            420                 425                 430
Ile Gln Lys Thr Lys Ile Ile Asn Ile Pro Phe Gln Ile Lys Ala Thr
            435                 440                 445
Ser Ala Met Phe Leu Asp Leu Pro His Glu Val Ser Gly Gln Tyr Gly
450                 455                 460
Lys Val Glu Gln Lys Thr Arg Gly Lys Leu Phe Thr Asp Ser Ser Leu
465                 470                 475                 480
Leu Asn Pro Tyr Tyr Val Ser Gly Leu Thr Trp Tyr Arg Val Glu Ala
                485                 490                 495
Phe Ile Arg Asn Asn Glu Glu Gly Lys Lys His Arg Arg Ala Arg Trp
            500                 505                 510
His Ile Met Met Val Ile Lys Tyr Leu Ile Ser Asp Leu Lys Asn Pro
            515                 520                 525
Ser Lys Ile Ile Asp Lys Asn Ala Glu Lys Ile Ser Glu Lys Val Glu
530                 535                 540
Lys Val Met Leu Asn Asp Ala Lys Ser Leu Glu Ile Ile Glu Asn Ala
545                 550                 555                 560
Leu Ser Leu Ile Lys Glu Phe Ile Ile Asn Glu Gly Ile Leu Asp Ile
                565                 570                 575
Ser Glu Asp Arg Lys Phe Phe Glu Arg Lys Glu Thr Thr Thr Gly Leu
            580                 585                 590
Ile Glu Met Leu Lys Asn Arg Leu Lys Thr Leu Ser
            595                 600

<210> SEQ ID NO 6
<211> LENGTH: 851
<212> TYPE: PRT
<213> ORGANISM: Bacillus subtilis
<220> FEATURE:
<223> OTHER INFORMATION: >ABP10182

<400> SEQUENCE: 6

Met Glu His Ser Asn Lys Leu Asn Ile Val Tyr Lys Ser Ile Gln Gln
1               5                   10                  15
Met Lys Glu Ser Tyr Gly Lys Leu Leu Lys Val Glu Phe His Ile His
            20                  25                  30
Thr Pro Ala Ser His Asp Tyr Arg Leu Leu Pro Gly Lys Leu Phe Lys
        35                  40                  45
```

```
Asn Met Lys Leu Thr Glu Val Phe Asp Val Ala Leu Asn Glu Gly Leu
 50                  55                  60

Tyr Ser Lys Glu Phe Leu Glu Arg Ile Gln Lys Glu Asp Phe Ala Ile
 65                  70                  75                  80

Phe Glu Lys Gln Val Ile Glu Asp Ile Asn Arg Asp Phe His Val Ser
                     85                  90                  95

Phe Ser Asn Phe Lys Glu Ile Leu Gly Tyr Gln Leu Ile Ala His Ser
                    100                 105                 110

Leu Tyr Lys Asn Asn Ile His Ala Ala Val Ile Ser Asp His Asn Thr
                115                 120                 125

Ile Asn Gly Phe Lys Lys Leu Gln Ala Val Leu Val Asp Tyr Tyr Lys
130                 135                 140

Ser Arg Ile Lys Gly Asn Thr Gln Arg Lys Ser Ile Lys Leu Phe Leu
145                 150                 155                 160

Gly Ile Glu Ile Ser Cys Ser Asp Tyr Tyr His Leu Val Gly Ile Phe
                    165                 170                 175

Asp Glu His Lys Tyr Thr Asp Leu Lys Asn Phe Val Ser Lys Tyr Ile
                180                 185                 190

His Ser Glu Glu Glu Gly Thr Tyr Ile Ser Cys Leu Asp Met Val Asn
                195                 200                 205

Arg Ile Thr Glu Asn Gly Gly Ile Pro Tyr Ile Ala His Ile Asn Thr
210                 215                 220

Ser Asp Phe Leu Gly Thr Asn Leu Tyr Lys Arg Ser Leu Phe Gly Phe
225                 230                 235                 240

Ser Gly Leu Lys Ile Leu Gly Leu Thr Asn Ile Asp Ser Lys Glu Arg
                245                 250                 255

Ile Ser Asn Arg Ile Lys Lys Tyr Gln Glu Ser Ser Lys Gly Asp Phe
                260                 265                 270

Cys Phe Ile His Glu Gly Asp Ser His Glu Leu Asn Gln Leu Gly Lys
                275                 280                 285

Lys Asn Thr Trp Ile Lys Phe Asn Asn Leu Ser Phe Lys Ser Leu Lys
                290                 295                 300

Lys Ala Phe Lys Asn Tyr Gln Phe Cys Ile Tyr Ile Asp Lys Pro Ile
305                 310                 315                 320

Tyr Asn Asp Arg Phe Leu Lys Gly Ile Tyr Ile Glu Pro Gly Glu Lys
                325                 330                 335

Gly Phe Leu Gly Asp Lys Glu Gln Pro Glu Lys Pro Phe Ile Val Asp
                340                 345                 350

Phe Ser Arg Asp Leu Asn Cys Ile Ile Gly Gly Arg Gly Val Gly Lys
                355                 360                 365

Ser Thr Ile Leu Ser Ile Leu Glu Thr Ala Phe Thr Leu Glu Val Thr
370                 375                 380

Asn Ile Asn Gln Leu Glu Tyr Ile Ser Arg His Asn Leu Ile Tyr Ile
385                 390                 395                 400

Val Phe Asn Tyr Lys Asn Met Asp Tyr Ile Leu Asn Phe Ile Pro Gln
                405                 410                 415

Ile Thr Glu Ser Gly Tyr Ser Gly Asn Asn Tyr Phe Leu Arg Lys Ala
                420                 425                 430

Phe Ser Glu Thr Thr Glu Thr Glu Ser Gly Thr Arg Arg Leu Ser Gln
                435                 440                 445

Asn Trp Ile Asn Leu Tyr Arg Val Ser Gln Val Glu Ser Ser Asn Gly
450                 455                 460
```

```
Tyr Lys Phe Gln Glu Leu Asn Tyr Asn Glu Thr Thr Thr Ile Ile Glu
465                 470                 475                 480

Ser Val Tyr Lys Lys Ser Tyr Ser Ile Asn Asn Ile Val Glu Leu Ser
                485                 490                 495

Asn Thr Gly Arg Ile Ser Glu Phe Ile Arg Asp Ile Val Leu Asn Gly
            500                 505                 510

Glu Arg Leu Asn Gly Ser Lys Ile Val Leu Ser Lys Leu Asn Lys Leu
        515                 520                 525

His Lys Asn Asn Tyr Arg Lys Tyr Leu Arg Glu Asn Ile Gln Ser Val
    530                 535                 540

Leu Val Asn Ile Lys Lys Arg Glu Glu Asn Val Lys Met Ala Ile Glu
545                 550                 555                 560

Glu Phe Asn Arg Leu Asn Asn Lys Leu Ile Gln Ile Val Tyr Ser Pro
                565                 570                 575

Lys Leu Lys Asp Pro Thr Phe Tyr Leu Lys Glu Leu Glu Leu Arg Tyr
            580                 585                 590

Asp Pro Ile Phe Asp Arg Glu Lys Gly Lys Arg Val Leu Asn Thr Tyr
        595                 600                 605

Leu Thr Trp Asp Asp Ile Asp Glu Phe Val Tyr Glu Ala Thr Lys Lys
610                 615                 620

Phe Gly Tyr Leu Glu Phe Leu Glu Leu Ile Leu Asn Lys Glu His Lys
625                 630                 635                 640

Gln Ile Glu Asn Glu Leu Ser Leu Asn Asn Phe Ile Ser Gly Thr Ile
                645                 650                 655

Thr Gly Glu Tyr Glu Asn Val Ser Ile Lys Asn Met Val Arg Val Tyr
            660                 665                 670

Asn Lys Ile Glu Glu Arg Ile Phe Arg Asn Ile Glu Lys Val Thr Asn
        675                 680                 685

Ser Phe Lys Leu Leu Phe Glu Ile Ile Asp Glu Phe Ser Leu Lys Phe
690                 695                 700

Asn Ile Asn Ser Lys Glu Thr Ile Arg Thr Glu Lys Val Val Met Lys
705                 710                 715                 720

Asp Ile Asp Glu Leu Ser Leu Gly Gln Lys Val Val Ala Ile Leu Thr
                725                 730                 735

Leu Ile Phe Asn Tyr Gly Glu His Ser Val Asp Ser Thr Pro Leu Val
            740                 745                 750

Ile Asp Gln Pro Glu Asp Asn Leu Asp Asn Leu Tyr Ile Tyr Gln Asn
        755                 760                 765

Leu Val Lys Ser Leu Arg Lys Ile Lys Asn Lys Arg Gln Val Ile Ile
770                 775                 780

Ala Thr His Ser Ala Thr Ile Val Thr Asn Ala Asp Ala Glu Gln Val
785                 790                 795                 800

Ile Ile Leu Glu Ser Asp Asn Lys Arg Gly Trp Leu Ser Lys Lys Gly
                805                 810                 815

Tyr Pro Asp Asp Glu Val Val Leu Lys His Ile Val Ser Ile Leu Glu
            820                 825                 830

Gly Gly Arg Glu Ser Phe Ile His Lys Lys Glu Thr Tyr Met Thr Val
        835                 840                 845

Leu Asp Ile
    850

<210> SEQ ID NO 7
<211> LENGTH: 316
<212> TYPE: PRT
```

<213> ORGANISM: Bacillus subtilis
<220> FEATURE:
<223> OTHER INFORMATION: >ABP10654

<400> SEQUENCE: 7

```
Met Thr Gln Ser Pro Ile Phe Leu Thr Pro Val Phe Lys Glu Lys Ile
1               5                   10                  15

Trp Gly Gly Thr Ala Leu Arg Asp Arg Phe Gly Tyr Ser Ile Pro Ser
            20                  25                  30

Glu Thr Thr Gly Glu Cys Trp Ala Ile Ser Ala His Pro Lys Gly Pro
        35                  40                  45

Ser Thr Val Ala Asn Gly Pro Tyr Lys Gly Lys Thr Leu Ile Glu Leu
    50                  55                  60

Trp Glu Glu His Arg Glu Val Phe Gly Gly Val Glu Gly Asp Arg Phe
65                  70                  75                  80

Pro Leu Leu Thr Lys Leu Leu Asp Val Lys Glu Asp Thr Ser Ile Lys
                85                  90                  95

Val His Pro Asp Asp Tyr Tyr Ala Gly Glu Asn Glu Glu Gly Glu Leu
            100                 105                 110

Gly Lys Thr Glu Cys Trp Tyr Ile Ile Asp Cys Lys Glu Asn Ala Glu
        115                 120                 125

Ile Ile Tyr Gly His Thr Ala Arg Ser Lys Thr Glu Leu Val Thr Met
    130                 135                 140

Ile Asn Ser Gly Asp Trp Glu Gly Leu Leu Arg Arg Ile Lys Ile Lys
145                 150                 155                 160

Pro Gly Asp Phe Tyr Tyr Val Pro Ser Gly Thr Leu His Ala Leu Cys
                165                 170                 175

Lys Gly Ala Leu Val Leu Glu Thr Gln Gln Asn Ser Asp Ala Thr Tyr
            180                 185                 190

Arg Val Tyr Asp Tyr Asp Arg Leu Asp Ser Asn Gly Ser Pro Arg Glu
        195                 200                 205

Leu His Phe Ala Lys Ala Val Asn Ala Ala Thr Val Pro His Val Asp
    210                 215                 220

Gly Tyr Ile Asp Glu Ser Thr Glu Ser Arg Lys Gly Ile Thr Ile Lys
225                 230                 235                 240

Thr Phe Val Gln Gly Glu Tyr Phe Ser Val Tyr Lys Trp Asp Ile Asn
                245                 250                 255

Gly Glu Ala Glu Met Ala Gln Asp Glu Ser Phe Leu Ile Cys Ser Val
            260                 265                 270

Ile Glu Gly Ser Gly Leu Leu Met Tyr Glu Asp Lys Thr Cys Leu Leu
        275                 280                 285

Lys Lys Gly Asp His Phe Ile Leu Pro Ala Gln Met Pro Asp Phe Thr
    290                 295                 300

Ile Lys Gly Thr Cys Thr Leu Ile Val Ser His Ile
305                 310                 315
```

<210> SEQ ID NO 8
<211> LENGTH: 880
<212> TYPE: PRT
<213> ORGANISM: Bacillus subtilis
<220> FEATURE:
<223> OTHER INFORMATION: >ABP10655

<400> SEQUENCE: 8

```
Met Lys Lys Arg Leu Ile Ala Pro Met Leu Leu Ser Ala Ala Ser Leu
1               5                   10                  15
```

```
Ala Phe Phe Ala Met Ser Gly Ser Ala Gln Ala Ala Tyr Thr Asp
                20                  25                  30
Tyr Ser Leu Tyr Lys Val Glu Pro Ser Asn Thr Phe Ser Thr Glu Ser
            35                  40                  45
Gln Ala Ser Gln Ala Val Ala Lys Leu Glu Lys Asp Thr Gly Trp Asp
        50                  55                  60
Ala Ser Tyr Gln Ala Ser Gly Thr Thr Thr Tyr Gln Ile Ser Ala
65                  70                  75                  80
Ser Gly Ile His Ser Glu Ser Glu Ala Lys Ala Ile Leu Ser Gly Leu
                85                  90                  95
Ala Lys Gln Thr Ser Ile Thr Gly Thr Ser Pro Val Gly Ser Lys
            100                 105                 110
Gln Pro Tyr Val Thr Ile Ser Ser Gly Ala Ile Ser Gly Glu Lys Gln
        115                 120                 125
Ala Asn Thr Ile Leu Ala Lys Leu Lys Gln Glu Thr Gly Val Ala Gly
    130                 135                 140
Ala Val Lys Ala Tyr Gly Ala Ala Gln Pro Tyr Met Asn Val Met Thr
145                 150                 155                 160
Ser Asp Ile Ala Asp Glu Thr Lys Val Lys Ala Leu Ile Gln Ser Leu
                165                 170                 175
Ala Lys Gln Thr Gly Ile Lys Ser Ser Tyr Gln Pro Ile Thr His Thr
            180                 185                 190
Val Ser Val Thr Thr Ile Gln Ser Gly Thr Ile Val Gly Asp Ser Arg
        195                 200                 205
Ala Ala Gln Ile Lys Asn Ala Phe Gln Lys Glu Ser Gly Leu Gln Ala
    210                 215                 220
Ser Leu Lys Glu Thr Val Lys Gly Gln Ala Tyr Tyr Thr Phe Thr Thr
225                 230                 235                 240
Ala Ala Ile Ser Gly Glu Ala Asn Ala Lys Thr Leu Gln Gln Leu
                245                 250                 255
Lys Gln Ser Thr Gly Ile Thr Gly Ser Tyr Lys Ser Ile Asn Gln Lys
            260                 265                 270
Thr Thr Val Glu Ser Tyr Asn Val Gln Ser Ala Tyr Phe Lys Gly Leu
        275                 280                 285
Asn Thr Val Lys Asp Ala Ile Ser Gln Ile Lys Lys Asn Thr Gly Val
    290                 295                 300
Ser Gly Ser Tyr Gln Gln Val Gly Lys Ser Thr Ser Tyr Thr Val Asn
305                 310                 315                 320
Met Lys Gly Ile Thr Lys Gln Gln Leu Gln Lys Ile Asp Thr Phe Phe
                325                 330                 335
Lys Lys Lys Lys Trp His Tyr Thr Ser Ser Val Lys Lys Thr Thr
            340                 345                 350
Thr Ser Ala Ala Tyr Gln Ile Thr Thr Ala Lys Ile Leu Gly Glu Gln
        355                 360                 365
Gln Ala Asn Lys Ala Ala Phe Phe Ala Gln Lys Val Lys Ala
    370                 375                 380
Thr Lys Thr Thr Ala Gly Thr Thr Ala Glu Asn Gln Tyr Gln Leu Ile
385                 390                 395                 400
Ser Glu Glu Thr Ser Asp Gln Ser Lys Val Thr Lys Gly Leu Asn Ile
                405                 410                 415
Leu Lys Lys Asn Gln Leu Ser Ala Ser Ala Lys Ser Val Lys Lys Gln
            420                 425                 430
Ile Ala Asp Thr Phe Lys Ile Thr Thr Glu Ser Leu Leu Asp Gln Thr
```

```
            435                 440                 445
Lys Val Asn Gln Ala Leu Thr Phe Phe Lys Ser Asn His Ile Ser Ala
450                 455                 460

Ala Ser Gln Lys Thr Gly Gln Thr Ala Ala Ser Ser Tyr Gln Ile Thr
465                 470                 475                 480

Thr Glu Ala Ile Ile Ser Gln Glu Glu Ile Asp Arg Val Leu Thr Phe
                    485                 490                 495

Phe Lys Gln Asn Lys Ile Ala Val Thr Thr Ser Lys Thr Gly Gln Thr
                500                 505                 510

Ala Tyr Thr Gln Tyr Lys Ile Val Thr Ala Gln Leu Ser Ser Lys Thr
            515                 520                 525

Ala Leu Asn Asn Gly Leu Thr Tyr Leu Lys Ser Gln Gly Leu Thr Pro
530                 535                 540

Ser Tyr Thr Thr Lys Ser Asn Thr Leu Tyr Lys Ile Ser Val Asn Glu
545                 550                 555                 560

Gln Phe Thr Gly Asn Asp Thr Ala Ala Ala Ser Ser Lys Leu Lys
                565                 570                 575

Gln Leu Tyr Gly Trp Ala Ser Ser Ile Val Lys Val Lys Asn Gly Pro
                580                 585                 590

Gln Ile Met Lys Thr Asn Tyr Asn Leu Ser Leu Arg Asp Met Val Gln
                595                 600                 605

Lys Gln Met Thr Val Ser Pro Gln Thr Asp Gly Ala Ala Tyr Val Ser
610                 615                 620

Leu Thr Tyr Ile Asn Thr Ala Thr Ser Thr Val Thr Ala Asp Ala Leu
625                 630                 635                 640

Asn Ile Arg Ser Thr Pro Glu Val Ser Pro Thr Asn Val Ile Gly Gln
                645                 650                 655

Phe Lys Lys Gly Asp Lys Val Lys Ile Ile Gly Gln Thr Asn Gly Trp
                660                 665                 670

Ala Lys Ile Asn Leu Gly Trp Arg Asn Ala Ser Ser Asp Glu Val Val
            675                 680                 685

Gln Tyr Val Asp Pro Asn Asn Phe Ser Arg Asp Ser Lys Tyr Tyr Phe
690                 695                 700

Gln Phe Leu Lys Leu Ser Gln Thr Ala Gly Leu Asn Ala Thr Glu Val
705                 710                 715                 720

Asn Gln Lys Val Leu Ala Gly Lys Gly Ile Leu Thr Gly Lys Ala Lys
                725                 730                 735

Ala Phe Ile Asp Ala Ala Asn Lys Tyr Gly Ile Asn Glu Leu Tyr Leu
                740                 745                 750

Ile Ser His Ala Leu Leu Glu Thr Gly Asn Gly Thr Ser Asp Leu Ala
            755                 760                 765

Asn Gly Leu Thr Tyr Asn Gly Lys Thr Val Tyr Asn Met Tyr Gly Ile
770                 775                 780

Gly Ala Tyr Asp Ser Asn Pro Asn Tyr Gly Ala Lys Tyr Ala Tyr
785                 790                 795                 800

Glu Gln Gly Trp Phe Thr Pro Glu Ala Ala Ile Ile Gly Gly Ala Lys
                805                 810                 815

Phe Ile Gly Ser Ser Tyr Ile His Asn Thr Ala Tyr Asn Gln Asp Thr
                820                 825                 830

Leu Tyr Lys Met Arg Trp Ser Ala Thr Ala Thr His Gln Tyr Ala Thr
            835                 840                 845

Asp Ile Gly Trp Ala Tyr Lys Gln Val Asn Arg Met Tyr Ser Leu Tyr
850                 855                 860
```

Ser Leu Leu Asp Gly Tyr Thr Leu Tyr Phe Asp Val Pro Glu Phe Lys
865                 870                 875                 880

<210> SEQ ID NO 9
<211> LENGTH: 37
<212> TYPE: PRT
<213> ORGANISM: Bacillus subtilis
<220> FEATURE:
<223> OTHER INFORMATION: >ABP10656

<400> SEQUENCE: 9

Met Tyr Tyr Leu Glu Ile Met Ile Lys Met Leu Lys Glu Ile Arg Lys
1               5                   10                  15

Glu Pro Lys Lys Phe Asp Ile Ile Phe Val Ser Ser Pro Pro Phe Leu
            20                  25                  30

Leu Leu Leu Ser Gly
        35

<210> SEQ ID NO 10
<211> LENGTH: 254
<212> TYPE: PRT
<213> ORGANISM: Bacillus subtilis
<220> FEATURE:
<223> OTHER INFORMATION: >ABP10657

<400> SEQUENCE: 10

Met Lys Gly Val Lys Val Phe His His Pro Ile Ile Val Glu Ser Phe
1               5                   10                  15

Arg Ile Leu Glu Lys Leu Leu Tyr Lys Lys Ala Asp His Ile Val Ile
            20                  25                  30

Asn Ser Glu Gly Phe Leu His Tyr Leu Asn Glu His Ser Pro Leu Val
        35                  40                  45

Lys Glu Lys Val Thr Phe Ile Pro Asn Ser Ala Arg Glu Lys Glu Leu
    50                  55                  60

Leu Ile Ser Ser Asn Asp Ala Lys Thr Ala Leu Lys Ile Ile Tyr Val
65                  70                  75                  80

Gly Asn Ile Gly Leu Ala Gln Asn Val His Ile Ile Arg Asn Leu Ala
                85                  90                  95

Glu Lys Leu His Glu His Gln Ile Glu Phe Leu Ile Val Gly Tyr Gly
            100                 105                 110

Val Glu Lys Lys Glu Leu Leu Asn Tyr Ile Arg Glu Lys Asn Leu Met
        115                 120                 125

Asn Val Lys Ile Val Asn Pro Met Thr Arg Lys Glu Cys Leu Glu Leu
    130                 135                 140

Met Ser Gly Cys Asp Ile Gly Ile Val Thr Leu Lys Asp Ser Thr Val
145                 150                 155                 160

Phe Glu Thr Val Leu Pro Gly Arg Ile Ile Asp Tyr Ile Thr Cys Gly
                165                 170                 175

Ile Pro Ile Val Gly Ser Ile Ala Gly Tyr Ser Lys Thr Ile Ile Glu
            180                 185                 190

Gln Glu Gly Val Gly Leu Val Thr Ser Asn Ser Ser Glu Glu Met
        195                 200                 205

Leu Ala Asn Ile Met Lys Ile Tyr Asn Asp Pro Gly Leu Leu Lys Lys
    210                 215                 220

Met Gln Lys Asn Cys His Lys Leu Ile Arg Glu Asn Phe Met Trp Glu
225                 230                 235                 240

Thr Asn Ile Glu Lys Leu Ile Asn Val Ile Glu Asp Thr Arg

<210> SEQ ID NO 11
<211> LENGTH: 422
<212> TYPE: PRT
<213> ORGANISM: Bacillus subtilis
<220> FEATURE:
<223> OTHER INFORMATION: >ABP10658

<400> SEQUENCE: 11

| Met | Arg | Lys | Lys | Val | Cys | Met | Phe | Val | Trp | Asn | His | Phe | Thr | Asn | Asp |
|-----|-----|-----|-----|-----|-----|-----|-----|-----|-----|-----|-----|-----|-----|-----|-----|
| 1 | | | | 5 | | | | | 10 | | | | | 15 | |
| Ala | Arg | Val | Leu | Arg | Glu | Cys | Thr | Ala | Leu | Ser | Asp | Lys | Tyr | Tyr | Asp |
| | | | 20 | | | | | 25 | | | | | 30 | | |
| Val | Asp | Leu | Ile | Cys | Ile | His | Asp | Pro | Asn | Asn | Pro | Asp | Leu | Asp | Leu |
| | | | 35 | | | | | 40 | | | | | 45 | | |
| Ile | Gln | Lys | Tyr | Asn | Asp | His | Phe | Thr | Val | Tyr | Arg | Val | Lys | Arg | Ser |
| | 50 | | | | | 55 | | | | | 60 | | | | |
| Pro | Leu | Leu | Phe | Tyr | Ile | Gln | Phe | Ile | Tyr | Lys | Leu | Phe | Lys | Asn | Lys |
| 65 | | | | | 70 | | | | | 75 | | | | | 80 |
| Trp | Ser | Ile | Leu | Phe | Phe | Leu | Leu | Ile | Trp | Ile | Cys | Leu | Leu | Arg | Met |
| | | | | 85 | | | | | 90 | | | | | 95 | |
| Phe | Pro | Leu | Leu | Thr | Ile | Gly | Phe | Ser | Leu | Phe | Ala | Val | Ile | Val | Leu |
| | | | 100 | | | | | 105 | | | | | 110 | | |
| Lys | Thr | Lys | Leu | Lys | Thr | Met | Leu | Val | Arg | Gly | Ser | Ile | Ile | Met | Arg |
| | | | 115 | | | | | 120 | | | | | 125 | | |
| Met | Ile | Leu | Lys | Gly | Tyr | Ser | Lys | Lys | Tyr | Asp | Ile | Tyr | His | Ser | Asn |
| 130 | | | | | 135 | | | | | 140 | | | | | |
| Asp | Leu | Asn | Thr | Leu | Pro | Gln | Gly | Phe | Ile | Cys | Ser | Lys | Phe | Arg | Phe |
| 145 | | | | | 150 | | | | | 155 | | | | | 160 |
| Lys | Lys | Arg | Lys | Leu | Ile | Tyr | Asp | Ser | His | Glu | Val | Gln | Thr | Ser | Arg |
| | | | | 165 | | | | | 170 | | | | | 175 | |
| Thr | Gly | Tyr | Asp | Ser | Pro | Phe | Tyr | Ser | Lys | Met | Glu | Ala | Tyr | Leu | Ile |
| | | | 180 | | | | | 185 | | | | | 190 | | |
| Arg | Lys | Ile | Asp | Ile | Met | Ile | Val | Glu | Asn | His | Thr | Arg | Ala | Ala | Tyr |
| | | 195 | | | | | 200 | | | | | 205 | | | |
| Asn | Lys | Glu | Leu | Tyr | Gly | Phe | Tyr | Pro | Lys | Val | Leu | His | Asn | Tyr | Pro |
| | 210 | | | | | 215 | | | | | 220 | | | | |
| Phe | Leu | Leu | Glu | Glu | Thr | Lys | Glu | Gln | Ile | Asp | Ile | His | His | Met | Leu |
| 225 | | | | | 230 | | | | | 235 | | | | | 240 |
| Gly | Leu | Pro | Lys | Asn | Glu | Lys | Ile | Leu | Leu | Tyr | Gln | Gly | Gly | Ile | Gln |
| | | | | 245 | | | | | 250 | | | | | 255 | |
| Val | Gly | Arg | Gly | Leu | Asp | Lys | Leu | Ile | Lys | Ala | Met | Pro | Phe | Ile | Asn |
| | | | 260 | | | | | 265 | | | | | 270 | | |
| Glu | Gly | Thr | Leu | Leu | Phe | Ile | Gly | Asp | Gly | Arg | Ile | Lys | Lys | Asp | Leu |
| | | | 275 | | | | | 280 | | | | | 285 | | |
| Glu | Asn | Met | Val | Asn | Asn | Met | Glu | Leu | Gln | His | Arg | Val | Arg | Phe | Leu |
| | 290 | | | | | 295 | | | | | 300 | | | | |
| Pro | Lys | Val | Pro | Leu | Ser | Glu | Leu | Pro | Lys | Tyr | Thr | Arg | Ser | Ala | Tyr |
| 305 | | | | | 310 | | | | | 315 | | | | | 320 |
| Leu | Gly | Phe | Gln | Val | Leu | Asn | Asn | Val | Cys | Phe | Asn | His | Tyr | Ser | Ala |
| | | | | 325 | | | | | 330 | | | | | 335 | |
| Ser | Ser | Asn | Lys | Leu | Phe | Glu | Tyr | Ile | Met | Ala | Gly | Val | Pro | Val | Ile |
| | | | 340 | | | | | 345 | | | | | 350 | | |
| Gly | Cys | Asp | Phe | Pro | Glu | Ile | Lys | Lys | Val | Ile | Gln | Gly | Glu | Lys | Val |

```
                355                 360                 365
Gly Leu Val Val Asp Ser His Asp His Leu Ser Ile Ala Lys Gly Val
    370                 375                 380

Asn Thr Leu Leu Glu Asn Ala Asp Leu His Tyr Glu Phe His Lys Asn
385                 390                 395                 400

Cys Asp Lys Ala Lys Arg Lys Tyr Asn Trp Glu Thr Glu Lys Ser Gln
                405                 410                 415

Leu Leu Ser Leu Tyr Asn
            420

<210> SEQ ID NO 12
<211> LENGTH: 74
<212> TYPE: PRT
<213> ORGANISM: Bacillus subtilis
<220> FEATURE:
<223> OTHER INFORMATION: >ABP10659

<400> SEQUENCE: 12

Met Gln Ile Lys Lys Asn Gln Lys Asn Gln Glu Leu Ala Asp Lys Tyr
1               5                   10                  15

Asn Asp Leu Lys Ile Lys Tyr His Lys Ser Leu Glu Val Gln Glu Asp
            20                  25                  30

Leu Ile Thr Leu Cys Gln Glu Leu Ile Arg Glu Lys Glu Tyr Ile Glu
        35                  40                  45

Ala Arg Tyr Asn Asn Leu Lys Glu Ser Lys Leu Gly Arg Leu Thr Val
    50                  55                  60

Trp Met Trp Lys Arg Arg Arg Asn Lys
65                  70

<210> SEQ ID NO 13
<211> LENGTH: 771
<212> TYPE: PRT
<213> ORGANISM: Bacillus subtilis
<220> FEATURE:
<223> OTHER INFORMATION: >ABP10660

<400> SEQUENCE: 13

Met Lys Gln Ser Lys Asp Ile Lys Thr Leu Ser Lys Gln Leu Glu
1               5                   10                  15

Lys Val Arg Arg Glu Lys Glu Ile Leu Ile Gly Leu Lys Glu Lys Glu
            20                  25                  30

Val Ser Ile Thr Gly Phe Asp Asp Phe Phe Asp Thr Pro Met Arg
        35                  40                  45

Ile Leu Ala Glu Tyr Asn Lys Gln Thr Leu Glu Val Asp Ala Glu Lys
    50                  55                  60

Val Tyr Leu Ser Leu Phe Glu Arg Thr Thr Asn Phe Ser Ile Pro Ser
65                  70                  75                  80

Asn Lys Glu Ile Tyr Lys Leu Thr Gly Asp Arg Ile Ile Asp Pro
                85                  90                  95

Phe Ile Thr Leu Ser Gly Ser Val Lys Gly Gln Ile Tyr Ile Ala Phe
            100                 105                 110

Tyr Lys Asn Asn Glu Leu Tyr Ser Thr Lys Ile Phe Glu Ala Pro Phe
        115                 120                 125

Asp Lys Ile Ser Ala Asp Val Pro Glu Asn Thr Thr Ser Tyr Arg Phe
    130                 135                 140

Ala Leu Arg Leu Glu Gly Lys Gly Tyr Leu Gln Leu Asn Lys Leu Lys
145                 150                 155                 160
```

-continued

```
Ile Lys Gln Val Phe Lys Glu Gln Ile Ala Ser Lys Asn Ile Gly Val
                165                 170                 175
Asn Arg Ser Ile Thr Ile Ser Lys Ala Ser Lys Ile Gln Gln Phe Ile
            180                 185                 190
Asp Ser Ile Glu Ala Glu Thr Gln Asn Tyr Lys Asn Glu Lys Lys Glu
        195                 200                 205
Leu Arg Ile Ala Ala Ile Leu Asp Glu Phe Ser Tyr Glu Cys Phe Lys
    210                 215                 220
His Asp Ala Glu Ile Leu Arg Leu Ser Asn Thr Asp Trp Asp Asn Glu
225                 230                 235                 240
Ile Leu Glu Phe Asn Pro His Phe Val Phe Glu Ser Cys Trp Gln
                245                 250                 255
Gly Asn Gln Gly His Trp Gln Tyr Glu Val Ala Asn Leu His Lys Asn
                260                 265                 270
Lys His Arg Thr Ala Leu Lys Lys Leu Thr Glu Tyr Cys Lys Ser Lys
            275                 280                 285
Asn Ile Lys Thr Val Phe Trp Asp Lys Glu Gly Tyr Glu Asn Phe Glu
        290                 295                 300
Phe Phe Lys Thr Ala Ala Ser Tyr Phe Asp Tyr Val Met Thr Ala Asp
305                 310                 315                 320
Glu Asn Thr Val Lys Lys Phe Lys Glu Thr Ser Ser Ile Asn Asn Val
                325                 330                 335
Gly Ile Leu Pro Phe Ala Ala Gln Pro Arg Ile His Asn Pro Ile Asn
                340                 345                 350
Lys Asn Leu His His Leu Gly Gly Ile Ala Phe Ala Gly Ser Tyr Tyr
            355                 360                 365
Asn Asn Lys His Glu Ser Arg Lys Arg Asp Ile Glu Glu Ile Ile Lys
        370                 375                 380
Pro Ala Leu Asp Phe Gly Ile Asp Ile Tyr Asp Arg Tyr Tyr Asn Val
385                 390                 395                 400
Pro Ala Ala Lys Lys Val Asn Asn Thr Trp Pro Glu Glu Tyr Gln Arg
                405                 410                 415
His Ile Val Gly Ser Leu Asn Tyr Ser Gln Met Asn Val Ala Tyr Lys
            420                 425                 430
Asn Tyr Asn Met Phe Val Asn Val Asn Ser Val Gln Asn Ser Lys His
        435                 440                 445
Met Phe Ala Arg Arg Val Phe Glu Leu Leu Ala Ser Lys Thr Met Val
    450                 455                 460
Ile Ser Gly Pro Ser Lys Gly Val Gln Glu Tyr Phe Gly Asp Leu Val
465                 470                 475                 480
Pro Val Ala Cys Ser Lys Glu Glu Thr Val Asn Ile Leu Lys Thr Phe
                485                 490                 495
Leu Tyr Asn Pro Val Tyr Arg Glu Met Tyr Glu Lys Lys Gly His Arg
            500                 505                 510
Leu Val Leu Asn Ser His Thr Tyr Lys Asn Arg Leu Gln Glu Ile Cys
        515                 520                 525
Asp His Ile Gly Ile Asp Ile Asn Leu Leu Glu Lys Pro Arg Ile Ser
    530                 535                 540
Ile Ile Ser Ser Thr Gln Arg Thr Glu Tyr Met Glu Asn Leu Tyr Asn
545                 550                 555                 560
Asn Ala Arg His Gln Thr Tyr Gln Asn Leu Glu Leu Ile Ile Ile Leu
                565                 570                 575
Asn Lys Asn Ser Met Asp Ala Glu Glu Trp Lys Gln Lys Phe Ser Ser
```

-continued

```
                580                 585                 590
Leu His Phe Pro Val Thr Ile Leu Gln Val Asp Glu Asn Val Ser Leu
            595                 600                 605

Gly His Cys Leu Asn Lys Ala Val Gln Arg Ser Thr Gly Glu Ile Ile
    610                 615                 620

Ala Lys Phe Asp Asp Asp Tyr Tyr Ala Pro His Tyr Leu Glu Asp
625                 630                 635                 640

Met Leu His Ser Met Glu Tyr Ser Gly Ala Asp Ile Val Gly Lys Ser
                645                 650                 655

Ala His Tyr Val Tyr Leu Glu Glu Arg Glu Leu Leu Ile Leu Lys Thr
            660                 665                 670

Val Gly Ser Gly Ala Glu Arg Tyr Ser Asp Phe Ile Ser Gly Ala Thr
        675                 680                 685

Leu Val Phe Lys Lys Glu Val Phe Val Ser Leu Gly Gly Phe Ser Asp
            690                 695                 700

Lys Asn Arg Gly Glu Asp Ser Asp Phe Leu Lys Arg Ala Lys Glu Asn
705                 710                 715                 720

Gly Asn Ile Ile Tyr Ser Asn Asp Ser Trp Asn Phe Cys Leu Val Arg
                725                 730                 735

Arg Ala Asn Arg Asn Ser His Thr Trp Asn Ile Thr Ala Asp Asp Leu
            740                 745                 750

Leu Arg Asn Ser Thr Val His Ser Met Cys Lys Asp Tyr Lys Lys Pro
        755                 760                 765

Ile Thr Ile
    770

<210> SEQ ID NO 14
<211> LENGTH: 425
<212> TYPE: PRT
<213> ORGANISM: Bacillus subtilis
<220> FEATURE:
<223> OTHER INFORMATION: >ABP10661

<400> SEQUENCE: 14

Met Lys Val Cys Val Ile Gly Leu Gly Tyr Ile Gly Leu Pro Thr Ser
1               5                   10                  15

Val Met Phe Ala Lys Tyr Gly Val Asp Val Ile Gly Val Asp Val Gln
                20                  25                  30

Pro His Val Val Asp Ser Leu Asn Asn Gly Glu Ala His Leu Glu Glu
            35                  40                  45

Pro Gly Leu Gln Glu Phe Leu Asp Glu Ala Leu Ala Asn Gly Asn Phe
        50                  55                  60

Lys Ala Gln Leu Val Pro Glu Pro Ala Asp Ala Phe Ile Ile Ala Val
65                  70                  75                  80

Pro Thr Pro Asn Asn Ile Asn Asp Asn Met Ser Cys Asp Leu Thr Tyr
                85                  90                  95

Val Leu Gln Ala Val Asp Asn Ile Ile Pro Tyr Ile Arg Lys Gly Ser
            100                 105                 110

Thr Ile Ile Val Glu Ser Thr Ile Ala Pro Arg Ser Ile Glu Asp Tyr
        115                 120                 125

Val Gln Pro Leu Leu Glu Gln Asn Gly Phe Thr Ile Gly Glu Asp Ile
    130                 135                 140

Tyr Leu Val His Cys Pro Glu Arg Val Met Pro Gly Asn Ile Phe His
145                 150                 155                 160

Glu Leu Ala Asn Asn Met Arg Ile Val Gly Gly Ile Thr Pro Ser Cys
```

```
                    165                 170                 175
Ser Glu Ala Gly Glu Lys Val Tyr Arg Thr Phe Val Lys Ser Lys Ile
                180                 185                 190

Val Lys Thr Asp Ala Lys Thr Ala Glu Met Ser Lys Leu Met Glu Asn
            195                 200                 205

Thr Tyr Arg Asp Val Asn Ile Ala Leu Ala Asn Glu Leu Thr Lys Ile
        210                 215                 220

Cys Asn Asp Leu His Ile Asn Ala Leu Asp Val Ile Glu Met Ala Asn
225                 230                 235                 240

Met His Pro Arg Val Asn Ile His Ser Pro Gly Pro Val Gly Gly
                245                 250                 255

His Cys Leu Ala Val Asp Pro Tyr Phe Ile Val Ala Lys Ala Pro Glu
                260                 265                 270

Thr Ala Asp Leu Ile Ser Arg Ser Arg Ser Ile Asn Ser Ser Met Pro
            275                 280                 285

Ile Tyr Ile Val Glu Lys Val Arg Glu Ile Met Glu Met Val Asn Gly
        290                 295                 300

Arg Thr Ile Thr Ile Gly Gly Leu Ala Tyr Lys Gly Asp Ile Asp Asp
305                 310                 315                 320

Leu Arg Glu Ser Pro Ala Leu Glu Ile Leu Glu Met Leu Lys Ser Glu
                325                 330                 335

Lys Lys Tyr Glu Val Arg Ala Tyr Asp Pro Tyr Val Asn His Ser Glu
            340                 345                 350

Asn Ala Gln Asn Leu Thr Glu Ala Leu Gly Gly Ser Asp Leu Phe Leu
        355                 360                 365

Ile Leu Thr Asp His Ser Leu Phe Lys Thr Ile Asn Asp Glu Asp Thr
    370                 375                 380

Asn Arg Met Ser Asn Lys Val Ile Phe Asp Thr Arg Asn Ile Val Arg
385                 390                 395                 400

Asn Val Pro Glu Asp Cys Glu Cys Ile Asn Leu Gly Ser Ile His Asn
                405                 410                 415

Phe Leu Asn Asn Ala Val Leu Asn Val
            420                 425

<210> SEQ ID NO 15
<211> LENGTH: 710
<212> TYPE: PRT
<213> ORGANISM: Bacillus subtilis
<220> FEATURE:
<223> OTHER INFORMATION: ABP10662

<400> SEQUENCE: 15

Met Arg Lys Tyr Leu Cys Leu Phe Ser Phe Val Ile Leu Phe Phe Leu
1               5                   10                  15

Thr Leu Ser Phe Tyr Gly Glu Arg Val Leu Ala Tyr Thr Asp Thr Ser
            20                  25                  30

Thr Tyr Lys Val Thr Ile Lys Asp Glu Phe Thr Ser Glu Asp Lys Val
        35                  40                  45

Lys Gly Ile Ser Asn Lys Ile Asn Asn Glu Thr Gly Trp Asp Ala Asn
    50                  55                  60

Tyr Lys Leu Thr Gly Asn Thr Thr Arg Ala Phe Lys Ile Ile Thr Gly
65                  70                  75                  80

Gly Phe Tyr Gly Glu Asp Lys Val Lys Asp Val Leu Asn Asp Phe Glu
                85                  90                  95

Gln Asn Thr Gly Ile Asn Gly Ser Tyr Ser Glu Asn Gly Asn Val Gln
```

```
               100                 105                 110
Thr Ile Tyr Gln Ile Thr Thr Gly Gly Phe Thr Gly Glu Ser Lys Val
            115                 120                 125

Lys Gln Val Leu Asp Ile Leu Gln Ser Gln Thr Gly Val Lys Gly Thr
            130                 135             140

Tyr Thr Ser Thr Gly Glu Lys Gln Tyr Tyr Arg Ile Val Ser Gly
145                 150                 155                 160

Gly Phe Gln Ser Glu Gln Arg Ile Lys Glu Val Leu Ser Lys Phe Glu
                165                 170                 175

Asn Glu Thr Ser Ile Lys Gly Ser Tyr Glu Pro Ile Gly Asn Ser Lys
            180                 185                 190

Ile Thr Tyr Thr Val Leu Ser Gly Gly Phe Ser Thr Glu Asp Asn Val
            195                 200                 205

Lys Lys Ala Ala Ala Glu Thr Lys Ser Gln Thr Gly Ile Glu Ala Ser
        210                 215                 220

Tyr Glu Lys Ile Pro Asp Ser Glu Ser Tyr Arg Leu Val Ile Ser Asn
225                 230                 235                 240

Ile Thr Glu Ser Glu Leu Thr Gly Ile Glu Ser Phe Phe Gly Lys Lys
                245                 250                 255

Asn Trp Trp Tyr Val Lys Lys Glu Val Lys Asn Gln Ser Tyr Arg Leu
                260                 265                 270

Ile Ser Glu Pro Ile Leu Asp Asp Gln Ile Ile Asp Lys Gly Leu Ser
            275                 280                 285

Phe Phe Glu Ser Asn Lys Trp Trp Ala Ser Lys Gln Lys Thr Asp Gln
        290                 295                 300

Leu Gly Glu Asn Lys Phe Arg Ile Thr Thr Glu Lys Ile Ser Asp Glu
305                 310                 315                 320

Thr Lys Leu Leu Lys Ala Leu Asn Phe Phe Glu Ser Asn Lys Trp Trp
                325                 330                 335

Ala Val Ser Gln Lys Thr Thr Ile Lys Gly Tyr Arg Ile Thr Ser Glu
            340                 345                 350

Val Ile Asn Ser Glu Ala Val Leu Asn Lys Gly Leu Asp Phe Phe Lys
            355                 360                 365

Ser Lys Asn Leu Trp Ala Thr Tyr Ser Asn Leu Ser Lys Asp Thr Tyr
        370                 375                 380

Ile Ile Asn Leu Asn Glu Glu Phe Thr Gly Ile Glu Asn Ala Thr Ser
385                 390                 395                 400

Ala Val Asn Lys Leu Ser Asn Val Tyr Gly Leu Asn Ala Glu Val Val
                405                 410                 415

Lys Ile Lys Asp Gly Pro Gln Ile Met Asn Thr Asn Tyr Asn Leu Thr
            420                 425                 430

Leu Ser Asp Met Ile Ser Lys Gln Met Asn Ala Asn Pro Gln Thr Asp
        435                 440                 445

Ser Ala Ala Tyr Val Ser Leu Ser Tyr Ile Asn Thr Ser Thr Ser Thr
450                 455                 460

Val Thr Ala Asp Tyr Leu Asn Val Arg Ser Thr Pro Glu Val Lys Ser
465                 470                 475                 480

Asp Asn Ile Ile Gly Gln Val Gln Lys Ser Asp Lys Val Thr Ile Ile
                485                 490                 495

Ser Lys Glu Gly Asn Trp Ala Lys Ile Asn Met Gly Trp Arg Lys Ala
            500                 505                 510

Ser Arg Glu Glu Val Thr Tyr Tyr Ile Asn Pro Glu Asn Phe Ser Ile
            515                 520                 525
```

Ser Ser Lys Tyr Tyr Phe Gln Phe Leu Lys Leu Ser Gln Tyr Ala Gly
        530                 535                 540

Leu Thr Ala Thr Glu Val Asn Asn Lys Ile Leu Lys Gly Lys Gly Ile
545                 550                 555                 560

Leu Glu Gly Lys Gly Glu Ser Phe Ile Lys Ala Ala Glu Ser Asn Asn
                565                 570                 575

Ile Asn Glu Leu Tyr Leu Ile Ala His Ser Leu Leu Glu Thr Gly Asn
                580                 585                 590

Gly Ser Ser Glu Leu Ala Asn Gly Val Met Tyr Asn Gly Lys Lys Val
            595                 600                 605

Tyr Asn Met Tyr Gly Ile Gly Ala Tyr Asp Gly Asp Ala Val Thr Lys
            610                 615                 620

Gly Ala Gln Tyr Ala Tyr Asn Gln Gly Trp Phe Thr Pro Glu Ala Ala
625                 630                 635                 640

Ile Leu Gly Gly Ala Lys Phe Ile Gly Ser Ser Tyr Ile His Asn Ala
                645                 650                 655

Thr Tyr His Gln Asp Thr Leu Tyr Lys Met Arg Trp Glu Pro Thr Val
                660                 665                 670

Ser His Gln Tyr Ala Thr Asp Ile Gly Trp Ala Tyr Lys Gln Val Asn
            675                 680                 685

Arg Met Tyr Ser Leu Tyr Thr Leu Leu Asp Asn Tyr Thr Leu Tyr Tyr
            690                 695                 700

Asp Ile Pro Lys Tyr Lys
705             710

<210> SEQ ID NO 16
<211> LENGTH: 280
<212> TYPE: PRT
<213> ORGANISM: Bacillus subtilis
<220> FEATURE:
<223> OTHER INFORMATION: >ABP10663

<400> SEQUENCE: 16

Met Glu Ile Asn Gln Leu Arg Lys Glu Thr Ile Lys Phe Ile Asp Leu
1               5                   10                  15

Lys Glu Tyr Lys Ile Arg Ile Glu Glu Pro Tyr Leu Leu Cys Val Thr
                20                  25                  30

Thr Glu Asp Gly Val Pro Phe Glu Phe Leu Ile Asn Ile Arg Leu Asn
            35                  40                  45

Gln Asn Lys Leu Leu Ile Leu Ser Ser Gly Ala Tyr Asp Asn Val Lys
        50                  55                  60

Leu Lys Pro Pro Ile Phe Gln Arg Tyr Thr Trp Met Thr Glu Phe Asn
65                  70                  75                  80

His Ser Val Val Tyr Phe Asn Asp Pro Thr Leu Tyr Ile Asn Gln Lys
                85                  90                  95

Leu Ser Ile Gly Trp Gly Gln Gly Thr Lys Asn His Phe Tyr Leu Ala
                100                 105                 110

Thr Ile Thr Asn Val Ile Arg Glu Leu Ala Tyr Lys Ile Lys Val Asn
            115                 120                 125

Thr Lys Asp Ile Phe Phe Tyr Gly Ser Ser Ala Gly Gly Phe Met Ser
        130                 135                 140

Leu Ile Leu Ala Ser Phe Leu Arg Ala Asn Ala Ile Val Asn Asn Pro
145                 150                 155                 160

Gln Thr Asp Val Cys Thr Phe Tyr Gln Ser His Val Asp Arg Leu Phe
                165                 170                 175

```
Glu Thr Leu Tyr Pro Asn Glu Asp Lys His Glu Val Ile Lys Gln Phe
            180                 185                 190

Arg Tyr Arg Leu Asn Val Cys Ala Phe Gln Lys Leu Lys Gln Val
            195                 200                 205

Pro Lys Ile Phe Tyr Tyr Gln Asn Tyr Ala Cys Ser Phe Asp Val Glu
            210                 215                 220

Thr Gln Leu Ile Pro Phe Leu Asn Ser Ile Lys Ser Glu Lys Thr Leu
225                 230                 235                 240

Ala His Leu Thr Ala Asp Lys Glu Ile Glu Leu His Leu Tyr Tyr Asp
                245                 250                 255

Ala Glu Leu Gly His Asn Pro Leu Asn Lys Gln Lys Thr Met Glu Ile
            260                 265                 270

Ile His Lys Ala Met Phe Gly Ser
            275                 280

<210> SEQ ID NO 17
<211> LENGTH: 623
<212> TYPE: PRT
<213> ORGANISM: Bacillus subtilis
<220> FEATURE:
<223> OTHER INFORMATION: ABP10664

<400> SEQUENCE: 17

Met Arg Tyr Lys Val Lys Leu Ala Arg Lys Ile Lys Asn Arg Leu Phe
1               5                   10                  15

Arg Ser Lys Lys Lys Thr Gln Lys Glu Asn Ala Ala Val Ile Val His
            20                  25                  30

Pro Ala Asp Asn Arg Val Phe Ser Leu Phe Asp Lys Thr Lys Arg Ile
            35                  40                  45

Glu Glu Asn Gln Gln Val Pro Val Arg Lys Ile Ser Glu Phe Ser Trp
    50                  55                  60

Asn Gly Ser Ile Leu Lys Ile Ala Gly Tyr Met Tyr Ile Lys Gly Leu
65                  70                  75                  80

Pro Leu Gln Lys Glu Asp Gln Val Arg Lys Leu Leu Leu Val Asn
                85                  90                  95

Asn Gly Val Leu Phe Thr Ala Val Ser Leu Arg Asp Val Pro Val Asp
            100                 105                 110

Lys Leu Ser Ile Asp Thr Ser Asn Val Pro Gly Ala Tyr Lys Trp Ala
            115                 120                 125

Gly Phe Ser Gln Gln Ile Asn Phe Ser Lys Leu Met Asn Asp Lys Pro
        130                 135                 140

Leu Pro Gln Gly Glu Tyr Lys Leu Phe Leu Glu Ile Glu Ala Val Asp
145                 150                 155                 160

Asp Gln Asn Val Lys His Gln Glu Val His Thr Val Gly Asn Val Ser
                165                 170                 175

Asn Phe Leu Ser Asn Asp Val Tyr Ala Thr Lys Met Glu Phe His Ser
            180                 185                 190

Ala Lys Lys Leu Met Lys Phe Asn Leu Ile Val Asn Tyr Asp Glu Gly
            195                 200                 205

Glu Lys Thr Ile Asn Leu Ser Cys Asn Lys Leu Gln Glu Ile Asp Pro
        210                 215                 220

Ser Leu Leu Glu Leu Asp Thr Gly Lys Glu Ala Asn Arg Phe Leu Arg
225                 230                 235                 240

Lys Leu Asn Thr Ser Leu Phe His Phe Ala Tyr Asp Val Phe Arg Leu
                245                 250                 255
```

Leu Pro Ile Lys Ser Asn Lys Ile Val Phe Ala Ser Asp Ser Arg Leu
            260                 265                 270

Asp Met Thr Gly Asn Phe Glu Phe Val Tyr Glu Glu Leu Lys Arg
        275                 280                 285

Glu Glu Asn Phe Asp Phe Lys Phe Phe Leu Lys Ser Ser Ile Arg Asp
290                 295                 300

Arg Lys Ser Leu Ser Glu Leu Met Ser Met Ala Tyr His Phe Ala Thr
305                 310                 315                 320

Ser Lys Ile Ile Phe Ile Asp Asp Phe Tyr Pro Ile Ile Tyr Pro Leu
                325                 330                 335

Lys Ile Arg Lys Asn Ala Asp Leu Val Gln Leu Trp His Ala Val Gly
                340                 345                 350

Ala Phe Lys Thr Phe Gly Tyr Ser Arg Ile Gly Leu Pro Gly Gly Pro
            355                 360                 365

Ser Pro His Ser Lys Asn His Arg Asn Tyr Thr Lys Val Ile Val Ser
        370                 375                 380

Ser Glu Asn Ile Arg Lys His Tyr Ala Glu Gly Phe Gly Val Asp Ile
385                 390                 395                 400

Glu Asn Val Ile Ala Thr Gly Val Pro Arg Thr Asp Phe Phe Phe Asp
                405                 410                 415

Glu Ala Lys Lys Ala Phe Val Lys Glu Arg Leu Tyr Thr Glu Tyr Pro
            420                 425                 430

Phe Leu Lys Asp Lys Lys Val Ile Leu Phe Ala Pro Thr Phe Arg Gly
        435                 440                 445

Asn Gly Gln Gln Ser Ala His Tyr Pro Phe Glu Val Leu Asp Phe Asp
450                 455                 460

Arg Leu Tyr Arg Glu Leu Lys Asp Glu Tyr Ile Phe Leu Phe Lys Ile
465                 470                 475                 480

His Pro Phe Val Arg Asn Asp Ala Asn Ile Pro Tyr Gln Tyr Ser Asp
                485                 490                 495

Phe Phe Tyr Asp Phe Ser Ser Phe Arg Glu Ile Asn Glu Leu Leu Leu
            500                 505                 510

Val Thr Asp Ile Leu Ile Thr Asp Tyr Ser Ser Val Cys Phe Glu Tyr
        515                 520                 525

Ala Leu Leu Asn Lys Pro Met Ile Phe Phe Ser Tyr Asp Val Asp Asp
530                 535                 540

Tyr Ile Arg Lys Arg Asp Phe Tyr Tyr Asp Tyr Phe Asp Phe Ile Pro
545                 550                 555                 560

Gly Pro Leu Ala Lys Thr Ser Glu Gln Met Ile Ser Ile Ile Lys Glu
                565                 570                 575

Glu Lys Tyr Asn Phe Glu Gln Ile Asp Ser Phe Val His Tyr Phe Phe
            580                 585                 590

Asp Asp Leu Asp Gly Lys Ala Ser Glu Arg Val Val Asp Gln Ile Val
        595                 600                 605

Phe Pro Gln Glu Glu Glu Pro Ser Glu Asp Lys Val Leu Lys Arg
        610                 615                 620

<210> SEQ ID NO 18
<211> LENGTH: 389
<212> TYPE: PRT
<213> ORGANISM: Bacillus subtilis
<220> FEATURE:
<223> OTHER INFORMATION: >ABP10665

<400> SEQUENCE: 18

```
Met Lys Thr Phe Leu Thr Arg Ile Val Lys Gly Val Phe Gly Thr Ala
1               5                   10                  15
Tyr Lys Leu Leu Ser Ala Leu Leu Pro Val Gln His Asn Lys Ile Val
            20                  25                  30
Ile Ala Ser Tyr Arg Glu Asp His Leu Ser Asp Asn Phe Lys Gly Val
        35                  40                  45
Tyr Glu Lys Leu Lys Gln Asp Pro Ser Leu Arg Ile Thr Leu Leu Phe
    50                  55                  60
Arg Lys Met Asp Lys Gly Leu Ile Gly Arg Val Ala Tyr Leu Leu His
65              70                  75                  80
Leu Phe Ser Ser Leu Tyr His Leu Ala Thr Cys Arg Val Leu Leu Leu
            85                  90                  95
Asp Asp Tyr Tyr Phe Pro Leu Tyr Val Val Pro Lys Arg Lys Glu Thr
        100                 105                 110
Val Ala Ile Gln Leu Trp His Ala Cys Gly Ala Phe Lys Lys Phe Gly
    115                 120                 125
Tyr Ser Ile Val Asn Lys Pro Phe Gly Pro Ser Ser Asp Tyr Leu Lys
    130                 135                 140
Ile Val Pro Val His Ser Asn Tyr Asp Tyr Ala Ile Val Ser Ala Pro
145             150                 155                 160
Ala Ala Val Pro His Phe Ala Glu Ala Phe Gln Met Glu Gln Lys Gln
            165                 170                 175
Ile Leu Pro Leu Gly Ile Pro Arg Thr Asp Tyr Phe Tyr His Lys Glu
        180                 185                 190
His Ile Arg Thr Val Leu Asp Glu Phe His Arg Val Tyr Pro Glu Leu
        195                 200                 205
Lys His Lys Lys Lys Leu Leu Tyr Ala Pro Thr Phe Arg Gly Ser Gly
210                 215                 220
His His Gln Glu Gly Asp Ala Ile Pro Leu Asp Leu Leu Gln Leu Lys
225                 230                 235                 240
Ser Ala Leu Ser His Lys Asp Tyr Val Val Ile Leu His Leu His Pro
            245                 250                 255
Tyr Met Arg Lys His Ala His Thr Glu Glu Asp Asp Phe Val Leu Asp
        260                 265                 270
Leu Thr Asp Ser Tyr Ser Leu Tyr Asp Leu Met Ala Ile Ser Asp Gly
        275                 280                 285
Leu Ile Thr Asp Tyr Ser Ser Val Ile Phe Glu Tyr Ser Leu Leu Lys
        290                 295                 300
Arg Pro Met Tyr Phe Tyr Cys Pro Asp Leu Glu Asp Tyr Leu Glu Glu
305                 310                 315                 320
Arg Asp Phe Tyr Tyr Pro Phe Glu Ser Phe Val Pro Gly Pro Ile Ser
            325                 330                 335
Lys Asp Val Pro Ser Leu Val His Asp Ile Glu Ser Asp His Glu Ala
            340                 345                 350
Asp Thr Lys Arg Ile Glu Asp Phe Ser Gln Ala Phe Ile Thr His Gln
            355                 360                 365
Asp Gly Lys Ser Ser Gly Arg Val Ala Asp Phe Ile Ser Ser Phe Leu
    370                 375                 380
Thr Ser Gly Ala Asp
385

<210> SEQ ID NO 19
<211> LENGTH: 163
```

```
<212> TYPE: PRT
<213> ORGANISM: Bacillus subtilis
<220> FEATURE:
<223> OTHER INFORMATION: >ABP10666

<400> SEQUENCE: 19

Met Thr Leu Leu Leu Lys Lys Lys Tyr Pro Asp Ser Lys Val Phe Ile
1               5                   10                  15

Phe Gly Lys Thr Pro Tyr Lys Leu Asp His Phe Ser Phe Val Asp Ala
                20                  25                  30

Ala Tyr Gln Ile Asn Asp Ile Pro Glu Asp Val Arg Ile Asp His Ala
            35                  40                  45

Phe Glu Cys Val Gly Gly Arg Gly Ser Glu Ser Ala Ile Glu Gln Ile
        50                  55                  60

Ile Ala His Val His Pro Glu Ala Cys Val Ala Leu Leu Gly Val Ser
65                  70                  75                  80

Glu Tyr Pro Val Glu Ile Glu Thr Arg Met Val Leu Glu Lys Gly Ile
                85                  90                  95

Thr Leu Ile Gly Ser Ser Arg Ser Gly Arg Glu Asp Phe Ala Arg Thr
                100                 105                 110

Val Asp Phe Leu Ala Gln Tyr Pro Glu Val Val Asp Tyr Leu Glu Thr
            115                 120                 125

Leu Val Gly Gly Arg Phe Pro Val Arg Ser Ile Glu Glu Ile Thr Asn
        130                 135                 140

Ala Phe Glu Ala Asp Leu Thr Ser Ser Trp Gly Lys Thr Val Ile Glu
145                 150                 155                 160

Trp Glu Ile

<210> SEQ ID NO 20
<211> LENGTH: 178
<212> TYPE: PRT
<213> ORGANISM: Bacillus subtilis
<220> FEATURE:
<223> OTHER INFORMATION: >ABP10667

<400> SEQUENCE: 20

Met Ile Asn Gln Thr Tyr Arg Leu Val Ser Ala Arg Gln Phe Glu Val
1               5                   10                  15

Thr Tyr Lys Asp Lys Val Val His Ser Asp Lys Val Val Arg Pro
                20                  25                  30

Thr His Leu Ser Ile Cys Ala Ala Asp Gln Arg Tyr Tyr Thr Gly Ser
            35                  40                  45

Arg Gly Lys Glu Ala Met Asp Lys Lys Leu Pro Met Ala Leu Ile His
        50                  55                  60

Glu Gly Ile Gly Lys Val Met Phe Asp Pro Thr Gly Thr Phe Lys Val
65                  70                  75                  80

Gly Thr Arg Val Val Met Val Pro Asn Thr Pro Val Glu Glu His Glu
                85                  90                  95

Val Ile Ala Glu Asn Tyr Leu Arg Ser Ser Arg Phe Arg Ser Ser Gly
                100                 105                 110

Tyr Asp Gly Phe Met Gln Asp Tyr Met Phe Met Ala Pro Asp Arg Leu
            115                 120                 125

Val Glu Leu Pro Asp Ser Ile Asn Pro His Val Ala Ala Phe Thr Glu
        130                 135                 140

Leu Ile Thr Ile Ala Val His Ala Leu Ser Arg Phe Glu Arg Met Ala
145                 150                 155                 160
```

His Lys Lys Arg Asp Thr Phe Gly Val Trp Gly Thr Glu Ile Ser Asp
                165                 170                 175

Leu Ser

<210> SEQ ID NO 21
<211> LENGTH: 237
<212> TYPE: PRT
<213> ORGANISM: Bacillus subtilis
<220> FEATURE:
<223> OTHER INFORMATION: >ABP10668

<400> SEQUENCE: 21

Met Ile Tyr Ala Glu Ile Leu Ala Gly Gly Lys Gly Ser Arg Met Gly
1               5                   10                  15

Asn Val Asn Met Pro Lys Gln Phe Leu Pro Leu Asn Lys Arg Pro Ile
                20                  25                  30

Ile Ile His Thr Ile Glu Lys Phe Leu Leu Asn Asp Arg Phe Asp Lys
            35                  40                  45

Ile Leu Ile Val Ser Pro Lys Glu Trp Ile Asn His Thr Lys Asp Ile
        50                  55                  60

Leu Lys Lys Phe Ile Gly Gln Asp Asp Arg Leu Ile Val Val Glu Gly
65                  70                  75                  80

Gly Ser Asp Arg Asn Glu Ser Ile Met Ser Gly Ile Arg Tyr Ile Glu
                85                  90                  95

Lys Glu Phe Gly Ile Gln Asp Asp Val Ile Ile Thr His Asp Ser
                100                 105                 110

Val Arg Pro Phe Leu Thr His Arg Ile Ile Asp Glu Asn Ile Asp Ala
            115                 120                 125

Val Leu Gln Tyr Gly Ala Val Asp Thr Val Ile Ser Ala Ile Asp Thr
        130                 135                 140

Ile Ile Ala Ser Glu Asp Gln Glu Phe Ile Ser Asp Ile Pro Val Arg
145                 150                 155                 160

Asp Asn Met Tyr Gln Gly Gln Thr Pro Gln Ser Phe Arg Ile Ser Lys
                165                 170                 175

Leu Val Glu Leu Tyr Asn Lys Leu Ser Asp Glu Gln Lys Ala Val Leu
                180                 185                 190

Thr Asp Ala Cys Lys Ile Cys Ser Leu Ala Gly Glu Lys Val Lys Leu
            195                 200                 205

Val Arg Gly Glu Val Phe Asn Ile Lys Val Thr Thr Pro Tyr Asp Leu
        210                 215                 220

Lys Val Ala Asn Ala Ile Leu Gln Glu Arg Ile Ser Gln
225                 230                 235

<210> SEQ ID NO 22
<211> LENGTH: 355
<212> TYPE: PRT
<213> ORGANISM: Bacillus subtilis
<220> FEATURE:
<223> OTHER INFORMATION: >ABP10669

<400> SEQUENCE: 22

Met Thr Leu Leu Val Ser Phe Pro Asp Asn Ala Arg Ala Ile Leu Lys
1               5                   10                  15

Glu Tyr Gln Met Gly His Tyr Ser Phe Pro Ile His Val Leu Leu Thr
                20                  25                  30

Gln His Ala Lys Ser Leu Glu Thr Glu Phe Pro Glu Leu Thr Val Ser
            35                  40                  45

Val Ile Asn Glu Lys His Pro Leu His Ile Tyr Lys Ala Val Phe Ser
 50                  55                  60

Met Leu Ser Ser Lys Ala Val Ile Val Asp Asn Tyr Phe Val Leu Thr
 65                  70                  75                  80

Thr Val Leu Thr Cys Arg Pro Asp Ile Glu Cys Ile Gln Val Trp His
                 85                  90                  95

Ala Asn Gly Ala Phe Lys Arg Phe Gly Leu Lys Asp Ile Asn Thr Gln
                100                 105                 110

Asn Arg Ser Arg Ala Asp Val Arg Phe Arg Lys Val Tyr Ala Ser
            115                 120                 125

Phe Asp Arg Ile Val Val Gly Ser Glu His Met Ala Asp Ile Phe Lys
130                 135                 140

Glu Phe Phe Asp Ile Lys Gly Asp Lys Phe Leu Arg Phe Gly Val Pro
145                 150                 155                 160

Leu Thr Asp Ala Tyr Tyr Glu Val Gln Glu Asn Ser Asn Asp Leu Lys
                165                 170                 175

Asn Lys Tyr His Leu Pro Ala Asp Lys Lys Ile Ile Leu Tyr Ala Pro
            180                 185                 190

Thr Phe Arg Asp His Gln Phe Glu Ser Phe Ser Leu Pro Phe Ser Glu
            195                 200                 205

Lys Gln Leu Gln His Asp Leu Lys Gly Glu Tyr Leu Leu Ala Val Lys
210                 215                 220

Leu His Pro Val Met Lys Gln Ser Ala Glu Leu Pro Gly Asp Ser Ala
225                 230                 235                 240

Trp Ile Lys Asp Val Ser Asp Leu Pro Leu Ala Asp Leu Leu Lys Met
                245                 250                 255

Ser Asp Leu Leu Ile Ser Asp Tyr Ser Ser Val Pro Phe Glu Phe Ala
            260                 265                 270

Leu Leu Asp Lys Pro Ile Leu Phe Tyr Thr Tyr Asp Met Glu Ala Tyr
275                 280                 285

Asn Arg Thr Arg Gly Leu Ile Arg Asn Tyr Ser Glu Val Ile Pro Gly
            290                 295                 300

Val Pro Cys Cys Asp Ser Arg Ala Leu Leu Asp Gln Leu Lys Val Met
305                 310                 315                 320

Asp Asn Leu Gln Ser Glu Phe Glu Arg Phe Ser Arg Glu Trp Asn Leu
                325                 330                 335

Tyr Ser Arg Gly Asn Ala Ser Lys Gln Leu Leu Ser Tyr Ile Asn Glu
            340                 345                 350

Lys Ser Ile
        355

<210> SEQ ID NO 23
<211> LENGTH: 65
<212> TYPE: PRT
<213> ORGANISM: Bacillus subtilis
<220> FEATURE:
<223> OTHER INFORMATION: >ABP10670

<400> SEQUENCE: 23

Met Thr Ser Arg Phe Asp Pro Lys Gln Gln Cys Ala Asp Asp Phe Asp
 1               5                   10                  15

Glu Gln Ile Val Lys Lys Arg Lys Pro Gly Phe Gln Ser Val Ile Ser
                20                  25                  30

Ser Lys Arg Leu Pro Arg Ile Val Gly Arg His Ser Glu Arg Phe Met
            35                  40                  45

```
His Phe Ile Thr Tyr His Ser Ser Phe Lys Ala His Tyr Arg Trp Arg
    50                  55                  60

Asp
65

<210> SEQ ID NO 24
<211> LENGTH: 257
<212> TYPE: PRT
<213> ORGANISM: Bacillus subtilis
<220> FEATURE:
<223> OTHER INFORMATION: >ABP10671

<400> SEQUENCE: 24

Met Gln Thr Lys Pro Ile Asn Gln Leu Asp Phe Val Asp Gly Glu Leu
1               5                   10                  15

Thr Ser Phe Val Ser His Leu Glu Thr Ser Phe Leu Asp Gln Asn Lys
            20                  25                  30

Gly Ala Phe Ile Val Thr Ala Asn Pro Glu Ile Gly Phe Glu Ala Met
        35                  40                  45

Gln Asn Pro Arg Tyr Glu Ala Val Leu Ser Ser Ala Asp Phe Ile Leu
    50                  55                  60

Pro Asp Gly Ile Gly Val Val Leu Val Ser Lys Leu Ile Gly Lys Pro
65                  70                  75                  80

Leu Gln Ser Arg Ile Ala Gly Tyr Asp Leu Phe Thr Ser Leu Leu Glu
                85                  90                  95

Lys Ala Asp Gln Lys Lys Arg Val Phe Phe Tyr Gly Ala Ala Lys
            100                 105                 110

His Val Ile Ala Gln Thr Ile Glu Arg Ile Glu Arg Asp Tyr Pro Gly
        115                 120                 125

Ile Glu Ile Ala Gly Tyr Ser Asp Gly Tyr Val Lys Asn Gln Arg Glu
    130                 135                 140

Val Ala Asp Lys Ile Ala Ala Thr Asn Pro Asp Met Val Phe Val Ala
145                 150                 155                 160

Leu Gly Tyr Pro Asn Gln Glu Phe Phe Ile His Lys Tyr Arg His Leu
                165                 170                 175

Phe Pro Gln Ala Val Ser Val Gly Leu Gly Gly Ser Phe Asp Val Phe
            180                 185                 190

Ser Gly Asn Val Lys Arg Ala Pro Ser Phe Phe Ile Arg Phe His Leu
        195                 200                 205

Glu Trp Met Tyr Arg Leu Ile Thr Asn Pro Ala Arg Trp Arg Arg Met
    210                 215                 220

Leu Ser Ile Pro Lys Tyr Val Thr Ala Val Leu Lys His Glu Arg Thr
225                 230                 235                 240

Ser Ala Lys Pro Gln Tyr Thr Gly Gln Val Lys Asp Gln Ser Arg His
                245                 250                 255

Leu

<210> SEQ ID NO 25
<211> LENGTH: 130
<212> TYPE: PRT
<213> ORGANISM: Bacillus subtilis
<220> FEATURE:
<223> OTHER INFORMATION: >ABP10672

<400> SEQUENCE: 25

Met Lys Lys Val Ile Thr Tyr Gly Thr Phe Asp Leu Phe His Tyr Gly
1               5                   10                  15
```

His Met Lys Leu Leu Glu Arg Ala Arg Cys Leu Gly Asp Tyr Leu Ile
            20                  25                  30

Val Gly Leu Ser Thr Asp Asp Phe Asn Leu Gln Lys Gln Lys Lys Ser
        35                  40                  45

His His Ser Tyr Glu His Arg Lys Leu Ile Leu Glu Thr Ile Asp Phe
    50                  55                  60

Val Asn Leu Val Ile Pro Glu Lys Ser Trp Glu Gln Lys Ile Thr Asp
65                  70                  75                  80

Ile Lys Lys Tyr Gly Val Asp Thr Phe Val Ile Gly Asp Asp Trp Lys
                85                  90                  95

Gly Lys Phe Asp Tyr Leu Asn Glu Tyr Cys Lys Val Ile Tyr Leu Pro
            100                 105                 110

Arg Thr Glu Gly Ile Ser Ser Thr Lys Ile Lys Lys Glu Ile Ser Asp
        115                 120                 125

Leu Ser
    130

<210> SEQ ID NO 26
<211> LENGTH: 275
<212> TYPE: PRT
<213> ORGANISM: Bacillus subtilis
<220> FEATURE:
<223> OTHER INFORMATION: >ABP10673

<400> SEQUENCE: 26

Met Asn Ala Leu Val Arg Ile Val Lys Glu Gln Val Thr Ser Phe Pro
1               5                   10                  15

Leu Ile Leu Arg Leu Ala Ser Tyr Glu Thr Lys Ser Gln Tyr Gln Met
            20                  25                  30

Asn Tyr Leu Gly Val Leu Trp Gln Phe Leu Asn Pro Leu Ile Gln Met
        35                  40                  45

Leu Ala Tyr Trp Phe Val Phe Gly Met Gly Ile Arg Asn Ser Lys Pro
    50                  55                  60

Val Leu Thr Gly Ala Gly Glu Val Pro Phe Ile Val Trp Met Leu Ala
65                  70                  75                  80

Gly Leu Ile Pro Trp Phe Phe Ile Ser Pro Thr Ile Leu Asp Gly Ser
                85                  90                  95

Asn Ser Val Phe Lys Arg Ile Asn Met Val Ala Lys Met Asn Phe Pro
            100                 105                 110

Ile Ser Ser Leu Pro Ser Val Val Ile Ala Ser Asn Leu Phe Ser Tyr
        115                 120                 125

Phe Val Met Met Gly Ile Tyr Val Ile Val Leu Phe Ala Ser Gly Val
    130                 135                 140

Tyr Pro Ser Met His Trp Ile Gln Tyr Ile Tyr Tyr Leu Ile Cys Met
145                 150                 155                 160

Ile Ala Phe Met Phe Ser Phe Ser Leu Phe Asn Ser Thr Ile Ser Val
                165                 170                 175

Leu Val Arg Asp Tyr Gln Phe Leu Gln Ala Val Thr Arg Leu Leu
            180                 185                 190

Phe Phe Leu Leu Pro Ile Phe Trp Asn Ile Ser Glu Gln Leu Gly Lys
        195                 200                 205

Asn His Pro Asn Leu Leu Pro Val Leu Lys Leu Asn Pro Ile Phe Tyr
    210                 215                 220

Leu Ile Glu Gly Phe Arg Asn Ser Phe Leu Asp Gly Lys Trp Phe Phe
225                 230                 235                 240

```
Gln Asp Met Lys Tyr Thr Leu Tyr Phe Trp Leu Phe Thr Phe Leu Leu
                245                 250                 255
Leu Leu Val Gly Ser Ile Leu His Met Lys Phe Arg Asp Lys Phe Val
            260                 265                 270
Asp Phe Leu
        275

<210> SEQ ID NO 27
<211> LENGTH: 527
<212> TYPE: PRT
<213> ORGANISM: Bacillus subtilis
<220> FEATURE:
<223> OTHER INFORMATION: >ABP10674

<400> SEQUENCE: 27

Met Lys Leu Lys Val Ser Phe Arg Asn Val Ser Lys Gln Tyr His Leu
1               5                   10                  15
Tyr Lys Lys Gln Ser Asp Lys Ile Lys Gly Leu Phe Phe Pro Ala Lys
                20                  25                  30
Asp Asn Gly Phe Phe Ala Val Arg Asn Val Ser Phe Asp Val Tyr Glu
            35                  40                  45
Gly Glu Thr Ile Gly Phe Val Gly Ile Asn Gly Ser Gly Lys Ser Thr
50                  55                  60
Met Ser Asn Leu Leu Ala Lys Ile Ile Pro Thr Ser Gly Glu Ile
65                  70                  75                  80
Glu Met Asn Gly Gln Pro Ser Leu Ile Ala Ile Ala Ala Gly Leu Asn
                85                  90                  95
Asn Gln Leu Thr Gly Arg Asp Asn Val Arg Leu Lys Cys Leu Met Met
            100                 105                 110
Gly Leu Thr Asn Lys Glu Ile Asp Asp Met Tyr Asp Ser Ile Val Glu
        115                 120                 125
Phe Ala Glu Ile Gly Asp Phe Ile Asn Gln Pro Val Lys Asn Tyr Ser
130                 135                 140
Ser Gly Met Lys Ser Arg Leu Gly Phe Ala Ile Ser Val His Ile Asp
145                 150                 155                 160
Pro Asp Ile Leu Ile Ile Asp Glu Ala Leu Ser Val Gly Asp Gln Thr
                165                 170                 175
Phe Tyr Gln Lys Cys Val Asp Arg Ile Asn Glu Phe Lys Lys Gln Gly
            180                 185                 190
Lys Thr Ile Phe Phe Val Ser His Ser Ile Gly Gln Ile Glu Lys Met
        195                 200                 205
Cys Asp Arg Val Ala Trp Met His Tyr Gly Glu Leu Arg Met Phe Asp
210                 215                 220
Glu Thr Lys Thr Val Val Lys Glu Tyr Lys Ala Phe Ile Asp Trp Phe
225                 230                 235                 240
Asn Lys Leu Ser Lys Lys Glu Lys Glu Thr Tyr Lys Lys Glu Gln Thr
                245                 250                 255
Glu Glu Arg Lys Lys Glu Asp Pro Glu Ala Phe Ala Arg Phe Arg Gln
            260                 265                 270
Lys Lys Lys Lys Pro Lys Ser Leu Ala Asn Ala Val Gln Ile Ala Ile
        275                 280                 285
Leu Ser Ile Leu Thr Val Phe Met Ala Gly Thr Met Phe Phe Asn Ala
        290                 295                 300
Pro Leu Arg Thr Ile Ala Ser Phe Gly Ala Ile Pro Gln Asn Glu Val
305                 310                 315                 320
```

Lys Asn His His Gly Asn Ala Lys Gly Lys Ser Glu Glu Arg Leu Thr
             325                 330                 335

Ala Val Asn Lys Gln Gly Phe Ile Ala Asn Glu Lys Ala Ala Ala Tyr
         340                 345                 350

Lys Asp Gln Gly Leu Lys Gln Lys Ala Asp Val Thr Leu Pro Phe Gly
     355                 360                 365

Thr Glu Val Thr Val Ala Ala Lys Gly Lys Gln Ala Ala Lys Ile Lys
370                 375                 380

Phe Asp Gly His Ser Tyr Tyr Val Lys Ser Ala Val Ala Ala Asn
385                 390                 395                 400

Met Lys His Ala Glu Leu His Ala Ala Phe Thr Ser Tyr Val Ser
             405                 410                 415

Gln Asn Ala Ala Ser Ser Tyr Glu Tyr Phe Leu Lys Phe Leu Gly Asp
         420                 425                 430

Ser Arg Thr Ser Ile Gln Ser Lys Leu Asn Gly Tyr Thr Glu Gly Asp
     435                 440                 445

Thr Ala Asp Gly Arg Lys Thr Leu Asp Phe Asp Tyr Glu Lys Ile Ser
450                 455                 460

Tyr Val Leu Glu Asn Asp Lys Ala Thr Glu Leu Ile Phe His Asn Ile
465                 470                 475                 480

Ser Pro Ile Thr Pro Ala Ser Leu Ser Leu Ser Asp Ser Asp Val Leu
             485                 490                 495

Tyr Asp Ser Ser Lys Lys Arg Phe Leu Val Asn Thr Ala Asp Gln Val
         500                 505                 510

Phe Ala Val Asp Asn Glu Glu His Thr Leu Thr Leu Met Leu Lys
     515                 520                 525

<210> SEQ ID NO 28
<211> LENGTH: 294
<212> TYPE: PRT
<213> ORGANISM: Bacillus subtilis
<220> FEATURE:
<223> OTHER INFORMATION: >ABP10675

<400> SEQUENCE: 28

Met Lys Leu Lys Lys Val Arg Lys Ala Ile Pro Ala Ala Gly Leu
1               5                   10                  15

Gly Thr Arg Phe Leu Pro Ala Thr Lys Ala Met Pro Lys Glu Met Leu
             20                  25                  30

Pro Ile Val Asp Lys Pro Thr Ile Gln Tyr Ile Ile Glu Glu Ala Val
         35                  40                  45

Glu Ala Gly Ile Glu Asp Ile Ile Val Thr Gly Lys Ser Lys Arg
     50                  55                  60

Ala Ile Glu Asp His Phe Asp Tyr Ser Pro Glu Leu Glu Arg Asn Leu
65                  70                  75                  80

Glu Glu Lys Gly Lys Thr Glu Leu Leu Glu Lys Val Lys Lys Ala Ser
             85                  90                  95

Asn Leu Ala Asp Ile His Tyr Ile Arg Gln Lys Glu Pro Lys Gly Leu
         100                 105                 110

Gly His Ala Val Trp Cys Ala Arg Asn Phe Ile Gly Asp Glu Pro Phe
     115                 120                 125

Ala Val Leu Leu Gly Asp Asp Ile Val Gln Ala Glu Thr Pro Gly Leu
130                 135                 140

Arg Gln Leu Met Asp Glu Tyr Glu Lys Thr Leu Ser Ser Ile Ile Gly
145                 150                 155                 160

```
Val Gln Gln Val Pro Glu Glu Thr His Arg Tyr Gly Ile Ile Asp
                165                 170                 175

Pro Leu Thr Ser Glu Gly Arg Arg Tyr Gln Val Lys Asn Phe Val Glu
            180                 185                 190

Lys Pro Pro Lys Gly Thr Ala Pro Ser Asn Leu Ala Ile Leu Gly Arg
        195                 200                 205

Tyr Val Phe Thr Pro Glu Ile Phe Met Tyr Leu Glu Glu Gln Gln Val
    210                 215                 220

Gly Ala Gly Gly Glu Ile Gln Leu Thr Asp Ala Ile Gln Lys Leu Asn
225                 230                 235                 240

Glu Ile Gln Arg Val Phe Ala Tyr Asp Phe Glu Gly Lys Arg Tyr Asp
                245                 250                 255

Val Gly Glu Lys Leu Gly Phe Ile Thr Thr Leu Glu Phe Ala Met
            260                 265                 270

Gln Asp Lys Glu Leu Arg Asp Gln Leu Val Pro Phe Met Glu Gly Leu
        275                 280                 285

Leu Asn Lys Glu Glu Ile
        290

<210> SEQ ID NO 29
<211> LENGTH: 509
<212> TYPE: PRT
<213> ORGANISM: Bacillus subtilis
<220> FEATURE:
<223> OTHER INFORMATION: >ABP10676

<400> SEQUENCE: 29

Met Lys Thr Val Phe Met Val Val Tyr Thr Ile Asp Val Asn Lys Gly
1               5                   10                  15

Gly Met Thr Thr Ala Met Leu Asn Arg Ser Lys Met Leu Val His Asn
            20                  25                  30

Gly Tyr Lys Ser Asp Leu Val Thr Phe Asp Tyr Asn Pro Tyr Tyr Glu
        35                  40                  45

Asn Ile Thr Ser Glu Leu Arg Gln Ile Gly Lys Leu Asp Pro Asp Val
    50                  55                  60

Asn Ile Leu Asn Val Asn Asp Tyr Tyr Arg Asp Leu Asn Thr Glu Gly
65                  70                  75                  80

Asn Val Asp Pro Ser Tyr Tyr Glu Asp Glu Ala Lys Thr Glu Gln Glu
                85                  90                  95

Gly Tyr Phe Ile Gln Asp Ser Glu Tyr Asp Thr Lys Gln Tyr Ile Arg
            100                 105                 110

Tyr Phe Lys Gln Gly Ser Tyr Val Lys Tyr Lys Lys Trp Thr Glu Asp
        115                 120                 125

Gly Tyr Leu Ser His Ile Asp Phe Phe Asn Glu Asn Arg Gln Arg Ile
    130                 135                 140

Lys Arg Glu Glu Phe His Lys Asn Lys Tyr Lys His Arg Glu Ile Ser
145                 150                 155                 160

Phe Asp Pro Ser Asn Asn Lys Met Asn Tyr Glu Lys Tyr Tyr Thr Pro
                165                 170                 175

Asp Gly Phe Cys Tyr Leu Ile Arg Trp Tyr Asn Ser Glu Thr Glu Lys
            180                 185                 190

Gln Gln Gln Val Phe Leu Phe Asn Arg Asn Ser Asn Lys Val Leu Met
        195                 200                 205

Phe Lys Asn Asn Ala Glu Phe His Thr Tyr Trp Leu Asn Glu Ile Ala
    210                 215                 220
```

```
Ala Ala Glu Asn Glu Lys Pro Ile Phe Ile Cys Asp Gly Pro Gly Ser
225                 230                 235                 240

Ser Gly Lys Val Arg Gly Met Lys Lys Glu Leu Ala His Arg Ile Tyr
            245                 250                 255

Met Val His Ile Asn His Phe Glu Thr Pro Tyr Thr Tyr Gly Ser Lys
        260                 265                 270

Val Lys Gln Asp His Ile Asp Phe Leu Ser Asn Ile Asp Lys Leu Asp
    275                 280                 285

Ala Leu Val Val Leu Thr Asn Asp Gln Lys Lys Asp Ile Glu Lys Gln
290                 295                 300

Phe Gly Glu His Gly Asn Ile Phe Ile Ile Pro Asn Ser Met Pro Tyr
305                 310                 315                 320

Thr Asp Leu Pro Asp Ile Lys Lys Asp Asn Lys Lys Val Ser Met Phe
                325                 330                 335

Val Arg Tyr His Lys Gln Lys Ala Ile Asp Glu Ala Ile Lys Ala Phe
            340                 345                 350

Val Arg Val Ile Lys Lys Val Pro Asp Ala Arg Leu Glu Ile Phe Gly
            355                 360                 365

His Gly Ala Glu Lys Ser Arg Leu Glu Gln Leu Ile Ile Glu Leu Asn
370                 375                 380

Leu Gln Gln Asn Val Phe Ile Lys Gly Tyr Ala Lys Asn Val Arg Glu
385                 390                 395                 400

Glu Met Gly Ser Ser Leu Ile Thr Leu Leu Thr Ser Asn Tyr Glu Ala
                405                 410                 415

Phe Gly Leu Ser Ile Thr Glu Ser Phe Met Asn Gly Thr Pro Val Ile
            420                 425                 430

Ser Tyr Asp Cys Asn Tyr Gly Pro Arg Asp Val Ile Ser Asp Gly Ile
        435                 440                 445

Asp Gly Tyr Ile Val Pro Gln Lys Asp Gln Lys Ala Leu Ala Asn Gln
    450                 455                 460

Ile Ile Lys Leu Leu Asn Asn Pro Asp Leu Ala Lys Glu Met Gly Leu
465                 470                 475                 480

Lys Gly Arg Glu Lys Val Leu Thr Glu Tyr Thr Asn Glu Val Val Leu
                485                 490                 495

Asn Lys Trp Leu Gln Leu Phe Asn Val Leu Glu Lys Lys
            500                 505

<210> SEQ ID NO 30
<211> LENGTH: 79
<212> TYPE: PRT
<213> ORGANISM: Bacillus subtilis
<220> FEATURE:
<223> OTHER INFORMATION: >ABP10677

<400> SEQUENCE: 30

Met Tyr Asp Phe Leu Asn Val Pro Gln Pro Asp Tyr Ser Trp Ile Glu
1               5                   10                  15

His Pro Ile Glu Glu Ala Gly Leu Thr Tyr Ile Lys Val Pro Glu Lys
            20                  25                  30

Pro Val Tyr Arg Tyr Tyr Gly Lys Tyr Val Lys Tyr Gln Arg Phe Ser
        35                  40                  45

Ser Ser Val Asn Trp Leu Tyr Gln Val Ile Leu Met Thr Ala Gln Ala
    50                  55                  60

Lys Val Gln Lys Arg Arg Val Arg Lys Thr Arg Thr Gln Arg Ile
65                  70                  75
```

-continued

<210> SEQ ID NO 31
<211> LENGTH: 61
<212> TYPE: PRT
<213> ORGANISM: Bacillus subtilis
<220> FEATURE:
<223> OTHER INFORMATION: >ABP10678

<400> SEQUENCE: 31

Met Phe Leu Thr Tyr Thr Asn Gly Glu Gly Tyr Glu His Tyr Gln Tyr
1               5                   10                  15

Leu Ile Asn Glu Leu Ser Leu Ile Ile Phe Glu Gly Ile Phe Gly Lys
            20                  25                  30

Ile Ser Ile Ile Leu Ser Gly Gly Ala Trp His Phe Ile Gln Asn Asn
        35                  40                  45

Lys Ala Ser Ala Leu Ser Phe Val Asn His Phe Leu Ser
    50                  55                  60

<210> SEQ ID NO 32
<211> LENGTH: 106
<212> TYPE: PRT
<213> ORGANISM: Bacillus subtilis
<220> FEATURE:
<223> OTHER INFORMATION: >ABP10825

<400> SEQUENCE: 32

Met Ala Trp Phe Leu Leu Val Ile Ala Gly Ile Glu Glu Ile Ile Ala
1               5                   10                  15

Ala Ile Ala Met Lys Tyr Ile Asp Gly Thr Arg Lys Lys Trp Pro Ile
            20                  25                  30

Ile Val Met Thr Val Gly Phe Gly Leu Ser Phe Tyr Cys Leu Ser Gln
        35                  40                  45

Ala Met Ile Val Leu Pro Ala Gly Val Ala Tyr Ala Val Trp Thr Gly
    50                  55                  60

Ile Gly Ser Ile Gly Val Ser Ala Val Gly Phe Ile Trp Phe Lys Glu
65                  70                  75                  80

Arg Phe Gln Leu Ser Gln Val Ile Ser Leu Cys Leu Ile Leu Ala Gly
                85                  90                  95

Val Ile Gly Leu Arg Leu Thr Ser Ser Ser
            100                 105

<210> SEQ ID NO 33
<211> LENGTH: 111
<212> TYPE: PRT
<213> ORGANISM: Bacillus subtilis
<220> FEATURE:
<223> OTHER INFORMATION: >ABP10826

<400> SEQUENCE: 33

Met Asn Trp Val Leu Val Phe Ile Ala Gly Leu Leu Glu Val Val Trp
1               5                   10                  15

Ala Ser Ser Leu Lys His Ala Asp Ser Leu Leu Asp Trp Ile Ile Ile
            20                  25                  30

Phe Ile Leu Ile Ala Val Ser Phe Ile Leu Leu Ile Arg Ser Tyr Gln
        35                  40                  45

Lys Ile Pro Met Ala Ala Ala Tyr Thr Val Phe Val Gly Ile Gly Thr
    50                  55                  60

Val Gly Thr Tyr Leu Thr Gly Ile Val Leu Gly Glu Ser Phe Ser Ala
65                  70                  75                  80

Ala Gln Met Phe Phe Leu Ala Leu Leu Leu Ala Gly Ile Leu Gly Met 85                  90                  95

Lys Leu Phe Thr Lys Glu Ser Lys Ser Gln Pro Gly Gly Glu Gln
                    100                 105                 110

<210> SEQ ID NO 34
<211> LENGTH: 194
<212> TYPE: PRT
<213> ORGANISM: Bacillus subtilis
<220> FEATURE:
<223> OTHER INFORMATION: >ABP10827

<400> SEQUENCE: 34

Met Pro Lys Gln Thr Ser Gly Lys Tyr Glu Lys Ile Leu Gln Ala Ala
1               5                   10                  15

Ile Glu Val Ile Ser Glu Lys Gly Leu Asp Lys Ala Ser Ile Ser Asp
                20                  25                  30

Ile Val Lys Lys Ala Gly Thr Ala Gln Gly Thr Phe Tyr Leu Tyr Phe
            35                  40                  45

Ser Ser Lys Asn Ala Leu Ile Pro Ala Ile Ala Glu Asn Leu Leu Thr
50                  55                  60

His Thr Leu Asp Gln Ile Lys Gly Arg Leu His Gly Asp Glu Asp Phe
65                  70                  75                  80

Trp Thr Val Leu Asp Ile Leu Ile Asp Glu Thr Phe Leu Ile Thr Glu
                85                  90                  95

Arg His Lys Asp Ile Ile Val Leu Cys Tyr Ser Gly Leu Ala Ile Asp
                100                 105                 110

His Ser Met Glu Lys Trp Glu Thr Ile Tyr Gln Pro Tyr Tyr Ser Trp
            115                 120                 125

Leu Glu Lys Ile Ile Asn Lys Ala Ile Ala Asn Leu Glu Val Thr Glu
        130                 135                 140

Glu Ile Asn Ser Lys Trp Thr Ala Arg Thr Ile Ile Asn Leu Val Glu
145                 150                 155                 160

Asn Thr Ala Glu Arg Phe Tyr Ile Gly Phe Glu Gln Asp Glu Asn Val
                165                 170                 175

Glu Val Tyr Lys Lys Glu Ile Phe Ser Phe Leu Lys Arg Ser Leu Gly
            180                 185                 190

Thr Ala

<210> SEQ ID NO 35
<211> LENGTH: 520
<212> TYPE: PRT
<213> ORGANISM: Bacillus subtilis
<220> FEATURE:
<223> OTHER INFORMATION: >ABP10828

<400> SEQUENCE: 35

Met Ser Lys Gln Gly Asn Phe Gln Lys Ser Met Ser Leu Phe Asp Leu
1               5                   10                  15

Ile Leu Ile Gly Met Gly Ala Ile Phe Gly Ser Ala Trp Leu Phe Ala
                20                  25                  30

Val Ser Asn Val Ala Ser Lys Ala Gly Pro Ser Gly Ala Phe Ser Trp
            35                  40                  45

Ile Leu Gly Gly Ala Ile Ile Leu Leu Ile Gly Leu Val Tyr Ala Glu
        50                  55                  60

Leu Gly Ala Ala Leu Pro Arg Thr Gly Gly Ile Ile Arg Tyr Pro Val
65                  70                  75                  80

Tyr Ser His Gly His Leu Val Gly Tyr Leu Ile Ser Phe Val Thr Ile

```
                    85                  90                  95
Val Ala Tyr Thr Ser Leu Ile Ser Ile Glu Val Thr Ala Val Arg Gln
                   100                 105                 110
Tyr Val Ala Tyr Trp Phe Pro Gly Leu Thr Ile Lys Gly Ser Asp Ser
                   115                 120                 125
Pro Thr Ile Ser Gly Trp Ile Leu Gln Phe Ala Leu Leu Cys Leu Phe
                   130                 135                 140
Phe Leu Leu Asn Tyr Trp Ser Val Lys Thr Phe Ala Lys Ala Asn Phe
145                150                 155                 160
Ile Ile Ser Ile Phe Lys Tyr Ile Val Pro Ile Thr Ile Ile Ile Val
                   165                 170                 175
Leu Ile Phe His Phe Gln Pro Glu Asn Leu Ser Val Gln Gly Phe Ala
                   180                 185                 190
Pro Phe Gly Phe Thr Gly Ile Gln Ala Ala Ile Ser Thr Gly Gly Val
                   195                 200                 205
Met Phe Ala Tyr Leu Gly Leu His Pro Ile Val Ser Val Ala Gly Glu
210                215                 220
Val Gln Asn Pro Lys Arg Asn Ile Pro Ile Ala Leu Ile Ile Cys Ile
225                230                 235                 240
Ile Val Ser Thr Ile Ile Tyr Thr Val Leu Gln Val Thr Phe Ile Gly
                   245                 250                 255
Ala Ile Pro Thr Glu Thr Leu Lys His Gly Trp Pro Ala Ile Gly Arg
                   260                 265                 270
Glu Phe Ser Leu Pro Phe Lys Asp Ile Ala Val Met Leu Gly Leu Gly
                   275                 280                 285
Trp Leu Ala Thr Leu Val Ile Leu Asp Ala Ile Leu Ser Pro Gly Gly
                   290                 295                 300
Asn Gly Asn Ile Phe Met Asn Thr Thr Ser Arg Leu Val Tyr Ala Trp
305                310                 315                 320
Ala Arg Asn Gly Thr Leu Phe Gly Ile Phe Ser Lys Val Asn Lys Asp
                   325                 330                 335
Thr Gly Thr Pro Arg Ala Ser Leu Trp Leu Ser Phe Ala Leu Ser Ile
                   340                 345                 350
Phe Trp Thr Leu Pro Phe Pro Ser Trp Asn Ala Leu Val Asn Val Cys
                   355                 360                 365
Ser Val Ala Leu Ile Leu Ser Tyr Ala Ile Ala Pro Ile Ser Ser Ala
370                375                 380
Ala Leu Arg Val Asn Ala Lys Asp Leu Asn Arg Pro Phe Tyr Leu Lys
385                390                 395                 400
Gly Met Ser Ile Ile Gly Pro Leu Ser Phe Ile Phe Thr Ala Phe Ile
                   405                 410                 415
Val Tyr Trp Ser Gly Trp Lys Thr Val Ser Trp Leu Leu Gly Ser Gln
                   420                 425                 430
Leu Val Met Phe Leu Ile Tyr Leu Cys Phe Ser Lys Tyr Thr Pro Lys
                   435                 440                 445
Glu Asp Val Ser Leu Ala Gln Gln Leu Lys Ser Ala Trp Trp Leu Ile
450                455                 460
Gly Phe Tyr Ile Met Met Leu Ile Phe Ser Tyr Ile Gly Ser Phe Gly
465                470                 475                 480
His Gly Leu Gly Ile Ile Ser Asn Pro Val Asp Leu Ile Leu Val Ala
                   485                 490                 495
Ile Gly Ser Leu Ala Ile Tyr Tyr Trp Ala Lys Tyr Thr Gly Leu Pro
                   500                 505                 510
```

-continued

Lys Ala Ala Ile Asp Tyr Asp Lys
                515                 520

<210> SEQ ID NO 36
<211> LENGTH: 516
<212> TYPE: PRT
<213> ORGANISM: Bacillus subtilis
<220> FEATURE:
<223> OTHER INFORMATION: >ABP10829

<400> SEQUENCE: 36

Met Asn Tyr Ile Lys Ala Gly Lys Trp Leu Thr Val Phe Leu Thr Phe
1               5                   10                  15

Leu Gly Ile Leu Leu Phe Ile Asp Leu Phe Pro Lys Glu Glu His Asp
            20                  25                  30

Gln Lys Thr Lys Ser Lys Gln Lys Pro Asp Tyr Arg Ala Ala Tyr His
        35                  40                  45

Phe Thr Thr Pro Asp Lys Trp Lys Asn Asp Pro Gln Lys Pro Ile Tyr
    50                  55                  60

Phe Asp Gly Lys Tyr His Tyr Phe Tyr Leu Tyr Asn Arg Asp Tyr Pro
65                  70                  75                  80

Lys Gly Asn Gly Thr Glu Trp Arg His Ala Val Ser Glu Asp Leu Val
                85                  90                  95

His Trp Thr Asp Glu Gly Val Ala Ile Pro Lys Tyr Thr Asn Pro Asp
            100                 105                 110

Gly Asp Ile Trp Thr Gly Ser Val Val Val Asp Lys Glu Asn Thr Ala
        115                 120                 125

Gly Phe Gly Lys Asn Ala Leu Val Ala Ile Val Thr Gln Pro Ser Ala
    130                 135                 140

Lys Asp Lys Lys Gln Glu Gln Tyr Leu Trp Tyr Ser Thr Asp Lys Gly
145                 150                 155                 160

Lys Ser Phe Lys Phe Tyr Ser Gly Asn Pro Val Met Pro Asn Pro Gly
                165                 170                 175

Thr Asp Asp Phe Arg Asp Pro Lys Val Ile Trp Asp Gln Asp Asn
            180                 185                 190

Lys Trp Val Met Val Met Ala Glu Gly Ser Lys Ile Gly Phe Tyr Glu
        195                 200                 205

Ser Asp Asn Leu Lys Asp Trp His Tyr Thr Ser Gly Phe Phe Pro Glu
    210                 215                 220

Gln Ala Gly Met Val Glu Cys Pro Asp Leu Tyr Met Met Arg Ala Ser
225                 230                 235                 240

Asp Gly Ala Asn Lys Trp Val Leu Gly Ala Ser Ala Asn Gly Lys Pro
                245                 250                 255

Trp Gly Lys Pro Asn Thr Tyr Ala Tyr Trp Thr Gly Ser Phe Asp Gly
            260                 265                 270

Lys Glu Phe Lys Ala Asp Gln Thr Glu Ala Gln Trp Leu Asp Tyr Gly
        275                 280                 285

Phe Asp Trp Tyr Gly Gly Val Thr Phe Glu Asp Ser Lys Ser Thr Asp
    290                 295                 300

Pro Leu Glu Lys Arg Tyr Ala Leu Ala Trp Met Asn Asn Trp Asp Tyr
305                 310                 315                 320

Ala Asn Asn Thr Pro Thr Met Lys Asn Gly Phe Asn Gly Thr Asp Ser
                325                 330                 335

Val Ile Arg Glu Leu Arg Leu Lys Glu Gln Asp Gly Thr Tyr Ser Leu
            340                 345                 350

```
Val Ser Gln Pro Ile Glu Ala Leu Glu Gln Leu Thr Val Ser Thr Glu
        355                 360                 365
Glu Ile Glu Asp Gln Asp Val Asn Gly Ser Lys Thr Leu Ser Ile Thr
370                 375                 380
Gly Asp Thr Tyr Gln Leu Asp Thr Asp Leu Ser Trp Ser Glu Leu Lys
385                 390                 395                 400
Asn Ala Gly Val Arg Leu Arg Glu Ser Glu Asp Gln Lys Arg His Ile
                405                 410                 415
Asp Val Gly Ile Phe Ala Glu Gly Gly Tyr Ser Tyr Val Asn Arg Ala
                420                 425                 430
Ala Thr Asn Gln Pro Asp Lys Ser Asn Thr Tyr Val Glu Ser Lys Ala
            435                 440                 445
Pro Tyr Asp Val Ser Lys Arg Lys Val His Leu Lys Ile Leu Val Asp
        450                 455                 460
Lys Thr Thr Ile Glu Val Phe Val Gly Asp Gly Lys Thr Ile Phe Ser
465                 470                 475                 480
Asn Glu Val Phe Pro Lys Pro Glu Asp Lys Gly Ile Thr Leu Phe Ser
                485                 490                 495
Asp Gly Gly Thr Ala Ser Phe Lys Asn Ile Thr Val Lys His Phe Asp
                500                 505                 510
Ser Ile His Lys
        515

<210> SEQ ID NO 37
<211> LENGTH: 473
<212> TYPE: PRT
<213> ORGANISM: Bacillus subtilis
<220> FEATURE:
<223> OTHER INFORMATION: >ABP10830

<400> SEQUENCE: 37

Met Asn Ile Lys Lys Phe Ala Lys Gln Ala Thr Val Leu Thr Phe Thr
1               5                   10                  15
Thr Ala Leu Leu Ala Gly Gly Ala Thr Gln Ala Phe Ala Lys Glu Thr
            20                  25                  30
Asn Gln Lys Pro Tyr Lys Glu Thr Tyr Gly Ile Ser His Ile Thr Arg
        35                  40                  45
His Asp Met Leu Gln Ile Pro Glu Gln Gln Lys Asn Glu Lys Tyr Gln
    50                  55                  60
Val Pro Glu Phe Asp Ser Ser Thr Ile Lys Asn Ile Ser Ser Ala Lys
65                  70                  75                  80
Gly Leu Asp Val Trp Asp Ser Trp Pro Leu Gln Asn Ala Asp Gly Thr
                85                  90                  95
Val Ala Asn Tyr His Gly Tyr His Ile Val Phe Ala Leu Ala Gly Asp
                100                 105                 110
Pro Lys Asn Ala Asp Asp Thr Ser Ile Tyr Met Phe Tyr Gln Lys Val
            115                 120                 125
Gly Glu Thr Ser Ile Asp Ser Trp Lys Asn Ala Gly Arg Val Phe Lys
        130                 135                 140
Asp Ser Asp Lys Phe Asp Ala Asn Asp Ser Ile Leu Lys Asp Gln Thr
145                 150                 155                 160
Gln Glu Trp Ser Gly Ser Ala Thr Tyr Thr Ser Asp Gly Lys Ile Arg
                165                 170                 175
Leu Phe Tyr Thr Asp Phe Ser Gly Lys His Tyr Gly Lys Gln Thr Leu
                180                 185                 190
```

Thr Thr Ala Gln Val Asn Val Ser Ala Ser Asp Ser Ser Leu Asn Ile
            195                 200                 205

Asn Gly Val Glu Asp Tyr Lys Ser Ile Phe Asp Gly Asp Gly Lys Thr
        210                 215                 220

Tyr Gln Asn Val Gln Gln Phe Ile Asp Glu Gly Asn Tyr Ser Ser Gly
225                 230                 235                 240

Asp Asn His Thr Leu Arg Asp Pro His Tyr Val Glu Asp Lys Gly His
                245                 250                 255

Lys Tyr Leu Val Phe Glu Ala Asn Thr Gly Thr Glu Asp Gly Tyr Gln
            260                 265                 270

Gly Glu Glu Ser Leu Phe Asn Lys Ala Tyr Tyr Gly Lys Ser Thr Ser
        275                 280                 285

Phe Phe Arg Gln Glu Ser Gln Lys Leu Leu Gln Ser Asp Lys Lys Arg
        290                 295                 300

Thr Ala Glu Leu Ala Asn Gly Ala Leu Gly Met Ile Glu Leu Asn Asp
305                 310                 315                 320

Asp Tyr Thr Leu Lys Lys Val Met Lys Pro Leu Ile Ala Ser Asn Thr
                325                 330                 335

Val Thr Asp Glu Ile Glu Arg Ala Asn Val Phe Lys Met Asn Gly Lys
            340                 345                 350

Trp Tyr Leu Phe Thr Asp Ser Arg Gly Ser Lys Met Thr Ile Asp Gly
        355                 360                 365

Ile Thr Ser Asn Asp Ile Tyr Met Leu Gly Tyr Val Ser Asn Ser Leu
370                 375                 380

Thr Gly Pro Tyr Lys Pro Leu Asn Lys Thr Gly Leu Val Leu Lys Met
385                 390                 395                 400

Asp Leu Asp Pro Asn Asp Val Thr Phe Thr Tyr Ser His Phe Ala Val
                405                 410                 415

Pro Gln Ala Lys Gly Asn Asn Val Val Ile Thr Ser Tyr Met Thr Asn
            420                 425                 430

Arg Gly Phe Tyr Ala Asp Lys Gln Ser Thr Phe Ala Pro Ser Phe Leu
        435                 440                 445

Leu Asn Ile Lys Gly Lys Lys Thr Ser Val Val Lys Asp Ser Ile Leu
        450                 455                 460

Glu Gln Gly Gln Leu Thr Val Asn Lys
465                 470

<210> SEQ ID NO 38
<211> LENGTH: 451
<212> TYPE: PRT
<213> ORGANISM: Bacillus subtilis
<220> FEATURE:
<223> OTHER INFORMATION: >ABP10831

<400> SEQUENCE: 38

Met Lys Gln Asn Lys Arg Lys Asn Leu Gln Thr Leu Phe Glu Thr Leu
1               5                   10                  15

Gly Glu Lys His Gln Phe Asn Gly Thr Val Leu Ala Ala Glu Gly Gly
            20                  25                  30

Asp Ile Leu Tyr His His Ser Phe Gly Tyr Ala Glu Met Thr Glu Lys
        35                  40                  45

Arg Pro Leu Lys Thr Asn Ser Leu Phe Glu Leu Ala Ser Leu Ser Lys
    50                  55                  60

Pro Phe Thr Ala Leu Gly Ile Ile Leu Leu Glu Glu Lys Gly Ile Leu
65                  70                  75                  80

Gly Tyr Glu Asp Lys Val Asp Arg Trp Leu Pro Gly Phe Pro Tyr Gln
            85                  90                  95

Gly Val Thr Ile Arg His Leu Leu Asn His Thr Ser Gly Leu Pro Asp
            100                 105                 110

Tyr Met Gly Trp Phe Phe Ala Asn Trp Asp Pro His Lys Ile Ala Val
            115                 120                 125

Asn Gln Asp Ile Val Asp Met Leu Met Asn Glu Gly Leu Ser Gly Tyr
130                 135                 140

Phe Glu Pro Asn Glu Gly Trp Met Tyr Ser Asn Thr Gly Tyr Val Leu
145                 150                 155                 160

Leu Ala Val Ile Ile Glu Lys Ala Ser Gly Met Ser Tyr Ala Asp Phe
                165                 170                 175

Met Lys Thr Ser Ile Phe Leu Pro Ala Gly Met Asn Glu Thr Arg Val
            180                 185                 190

Tyr Asn Arg Arg Leu Ser Pro Glu Arg Ile Asp His Tyr Ala Tyr Gly
            195                 200                 205

Tyr Val Tyr Asp Val His Ser Glu Thr Tyr Val Leu Pro Asp Glu Leu
            210                 215                 220

Glu Glu Thr Asn Tyr Val Val Tyr Leu Asp Gly Ile Gln Gly Asp Gly
225                 230                 235                 240

Thr Val Asn Ser Val Thr Ser Asp Leu Phe Arg Phe Asp Gln Ala Leu
                245                 250                 255

Tyr Gln Asp Asp Phe Ile Ser Lys Ala Ser Lys Glu Ser Ala Phe Ser
            260                 265                 270

Pro Val Arg Leu Asn Asn Gly Glu Thr Ile Asp Tyr Gly Phe Gly Trp
            275                 280                 285

Val Leu Gln Asn Ser Pro Glu Lys Gly Arg Ile Val Ser His Ser Gly
            290                 295                 300

Gly Trp Pro Gly Tyr Ser Thr Leu Met Ile Arg Tyr Ile Asp His Arg
305                 310                 315                 320

Lys Thr Leu Ile Tyr Leu Ser Asn Lys Glu Glu Asp Thr Glu Tyr Glu
                325                 330                 335

Gln Ala Ile Leu Lys Ala Ala Glu His Ile Leu Phe Gly Gln Pro Tyr
            340                 345                 350

Glu Val Pro Glu Arg Pro Ala Asp Lys Lys Lys Ala Ile Asp Thr
            355                 360                 365

Ala Ile Tyr Ser Arg Tyr Val Gly Ser Tyr Leu Leu Gln Asp Gly Thr
370                 375                 380

Ala Ala Gln Val Thr Ala Glu Asn Glu Arg Leu Tyr Leu Glu Ile Ala
385                 390                 395                 400

Gly Gln Leu Arg Leu Glu Leu Phe Pro Ser Ser Glu Thr Arg Phe Phe
                405                 410                 415

Leu Arg Ala Leu Ser Val Glu Val Glu Phe Thr Leu Gly Val Asp Ala
            420                 425                 430

Ala Lys Ser Phe Ile Leu Tyr Glu Asp Gly Ser Glu Glu Glu Ala Val
            435                 440                 445

Arg Thr Lys
    450

<210> SEQ ID NO 39
<211> LENGTH: 227
<212> TYPE: PRT
<213> ORGANISM: Bacillus subtilis
<220> FEATURE:

<223> OTHER INFORMATION: >ABP10832

<400> SEQUENCE: 39

```
Met Ile Gly Ile Leu Ala Gly Met Gly Pro Lys Ser Thr Ser Pro Phe
1               5                   10                  15

Ile Asp Lys Val Ile Asp Tyr Cys Gln Lys Leu Tyr Gly Ala Ser Asn
            20                  25                  30

Asp Ile Asp Tyr Pro His Met Met Ile Tyr Ser Cys Pro Thr Pro Phe
        35                  40                  45

Tyr Ala Asp Arg Pro Ile Asp His Asp Glu Met Lys Lys Ala Ile Ile
    50                  55                  60

Asp Gly Ala Val Lys Leu Glu Lys Thr Gly Val Asp Phe Ile Ala Leu
65                  70                  75                  80

Pro Cys Asn Thr Ala His Val Tyr Tyr Glu Glu Ile Gln Gln Ala Leu
                85                  90                  95

Ser Val Pro Met Leu His Ile Val Glu Glu Thr Ile Lys Glu Ile Pro
            100                 105                 110

His Leu Ala Lys Lys Ala Val Val Leu Gly Thr Glu Pro Thr Ile Gln
        115                 120                 125

Ser Ala Ile Tyr Gln Lys Val Leu Lys Gly Asn Gly Gln Glu Val Ile
    130                 135                 140

His Lys Asp His Trp Gln Gln Ala Val Asn Gln Leu Ile Ala Ala Ile
145                 150                 155                 160

Lys Gln Pro Asn His Met Gln His Thr Gln Ala Leu Trp Gln Thr Leu
                165                 170                 175

Tyr Glu Glu Ile Ser Gln His Ala Asp Ile Ile Ser Ala Cys Thr
            180                 185                 190

Asp Leu Asn Ala Val Leu Asp His Ile Gln Ser Glu Ile Pro Ile Ile
        195                 200                 205

Asp Ser Ser Ala Cys Leu Ala Lys Ser Thr Val Ser Thr Tyr Leu Ala
    210                 215                 220

Tyr Gln Ser
225
```

<210> SEQ ID NO 40
<211> LENGTH: 151
<212> TYPE: PRT
<213> ORGANISM: Bacillus subtilis
<220> FEATURE:
<223> OTHER INFORMATION: >ABP10833

<400> SEQUENCE: 40

```
Met Lys Lys Pro Val Leu Lys Pro Phe Ala Ser Leu Glu Ile Lys Val
1               5                   10                  15

Asp Pro Pro Ile Thr Ile Gly Glu Thr Ser Leu Gly Leu Arg Arg Phe
            20                  25                  30

Ile Pro Ile Arg Ser Gly Thr Ile Thr Gly Glu Val Lys Gly Arg Ile
        35                  40                  45

Leu Pro Gly Gly Ala Asp Ser Gln Met Ile Arg Ala Asn Gly Arg Thr
    50                  55                  60

Asp Leu Ser Ala Arg Tyr Val Ile Glu Thr Ala Asp His Glu Leu Ile
65                  70                  75                  80

Tyr Ile Glu Asn Asn Gly Ile Arg Gln Val Ser Glu Pro Phe Arg Lys
                85                  90                  95

Gln Ala Ala Ala Gly Glu Ile Ile Glu Pro Glu His Val Tyr Phe Arg
            100                 105                 110
```

```
Thr Val Pro Thr Phe Glu Thr Gly Ser Glu Val Tyr Gln Trp Leu His
            115                 120                 125

Asp Arg Leu Phe Ile Gly Ser Ala Glu Arg Thr Pro Asp Tyr Val Leu
            130                 135                 140

Leu Asp Ile Tyr Glu Val Gln
145                 150

<210> SEQ ID NO 41
<211> LENGTH: 161
<212> TYPE: PRT
<213> ORGANISM: Bacillus subtilis
<220> FEATURE:
<223> OTHER INFORMATION: >ABP10834

<400> SEQUENCE: 41

Met Glu Asn Phe Ile Gly Ser His Met Ile Tyr Thr Tyr Glu Asn Gly
1               5                   10                  15

Trp Glu Tyr Glu Ile Tyr Ile Lys Asn Asp His Thr Ile Asp Tyr Arg
            20                  25                  30

Ile His Ser Gly Met Val Ala Gly Arg Trp Val Arg Asp Gln Glu Val
        35                  40                  45

Asn Ile Val Lys Leu Thr Glu Gly Val Tyr Lys Val Ser Trp Thr Glu
50                  55                  60

Pro Thr Gly Thr Asp Val Ser Leu Asn Phe Met Pro Asn Glu Lys Arg
65                  70                  75                  80

Met His Gly Ile Ile Phe Phe Pro Lys Trp Val His Glu His Pro Glu
                85                  90                  95

Ile Thr Val Cys Tyr Gln Asn Asp His Ile Asp Leu Met Lys Glu Ser
            100                 105                 110

Arg Glu Lys Tyr Glu Thr Tyr Pro Lys Tyr Val Pro Glu Phe Ala
        115                 120                 125

Glu Ile Thr Phe Leu Lys Asn Glu Gly Val Asp Asn Glu Glu Val Ile
    130                 135                 140

Ser Lys Ala Pro Tyr Glu Gly Met Thr Asp Asp Ile Arg Ala Gly Arg
145                 150                 155                 160

Leu

<210> SEQ ID NO 42
<211> LENGTH: 63
<212> TYPE: PRT
<213> ORGANISM: Bacillus subtilis
<220> FEATURE:
<223> OTHER INFORMATION: >ABP10835

<400> SEQUENCE: 42

Met Gly Lys Thr Gly Tyr Ile Gly Ala Ala Ile Val Ala Ala Cys
1               5                   10                  15

Ile Ile Ile Leu Ser Ala Val Val Cys Leu Arg Asp Thr Val Tyr Tyr
            20                  25                  30

Gln Pro Met Arg Trp Thr Gly Ile Ile Leu Phe Phe Ala Gly Ile Val
        35                  40                  45

Met Val Pro Ala Tyr Ser Ala Lys Arg Lys Pro Gly Lys Glu Lys
50                  55                  60

<210> SEQ ID NO 43
<211> LENGTH: 489
<212> TYPE: PRT
<213> ORGANISM: Bacillus subtilis
```

<220> FEATURE:
<223> OTHER INFORMATION: >ABP10836

<400> SEQUENCE: 43

```
Met Thr His Gln Ile Val Thr Thr Gln Tyr Gly Lys Val Lys Gly Thr
1               5                   10                  15

Thr Glu Asn Gly Val His Lys Trp Lys Gly Ile Pro Tyr Ala Lys Pro
            20                  25                  30

Pro Leu Gly Gln Trp Arg Phe Lys Ala Pro Glu Pro Glu Val Trp
        35                  40                  45

Glu Asp Val Leu Asp Ala Thr Ala Tyr Gly Pro Ile Cys Pro Gln Pro
        50                  55                  60

Ser Asp Leu Leu Ser Leu Ser Tyr Thr Glu Leu Pro Arg Gln Ser Glu
65                  70                  75                  80

Asp Cys Leu Tyr Val Asn Val Phe Ala Pro Asp Thr Pro Ser Gln Asn
                85                  90                  95

Leu Pro Val Met Val Trp Ile His Gly Gly Ala Phe Tyr Leu Gly Ala
            100                 105                 110

Gly Ser Glu Pro Leu Tyr Asp Gly Ser Lys Leu Ala Ala Gln Gly Glu
        115                 120                 125

Val Ile Val Val Thr Leu Asn Tyr Arg Leu Gly Pro Phe Gly Phe Leu
    130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Met Ser Ile Ala Ala Leu Leu Ala Met Pro Ala Ala Lys Gly Leu Phe
        195                 200                 205

Gln Lys Ala Ile Met Glu Ser Gly Ala Ser Arg Thr Met Thr Lys Glu
    210                 215                 220

Gln Ala Ala Ser Thr Ser Ala Ala Phe Leu Gln Val Leu Gly Ile Asn
225                 230                 235                 240

Glu Gly Gln Leu Asp Lys Leu His Thr Val Ser Ala Glu Asp Leu Leu
                245                 250                 255

Lys Ala Ala Asp Gln Leu Arg Ile Ala Glu Lys Glu Asn Ile Phe Gln
            260                 265                 270

Leu Phe Phe Gln Pro Ala Leu Asp Pro Lys Thr Leu Pro Glu Glu Pro
        275                 280                 285

Glu Lys Ala Ile Ala Glu Gly Ala Ala Ser Gly Ile Pro Leu Leu Ile
    290                 295                 300

Gly Thr Thr Arg Asp Glu Gly Tyr Leu Phe Phe Thr Pro Asp Ser Asp
305                 310                 315                 320

Val His Ser Gln Glu Thr Leu Asp Ala Ala Leu Glu Tyr Leu Leu Gly
                325                 330                 335

Lys Pro Leu Ala Glu Lys Val Ala Asp Leu Tyr Pro Arg Ser Leu Glu
            340                 345                 350

Ser Gln Ile His Met Met Thr Asp Leu Leu Phe Trp Arg Pro Ala Val
        355                 360                 365

Ala Tyr Ala Ser Ala Gln Ser His Tyr Ala Pro Val Trp Met Tyr Arg
    370                 375                 380

Phe Asp Trp His Pro Lys Lys Pro Pro Tyr Asn Lys Ala Phe His Ala
385                 390                 395                 400
```

Leu Glu Leu Pro Phe Val Phe Gly Asn Leu Asp Gly Leu Glu Arg Met
            405                 410                 415

Ala Lys Ala Glu Ile Thr Asp Glu Val Lys Gln Leu Ser His Thr Ile
            420                 425                 430

Gln Ser Ala Trp Ile Thr Phe Ala Lys Thr Gly Asn Pro Ser Thr Glu
            435                 440                 445

Ala Val Asn Trp Pro Ala Tyr His Glu Glu Thr Arg Glu Thr Leu Ile
            450                 455                 460

Leu Asp Ser Glu Ile Thr Ile Glu Asn Asp Pro Glu Ser Glu Lys Arg
465                 470                 475                 480

Gln Lys Leu Phe Pro Ser Lys Gly Glu
            485

<210> SEQ ID NO 44
<211> LENGTH: 152
<212> TYPE: PRT
<213> ORGANISM: Bacillus subtilis
<220> FEATURE:
<223> OTHER INFORMATION: >ABP10837

<400> SEQUENCE: 44

Met Ile Gly Arg Ile Ile Arg Leu Tyr Arg Lys Arg Lys Gly Tyr Ser
1               5                   10                  15

Ile Asn Gln Leu Ala Val Glu Ser Gly Val Ser Lys Ser Tyr Leu Ser
            20                  25                  30

Lys Ile Glu Arg Gly Val His Thr Asn Pro Ser Val Gln Phe Leu Lys
        35                  40                  45

Lys Val Ser Ala Thr Leu Glu Val Glu Leu Thr Glu Leu Phe Asp Ala
    50                  55                  60

Glu Thr Met Met Tyr Glu Lys Ile Ser Gly Glu Glu Glu Trp Arg
65                  70                  75                  80

Val His Leu Val Gln Ala Val Gln Ala Gly Met Glu Lys Glu Leu
            85                  90                  95

Phe Thr Phe Thr Asn Arg Leu Lys Lys Glu Gln Pro Glu Thr Ala Ser
            100                 105                 110

Tyr Arg Asn Arg Lys Leu Thr Glu Ser Asn Ile Glu Glu Trp Lys Ala
        115                 120                 125

Leu Met Ala Glu Ala Arg Glu Ile Gly Leu Ser Val His Glu Val Lys
    130                 135                 140

Ser Phe Leu Lys Thr Met Gly Arg
145                 150

<210> SEQ ID NO 45
<211> LENGTH: 234
<212> TYPE: PRT
<213> ORGANISM: Bacillus subtilis
<220> FEATURE:
<223> OTHER INFORMATION: >ABP10838

<400> SEQUENCE: 45

Met Asn Glu Asn Met Ser Phe Lys Glu Leu Tyr Ala Ile Val Arg His
1               5                   10                  15

Arg Phe Val Leu Ile Leu Leu Ile Thr Ile Gly Val Thr Leu Met Met
            20                  25                  30

Gly Phe Val Gln Phe Lys Val Ile Ser Pro Thr Tyr Gln Ala Ser Thr
        35                  40                  45

Gln Val Leu Val His Glu Ser Asp Gly Glu Glu Asn Ser Asn Leu Ser

```
            50                  55                  60
Asp Ile Gln Arg Asn Leu Gln Tyr Ser Ser Thr Phe Gln Ser Ile Met
 65                  70                  75                  80

Lys Ser Thr Ala Leu Met Glu Glu Val Lys Ala Glu Leu His Leu Ser
                 85                  90                  95

Glu Ser Ala Ser Ser Leu Lys Gly Lys Val Ile Thr Ser Ser Glu Asn
                100                 105                 110

Glu Ser Glu Ile Ile Asn Val Ala Val Gln Asp His Asp Pro Ala Lys
            115                 120                 125

Ala Ala Glu Ile Ala Asn Thr Leu Val Asn Lys Phe Glu Lys Glu Val
        130                 135                 140

Asp Glu Arg Met Asn Val Gln Gly Val His Ile Leu Ser Glu Ala Lys
145                 150                 155                 160

Ala Ser Glu Ser Pro Met Ile Lys Pro Ala Arg Leu Arg Asn Met Val
                165                 170                 175

Met Ala Phe Gly Ala Ala Val Met Gly Gly Ile Thr Leu Ala Phe Phe
                180                 185                 190

Leu His Phe Leu Asp Asp Thr Cys Lys Ser Ala Arg Gln Leu Ser Glu
            195                 200                 205

Arg Thr Gly Leu Pro Cys Leu Gly Ser Val Pro Asp Val His Lys Gly
        210                 215                 220

Arg Asn Arg Gly Ile Lys His Phe Gly Glu
225                 230

<210> SEQ ID NO 46
<211> LENGTH: 227
<212> TYPE: PRT
<213> ORGANISM: Bacillus subtilis
<220> FEATURE:
<223> OTHER INFORMATION: >ABP10839

<400> SEQUENCE: 46

Met Ile Phe Arg Lys Lys Ala Arg Arg Gly Leu Ala Gln Ile Ser
 1               5                  10                  15

Val Leu His Asn Lys Ser Val Val Ala Glu Gln Tyr Arg Thr Ile Arg
                 20                  25                  30

Thr Asn Ile Glu Phe Ser Ser Val Gln Thr Asn Leu Arg Ser Ile Leu
             35                  40                  45

Val Thr Ser Ser Val Pro Gly Glu Gly Lys Ser Phe Ser Ala Ala Asn
         50                  55                  60

Leu Ala Ala Val Phe Ala Gln Gln Gln Glu Lys Lys Val Leu Leu Val
 65                  70                  75                  80

Asp Ala Asp Leu Arg Lys Pro Thr Ile Asn Gln Thr Phe Gln Val Asp
                 85                  90                  95

Asn Val Thr Gly Leu Thr Asn Val Leu Val Gly Asn Ala Ser Leu Ser
                100                 105                 110

Glu Thr Val Gln Lys Thr Pro Ile Asp Asn Leu Tyr Val Leu Thr Ser
            115                 120                 125

Gly Pro Thr Pro Asn Pro Ala Glu Leu Leu Ser Ser Lys Ala Met
        130                 135                 140

Gly Asp Leu Ile Ser Glu Ile Tyr Glu Gln Phe Ser Leu Val Ile Phe
145                 150                 155                 160

Asp Ser Pro Pro Leu Leu Ala Val Ala Asp Ala Gln Ile Leu Ala Asn
                165                 170                 175

Gln Thr Asp Gly Ser Val Leu Val Val Leu Ser Gly Lys Thr Lys Thr
```

```
            180                 185                 190
Asp Thr Val Leu Lys Ala Lys Asp Ala Leu Glu Gln Ser Asn Ala Lys
            195                 200                 205

Leu Leu Gly Ala Leu Leu Asn Lys Lys Met Lys Lys Ser Glu His
            210                 215                 220

Tyr Ser Tyr
225

<210> SEQ ID NO 47
<211> LENGTH: 598
<212> TYPE: PRT
<213> ORGANISM: Bacillus subtilis
<220> FEATURE:
<223> OTHER INFORMATION: >ABP10840

<400> SEQUENCE: 47

Met Ile Ile Ala Leu Asp Thr Tyr Leu Val Leu Asn Ser Val Ile Ala
1               5                   10                  15

Gly Tyr Gln Phe Leu Lys Asp Ser Tyr Gln Phe Tyr Asp Ser Gly Ala
                20                  25                  30

Leu Leu Leu Thr Ala Val Ser Leu Leu Ser Tyr His Val Cys Ala
            35                  40                  45

Phe Leu Phe Asn Gln Tyr Lys Gln Val Trp Thr Tyr Thr Gly Leu Gly
50                  55                  60

Glu Leu Ile Val Leu Leu Lys Gly Ile Thr Leu Ser Ala Ala Val Thr
65                  70                  75                  80

Gly Ile Ile Gln Tyr Ala Val Tyr His Thr Met Phe Phe Arg Leu Leu
                85                  90                  95

Thr Ala Cys Trp Val Leu Gln Leu Leu Ser Ile Gly Gly Thr Arg Ile
            100                 105                 110

Leu Ser Arg Val Leu Asn Glu Ser Ile Arg Lys Lys Arg Cys Ala Ser
            115                 120                 125

Ser Arg Ala Leu Ile Ile Gly Ala Gly Ser Gly Gly Thr Leu Met Val
        130                 135                 140

Arg Gln Leu Leu Ser Lys Asp Glu Pro Asp Ile Ile Pro Val Ala Phe
145                 150                 155                 160

Ile Asp Asp Asp Gln Thr Lys His Lys Leu Glu Ile Met Gly Leu Pro
                165                 170                 175

Val Ile Gly Gly Lys Glu Ser Ile Met Pro Ala Val Gln Lys Leu Lys
                180                 185                 190

Ile Asn Phe Ile Ile Ile Ala Ile Pro Ser Leu Arg Thr His Glu Leu
            195                 200                 205

Gln Val Leu Tyr Lys Glu Cys Val Arg Thr Gly Val Ser Ile Lys Ile
        210                 215                 220

Met Pro His Phe Asp Glu Met Leu Leu Gly Thr Arg Thr Ala Gly Gln
225                 230                 235                 240

Ile Arg Asp Val Lys Ala Glu Asp Leu Leu Gly Arg Lys Pro Val Thr
                245                 250                 255

Leu Asp Thr Ser Glu Ile Ser Asn Arg Ile Lys Gly Lys Thr Val Leu
                260                 265                 270

Val Thr Gly Ala Gly Gly Ser Ile Gly Ser Glu Ile Cys Arg Gln Ile
            275                 280                 285

Ser Ala Phe Gln Pro Lys Glu Ile Ile Leu Leu Gly His Gly Glu Asn
        290                 295                 300

Ser Ile His Ser Ile Tyr Thr Glu Leu Asn Gly Arg Phe Gly Lys His
```

```
            305                 310                 315                 320
        Ile Val Phe His Thr Glu Ile Ala Asp Val Gln Asp Arg Asp Lys Met
                        325                 330                 335

Phe Thr Leu Met Lys Lys Tyr Glu Pro His Val Val Tyr His Ala Ala
                        340                 345                 350

Ala His Lys His Val Pro Leu Met Glu His Asn Pro Glu Glu Ala Val
                        355                 360                 365

Lys Asn Asn Ile Ile Gly Thr Lys Asn Val Ala Glu Ala Ala Asp Met
            370                 375                 380

Ser Gly Thr Glu Thr Phe Val Leu Ile Ser Ser Asp Lys Ala Val Asn
        385                 390                 395                 400

Pro Ala Asn Val Met Gly Ala Thr Lys Arg Phe Ala Glu Met Ile Ile
                        405                 410                 415

Met Asn Leu Gly Lys Val Ser Arg Thr Lys Phe Val Ala Val Arg Phe
                        420                 425                 430

Gly Asn Val Leu Gly Ser Arg Gly Ser Val Ile Pro Ile Phe Lys Lys
                        435                 440                 445

Gln Ile Glu Lys Gly Gly Pro Val Thr Val Thr His Pro Ala Met Thr
            450                 455                 460

Arg Tyr Phe Met Thr Ile Pro Glu Ala Ser Arg Leu Val Ile Gln Ala
        465                 470                 475                 480

Gly Ala Leu Ala Lys Gly Arg Gln Ile Phe Val Leu Asp Met Gly Glu
                        485                 490                 495

Pro Val Lys Ile Val Asp Leu Ala Lys Asn Leu Ile His Leu Ser Gly
                        500                 505                 510

Tyr Thr Thr Glu Gln Val Pro Ile Glu Phe Thr Gly Ile Arg Pro Gly
            515                 520                 525

Glu Lys Met Tyr Glu Glu Leu Leu Asn Lys Asn Glu Val His Ala Glu
            530                 535                 540

Gln Ile Phe Pro Lys Ile His Ile Gly Lys Ala Val Asp Gly Asp Trp
        545                 550                 555                 560

Pro Val Leu Met Arg Phe Ile Glu Asp Phe His Glu Leu Ser Glu Ala
                        565                 570                 575

Asp Leu Arg Ala Arg Leu Phe Ala Ala Ile Asn Thr Ser Asp Lys Met
                        580                 585                 590

Thr Ala Ala Ser Val His
                        595

<210> SEQ ID NO 48
<211> LENGTH: 381
<212> TYPE: PRT
<213> ORGANISM: Bacillus subtilis
<220> FEATURE:
<223> OTHER INFORMATION: >ABP10841

<400> SEQUENCE: 48

Met Thr Lys Lys Ile Leu Phe Cys Ala Thr Val Asp Tyr His Phe Lys
        1               5                   10                  15

Ala Phe His Leu Pro Tyr Phe Lys Trp Phe Lys Gln Arg Gly Trp Glu
                        20                  25                  30

Val His Val Ala Ala Asn Gly Gln Thr Lys Leu Pro Tyr Val Asp Glu
                        35                  40                  45

Lys Phe Ser Ile Pro Ile Arg Arg Ser Pro Phe Asp Pro Gln Asn Leu
            50                  55                  60

Ala Val Tyr Arg Gln Leu Lys Lys Val Ile Asp Thr Tyr Glu Tyr Asp
```

Ile Val His Cys His Thr Pro Val Gly Gly Val Leu Ala Arg Leu Ala
65                  70                  75                  80

Ala Arg Gln Ala Arg Arg His Gly Thr Lys Val Leu Tyr Thr Ala His
            85                  90                  95

Gly Phe His Phe Cys Lys Gly Ala Pro Met Lys Asn Trp Leu Leu Tyr
        100                 105                 110

Tyr Pro Val Glu Lys Trp Leu Ser Ala Tyr Thr Asp Cys Leu Ile Thr
    115                 120                 125

Ile Asn Glu Glu Asp Tyr Lys Arg Ala Lys Gly Leu Gln Arg Pro Gly
130                 135                 140

Gly Arg Thr Gln Lys Ile His Gly Ile Gly Val Asn Thr Glu Arg Phe
145                 150                 155                 160

Arg Pro Val Ser Pro Ile Glu Gln Gln Arg Leu Arg Glu Lys His Gly
            165                 170                 175

Phe Arg Glu Asp Asp Phe Ile Leu Val Tyr Pro Ala Glu Leu Asn Leu
        180                 185                 190

Asn Lys Asn Gln Lys Gln Leu Ile Glu Ala Ala Leu Leu Lys Glu
    195                 200                 205

Lys Ile Pro Ser Leu Arg Leu Val Phe Ala Gly Glu Gly Ala Met Glu
210                 215                 220

Gln Thr Tyr Gln Met Leu Ala Glu Lys Leu Gly Ala Ser Ala Asn Val
225                 230                 235                 240

Cys Phe Tyr Gly Phe Cys Ser Asp Ile His Glu Leu Ile Gln Leu Ala
            245                 250                 255

Asp Val Ser Val Ala Ser Ser Ile Arg Glu Gly Leu Gly Met Asn Val
        260                 265                 270

Leu Glu Gly Met Ala Ala Glu Lys Pro Ala Ile Ala Thr Asp Asn Arg
    275                 280                 285

Gly His Arg Glu Ile Ile Arg Asp Gly Glu Asn Gly Phe Leu Ile Lys
290                 295                 300

Ile Gly Asp Ser Ala Ala Phe Ala Arg Arg Ile Glu Gln Leu Tyr His
305                 310                 315                 320

Lys Pro Glu Ile Cys Arg Lys Leu Gly Gln Glu Gly Arg Lys Thr Ala
            325                 330                 335

Leu Arg Phe Ser Glu Ala Arg Thr Val Glu Glu Met Ala Asp Ile Tyr
        340                 345                 350

Ser Ala Tyr Met Asp Met Asp Thr Lys Glu Lys Ser Val
    355                 360                 365

<210> SEQ ID NO 49
<211> LENGTH: 278
<212> TYPE: PRT
<213> ORGANISM: Bacillus subtilis
<220> FEATURE:
<223> OTHER INFORMATION: >ABP10842

<400> SEQUENCE: 49

Met Asn Ser Gly Pro Lys Val Ser Val Ile Met Gly Ile Tyr Asn Cys
1               5                   10                  15

Glu Arg Thr Leu Ala Glu Ser Ile Glu Ser Ile Leu Ser Gln Ser Tyr
            20                  25                  30

Lys Asn Trp Glu Leu Ile Leu Cys Asp Asp Ala Ser Thr Asp Gly Thr
        35                  40                  45

Leu Arg Ile Ala Lys Gln Tyr Ala Ala His Tyr Ser Asp Arg Ile Lys

```
                50                  55                  60
Leu Ile Gln Asn Lys Thr Asn Lys Arg Leu Ala Ala Ser Leu Asn His
 65                  70                  75                  80

Cys Leu Ser His Ala Thr Gly Asp Tyr Ile Ala Arg Gln Asp Gly Asp
                 85                  90                  95

Asp Leu Ser Phe Pro Arg Arg Leu Glu Lys Gln Val Ala Phe Leu Glu
                100                 105                 110

Lys His Arg His Tyr Gln Val Val Gly Thr Gly Met Leu Val Phe Asp
                115                 120                 125

Glu Phe Gly Val Arg Gly Thr Arg Ile Leu Pro Ser Val Pro Glu Pro
130                 135                 140

Gly Ile Met Ala Lys Gly Thr Pro Phe Cys His Gly Thr Ile Met Met
145                 150                 155                 160

Arg Ala Ser Ala Tyr Arg Thr Leu Lys Gly Tyr Arg Ser Val Arg Arg
                165                 170                 175

Thr Arg Arg Met Glu Asp Ile Asp Leu Trp Leu Arg Phe Phe Glu Glu
                180                 185                 190

Gly Phe Arg Gly Tyr Asn Leu Gln Glu Ala Leu Tyr Lys Val Arg Glu
                195                 200                 205

Asp Ser Asp Ala Phe Lys Arg Arg Ser Phe Thr Tyr Ser Ile Asp Asn
210                 215                 220

Ala Ile Leu Val Tyr Gln Ala Cys Arg Arg Leu Lys Leu Pro Leu Ser
225                 230                 235                 240

Asp Tyr Ile Tyr Ile Ala Lys Pro Leu Ile Arg Ala Phe Met Pro Ala
                245                 250                 255

Ala Val Met Asn Arg Tyr His Lys Lys Arg Val Met Asn Gln Lys Glu
                260                 265                 270

Gly Leu Val Lys His Glu
            275

<210> SEQ ID NO 50
<211> LENGTH: 384
<212> TYPE: PRT
<213> ORGANISM: Bacillus subtilis
<220> FEATURE:
<223> OTHER INFORMATION: >ABP10843

<400> SEQUENCE: 50

Met Asn Ser Ser Gln Lys Arg Val Leu His Val Leu Ser Gly Met Asn
 1               5                  10                  15

Arg Gly Gly Ala Glu Thr Met Val Met Asn Leu Tyr Arg Lys Met Asp
                 20                  25                  30

Lys Ser Lys Val Gln Phe Asp Phe Leu Thr Tyr Arg Asn Asp Pro Cys
             35                  40                  45

Ala Tyr Asp Glu Glu Ile Leu Ser Leu Gly Gly Arg Leu Phe Tyr Val
 50                  55                  60

Pro Ser Ile Gly Gln Ser Asn Pro Leu Thr Phe Val Arg Asn Val Arg
 65                  70                  75                  80

Asn Ala Ile Lys Glu Asn Gly Pro Phe Ser Ala Val His Ala His Thr
                 85                  90                  95

Asp Phe Gln Thr Gly Phe Ile Ala Leu Ala Ala Arg Leu Ala Gly Val
                100                 105                 110

Pro Val Arg Val Cys His Ser His Asn Thr Ser Trp Lys Thr Gly Phe
                115                 120                 125

Asn Trp Lys Asp Arg Leu Gln Leu Leu Val Phe Arg Arg Leu Ile Leu
```

```
                130                 135                 140
Ala Asn Ala Thr Ala Leu Cys Ala Cys Gly Glu Asp Ala Gly Arg Phe
145                 150                 155                 160

Leu Phe Gly Gln Ser Asn Met Glu Arg Glu Arg Val His Leu Leu Pro
                165                 170                 175

Asn Gly Ile Asp Leu Glu Leu Phe Ala Pro Asn Gly Gln Ala Ala Asp
                180                 185                 190

Glu Glu Lys Ala Ala Arg Gly Ile Ala Ala Asp Arg Leu Ile Ile Gly
            195                 200                 205

His Val Ala Arg Phe His Glu Val Lys Asn His Ala Phe Leu Leu Lys
        210                 215                 220

Leu Ala Ala His Leu Lys Glu Arg Gly Ile Arg Phe Gln Leu Val Leu
225                 230                 235                 240

Ala Gly Asp Gly Pro Leu Arg Gly Glu Ile Glu Glu Ala Arg Gln
                245                 250                 255

Gln Asn Leu Leu Ser Asp Val Leu Phe Leu Gly Thr Glu Glu Arg Ile
                260                 265                 270

His Glu Leu Met Arg Thr Phe Asp Val Phe Met Pro Ser Leu Tyr
        275                 280                 285

Glu Gly Leu Pro Val Val Leu Val Glu Ala Gln Ala Ser Gly Leu Pro
            290                 295                 300

Cys Ile Ile Ser Asp Ser Ile Thr Glu Lys Val Asp Ala Gly Leu Gly
305                 310                 315                 320

Leu Val Thr Arg Leu Ser Leu Ser Glu Pro Ile Ser Val Trp Ala Glu
                325                 330                 335

Thr Ile Ala Arg Ala Ala Ala Gly Arg Pro Lys Arg Glu Phe Ile
                340                 345                 350

Lys Glu Thr Leu Ala Gln Leu Gly Tyr Asp Ala Gln Gln Asn Val Gly
                355                 360                 365

Ala Leu Leu Asn Val Tyr Asn Ile Ser Thr Glu Lys Asp His Asn Arg
            370                 375                 380

<210> SEQ ID NO 51
<211> LENGTH: 367
<212> TYPE: PRT
<213> ORGANISM: Bacillus subtilis
<220> FEATURE:
<223> OTHER INFORMATION: >ABP10844

<400> SEQUENCE: 51

Met Ile Val Tyr Ala Val Asn Met Gly Ile Val Phe Ile Trp Ser Trp
1               5                   10                  15

Phe Ala Lys Met Cys Gly Gly Arg Asp Asp Ser Leu Ala Thr Gly Tyr
            20                  25                  30

Arg Pro Asn Lys Leu Leu Ile Trp Ile Pro Leu Ala Ser Leu Val Leu
        35                  40                  45

Val Ser Gly Leu Arg Tyr Arg Val Gly Thr Asp Phe Gln Thr Tyr Thr
    50                  55                  60

Leu Leu Tyr Glu Leu Ala Gly Asp Tyr Gln Asn Val Trp Gln Ile Phe
65                  70                  75                  80

Gly Phe Gly Thr Ala Lys Thr Ala Thr Asp Pro Gly Phe Thr Ala Leu
                85                  90                  95

Leu Trp Leu Met Asn Phe Ile Thr Glu Asp Pro Gln Ile Met Tyr Phe
            100                 105                 110

Thr Val Ala Val Val Thr Tyr Ser Phe Ile Met Lys Thr Leu Ala Asp
```

```
                115                 120                 125
Tyr Gly Arg Pro Phe Glu Leu Ser Val Phe Leu Phe Leu Gly Thr Phe
            130                 135                 140

His Tyr Tyr Ala Ser Phe Asn Gly Ile Arg Gln Tyr Met Val Ala Ala
145                 150                 155                 160

Val Leu Phe Trp Ala Ile Arg Tyr Ile Ile Ser Gly Asn Trp Lys Arg
                165                 170                 175

Tyr Phe Leu Ile Val Leu Val Ser Ser Leu Phe His Ser Ser Ala Leu
            180                 185                 190

Ile Met Ile Pro Val Tyr Phe Ile Val Arg Arg Lys Ala Trp Ser Pro
        195                 200                 205

Ala Ile Phe Gly Leu Ser Ala Leu Phe Leu Gly Met Thr Phe Leu Tyr
            210                 215                 220

Gln Lys Phe Ile Ser Val Phe Val Val Leu Glu Asn Ser Ser Tyr
225                 230                 235                 240

Ser His Tyr Glu Lys Trp Leu Met Thr Asn Thr Asn Gly Met Asn Val
                245                 250                 255

Ile Lys Ile Ala Val Leu Val Leu Pro Leu Phe Leu Ala Phe Cys Tyr
            260                 265                 270

Lys Glu Arg Leu Arg Ser Leu Trp Pro Gln Ile Asp Ile Val Val Asn
                275                 280                 285

Leu Cys Leu Leu Gly Phe Leu Phe Gly Leu Leu Ala Thr Lys Asp Val
        290                 295                 300

Ile Phe Ala Arg Phe Asn Ile Tyr Phe Gly Leu Tyr Gln Met Ile Leu
305                 310                 315                 320

Val Pro Tyr Phe Val Arg Ile Phe Asp Glu Lys Ser Asn Ala Leu Ile
                325                 330                 335

Tyr Ile Ala Ile Val Val Cys Tyr Phe Leu Tyr Ser Tyr Leu Leu Met
            340                 345                 350

Pro Val Asp Ser Ser Val Leu Pro Tyr Arg Thr Ile Phe Ser Arg
        355                 360                 365

<210> SEQ ID NO 52
<211> LENGTH: 344
<212> TYPE: PRT
<213> ORGANISM: Bacillus subtilis
<220> FEATURE:
<223> OTHER INFORMATION: >ABP10845

<400> SEQUENCE: 52

Met Glu Thr Pro Ala Val Ser Leu Leu Val Ala Val Tyr Asn Thr Glu
1               5                   10                  15

Thr Tyr Ile Arg Thr Cys Leu Glu Ser Leu Arg Asn Gln Thr Met Asp
            20                  25                  30

Asn Ile Glu Ile Ile Val Asn Asp Gly Ser Ala Asp Ala Ser Pro
        35                  40                  45

Asp Ile Ala Glu Glu Tyr Ala Lys Met Asp Asn Arg Phe Lys Val Ile
    50                  55                  60

His Gln Glu Asn Gln Gly Leu Gly Ala Val Arg Asn Lys Gly Ile Glu
65                  70                  75                  80

Ala Ala Arg Gly Glu Phe Ile Ala Phe Ile Asp Ser Asp Asp Trp Ile
                85                  90                  95

Glu Pro Asp Tyr Cys Glu Gln Met Leu Arg Ala Ala Gly Asp Glu Thr
            100                 105                 110

Asp Leu Val Ile Cys Asn Tyr Ala Ala Glu Phe Glu Asp Thr Gly Lys
```

```
                115                 120                 125
Thr Met Asp Ser Asp Ile Ala Gln Thr Tyr Gln Asp Gln Pro Lys Glu
    130                 135                 140

His Tyr Ile Lys Ala Leu Phe Glu Gly Lys Val Arg Gly Phe Ser Trp
145                 150                 155                 160

Asn Lys Leu Tyr Arg Arg Ser Met Ile Asp Ala His Arg Leu Ser Phe
                165                 170                 175

Pro Leu Arg Gly Glu Leu Glu His Val Glu Asp Gln Phe Phe Ser Phe
            180                 185                 190

Arg Ala His Phe Phe Ala Arg Ser Val Ser Tyr Val Lys Thr Pro Leu
        195                 200                 205

Tyr His Tyr Arg Ile His Leu Ser Ser Ile Val Gln Arg Tyr Gln Lys
    210                 215                 220

Lys Leu Phe Glu Ser Gly Leu Ala Leu Tyr Glu Ala Asn Ala Ala Phe
225                 230                 235                 240

Leu Gln Glu Asn Asn Lys Leu Glu Glu Tyr Arg Lys Glu Leu Asp Thr
                245                 250                 255

Phe Ile Val Leu His Ser Ser Ile Cys Met Leu Asn Glu Trp Lys Thr
            260                 265                 270

Ser Gly Ser Arg Arg Leu Phe Glu Lys Leu Arg Asn Val Gly Val Ile
        275                 280                 285

Cys Ala Asp Pro Val Phe Gln Glu Ser Leu Ser Lys Thr Gly Thr Ala
    290                 295                 300

Pro Phe Asp Ala Lys Arg Ser Cys Leu Leu Met Ala Lys Tyr Arg
305                 310                 315                 320

Met Ile Pro Phe Val Ala Met Ala Ser Ala Val Tyr Gln Arg Val Ile
                325                 330                 335

Glu Tyr Lys Met Arg Asn Arg Gly
            340

<210> SEQ ID NO 53
<211> LENGTH: 358
<212> TYPE: PRT
<213> ORGANISM: Bacillus subtilis
<220> FEATURE:
<223> OTHER INFORMATION: >ABP10846

<400> SEQUENCE: 53

Met Ser Leu Gln Ser Leu Lys Ile Asn Phe Ala Glu Trp Leu Leu Leu
1               5                   10                  15

Lys Val Lys Tyr Pro Ser Gln Tyr Trp Leu Gly Ala Ala Asp Gln Pro
            20                  25                  30

Ile Lys Ala Ala His Gln Lys Lys Ile Ile Leu Thr Leu Leu Pro
        35                  40                  45

Ser His Asp Asn Leu Gly Asp His Ala Ile Ala Tyr Ala Ser Lys Ala
    50                  55                  60

Phe Leu Glu Gln Glu Tyr Pro Asp Phe Asp Ile Val Glu Val Asp Met
65                  70                  75                  80

Lys Asp Ile Tyr Lys Ser Ala Lys Ser Leu Ile Arg Ser Arg His Pro
                85                  90                  95

Glu Asp Met Val Phe Ile Ile Gly Gly Asn Met Gly Asp Leu Tyr
            100                 105                 110

Arg Tyr Glu Glu Trp Thr Arg Arg Phe Ile Ile Lys Thr Phe His Asp
        115                 120                 125

Tyr Arg Val Val Gln Leu Pro Ala Thr Ala His Phe Ser Asp Thr Lys
```

```
              130                 135                 140
Lys Gly Arg Lys Glu Leu Lys Arg Ala Gln Lys Ile Tyr Asn Ala His
145                 150                 155                 160

Pro Gly Leu Leu Leu Met Ala Arg Asp Glu Thr Thr Tyr Gln Phe Met
                165                 170                 175

Lys Gln His Phe His Glu Lys Thr Ile Leu Lys Gln Pro Asp Met Val
                180                 185                 190

Leu Tyr Leu Asp Arg Ser Lys Pro Pro Ala Glu Arg Glu Gly Val Tyr
                195                 200                 205

Met Cys Leu Arg Glu Asp Gln Glu Ser Val Leu Gln Glu Asp Gln Arg
                210                 215                 220

Asn Arg Val Lys Ala Ala Leu Phe Glu Glu Phe Gly Glu Ile Lys Ser
225                 230                 235                 240

Phe Thr Thr Thr Ile Gly Arg Arg Val Ser Arg Asp Thr Arg Glu Gln
                245                 250                 255

Glu Leu Glu Ala Leu Trp Ser Lys Leu Gln Ser Ala Glu Ala Val Val
                260                 265                 270

Thr Asp Arg Leu His Gly Met Ile Phe Cys Ala Leu Thr Gly Thr Pro
                275                 280                 285

Cys Val Val Ile Arg Ser Phe Asp His Lys Val Met Glu Gly Tyr Gln
290                 295                 300

Trp Leu Lys Asp Ile Pro Phe Met Lys Leu Ile Glu His Pro Glu Pro
305                 310                 315                 320

Glu Arg Val Thr Ala Ala Val Asn Glu Leu Leu Thr Lys Glu Thr Pro
                325                 330                 335

Arg Ala Gly Phe Pro Arg Asp Val Tyr Phe Lys Gly Leu Arg Asp Lys
                340                 345                 350

Ile Ser Gly Glu Ala Gln
                355

<210> SEQ ID NO 54
<211> LENGTH: 344
<212> TYPE: PRT
<213> ORGANISM: Bacillus subtilis
<220> FEATURE:
<223> OTHER INFORMATION: >ABP10847

<400> SEQUENCE: 54

Met Thr Pro Leu Val Ser Ile Ile Val Pro Met Tyr Asn Val Glu Pro
1               5                   10                  15

Phe Ile Glu Glu Cys Ile Asp Ser Leu Leu Cys Gln Thr Leu Ser Asp
                20                  25                  30

Ile Glu Ile Ile Leu Val Asn Asp Gly Thr Pro Asp Arg Ser Gly Glu
            35                  40                  45

Ile Ala Glu Asp Tyr Ala Lys Arg Asp Ala Arg Ile Arg Val Ile His
        50                  55                  60

Gln Ala Asn Gly Gly Leu Ser Ser Ala Arg Asn Thr Gly Ile Lys Gly
65                  70                  75                  80

Ala Arg Gly Thr Tyr Ile Gly Phe Val Asp Gly Asp Tyr Val Ser
                85                  90                  95

Ser Ala Met Phe Gln Arg Leu Thr Glu Glu Ala Glu Gln Asn Gln Leu
                100                 105                 110

Asp Ile Val Gly Cys Gly Phe Tyr Lys Gln Ser Ser Asp Arg Arg Thr
            115                 120                 125

Tyr Val Pro Pro Gln Leu Glu Ala Asn Arg Val Leu Thr Lys Pro Glu
```

-continued

```
                130                 135                 140
Met Thr Glu Gln Leu Lys His Ala His Glu Thr Arg Phe Ile Trp Tyr
145                 150                 155                 160

Val Trp Arg Tyr Leu Tyr Arg Arg Glu Leu Phe Glu Arg Ala Asn Leu
                165                 170                 175

Leu Phe Asp Glu Asp Ile Arg Phe Ala Glu Asp Ser Pro Phe Asn Leu
                180                 185                 190

Ser Ala Phe Cys Glu Ala Glu Arg Val Lys Met Leu Asp Glu Gly Leu
                195                 200                 205

Tyr Ile Tyr Arg Glu Asn Pro Asn Ser Leu Thr Glu Ile Pro Tyr Lys
                210                 215                 220

Pro Ala Met Asp Glu His Leu Gln Lys Gln Tyr Gln Ala Lys Ile Ala
225                 230                 235                 240

Phe Tyr Asn His Tyr Gly Leu Ala Gly Ala Cys Lys Glu Asp Leu Asn
                245                 250                 255

Val Tyr Ile Cys Arg His Gln Leu Pro Met Leu Leu Ala Asn Ala Cys
                260                 265                 270

Ala Ser Gln Asn Ser Pro Lys Asp Ile Lys Lys Ile Arg Gln Ile
                275                 280                 285

Leu Ser Tyr Asp Met Val Arg Gln Ala Val Arg His Thr Pro Ile Gln
                290                 295                 300

His Glu Lys Leu Leu Arg Gly Glu Arg Leu Val Leu Ala Leu Cys Lys
305                 310                 315                 320

Trp Arg Leu Thr Phe Leu Ile Lys Leu Phe Glu Gln Arg Gly Thr
                325                 330                 335

Met Lys Gly Ser Ala Lys Gln Ala
                340

<210> SEQ ID NO 55
<211> LENGTH: 482
<212> TYPE: PRT
<213> ORGANISM: Bacillus subtilis
<220> FEATURE:
<223> OTHER INFORMATION: >ABP10848

<400> SEQUENCE: 55

Met Thr Pro Phe Ile Val Lys Thr Leu Gly Val Glu Ala Phe Gly Phe
1               5                   10                  15

Val His Leu Thr Gln Asn Val Ile Asn Tyr Phe Ser Ile Ile Thr Val
                20                  25                  30

Ala Leu Ser Ser Val Val Arg Phe Phe Ser Val Ala Ala His Arg
                35                  40                  45

Gly Glu Arg Glu Lys Ala Asn Ala Tyr Ile Ser Asn Tyr Leu Ala Ala
                50                  55                  60

Ser Val Leu Ile Ser Leu Leu Leu Leu Pro Leu Ala Gly Ser Ala
65                  70                  75                  80

Phe Phe Ile Asp Arg Val Met Asn Val Pro Gln Ala Leu Leu Ala Asp
                85                  90                  95

Val Arg Leu Ser Ile Leu Ile Gly Ser Val Leu Phe Ile Leu Thr Phe
                100                 105                 110

Leu Met Ala Gly Phe Gly Ala Ala Pro Phe Tyr Ala Asn Arg Leu Tyr
                115                 120                 125

Ile Thr Ser Ser Ile Gln Ala Val Gln Met Leu Ile Arg Val Leu Ser
                130                 135                 140

Val Leu Leu Leu Phe Ala Cys Phe Ala Pro Lys Ile Trp Gln Ile Gln
```

```
            145                 150                 155                 160
Leu Ala Ala Leu Ala Gly Ala Val Met Ala Ser Val Leu Ser Phe Tyr
                165                 170                 175

Phe Phe Lys Lys Leu Ile Pro Trp Phe Ser Phe Arg Met Lys Asp Leu
                180                 185                 190

Ser Phe Arg Thr Ser Lys Glu Leu Phe Gln Ala Gly Ala Trp Ser Ser
                195                 200                 205

Val Asn Gln Ile Gly Val Leu Leu Phe Leu Gln Ile Asp Leu Leu Thr
    210                 215                 220

Ala Asn Leu Met Leu Gly Ala Ser Ala Ser Gly Lys Tyr Ala Ala Ile
225                 230                 235                 240

Ile Gln Phe Pro Leu Leu Leu Arg Ser Leu Ala Gly Thr Val Ala Ser
                245                 250                 255

Leu Phe Ala Pro Ile Met Thr Ser Tyr Tyr Ser Lys Gly Asp Met Asp
                260                 265                 270

Gly Leu Met Asn Tyr Ala Asn Lys Ala Val Arg Leu Asn Gly Val Leu
                275                 280                 285

Leu Ala Leu Pro Ala Ala Leu Leu Gly Gly Leu Ala Gly Pro Phe Leu
    290                 295                 300

Thr Ile Trp Leu Gly Pro Ser Phe Ser Ser Ile Ala Pro Leu Leu Phe
305                 310                 315                 320

Ile His Ala Gly Tyr Leu Val Val Ser Leu Ala Phe Met Pro Leu Phe
                325                 330                 335

Tyr Ile Trp Thr Ala Phe Asn Gln Gln Lys Thr Pro Ala Ile Val Thr
                340                 345                 350

Leu Leu Leu Gly Ala Val Asn Val Val Leu Ala Val Thr Leu Ser Gly
                355                 360                 365

Pro Ala His Leu Gly Leu Tyr Gly Ile Thr Leu Ala Gly Ala Ile Ser
    370                 375                 380

Leu Ile Leu Lys Asn Ala Ile Phe Thr Pro Leu Tyr Val Ser Arg Ile
385                 390                 395                 400

Thr Gly Tyr Lys Lys His Val Phe Phe Lys Gly Ile Ile Gly Pro Leu
                405                 410                 415

Ser Ala Ala Val Phe Ala Trp Thr Val Cys Lys Ala Ile Gln Phe Ile
                420                 425                 430

Val Lys Ile Asp Ser Trp Pro Ser Leu Ile Ala Ala Gly Val Thr Val
    435                 440                 445

Ser Phe Phe Tyr Ala Val Phe Ala Phe Met Leu Val Cys Thr Lys Glu
    450                 455                 460

Glu Arg Gln Leu Val Leu Lys Arg Phe Arg Lys Thr Lys Gly Ala Val
465                 470                 475                 480

Asn Leu

<210> SEQ ID NO 56
<211> LENGTH: 202
<212> TYPE: PRT
<213> ORGANISM: Bacillus subtilis
<220> FEATURE:
<223> OTHER INFORMATION: >ABP10849

<400> SEQUENCE: 56

Met Ile Leu Lys Arg Leu Phe Asp Leu Thr Ala Ala Ile Phe Leu Leu
1               5                   10                  15

Cys Cys Thr Ser Val Ile Ile Leu Phe Thr Ile Ala Val Val Arg Leu
                20                  25                  30
```

Lys Ile Gly Ser Pro Val Phe Phe Lys Gln Val Arg Pro Gly Leu His
                35                  40                  45

Gly Lys Pro Phe Thr Leu Tyr Lys Phe Arg Thr Met Thr Asp Glu Arg
 50                  55                  60

Asp Gly Glu Gly Asn Leu Leu Pro Asp Glu Val Arg Leu Thr Lys Thr
 65                  70                  75                  80

Gly Arg Leu Ile Arg Lys Leu Ser Ile Asp Glu Leu Pro Gln Leu Leu
                 85                  90                  95

Asn Val Leu Lys Gly Asp Leu Ser Leu Val Gly Pro Arg Pro Leu Leu
            100                 105                 110

Met Asp Tyr Leu Pro Leu Tyr Thr Glu Lys Gln Ala Arg Arg His Glu
            115                 120                 125

Val Lys Pro Gly Ile Thr Gly Trp Ala Gln Ile Asn Gly Arg Asn Ala
        130                 135                 140

Ile Ser Trp Glu Lys Lys Phe Glu Leu Asp Val Trp Tyr Val Asp Asn
145                 150                 155                 160

Arg Ser Phe Ile Leu Asp Leu Lys Ile Leu Cys Leu Thr Val Arg Lys
                165                 170                 175

Val Leu Val Ser Glu Gly Ile Gln Gln Thr Asn His Val Thr Ala Glu
            180                 185                 190

Arg Phe Thr Gly Ser Gly Asp Val Ser Ser
        195                 200

<210> SEQ ID NO 57
<211> LENGTH: 216
<212> TYPE: PRT
<213> ORGANISM: Bacillus subtilis
<220> FEATURE:
<223> OTHER INFORMATION: >ABP10850

<400> SEQUENCE: 57

Met Lys Asn Val Ala Ile Val Gly Asp Gly Gly His Gly Lys Val Ile
1               5                   10                  15

Arg Glu Leu Ile Asn Ala Arg Ser Asp Thr Arg Leu Ala Ala Val Leu
            20                  25                  30

Asp Asp Lys Phe Lys Thr Phe Glu Gly Gly Lys Glu Trp Tyr Thr Gly
        35                  40                  45

Pro Pro Glu Ala Val Thr Glu Leu Arg Arg Leu Ile Pro Asp Val Leu
 50                  55                  60

Phe Leu Ile Ala Val Gly Asn Asn Ser Val Arg Lys Gln Leu Ala Glu
 65                  70                  75                  80

Arg Leu Gly Leu Arg Lys Asp Asp Phe Ile Thr Leu Ile His Pro Ser
                 85                  90                  95

Ala Ile Val Ser Arg Ser Ala Val Ile Gly Glu Gly Thr Val Ile Met
            100                 105                 110

Ala Gly Ala Ile Ile Gln Ala Asp Ala Arg Ile Gly Ala His Cys Ile
            115                 120                 125

Ile Asn Thr Gly Ala Val Ala Glu His Asp Asn Gln Ile Ser Asp Tyr
        130                 135                 140

Val His Leu Ser Pro Arg Val Thr Leu Ser Gly Ala Val Ser Val Gln
145                 150                 155                 160

Glu Gly Ala His Val Gly Thr Gly Ala Ser Ile Pro Gln Ile Thr
                165                 170                 175

Ile Gly Ala Trp Ser Ile Val Gly Ala Gly Ser Ala Val Ile Arg Pro
            180                 185                 190

Ile Pro Asp Arg Val Thr Ala Ala Gly Ala Pro Ala Arg Ile Ile Ser
        195                 200                 205

Ser Ile Gln Thr Ser Asn Lys Gly
    210                 215

<210> SEQ ID NO 58
<211> LENGTH: 388
<212> TYPE: PRT
<213> ORGANISM: Bacillus subtilis
<220> FEATURE:
<223> OTHER INFORMATION: >ABP10851

<400> SEQUENCE: 58

Met His Lys Lys Ile Tyr Leu Ser Pro Pro His Met Ser Gly Arg Glu
1               5                   10                  15

Gln His Tyr Ile Ser Glu Ala Phe Arg Ser Asn Trp Ile Ala Pro Leu
            20                  25                  30

Gly Pro Leu Val Asn Ser Phe Glu Glu Gln Leu Ala Glu Arg Val Gly
        35                  40                  45

Val Lys Ala Ala Ala Val Ser Ser Gly Thr Ala Ala Ile His Leu
    50                  55                  60

Ala Leu Arg Leu Leu Glu Val Lys Glu Gly Asp Ser Val Phe Cys Gln
65                  70                  75                  80

Ser Phe Thr Phe Val Ala Thr Ala Asn Pro Ile Leu Tyr Glu Lys Ala
                85                  90                  95

Val Pro Val Phe Ile Asp Ser Glu Pro Asp Thr Trp Asn Met Ser Pro
            100                 105                 110

Thr Ala Leu Glu Arg Ala Leu Glu Glu Ala Lys Arg Asn Gly Thr Leu
        115                 120                 125

Pro Lys Ala Val Ile Ala Val Asn Leu Tyr Gly Gln Ser Ala Lys Met
    130                 135                 140

Asp Glu Ile Val Ser Leu Cys Asp Ala Tyr Gly Val Pro Val Ile Glu
145                 150                 155                 160

Asp Ala Ala Glu Ser Leu Gly Thr Val Tyr Lys Gly Lys Gln Ser Gly
                165                 170                 175

Thr Phe Gly Arg Phe Gly Ile Phe Ser Phe Asn Gly Asn Lys Ile Ile
            180                 185                 190

Thr Thr Ser Gly Gly Met Leu Val Ser Asn Asp Glu Ala Ala Ile
        195                 200                 205

Glu Lys Ala Arg Phe Leu Ala Ser Gln Ala Arg Glu Pro Ala Val His
    210                 215                 220

Tyr Gln His Ser Gln Ile Gly His Asn Tyr Arg Leu Ser Asn Ile Leu
225                 230                 235                 240

Ala Gly Val Gly Ile Ala Gln Leu Glu Val Leu Asp Glu Arg Val Glu
                245                 250                 255

Lys Arg Arg Thr Ile Phe Thr Arg Tyr Lys Asn Val Leu Gly His Ile
            260                 265                 270

Ala Gly Val Arg Phe Met Pro Glu Tyr Ala Ala Gly Val Ser Asn Arg
        275                 280                 285

Trp Leu Thr Thr Leu Thr Leu Asp Asn Gly Leu Ser Pro Tyr Asp Val
    290                 295                 300

Val Gln Cys Leu Ala Glu Glu Asn Ile Glu Ala Arg Pro Leu Trp Lys
305                 310                 315                 320

Pro Leu His Thr Gln Gln Leu Phe Asp Pro Ala Leu Phe Tyr Ser His
                325                 330                 335

```
Glu Asp Thr Gly Ser Val Cys Glu Asp Leu Phe Lys Arg Gly Ile Cys
            340                 345                 350

Leu Pro Ser Gly Ser Asn Met Thr Glu Asp Glu Gln Asp Arg Val Ile
            355                 360                 365

Glu Val Leu Leu His Leu Phe Gln Thr Ala Glu Val Lys Lys Trp Thr
370                 375                 380

Ala Ser Ile Arg
385

<210> SEQ ID NO 59
<211> LENGTH: 322
<212> TYPE: PRT
<213> ORGANISM: Bacillus subtilis
<220> FEATURE:
<223> OTHER INFORMATION: >ABP10852

<400> SEQUENCE: 59

Met Asp Ser Lys His Ser Met Ile Ser Leu Lys Gln Lys Leu Ser Gly
1               5                   10                  15

Leu Leu Asp Val Ile Pro Lys Gln Ser Glu Ile Ile Tyr Ala Asp Tyr
            20                  25                  30

Pro Leu Tyr Gly Asn Val Gly Asp Leu Phe Ile Met Lys Gly Thr Glu
        35                  40                  45

Ala Phe Phe Lys Glu His Gly Ile Arg Val Arg Lys Arg Trp Asn Pro
    50                  55                  60

Asp Asn Phe Pro Val Gly Arg Lys Leu Asp Pro Asn Leu Ile Ile Val
65                  70                  75                  80

Cys Gln Gly Gly Gly Asn Phe Gly Asp Leu Tyr Pro Tyr Tyr Gln Gly
                85                  90                  95

Phe Arg Glu Lys Ile Val Gln Thr Tyr Pro Asn His Lys Ile Val Ile
            100                 105                 110

Leu Pro Gln Ser Ile Tyr Phe Gln Asn Lys Asp Asn Leu Lys Arg Thr
        115                 120                 125

Ala Glu Ile Phe Ser Lys His Ala Asn Leu His Ile Met Thr Arg Glu
130                 135                 140

Lys Ala Ser Tyr Ala Thr Ala Gln Ala Tyr Phe Ser Lys Asn His Ile
145                 150                 155                 160

Gln Leu Leu Pro Asp Met Ala His Gln Leu Phe Pro Val Ile Pro Thr
                165                 170                 175

Gln Gln Pro Ser Asn Gln Lys Leu Arg Phe Ile Arg Thr Asp His Glu
            180                 185                 190

Ala Asn Gln Ala Leu Gln Glu His Thr Glu Thr Glu Ser Tyr Asp Trp
        195                 200                 205

Arg Thr Val Leu Ser Ala Ser Asp Arg Arg Thr Ile Ala Phe Leu Gln
    210                 215                 220

Thr Leu Asn Val Leu Asn Lys Lys Ala Gly Asn Pro Leu Pro Ile Ala
225                 230                 235                 240

Tyr Ile Trp Gly Lys Tyr Ser Asp Tyr Ile Val Gln Lys Ala Ile Arg
                245                 250                 255

Phe Phe Ser Arg Tyr Glu Ser Val Glu Thr Ser Arg Leu His Gly His
            260                 265                 270

Ile Leu Ser Ala Leu Leu Gln Lys Glu Asn Thr Val Ile Asp Asn Ser
        275                 280                 285

Tyr Gly Lys Asn Ala Asn Tyr Phe His Thr Trp Met Glu Gly Val Pro
    290                 295                 300
```

```
Gly Thr Arg Leu Ile Gln His Ala Ser Lys Lys Glu Asn Leu Pro Ala
305                 310                 315                 320

His Met
```

<210> SEQ ID NO 60
<211> LENGTH: 72
<212> TYPE: PRT
<213> ORGANISM: Bacillus subtilis
<220> FEATURE:
<223> OTHER INFORMATION: >ABP10853

<400> SEQUENCE: 60

```
Met Ser Glu Leu Phe Ser Val Pro Tyr Phe Ile Glu Asn Leu Lys Gln
1               5                   10                  15

His Ile Glu Met Asn Gln Ser Glu Asp Lys Ile His Ala Met Asn Ser
            20                  25                  30

Tyr Tyr Arg Ser Val Val Ser Thr Leu Val Gln Asp Gln Leu Thr Lys
        35                  40                  45

Asn Ala Val Val Leu Lys Arg Ile Gln His Leu Asp Glu Ala Tyr Asn
    50                  55                  60

Lys Val Lys Arg Gly Glu Ser Lys
65                  70
```

<210> SEQ ID NO 61
<211> LENGTH: 39
<212> TYPE: PRT
<213> ORGANISM: Bacillus subtilis
<220> FEATURE:
<223> OTHER INFORMATION: >ABP10854

<400> SEQUENCE: 61

```
Met Leu Thr Pro Leu Ser Ser Leu Tyr Met Ile Glu Ile Thr Pro Tyr
1               5                   10                  15

Thr Phe Met Lys Lys Glu Leu Pro Lys Lys Cys Leu Asn Phe Phe Pro
            20                  25                  30

Ser Leu Ile Leu Leu Arg Ile
        35
```

<210> SEQ ID NO 62
<211> LENGTH: 437
<212> TYPE: PRT
<213> ORGANISM: Bacillus subtilis
<220> FEATURE:
<223> OTHER INFORMATION: >ABP10855

<400> SEQUENCE: 62

```
Met Met Asp Met Lys Leu Gln Gln Val Gln Val Leu Lys Pro Gln Leu
1               5                   10                  15

Thr Gln Glu Leu Arg Gln Ala Ile Thr Leu Leu Gly Tyr His Ser Ala
            20                  25                  30

Glu Leu Ala Glu Tyr Ile Asp Glu Leu Ser Leu Glu Asn Pro Leu Ile
        35                  40                  45

Glu Arg Lys Glu Thr Asp Thr Pro Pro Leu Ser Tyr His Lys Thr Asn
    50                  55                  60

Lys Asn Arg Met Asn Ala Gln Glu Ala Gly Leu Gln Leu Ser Asn Pro
65                  70                  75                  80

Gln Lys Thr Leu Gln Asp Ala Leu Lys Gln Gln Ser Leu Asp Met Asn
                85                  90                  95

Leu Thr Asn Thr Glu Lys Lys Ile Phe Asn Tyr Leu Ile His Ser Leu
```

Asp Ser Asn Gly Tyr Leu Glu Glu Asp Val Glu Glu Ala Ala Arg Arg
    115                 120                 125

Leu Ser Val Ser Ala Lys Glu Thr Glu Ala Val Leu Ala Lys Leu Gln
130                 135                 140

Ser Leu Glu Pro Ala Gly Ile Gly Ala Arg Ser Leu Gln Glu Cys Ile
145                 150                 155                 160

Leu Leu Gln Leu Gln Arg Leu Pro Asn Arg Asn Glu Gln Ala Glu Met
                165                 170                 175

Leu Val Ser Ala His Phe Asp Ala Phe Ala Gln Lys Lys Trp Lys Ala
            180                 185                 190

Leu Ser Val Glu Thr Gly Ile Pro Leu His Thr Ile Gln Asp Ile Ser
        195                 200                 205

Asp Asp Ile Ala Ala Leu His Pro Arg Pro Gly Leu Leu Phe Ala Arg
210                 215                 220

Pro Glu Gln Asp Val Tyr Ile Glu Pro Asp Ile Phe Ile Thr Val Lys
225                 230                 235                 240

Asn Gly His Ile Ala Ala Glu Leu Asn Thr Arg Ser Phe Pro Glu Ile
                245                 250                 255

Asp Leu His Pro Gln Tyr Arg Thr Leu Leu Ser Ser Gly Ser Cys Gln
            260                 265                 270

Asp Thr Val Ser Tyr Leu Ser Ala Lys Tyr Gln Glu Trp Arg Trp Leu
        275                 280                 285

Ser Arg Ala Leu Arg Gln Arg Lys Gln Thr Ile Thr Arg Ile Ile Asn
290                 295                 300

Glu Leu Ile Thr Arg Gln Lys Asp Phe Phe Leu Lys Gly Arg Ser Ala
305                 310                 315                 320

Met Lys Pro Leu Thr Leu Arg Glu Val Ala Asp Cys Leu Ser Leu His
                325                 330                 335

Glu Ser Thr Val Ser Arg Ala Ile Lys Gly Lys Thr Ile Gln Thr Pro
            340                 345                 350

Tyr Gly Leu Phe Glu Met Lys Leu Phe Phe Ser Ala Lys Ala Glu Ala
        355                 360                 365

Ser Gly Glu Gly Asp Ala Ser Asn Tyr Ala Val Lys Met His Leu Glu
370                 375                 380

Asp Leu Ile Asn Gln Glu Asp Lys Thr Lys Pro Leu Ser Asp Gln Lys
385                 390                 395                 400

Leu Val Asp Leu Leu Tyr Glu Gln His Gly Ile Gln Ile Ser Arg Arg
                405                 410                 415

Thr Val Ala Lys Tyr Arg Asp Gln Met Lys Ile Pro Ser Ser Ala Ala
            420                 425                 430

Arg Lys Arg Tyr Lys
        435

<210> SEQ ID NO 63
<211> LENGTH: 563
<212> TYPE: PRT
<213> ORGANISM: Bacillus subtilis
<220> FEATURE:
<223> OTHER INFORMATION: >ABP10856

<400> SEQUENCE: 63

Met Gln Trp Thr Gln Ala Tyr Thr Pro Ile Gly Gly Asn Leu Leu Leu
1               5                   10                  15

Ser Ala Leu Ala Ala Leu Val Pro Ile Ile Phe Phe Trp Ala Leu

```
            20                  25                  30
Ala Ile Lys Arg Met Lys Gly Tyr Thr Ala Gly Leu Ala Thr Leu Gly
        35                  40                  45
Ile Ala Leu Ile Ile Ala Val Leu Val Tyr Arg Met Pro Ala Glu Lys
        50                  55                  60
Ala Leu Met Ser Ala Thr Gln Gly Ala Val Tyr Gly Leu Leu Pro Ile
65                  70                  75                  80
Gly Trp Ile Ile Val Thr Ser Val Phe Leu Tyr Lys Ile Thr Val Lys
                85                  90                  95
Thr Gly Gln Phe Asp Ile Ile Arg Ser Ser Val Leu Ser Ile Thr Asp
                100                 105                 110
Asp Arg Arg Leu Gln Ala Leu Leu Ile Ala Phe Ser Phe Gly Ala Phe
            115                 120                 125
Leu Glu Gly Ala Ala Gly Phe Gly Ala Pro Val Ala Ile Ser Ala Ala
        130                 135                 140
Leu Leu Val Gly Leu Gly Phe Asn Pro Leu Tyr Ala Ala Gly Ile Cys
145                 150                 155                 160
Leu Ile Ala Asn Thr Ala Pro Val Ala Phe Gly Ala Ile Gly Ile Pro
                165                 170                 175
Ile Thr Ala Val Glu Gly Pro Thr Gly Ile Pro Ala Met Glu Ile Ser
                180                 185                 190
Gln Met Val Gly Arg Gln Leu Pro Phe Leu Ser Val Phe Ile Pro Leu
            195                 200                 205
Tyr Leu Ile Ile Ile Met Ser Gly Phe Arg Lys Ala Leu Glu Val Trp
        210                 215                 220
Pro Ala Ile Leu Val Ser Gly Val Ser Phe Ala Val Val Gln Tyr Leu
225                 230                 235                 240
Ser Ser Asn Phe Leu Gly Pro Glu Leu Pro Asp Val Leu Ser Ala Leu
                245                 250                 255
Val Ser Met Ala Ala Leu Ala Val Phe Leu Lys Trp Trp Lys Pro Lys
                260                 265                 270
Thr Thr Phe Arg Phe Ala Gly Glu Gln Glu Ser Ala Ala Ser Ile Glu
            275                 280                 285
Thr Ala Arg Thr Asn Pro Ala Ala Pro Ala Tyr Ser Gly Gly Gln Ile
        290                 295                 300
Phe Lys Ala Trp Ser Pro Phe Leu Leu Leu Thr Ala Met Ile Ser Val
305                 310                 315                 320
Trp Gly Ile Pro Ser Val Lys Ser Ala Leu Thr Gly His Tyr Glu Gly
                325                 330                 335
Ser Ala Val Phe Leu Lys Trp Leu Asn Ala Val Gly Glu Lys Leu Thr
                340                 345                 350
Phe Ala Pro Gly Val Pro Phe Leu Asn Asn Gln Ile Val Asn Ala Asp
            355                 360                 365
Gly Thr Pro Ile Glu Ala Val Tyr Lys Leu Glu Val Leu Gly Ser Ala
        370                 375                 380
Gly Thr Ala Ile Leu Ile Ala Ala Val Leu Ser Lys Phe Ile Thr Ala
385                 390                 395                 400
Ile Ser Trp Lys Asp Trp Gly Thr Val Phe Lys Glu Thr Val Gln Glu
                405                 410                 415
Leu Lys Leu Pro Ile Leu Thr Ile Ala Ser Val Val Gly Phe Ala Tyr
            420                 425                 430
Val Thr Asn Ser Ser Gly Met Ser Thr Thr Leu Gly Met Thr Leu Ala
        435                 440                 445
```

```
Leu Thr Gly Ser Met Phe Thr Phe Phe Ser Pro Val Leu Gly Trp Leu
    450                 455                 460

Gly Val Phe Ile Thr Gly Ser Asp Thr Ser Ala Asn Leu Leu Phe Gly
465                 470                 475                 480

Asn Leu Gln Lys Val Thr Ala Leu Ser Val Gly Met Asp Pro Val Leu
                485                 490                 495

Ser Val Ala Ala Asn Ser Ser Gly Val Thr Gly Lys Met Ile Ser
                500                 505                 510

Pro Gln Ser Ile Ala Val Ala Cys Ala Ala Val Gly Leu Ala Gly Lys
            515                 520                 525

Glu Ser Asp Leu Phe Arg Phe Thr Ile Lys His Ser Leu Phe Leu Leu
530                 535                 540

Leu Leu Val Cys Ile Ile Thr Phe Leu Gln His His Val Phe Ser Trp
545                 550                 555                 560

Met Ile Pro

<210> SEQ ID NO 64
<211> LENGTH: 240
<212> TYPE: PRT
<213> ORGANISM: Bacillus subtilis
<220> FEATURE:
<223> OTHER INFORMATION: >ABP10857

<400> SEQUENCE: 64

Met Lys Tyr Lys Gln Ile Lys Thr Lys Lys Ile Tyr Glu Glu Val Ala
1               5                   10                  15

Asp Ala Leu Leu Asp Met Ile Lys Asn Gly Glu Leu Lys Pro Gly Asp
                20                  25                  30

Lys Leu Asp Ser Val Gln Ala Leu Ala Glu Ser Phe Gln Val Ser Arg
            35                  40                  45

Ser Ala Val Arg Glu Ala Leu Ser Ala Leu Lys Ala Met Gly Leu Val
        50                  55                  60

Glu Met Lys Gln Gly Glu Gly Thr Tyr Leu Lys Glu Phe Glu Leu Asn
65                  70                  75                  80

Gln Ile Ser Gln Pro Leu Ser Ala Ala Leu Leu Met Lys Lys Glu Asp
                85                  90                  95

Val Lys Gln Leu Leu Glu Val Arg Lys Leu Leu Glu Ile Gly Val Ala
            100                 105                 110

Ser Leu Ala Ala Glu Lys Arg Thr Glu Ala Asp Leu Glu Arg Ile Gln
        115                 120                 125

Asp Ala Leu Lys Glu Met Gly Ser Ile Glu Ala Asp Asp Glu Leu Gly
    130                 135                 140

Glu Lys Ala Asp Phe Ala Phe His Leu Ala Leu Ala Asp Ala Ser Gln
145                 150                 155                 160

Asn Glu Leu Leu Lys His Leu Met Asn His Val Ser Ser Leu Leu Leu
                165                 170                 175

Glu Thr Met Arg Glu Thr Arg Lys Ile Trp Leu Phe Ser Lys Lys Thr
            180                 185                 190

Ser Val Gln Arg Leu Tyr Glu Glu His Glu Arg Ile Tyr Asn Ala Val
        195                 200                 205

Ala Ala Gly Asn Gly Val Gln Ala Glu Ala Ala Met Leu Ala His Leu
    210                 215                 220

Thr Asn Val Glu Asp Val Leu Ser Gly Tyr Phe Glu Glu Asn Val Gln
225                 230                 235                 240
```

```
<210> SEQ ID NO 65
<211> LENGTH: 332
<212> TYPE: PRT
<213> ORGANISM: Bacillus subtilis
<220> FEATURE:
<223> OTHER INFORMATION: >ABP10858

<400> SEQUENCE: 65

Met Ala Thr Ile Lys Asp Ile Ala Gln Glu Ala Gly Phe Ser Ile Ser
1               5                   10                  15

Thr Val Ser Arg Val Leu Asn Asn Asp Glu Ser Leu Ser Val Pro Asp
            20                  25                  30

Glu Thr Arg Glu Lys Ile Tyr Glu Ala Ala Lys Leu Asn Tyr Arg
        35                  40                  45

Lys Lys Thr Val Arg Pro Leu Val Lys His Ile Ala Phe Leu Tyr Trp
    50                  55                  60

Leu Thr Asp Lys Glu Glu Leu Glu Asp Val Tyr Phe Lys Thr Met Arg
65                  70                  75                  80

Leu Glu Val Glu Lys Leu Ala Lys Ala Phe Asn Val Asp Met Thr Thr
                85                  90                  95

Tyr Lys Ile Ala Asp Gly Ile Glu Ser Ile Pro Glu His Thr Glu Gly
            100                 105                 110

Phe Ile Ala Val Gly Thr Phe Ser Asp Glu Glu Leu Ala Phe Leu Arg
        115                 120                 125

Asn Leu Thr Glu Asn Gly Val Phe Ile Asp Ser Thr Pro Asp Pro Asp
    130                 135                 140

His Phe Asp Ser Val Arg Pro Asp Leu Ala Gln Met Thr Lys Lys Thr
145                 150                 155                 160

Val Asn Ile Leu Thr Glu Lys Gly His Lys Ser Ile Gly Phe Ile Gly
                165                 170                 175

Gly Thr Tyr Lys Asn Pro Asn Thr Asn Gln Asp Glu Met Asp Ile Arg
            180                 185                 190

Glu Gln Thr Phe Arg Ser Tyr Met Arg Glu Lys Ala Met Leu Asp Glu
        195                 200                 205

Arg Tyr Ile Phe Cys His Arg Gly Phe Ser Val Glu Asn Gly Tyr Arg
    210                 215                 220

Leu Met Ser Ala Ala Ile Asp Ile Leu Gly Asp Gln Leu Pro Thr Ala
225                 230                 235                 240

Phe Met Ile Ala Ala Asp Pro Ile Ala Val Gly Cys Leu Gln Ala Leu
                245                 250                 255

Asn Glu Lys Gly Ile Ala Ile Pro Asn Arg Val Ser Ile Val Ser Ile
            260                 265                 270

Asn Asn Ile Ser Phe Ala Lys Tyr Val Ser Pro Pro Leu Thr Thr Phe
        275                 280                 285

His Ile Asp Ile His Glu Leu Cys Lys Asn Ala Val Gln Leu Leu Leu
    290                 295                 300

Glu Gln Val Gln Asp Lys Arg Arg Thr Val Lys Thr Leu Tyr Val Gly
305                 310                 315                 320

Ala Glu Leu Ile Val Arg Lys Ser Met Asn Glu Gly
                325                 330

<210> SEQ ID NO 66
<211> LENGTH: 421
<212> TYPE: PRT
<213> ORGANISM: Bacillus subtilis
<220> FEATURE:
```

<223> OTHER INFORMATION: >ABP10859

<400> SEQUENCE: 66

```
Met Lys Met Ala Lys Cys Ser Val Phe Met Leu Cys Ala Ala Val
1               5                   10                  15

Ser Leu Ser Leu Ala Ala Cys Gly Pro Lys Glu Ser Ser Ala Lys
            20                  25                  30

Ser Ser Ser Lys Gly Ser Glu Leu Val Trp Glu Asp Lys Glu Lys
        35                  40                  45

Ser Ile Gly Ile Lys Asp Ala Val Ala Phe Glu Lys Glu His Asp
    50                  55                  60

Val Lys Val Lys Val Val Glu Lys Pro Tyr Ala Lys Gln Ile Glu Asp
65                  70                  75                  80

Leu Arg Met Asp Gly Pro Ala Gly Thr Gly Pro Asp Val Leu Thr Met
                85                  90                  95

Pro Gly Asp Gln Ile Gly Thr Ala Val Thr Glu Gly Leu Leu Lys Glu
            100                 105                 110

Leu His Val Lys Lys Asp Val Gln Ser Leu Tyr Thr Asp Ala Ser Ile
        115                 120                 125

Gln Ser Gln Met Val Asp Gln Lys Leu Tyr Gly Leu Pro Lys Ala Val
130                 135                 140

Glu Thr Thr Val Leu Phe Tyr Asn Lys Asp Leu Ile Ser Glu Lys Glu
145                 150                 155                 160

Leu Pro Lys Thr Leu Glu Glu Trp Tyr Asp Tyr Ser Lys Lys Thr Ala
                165                 170                 175

Asn Gly Ser Lys Phe Gly Phe Leu Ala Leu Phe Asp Gln Ile Tyr Tyr
            180                 185                 190

Ala Glu Ser Val Met Ser Gly Tyr Gly Gly Tyr Ile Phe Gly Lys Ala
        195                 200                 205

Lys Asp Gly Ser Tyr Asn Pro Ser Asp Ile Gly Ile Asn Asn Glu Gly
210                 215                 220

Ala Val Lys Gly Ala Ala Leu Ile Gln Lys Phe Tyr Lys Asp Gly Leu
225                 230                 235                 240

Phe Pro Ala Gly Ile Ile Gly Glu Gln Gly Ile Asn Val Leu Glu Ser
                245                 250                 255

Leu Phe Thr Glu Gly Lys Ala Ala Ile Ile Ser Gly Pro Trp Asn
            260                 265                 270

Val Glu Ala Phe Ser Lys Ala Gly Ile Asn Tyr Gly Ile Thr Lys Leu
        275                 280                 285

Pro Lys Leu Glu Asn Gly Lys Asn Met Ser Ser Phe Ile Gly Val Lys
                295                 300

Ser Tyr Asn Val Ser Ala Phe Ser Lys Asn Glu Glu Leu Ala Gln Glu
305                 310                 315                 320

Leu Ala Val Phe Leu Ala Asn Glu Lys Asn Ser Lys Thr Arg Tyr Glu
                325                 330                 335

Glu Thr Lys Glu Val Pro Ala Val Lys Ser Leu Ala Asn Asp Pro Ala
            340                 345                 350

Ile Met Lys Ser Gly Ala Ala Arg Ala Val Thr Glu Gln Ser Arg Phe
        355                 360                 365

Ser Glu Pro Thr Pro Asn Ile Pro Glu Met Asn Glu Ile Trp Thr Pro
370                 375                 380

Ala Asp Ser Ala Leu Gln Thr Val Ala Thr Gly Lys Ala Asp Pro Lys
385                 390                 395                 400
```

```
Gln Ala Leu Asp Gln Ala Ala Glu Thr Ala Lys Gly Gln Ile Lys Ala
                405                 410                 415

Lys His Ser Gly Lys
            420

<210> SEQ ID NO 67
<211> LENGTH: 418
<212> TYPE: PRT
<213> ORGANISM: Bacillus subtilis
<220> FEATURE:
<223> OTHER INFORMATION: >ABP10860

<400> SEQUENCE: 67

Met Gln His Arg Gln Val Ala Leu Leu Leu Ser Ile Ile Pro Gly Leu
1               5                   10                  15

Gly Gln Phe Tyr Asn Lys Gln Trp Ile Lys Gly Ile Val Phe Leu Phe
            20                  25                  30

Leu Gly Ala Ser Phe Phe Ala Val Phe Gly Asp Leu Leu Asn Met Gly
        35                  40                  45

Phe Trp Gly Ile Phe Thr Leu Gly Thr Glu Val Pro Arg Asp Asn Ser
    50                  55                  60

Val Phe Leu Leu Ala Glu Gly Ile Ile Ala Val Ile Val Thr Cys Phe
65                  70                  75                  80

Gly Leu Ala Val Tyr Tyr Val Asn Leu Arg Asp Ala Phe Gln Ser Gly
                85                  90                  95

Lys Gln Arg Asp Glu Asn Lys Pro Leu Ser Ser Leu Lys Glu Gln Tyr
            100                 105                 110

Gln His Ile Ile Ser Glu Gly Tyr Pro Tyr Val Val Ser Gly Pro Ser
        115                 120                 125

Leu Phe Ile Leu Ile Phe Ala Val Ile Phe Pro Ile Leu Phe Ser Phe
    130                 135                 140

Ala Leu Ala Phe Thr Asn Tyr Asp Leu Tyr His Ser Pro Pro Ala Lys
145                 150                 155                 160

Leu Ile Asp Trp Val Gly Phe Gln Thr Phe Ala Asn Ile Phe Thr Val
                165                 170                 175

Asp Ile Trp Arg Ser Thr Phe Phe Asp Val Leu Ala Trp Thr Val Val
            180                 185                 190

Trp Thr Leu Ala Ala Ser Thr Leu Gln Val Ser Leu Gly Ile Phe Leu
        195                 200                 205

Ala Ile Ile Val Asn Gln Lys Asp Leu Arg Phe Lys Arg Phe Phe Arg
    210                 215                 220

Thr Ile Leu Ile Leu Pro Trp Ala Val Pro Gly Phe Val Thr Ile Leu
225                 230                 235                 240

Ile Phe Ala Gly Leu Phe Asn Asp Ser Phe Gly Ala Met Asn His Asp
                245                 250                 255

Ile Leu Ala Phe Phe Gly Ile Asp Pro Leu Pro Trp Met Thr Asp Ala
            260                 265                 270

Asn Trp Ser Arg Leu Ala Leu Ile Leu Met Gln Gly Trp Leu Gly Phe
        275                 280                 285

Pro Tyr Ile Phe Leu Val Ser Thr Gly Val Leu Gln Ser Ile Pro Asp
    290                 295                 300

Asp Leu Tyr Glu Ala Ala Thr Ile Asp Gly Ala Ser Val Phe Ser Lys
305                 310                 315                 320

Leu Arg Tyr Ile Thr Leu Pro Met Val Phe Ile Ala Met Ala Pro Ile
                325                 330                 335
```

-continued

```
Ile Ile Thr Gln Phe Thr Phe Asn Phe Asn Phe Asn Ile Ile Tyr
            340                 345                 350

Leu Phe Asn Gly Gly Pro Ala Val Thr Gly Ser Thr Ala Gly Gly
        355                 360                 365

Thr Asp Ile Leu Val Ser Trp Ile Tyr Lys Leu Thr Met Gln Ser Ser
    370                 375                 380

Gln Tyr Ser Leu Ala Ala Leu Thr Ile Leu Leu Ser Val Phe Val
385                 390                 395                 400

Ile Ser Ile Ala Leu Trp Gln Phe Arg Gln Thr Lys Ser Phe Lys Glu
                405                 410                 415

Glu Ala

<210> SEQ ID NO 68
<211> LENGTH: 52
<212> TYPE: PRT
<213> ORGANISM: Bacillus subtilis
<220> FEATURE:
<223> OTHER INFORMATION: >ABP10886

<400> SEQUENCE: 68

Met Arg Lys Asp Lys Leu Val Ser Thr Val Phe Lys Asn Asn Ala Ile
1               5                   10                  15

Glu Ile Tyr Thr Ile Ile Ile Leu Lys Asn Pro Asp Thr Leu Val Arg
            20                  25                  30

Ile Lys Glu Ile Gln Leu Phe His Thr Lys Lys Ser Leu Ala Ala Ser
        35                  40                  45

Ala Ala Lys Leu
    50

<210> SEQ ID NO 69
<211> LENGTH: 1015
<212> TYPE: PRT
<213> ORGANISM: Bacillus subtilis
<220> FEATURE:
<223> OTHER INFORMATION: >ABP10887

<400> SEQUENCE: 69

Met Phe Pro Glu Val Asn Asp Lys Asp Glu Leu Gln Lys Ile Phe Leu
1               5                   10                  15

Asn Val Ser Gly Lys Thr Ile His Ser Leu Ile Arg Asp Asp Thr Asn
            20                  25                  30

Ile Glu Gln Asn Thr Asn Ile Ile Asp Ile Asp Arg Val Leu Asp His
        35                  40                  45

Lys Lys Ser Asp Phe Leu Val Arg Asn Ser Glu Glu Phe Leu Glu His
    50                  55                  60

Asn Pro Phe Phe His Phe Ser Pro Phe Leu Ser Cys Lys Ile Glu
65                  70                  75                  80

Glu Phe Ile Val Lys Val Arg Ile Glu Asp Ala Val Asp Asn Glu Asp
                85                  90                  95

Glu Phe Val Lys Lys Val Ile Lys His Ile Leu Asp Leu Met Phe Glu
            100                 105                 110

Lys Ala Phe Arg Val Leu Val Leu Glu Val Asn Ile Ala Arg Leu Glu
        115                 120                 125

Gly Lys Leu Glu Gly Thr Thr Pro Glu Glu Arg Leu Asn His Phe Leu
    130                 135                 140

Ala Val Ser Leu Asn Asp Glu Ser Phe Leu Lys Ser Val Tyr Lys Glu
145                 150                 155                 160
```

```
Tyr Glu Val Leu Thr Ser Leu Leu Cys Val Thr Ile Asp Asp Tyr Phe
                165                 170                 175
Thr Tyr Val Met Glu Ile Ile Lys Asn Thr Lys Arg Glu Ile Ser Ser
            180                 185                 190
Leu Asn Ser Lys Phe Asn Ser Asp Asn Asp Leu Gly Ala Ile Thr Asn
        195                 200                 205
Ile Thr Thr Gly Leu Gly Asp Thr His Gln Lys Gly Lys Ser Val Ser
    210                 215                 220
Thr Ile Tyr Phe Lys Ser Gly Lys Lys Ile Ile Tyr Lys Pro Arg Asp
225                 230                 235                 240
Leu Thr Leu Glu Gln Gly Phe Gln Val Leu Tyr Trp Leu Asp Gly
                245                 250                 255
Lys Asn Ile Pro Gly Ile Leu Asn Phe Lys Arg Val Gln Ile His Thr
                260                 265                 270
Val Asn Asp Ser Gly Trp Met Glu His Ile Asp Tyr Lys Ser Cys Phe
                275                 280                 285
Asn Lys Asn Glu Ala Asn Asp Phe Tyr Thr Arg Ser Gly Asn Leu Leu
            290                 295                 300
Cys Leu Leu Tyr Leu Leu Asn Ala Val Asp Phe His His Glu Asn Leu
305                 310                 315                 320
Ile Ala His Gly Ser Phe Pro Val Leu Val Asp Leu Glu Ser Leu Phe
                325                 330                 335
His Ala Arg Leu Lys Val Asp Gln Ile Asp Lys Lys Ser Ala Phe Val
                340                 345                 350
Thr Ala Thr Glu Leu Val Asp Asn Ser Val Gln Ser Ile Ser Leu Leu
            355                 360                 365
Pro Thr Lys Ile Ser Lys Arg Val Gly Asp Lys Asp Ile Ser Leu Asp
        370                 375                 380
Ile Gly Gly Leu Gly Ala Tyr Lys Glu Gln Leu Ser Pro His Lys Ser
385                 390                 395                 400
Leu Val Ile Glu Asn Ala Gly Thr Asp Thr Ile Lys Ile Leu Arg Lys
                405                 410                 415
Asn Thr Phe Ile Lys Pro Gln Leu Asn Asn Pro Ser Ile Lys Thr Gly
                420                 425                 430
Ser Tyr Leu Tyr Ser Glu Asn Tyr Thr Gly Gln Ile Lys Asp Gly Phe
            435                 440                 445
Glu Ser Leu Tyr Ser Trp Val Met Leu Asn Lys Asp Glu Phe Trp Asp
        450                 455                 460
Lys Ile Ser Gln Thr Phe Lys Glu Thr Asn Ser Arg Phe Ile Phe Arg
465                 470                 475                 480
Pro Thr Tyr Leu Tyr Thr Gln Leu Leu Arg Ile Ser Ser His Pro Asp
                485                 490                 495
Phe Met Arg Asp Thr Tyr Arg Arg Lys Ile Ile Leu His Arg Ile Gly
                500                 505                 510
Ile Asp Tyr Ile Gln Glu Tyr Lys Asp Ile Leu Asn Ser Glu Tyr Lys
            515                 520                 525
Asp Leu Leu Thr Gly Asp Val Pro Phe Phe Arg Ser Ser Ile Glu His
        530                 535                 540
Glu His Leu Ile Asp Ser Arg Gly Gly Lys Ile His Asn Ile Leu Glu
545                 550                 555                 560
Glu Pro Pro Ile Lys Thr Val Lys Gln Lys Ile Phe Asn Leu Ser Lys
                565                 570                 575
Glu Asp Leu Lys Arg Gln Ile Asp Phe Ile Glu Met Ser Tyr Ile Ser
```

```
            580                 585                 590
Asn Glu Lys Arg Leu Lys Glu Val Thr Asp Ile Lys Phe Ser Lys Ala
            595                 600                 605

Ala Asn Leu Asn Lys Ile Lys Ser Glu Asn Trp Ile Asp Glu Ala Thr
            610                 615                 620

Gln Ile Gly Glu Phe Ile Val Glu Asn Ser Val Cys Gly Ile Asn Lys
625                 630                 635                 640

Lys Gln Lys Asp Arg Met Trp Ile Gly Pro Ser Leu Glu Gly Ile Glu
                645                 650                 655

Glu Asp Ile Trp Asn Ala Asn Val Leu Gly Phe Asp Ile Tyr Asn Gly
            660                 665                 670

Asn Ser Gly Ile Ala Leu Phe Leu Gly Tyr Leu Gly Glu Ile Leu Asn
            675                 680                 685

Arg Gln Asp Phe Lys Gln Ala Ala Ile Glu Thr Met Arg Pro Ile Gln
            690                 695                 700

Lys Phe Ile Ser Glu Ile Lys Glu Asp His Pro Tyr Leu Ile Gly Ala
705                 710                 715                 720

Phe Gln Gly Ile Ser Gly Tyr Phe Tyr Thr Leu Asn Lys Leu Ser Asn
                725                 730                 735

Leu Phe Glu Asp Ser Glu Leu Arg Lys Thr Thr Leu Glu Asn Ile Ser
                740                 745                 750

Val Leu Ser Lys Leu Gly Lys Phe Asp Lys Val Tyr Asp Leu Ile Gly
            755                 760                 765

Gly Ser Leu Gly Ser Leu Ala Val Met Leu Ser Ile Ile Pro Asn Ile
            770                 775                 780

Thr Glu Glu Asn Asn Lys Lys Glu Ile Leu Lys Ile Ser His Ile His
785                 790                 795                 800

Cys Asp His Ile Leu Ser Val Ala Lys Asn Phe Glu Glu Gln Ile Ser
                805                 810                 815

Trp Pro Gly Lys Phe Ser Ala Ala Tyr Ser Gly Phe Ser His Gly Asn
                820                 825                 830

Ser Gly Phe Ile Ala Tyr Leu Tyr Lys Phe Phe Lys Leu Thr Asn Asp
            835                 840                 845

Glu Gln Leu Leu Glu Val Ile Gln Arg Ala Leu Arg Phe Glu Arg Arg
            850                 855                 860

Leu Tyr Ser Glu Asp His Asn Asn Trp Tyr Thr Thr Glu Asn Lys Asp
865                 870                 875                 880

Lys Leu Ala Asn Gly Trp Cys His Gly Ala Pro Gly Ile Leu Leu Ser
                885                 890                 895

Lys Leu Ile Leu Lys Asp Asn Gly Phe Glu Asp Glu Tyr Ile Glu Lys
                900                 905                 910

Glu Ile Ser Thr Ala Ile Asp Ser Ile His Asn Gly Ile Gly Asn
            915                 920                 925

Asn Pro Thr Tyr Cys His Gly Asp Leu Gly Val Leu Ser Ile Leu Asn
            930                 935                 940

Tyr Ala Ser Asp Leu Thr Asn Asn Ile Asn Leu Lys Asn Arg Cys Leu
945                 950                 955                 960

Arg Thr Tyr Gln Asp Leu Phe Glu Asn Val Leu Ala Met Lys Trp Arg
                965                 970                 975

Lys Arg Asp Leu Val Cys Thr Arg Ser Tyr Ser Leu Met Ile Gly Leu
                980                 985                 990

Ser Gly Ile Gly Tyr Ser Met Ile Lys Asn Tyr Ala Pro Glu Ile Val
            995                 1000                1005
```

-continued

```
Pro Asn Phe Leu Trp Leu Glu
    1010                1015

<210> SEQ ID NO 70
<211> LENGTH: 66
<212> TYPE: PRT
<213> ORGANISM: Bacillus subtilis
<220> FEATURE:
<223> OTHER INFORMATION: >ABP10888

<400> SEQUENCE: 70

Met Lys Lys Asp Met Val Lys Asn Ala Ser Gly Phe Ile Glu Glu Asp
1               5                   10                  15

Glu Leu Ile Ser Leu Ala Asn Gly Glu Asn Ala Thr Gly Gly Gly Thr
            20                  25                  30

Pro Val Thr Ala Ile Ile Thr Ala Leu Thr Gly Thr Thr Phe Thr Val
        35                  40                  45

Thr Leu Ser Ala Ala Ser Cys Pro Thr Ser Ala Cys Thr Asn Leu Cys
    50                  55                  60

Asn Lys
65

<210> SEQ ID NO 71
<211> LENGTH: 982
<212> TYPE: PRT
<213> ORGANISM: Bacillus subtilis
<220> FEATURE:
<223> OTHER INFORMATION: >ABP10889

<400> SEQUENCE: 71

Met Asp Ile Ser Tyr Glu Asn Asn Phe Ile Arg Asp Ala Val Ile
1               5                   10                  15

Asn Phe Ser Ser Pro Thr Asn Glu Val Glu Lys Leu Arg Ile Lys Asn
            20                  25                  30

Lys Asp Tyr Phe Gly Asn Phe Tyr Thr Phe Phe Leu Asp Phe Tyr Gln
        35                  40                  45

Gln Arg Leu Phe Asn Thr Leu Glu Asn Ala Ser Lys Glu Asn Asn Leu
    50                  55                  60

Lys Leu Asn Lys Gln Lys Ile Ile Ser Ser Ala Leu Glu Ala Phe Ser
65                  70                  75                  80

Gln Glu Leu Ile Gln Leu Cys Ile Arg Thr Leu Ile Val Asp Ile Asn
                85                  90                  95

Asp Arg Lys Glu Lys Gly Leu Leu Glu Gly Lys Asp Ser Lys Leu Arg
            100                 105                 110

Tyr Lys Asn Tyr Asn Asn Leu Ile Phe Lys Ser Glu Tyr Val Ala Glu
        115                 120                 125

Ile Leu Asn Lys Tyr Pro Val Leu Thr Tyr Leu Ile Ser Ser Arg Ile
    130                 135                 140

Ser Asn Lys Ile Leu Tyr Leu Lys Glu Val Leu Glu Asn Leu Arg Lys
145                 150                 155                 160

Asn Arg Gln Asp Ile Tyr Arg Glu Leu Arg Ile Glu Phe Asp Glu Val
                165                 170                 175

Ser Asn Ile Tyr Phe Ser Ser Gly Asp Thr His Asn Gly Gly Lys Asn
            180                 185                 190

Val Leu Ile Ile Glu Thr Asn Gln Gly Lys Ile Val Tyr Lys Pro His
        195                 200                 205

Ser Leu Ser Pro Asp Ile Leu Phe Asn Ser Ile Val Asp Tyr Val Asn
```

```
            210                 215                 220
Asn Ser Asp Lys Ile Leu Lys Lys Ile Tyr Lys Ile Arg Thr Leu Asn
225                 230                 235                 240

Tyr Lys Asp Tyr Gly Tyr Gln Glu Phe Ile Asp Tyr Lys Glu Cys Glu
                245                 250                 255

Thr Ser Glu Lys Leu Asn Phe Tyr Phe Tyr Arg Val Gly Val Ser Leu
                260                 265                 270

Ser Ile Phe His Ile Ile Gly Cys Asp Asp Leu His His Glu Asn Leu
                275                 280                 285

Ile Ala His Gly Glu Tyr Pro Val Val Ile Asp Leu Glu Thr Leu Ile
                290                 295                 300

Lys Asn Asn Ser Ile Tyr Lys Pro Arg Asn Asn Leu Ile Asp Asn
305                 310                 315                 320

Phe His Glu Asp Ile Asn Tyr Ser Val Leu Gly Thr Met Leu Leu Pro
                325                 330                 335

Leu Asn Leu Gln Thr Ser Ile Phe Asp Phe Asp Leu Gly Gly Ile Ser
                340                 345                 350

Asn Asp Glu Asn Gln Thr Ser Glu Ile Trp Lys Ser Tyr Ile Ile Asp
                355                 360                 365

Phe Glu Gly Thr Asp Glu Ile Gln Leu Thr Lys Lys Ser Val Ile Met
                370                 375                 380

Asn Ser Thr Gln Asn Arg Ala Thr Tyr Asn Gly Lys Ala Ala Asp Pro
385                 390                 395                 400

Lys Asn Tyr Ile Glu Glu Ile Leu Lys Gly Phe Thr Asp Cys Tyr Asn
                405                 410                 415

Phe Val Leu Glu Asn Ile Ser Gly Phe His Asp Leu Val Lys Lys Val
                420                 425                 430

Gly Ser Ser Asn Leu Glu Val Arg Gln Val Leu Arg Ala Thr Ser Ile
                435                 440                 445

Tyr Ala Arg Phe Leu Glu Ala Ser Thr His Pro Asn Tyr Leu Ser Ser
                450                 455                 460

Phe Glu Glu Arg Lys Lys Leu Phe Lys Lys Ile Asn Ile Ala Glu Gly
465                 470                 475                 480

Val Thr Asp Lys Phe Ser Lys Lys Asn Leu Tyr Glu Leu Glu Ser Leu
                485                 490                 495

Met Cys Asn Asp Val Pro Tyr Phe Ser Thr Met Tyr Asn Ser Leu Asp
                500                 505                 510

Leu Ile Cys Asn Lys Ser Thr Ser Ile Val Asn Phe Phe Arg Glu Ser
                515                 520                 525

Leu Leu Asp Val Val Leu Asn Lys Thr Lys Ser Ile Ser Lys Ala Ser
530                 535                 540

Leu Lys Lys Gln Gln Tyr Tyr Ile Arg Met Ser Leu Thr Thr Thr Ile
545                 550                 555                 560

Lys Asp Ser Trp Lys Lys Thr Asn Lys His Asn Lys Lys Tyr Arg Pro
                565                 570                 575

Lys Leu Phe Gly Asn Asn Lys Asn Tyr Leu Glu Cys Ala Thr Glu
                580                 585                 590

Ile Gly Asp Leu Phe Leu Glu Thr Ala Ile Trp Asn Asn Asp Arg Ser
                595                 600                 605

Lys Cys Thr Trp Val Ala Pro Ile Ile Ser Glu Asn Asn Lys Val Lys
                610                 615                 620

Leu Gly Pro Leu Asn Phe Asp Leu Tyr Glu Gly Gly Val Ile Leu
625                 630                 635                 640
```

```
Phe Leu Ala Leu Leu Gly Lys Glu Asn Gly Lys Lys Glu Tyr Phe Asp
                645                 650                 655

Leu Ala Leu Ala Gly Met Arg Gly Ile Glu Glu Leu Phe Leu Ser Asp
            660                 665                 670

Asp Lys Met Asp Asp Arg Leu Ser Leu Phe Thr Gly Ile Gly Ser Leu
        675                 680                 685

Ser Tyr Ile Tyr Tyr His Leu Tyr Thr His Thr Asn Asp Tyr Lys Tyr
    690                 695                 700

Tyr Glu Lys Phe Lys Lys Tyr Ile Lys Lys Ile Asn Glu Met Asn Ile
705                 710                 715                 720

Ser Gly Asp Ile Ala Leu Asp Ile Val Gly Val Ser Ser Leu Ile
                725                 730                 735

Val Phe Leu Leu Asn Leu Tyr Lys Glu Thr Lys Leu Asp Ile Leu Asn
            740                 745                 750

Ser Val Cys Cys Lys Leu Gly Asn Thr Leu Tyr Gln Cys Leu Glu Asn
        755                 760                 765

Asp Lys His Asn Tyr Leu Thr Gly Leu Ser His Gly Tyr Ser Gly Phe
    770                 775                 780

Thr Trp Ala Leu Cys Tyr Leu Gly His Ile Thr Lys Glu Glu Lys Tyr
785                 790                 795                 800

Thr Thr Leu Gly Lys Glu Leu Leu Lys Ile Glu Asn Lys Phe Phe Asp
                805                 810                 815

Leu His Thr Ser Asn Trp Lys Asp Leu Arg Val Gly Glu Gly Asn Ser
            820                 825                 830

Asp Pro Val Tyr Trp Cys His Gly Ala Gly Ile Ala Leu Ser Arg
        835                 840                 845

Ala Phe Leu Lys Asp Leu Leu Lys Asn Lys Glu Asn Val Val Asp Lys
    850                 855                 860

Glu Ile Asp Lys Glu Val Asp Arg Asp Leu Ser Ser Ala Ile Cys Lys
865                 870                 875                 880

Leu Leu Ser Asp Gly Phe Lys Lys Thr Thr Asp His Ser Leu Cys His
                885                 890                 895

Gly Ser Phe Gly Asn Ile Asp Ile Leu Leu Lys Leu Ser Glu Phe Leu
            900                 905                 910

Asn Asp Ile Asp Leu Gln Glu Val Ala Phe Lys Glu Ala Gln Asn Ala
        915                 920                 925

Ile Asn Tyr Ile Arg Asp Lys Gly Phe Ile Pro Gly Leu Gln Asp His
    930                 935                 940

Phe Asp Leu Asn Thr Phe Met Leu Gly Leu Gly Val Gly Tyr Ser
945                 950                 955                 960

Leu Leu Arg Leu His Asn Pro Val Asn Pro Ser Leu Leu Ala Met Glu
                965                 970                 975

Val Arg Ser Tyr Asn Glu
            980

<210> SEQ ID NO 72
<211> LENGTH: 715
<212> TYPE: PRT
<213> ORGANISM: Bacillus subtilis
<220> FEATURE:
<223> OTHER INFORMATION: >ABP10890

<400> SEQUENCE: 72

Met Ile Val Lys Lys Lys Arg Ile Pro Ile Val Lys Gln Leu Gln
1               5                   10                  15
```

Gln Thr Glu Cys Gly Leu Cys Cys Ala Met Leu Ile Arg Phe Tyr
            20              25              30

Asn Ser Asn Glu Thr Leu Phe Glu Leu Arg Ser Phe Leu Glu Ala Gly
        35              40              45

Arg Asp Gly Leu Thr Ile Lys Gln Leu Lys Asn Leu Leu Val His Lys
50              55              60

Gly Phe Lys Ala Asp Ile Tyr Lys Ser Thr Ile Pro Gly Leu Lys Lys
65              70              75              80

Ile Asn Val Pro Phe Ile Ala Tyr Trp Asn Asn Glu His Phe Ile Val
            85              90              95

Val Glu Lys Thr Lys Lys Asn Phe Tyr Tyr Ile Ile Asp Pro Ala Asn
            100             105             110

Gly Arg Arg Lys Leu Thr Glu Glu Phe Arg Lys Gly Phe Ser Ser
        115             120             125

Tyr Ile Leu Tyr Ala Val Pro Ser Glu Asn Phe Thr Pro Asn Lys Arg
    130             135             140

Lys Asp Lys Asn Val Trp Phe Gly Val Leu Lys Asn Ile Thr Asn Tyr
145             150             155             160

Lys Leu Leu Phe Ser Ile Ile Val Phe Leu Ser Leu Ile Ser Tyr Leu
            165             170             175

Leu Thr Leu Tyr Val Pro Ile Leu Val Gln Lys Leu Ile Asp Thr Ser
        180             185             190

Ile Glu His Asn Asn Leu Asn Ser Ile Ser Asn Ile Val Trp Ile Thr
        195             200             205

Phe Leu Ile Ser Ile Leu Tyr Gly Met Phe Val Leu Phe Arg Gly Leu
        210             215             220

Lys Met Ile Ser Leu Asn Ile Phe Leu Ser Lys Asn Leu Val Val Asp
225             230             235             240

Thr Phe Ala His Leu Leu Lys Leu Pro Phe Lys Phe Asp Leu Arg
            245             250             255

Ser Pro Gly Asp Leu Leu Phe Arg Leu Asn Ser Met Asn Gly Phe Arg
        260             265             270

Glu Leu Leu Ser Thr Gln Leu Ile Ser Gly Leu Ile Asp Leu Gly Ala
        275             280             285

Val Val Phe Ile Leu Ala Tyr Met Phe Phe Lys Ser Ile Pro Leu Thr
    290             295             300

Leu Ile Thr Ile Leu Ile Phe Ala Ile Asn Thr Ile Phe Met Phe Leu
305             310             315             320

Thr Arg Pro Ala Val Ala Gln Ala Ile Asp Asp Glu Val Ala Glu Gln
            325             330             335

Ser Lys Ser Gln Ala Ile Gln Ile Glu Ser Ile Phe Ser Ile Ala Ala
        340             345             350

Ile Lys Ile Ser Gly Met Glu Asn Glu Ile Phe Ser Thr Trp Asn Asn
        355             360             365

Ser Phe Asn Asp Val Ile Lys Arg Phe Lys Arg Ser Ile Leu Gln
    370             375             380

Asn Ile Val Asn Thr Val Thr Gln Val Phe Gln Thr Ile Ala Pro Leu
385             390             395             400

Val Ile Leu Ile Leu Glu Leu Leu Phe Phe Asp Asn Lys Phe Thr
            405             410             415

Met Gly Glu Val Ile Ala Tyr His Ser Leu Ser Val Thr Phe Phe Gly
            420             425             430

Leu Thr Thr Ser Leu Phe Gly Thr Tyr Thr Gln Phe Ile Leu Ala Thr
            435                 440                 445

Ser Tyr Leu Glu Arg Val Lys Asp Ile Thr Thr Glu Cys Glu Lys
450                 455                 460

Asn Phe Glu Asn Ala Val Asn Leu Lys Leu Arg Gly Asn Val Lys Leu
465                 470                 475                 480

Glu Asn Val Ser Phe Ser Tyr Thr Lys His Ser Pro Lys Val Leu Lys
                485                 490                 495

Asn Ile Ser Leu Glu Ile Arg Glu Gly Gln Lys Ile Ala Ile Val Gly
                500                 505                 510

Ser Ser Gly Ser Gly Lys Ser Thr Leu Ser Lys Leu Ile Met Gly Leu
                515                 520                 525

Tyr Asp Pro Thr Glu Gly Gln Ile Cys Phe Asp Ser Ile Pro Leu Glu
                530                 535                 540

Lys Leu Asp Lys Lys Gln Leu Tyr Lys Gln Met Gly Ile Val Pro Gln
545                 550                 555                 560

Asp Ile Thr Leu Phe Asn Ser Ser Ile Leu Lys Asn Ile Thr Leu Asn
                565                 570                 575

Asn Lys Asn Thr Ser Ile Glu Lys Val Arg Lys Val Ala Lys Ala Ala
                580                 585                 590

Gln Ile Asp Lys Glu Ile Glu Ser Met Pro Met Lys Tyr Asn Thr Pro
                595                 600                 605

Ile Ser Glu Met Gly Met Asn Leu Ser Gly Gly Gln Arg Gln Arg Ile
                610                 615                 620

Val Leu Ala Arg Ala Leu Leu Asn Asp Pro Lys Ile Leu Ile Leu Asp
625                 630                 635                 640

Glu Ala Thr Ser Ser Leu Asp Leu Val Asn Glu Thr Leu Ile Ser Lys
                645                 650                 655

Tyr Leu Ser Glu Met Gly Cys Thr Arg Val Val Ile Ala His Arg Leu
                660                 665                 670

Ser Thr Ile Met Asp Ser Asp Phe Ile Ile Val Leu Asp Lys Gly Glu
                675                 680                 685

Val Val Glu Ile Gly Lys His Glu Glu Leu Ile Ala Leu Glu Gly Val
                690                 695                 700

Tyr Ser Asn Leu Tyr Arg Ser Gln Met Lys Arg
705                 710                 715

<210> SEQ ID NO 73
<211> LENGTH: 56
<212> TYPE: PRT
<213> ORGANISM: Bacillus subtilis
<220> FEATURE:
<223> OTHER INFORMATION: >ABP10891

<400> SEQUENCE: 73

Met Lys Asn Tyr Lys Gly Asp Gly Ala Val Phe Leu Val Ile Gly Phe
1               5                   10                  15

Cys Leu Gly Leu Phe Met Gly Val Val Phe Asp Ile Leu Pro Tyr Gly
                20                  25                  30

Leu Ser Leu Gly Ile Leu Ile Gly Ser Leu Ile Asp Phe Tyr Phe Tyr
                35                  40                  45

Ala Arg Tyr Lys Asn Asn Lys
                50              55

<210> SEQ ID NO 74
<211> LENGTH: 84

```
<212> TYPE: PRT
<213> ORGANISM: Bacillus subtilis
<220> FEATURE:
<223> OTHER INFORMATION: >ABP10892

<400> SEQUENCE: 74
```

Met Ser Met Ser Arg Lys Glu Thr Pro Asp Asp Asn Ala Phe Ile Glu
1               5                   10                  15

Ser Phe His Ser Ser Leu Lys Ser Lys Thr Leu Tyr Leu Asn Ser Ile
            20                  25                  30

Glu Arg Thr Ser Thr Ile Ile Val Glu Arg Asn Val Lys Asp Tyr Ile
        35                  40                  45

Tyr Tyr Asn Asn Ile Pro Tyr Ser Asn Glu Thr Lys Gln Pro Ile Thr
    50                  55                  60

Asp Lys Leu Ser Ala Ile Gly Cys Leu Lys Gly Val Leu Ile Pro Val
65                  70                  75                  80

Ser Lys Thr Gly

```
<210> SEQ ID NO 75
<211> LENGTH: 427
<212> TYPE: PRT
<213> ORGANISM: Bacillus subtilis
<220> FEATURE:
<223> OTHER INFORMATION: >ABP10981

<400> SEQUENCE: 75
```

Met Ile Asp Val Ile Arg Val Ser Gly Gly Tyr Gly Arg Lys Asp Val
1               5                   10                  15

Leu Gln Asp Ile Ser Phe Ala Val Lys Pro Gly Glu Phe Leu Gly Ile
            20                  25                  30

Leu Gly Pro Asn Gly Ser Gly Lys Thr Thr Leu Leu Lys Met Leu Ser
        35                  40                  45

Gly Ser Ile Thr Pro Arg Ser Gly Glu Val Leu Leu Glu Cys Arg Ser
    50                  55                  60

Val Gly Ser Tyr Lys Thr Lys Glu Leu Ala Arg Lys Val Ala Ala Leu
65                  70                  75                  80

Pro Gln Lys Thr Glu Gln Ala Phe Ser Phe Thr Val Glu Glu Thr Val
            85                  90                  95

Gln Phe Gly Arg Tyr Ala Tyr Gln Ser Gly Leu Phe Arg Gln Leu Thr
        100                 105                 110

Gly Glu Asp His Asp Ile Val Lys Arg Val Met Lys Gln Thr Asp Ile
    115                 120                 125

Leu Arg Phe Ala Lys Lys Ser Ile His Glu Leu Ser Gly Gly Glu Gln
130                 135                 140

Gln Arg Val Tyr Val Ala Gln Ala Leu Ala Gln Glu Pro Arg Tyr Leu
145                 150                 155                 160

Leu Leu Asp Glu Pro Thr Ser Phe Leu Asp Leu Ser Phe Gln Lys Ser
            165                 170                 175

Leu Leu Asp Leu Ile Lys Gln Glu Thr Val Ala Ser Lys Leu Ala Val
        180                 185                 190

Ile Gly Val Phe His Asp Val Asn Ile Ala Ser Leu Tyr Cys Asp Arg
    195                 200                 205

Leu Leu Leu Leu Lys Asp Gly Lys Ala Glu Val Leu Asp Arg Pro Glu
210                 215                 220

Ala Ala Leu Cys Ala Asp Arg Ile Glu Arg Val Tyr His Thr Asp Ile
225                 230                 235                 240

```
Thr Ala Leu Asp His Pro Glu Arg Ala Asn Pro Gln Phe Thr Ile Lys
                245                 250                 255

Ala Lys Thr Ile Pro Glu Lys Ala Glu Pro Leu Phe Leu Lys Glu Arg
            260                 265                 270

Ile Glu Gln Tyr Leu Pro Arg Gly Ile Thr Phe Ser Ala Asp Arg Pro
            275                 280                 285

Met Arg Val Leu Ser Ser Glu Gly Phe Ala Trp Arg Arg Lys Leu
    290                 295                 300

Val Phe Asp Ser Gly Asn Asn Ser Gly Trp Pro His Asp Leu Ser Thr
305                 310                 315                 320

Val Glu Gln Glu Ala Leu Phe Ile Gln His Asp Cys Lys Leu Thr Ala
                325                 330                 335

Cys His Ile Val Ser Glu Ser Asn Asp Leu Cys Ile Ile Gly Met Lys
                340                 345                 350

Asp Ala Lys Gly Arg Phe Ile Met Trp Val Val Ser Gly Cys Leu
            355                 360                 365

His Asp Gly Gln Phe Val Lys Val Ile Ser Ala Thr Lys Ala Ala
    370                 375                 380

Ala Gln His Arg Val Phe Cys Ser Asp Val Leu Ile Ala Ala Thr His
385                 390                 395                 400

Ser Gly Arg Leu Pro Asp Gln Thr Ile Leu Leu Thr Gln Ile Gln Asp
                405                 410                 415

Gln Thr Ala Ala Cys Val Lys Ala Leu Lys Asn
                420                 425

<210> SEQ ID NO 76
<211> LENGTH: 300
<212> TYPE: PRT
<213> ORGANISM: Bacillus subtilis
<220> FEATURE:
<223> OTHER INFORMATION: >ABP10982

<400> SEQUENCE: 76

Met Lys Val Glu Gly Ile Ile Pro Ala Ile Leu Thr Pro Ile Thr Lys
1               5                   10                  15

Glu Gln Asp Phe His Pro Gly Val Ala Glu Lys Leu Val Asn His Leu
                20                  25                  30

Ile Asp Ser Gly Val His Gly Ile Phe Ala Leu Gly Thr Asn Gly Glu
            35                  40                  45

Phe His Leu Phe Ser Gln Glu Lys Leu Gln Ile Ala Glu Thr Val
    50                  55                  60

Val Lys Ala Val Asn Lys Arg Val Pro Val Phe Ile Gly Ala Gly Glu
65                  70                  75                  80

Asn Ser Thr Glu Ala Thr Ile Ser Leu Ser Asn Gln Met Ala Asp Ile
                85                  90                  95

Gly Ala Asp Val Leu Ser Ile Ile Thr Pro Tyr Phe Val Ala Pro Ser
            100                 105                 110

Gln Lys Glu Leu Tyr Gln His Phe Arg Thr Ile Ser Glu Asn Val Ala
        115                 120                 125

Leu Pro Val Leu Leu Tyr Asn Ile Pro Ser Arg Thr Gly Val Ser Leu
    130                 135                 140

Glu Pro Glu Thr Val Glu Arg Leu Ala Ala Leu Pro Asn Ile Ile Gly
145                 150                 155                 160

Ile Lys Asp Ser Ser Gly Ser Phe Asp Asn Ile Lys Ala Tyr Leu Glu
                165                 170                 175
```

```
Arg Thr Lys Asp Gln Ser Phe Ser Val Leu Ala Gly Thr Asp Ser Leu
            180                 185                 190

Ile Leu Asp Thr Leu Lys Ala Gly Gly Thr Gly Ala Val Ala Ala Thr
        195                 200                 205

Ala Asn Val Leu Pro Gln Thr Val Val Ser Ile Tyr Glu Ser Tyr Lys
    210                 215                 220

Gln Gly Asn Ile Glu Glu Ser Glu Gln Tyr Gln Lys Gln Leu Asp Pro
225                 230                 235                 240

Leu Arg Ala Thr Phe Ser Leu Gly Ser Leu Pro Ala Pro Leu Lys Lys
                245                 250                 255

Ala Thr Glu Leu Ala Gly Ile Asp Val Gly Pro Pro Lys His Pro Ile
            260                 265                 270

Ala Glu Leu Ser Gly Glu Gly Leu Gln Lys Val Lys Lys Met Leu Glu
        275                 280                 285

Gly Tyr Gly Ile Glu Thr Lys Leu Val Lys Glu Gln
    290                 295                 300

<210> SEQ ID NO 77
<211> LENGTH: 390
<212> TYPE: PRT
<213> ORGANISM: Bacillus subtilis
<220> FEATURE:
<223> OTHER INFORMATION: >ABP10983

<400> SEQUENCE: 77

Met Lys Thr Leu Tyr His Phe Gln Thr Ala Ala Arg Ile Glu Ala Gly
1               5                   10                  15

Ala His Ser Leu Asn Phe Leu Gly Asp His Leu Asp Gln Thr Ser Gly
            20                  25                  30

Trp Asn Gln Ile Arg Ser Val Phe Ile Leu Thr Gln Pro Ser Ile Val
        35                  40                  45

Ser Leu Gly Tyr Ala Asp Gln Ile Lys Glu Val Leu Ala Glu Lys Gly
    50                  55                  60

Ile Ser Ser Glu Ile Asn Thr Asp Ile Gln Pro Glu Pro Thr Glu Gln
65                  70                  75                  80

Asn Ile Glu Glu Val Phe Gln Leu Phe Ser Ala Gly Ser His Asp Ala
                85                  90                  95

Ile Leu Gly Ile Gly Gly Gly Ser Val Leu Asp Ala Ala Lys Ile Leu
            100                 105                 110

Ser Val Leu Lys Thr Asn Lys Lys Pro Ile Ser Glu Leu Val Gly Thr
        115                 120                 125

Asn Leu Val Glu Lys Pro Gly Val Pro Leu Val Leu Ile Pro Thr Thr
    130                 135                 140

Ser Gly Thr Gly Ser Glu Val Thr Pro Asn Ala Ile Val Thr Phe Pro
145                 150                 155                 160

Glu Lys Glu Leu Lys Ile Gly Met Val Ser Pro Tyr Leu Leu Pro Ser
                165                 170                 175

Leu Val Ile Leu Asp Pro Val Leu Thr Ile Gly Leu Pro Lys Ala Ile
            180                 185                 190

Thr Ala Ala Thr Gly Met Asp Ala Phe Thr His Ala Leu Glu Ser Tyr
        195                 200                 205

Ile Ser Asn Lys Ala Asn Pro Phe Ser Asp Met Phe Ala Leu Glu Ser
    210                 215                 220

Met Arg Leu Ile Ser Ser Ser Ile Gln Glu Ala Tyr His His Gly Asp
225                 230                 235                 240
```

```
Lys Leu Glu Ala Arg Glu Lys Met Leu Ile Gly Ala Met Tyr Gly Gly
                245                 250                 255

Met Ala Leu Thr Ser Ala Gly Thr Ala Ala Val His Ala Met Ala Tyr
            260                 265                 270

Pro Leu Gly Gly Lys Tyr Lys Met Ser His Gly Val Ala Asn Ser Met
        275                 280                 285

Leu Leu Pro His Val Thr Ala Phe Asn Ala Asp His Val Thr Asp Arg
290                 295                 300

Leu Ser Asp Val Ala Gly Val Ile Gly Ile Glu Gln Lys Gly Ser Lys
305                 310                 315                 320

Ala Ser Gln Ala Glu Arg Val Ile Gln Lys Ile Glu Glu Trp Thr Ala
                325                 330                 335

Asp Leu Asn Ile Pro Gln Asn Leu Lys Ala Phe Gly Val Ser Lys Glu
            340                 345                 350

Asp Val Pro Thr Leu Ala Glu Ala Ala Asp Val Lys Arg Leu Met
        355                 360                 365

Asp Asn Asn Pro Lys Pro Met Ser Val Ala Glu Ile Glu Ala Val Tyr
370                 375                 380

Leu Lys Leu Leu Glu Val
385                 390

<210> SEQ ID NO 78
<211> LENGTH: 467
<212> TYPE: PRT
<213> ORGANISM: Bacillus subtilis
<220> FEATURE:
<223> OTHER INFORMATION: >ABP10984

<400> SEQUENCE: 78

Met Asp Val Leu Ser Gly Ser Val Ile Thr Phe Ile Leu Ala Val Ile
1               5                   10                  15

Val Val Tyr Ile Leu Phe Thr Thr Trp Leu Thr Met Arg Phe Arg Ser
            20                  25                  30

Lys Ser Ser Ala Glu Phe Asn Asn Ala Ala Lys Thr Leu Pro Ala Ile
        35                  40                  45

Val Val Gly Ile Leu Leu Met Ser Glu Phe Ile Gly Thr Lys Ser Thr
    50                  55                  60

Ile Gly Thr Ala Glu Ser Ala Tyr Thr His Gly Leu Ala Ala Ser Trp
65                  70                  75                  80

Ser Ile Val Thr Val Ser Ile Ala Phe Phe Ile Phe Ser Tyr Phe Leu
                85                  90                  95

Val Gly Lys Phe Tyr Lys Thr Gly Gln Tyr Thr Ile Ser Gly Ile Ile
            100                 105                 110

Ser Asp Lys Phe Gly Arg Ser Thr Lys Leu Val Val Ser Thr Ile Met
        115                 120                 125

Ile Val Ala Leu Leu Val Asn Leu Gly Asn Tyr Leu Ser Gly Ser
    130                 135                 140

Ala Ala Ile Ser Ser Ile Leu Gly Leu Pro Leu Met Thr Cys Ala Ile
145                 150                 155                 160

Ile Thr Ala Ile Val Ser Thr Phe Tyr Phe Thr Phe Gly Gly Met Lys
                165                 170                 175

Gly Val Ala Trp Val Thr Ile Leu His Ser Leu Val Lys Tyr Val Gly
            180                 185                 190

Val Leu Ile Thr Leu Gly Val Ala Leu Tyr Leu Thr Lys Gly Trp Glu
        195                 200                 205
```

Pro Met Thr Gln Gln Leu Pro Glu His Phe Phe Thr Trp Asp Gly Ser
    210                 215                 220

Ile Gly Trp Gly Thr Ile Gly Ala Trp Phe Ile Gly Asn Met Gly Ala
225                 230                 235                 240

Ile Phe Ala Thr Gln Phe Ile Ile Gln Ala Ile Thr Ser Ser Lys Ser
                245                 250                 255

Glu Lys Glu Ala Lys Arg Ser Thr Leu Tyr Ala Ala Leu Leu Cys Leu
                260                 265                 270

Pro Leu Ala Ile Ala Ile Gly Val Ile Gly Val Ala Ala Arg His Leu
            275                 280                 285

Tyr Pro Asp Ile Asp Ala Ile Tyr Ala Phe Pro Val Phe Met Gln Gln
    290                 295                 300

Met Asn Pro Val Leu Ser Ala Ile Val Ala Thr Ser Leu Val Ala Ser
305                 310                 315                 320

Ile Phe Val Gly Val Ser Thr Val Ala Leu Ala Thr Thr Thr Leu Ile
                325                 330                 335

Met Asp Asp Phe Tyr Val Pro Lys Ala Lys Pro Thr Pro Glu Gln Arg
            340                 345                 350

Met Lys Val Thr Arg Tyr Ala Ser Ile Ile Gly Phe Ile Pro Leu
            355                 360                 365

Leu Gly Val Ala Leu Ala Pro Glu Leu Leu Thr Leu Ser Phe Phe Thr
    370                 375                 380

Arg Ala Leu Arg Thr Ser Ile Ala Val Val Ala Ala Met Gly Phe Tyr
385                 390                 395                 400

Leu Pro Tyr Phe Asn Ser Asn Arg Gly Ala Thr Ile Gly Leu Val Leu
                405                 410                 415

Ser Gly Met Ala Thr Thr Val Trp Tyr Leu Leu Asp Asn Pro Phe Gly
            420                 425                 430

Ile Asp Asn Met Tyr Ile Ala Ile Ile Val Pro Phe Val Val Leu Val
        435                 440                 445

Leu Asp Arg Leu Ile Ser Ser Pro Ala Lys Lys Glu Ser Asn Val Lys
    450                 455                 460

Glu Glu Phe
465

<210> SEQ ID NO 79
<211> LENGTH: 392
<212> TYPE: PRT
<213> ORGANISM: Bacillus subtilis
<220> FEATURE:
<223> OTHER INFORMATION: >ABP10985

<400> SEQUENCE: 79

Met Lys Gln Ser Glu Val Ser Leu Leu Ile Asp Gly Arg Ile Arg Lys
1               5                   10                  15

Asn Glu Thr Asp Glu Ala Arg Lys Asp Ala Phe Leu Pro Thr Asp Cys
            20                  25                  30

Pro Gln Asn His Ala Ala Asn Leu Glu Leu Asp Asn Gly Asp Leu
            35                  40                  45

Leu Cys Val Trp Phe Gly Gly Thr Gln Glu Gly Ile Ala Asp Ile Ser
    50                  55                  60

Ile Tyr Met Ser Arg Leu Ala Lys Gly Ser Ser Glu Trp Thr Gln Ile
65                  70                  75                  80

Glu Lys Leu Ser Asp Asp Pro Ser Arg Ser Glu Gln Asn Pro Val Leu
                85                  90                  95

```
Phe Gln Glu Pro Ser Gly Arg Leu Trp Leu Met Tyr Thr Ala Gln Met
                100                 105                 110

Ser Gly Asn Gln Asp Thr Ala Ile Ile Arg Tyr Arg Thr Ser Asp Asp
            115                 120                 125

Arg Gly His Thr Trp Ser Gly Ile Asp Thr Leu Phe Gly Glu Ala Gly
        130                 135                 140

Thr Phe Ile Arg Gln Pro Leu Val Val Leu Asp Asn Gly Asp Trp Leu
145                 150                 155                 160

Leu Pro Val Phe Tyr Cys Ile Thr Leu Ala Asp Val Lys Trp Thr Gly
                165                 170                 175

Asn Arg Asp Ile Ser Ala Val Lys Ile Ser Ser Asp Lys Gly Lys Thr
            180                 185                 190

Trp Glu Glu Val Lys Val Pro Ser Ser Met Gly Cys Val His Met Asn
        195                 200                 205

Ile Glu Lys Leu His Asp Gly Thr Leu Ala Leu Phe Arg Ser Arg
            210                 215                 220

Phe Ala Asp Ser Ile Tyr Ala Ser Arg Ser Ile Asp Asn Gly Arg Thr
225                 230                 235                 240

Trp Ser Glu Pro Glu Pro Thr Glu Leu Pro Asn Asn Asn Ser Ser Ile
                245                 250                 255

Gln Phe Thr Ala Leu Gln Asp Gly Thr Leu Ala Leu Val Tyr Asn His
            260                 265                 270

Met Lys Ala Asn Glu Thr Thr Glu Arg Arg Ala Ser Leu Tyr Asp Glu
        275                 280                 285

Ile Glu Asp Glu Asp Asp Thr Arg Thr Gly Val Asp Thr Glu Ala Arg
            290                 295                 300

Pro Ala Phe Trp Gly Ala Pro Arg Ala Pro Met Thr Leu Ala Leu Ser
305                 310                 315                 320

His Asp Gly Gly Val Thr Trp Pro Val Lys Arg Asn Ile Glu Val Gly
                325                 330                 335

Asp Gly Tyr Ala Met Thr Asn Asn Ser Lys Asp Lys Leu Asn Arg Glu
            340                 345                 350

Phe Ser Tyr Pro Ser Ile Lys Gln Gly Lys Asp Gly Asp Leu His Ile
        355                 360                 365

Ala Phe Thr Tyr Tyr Arg Gln Ala Ile Lys Tyr Val Arg Val Pro Gln
370                 375                 380

Met Trp Ala Ser Ala Asp Gln Glu
385                 390

<210> SEQ ID NO 80
<211> LENGTH: 594
<212> TYPE: PRT
<213> ORGANISM: Bacillus subtilis
<220> FEATURE:
<223> OTHER INFORMATION: >ABP10986

<400> SEQUENCE: 80

Met Lys Ile Lys Val Leu Gly Ile Ala Pro Tyr Lys Gly Leu Gly Asp
1               5                   10                  15

Leu Leu Thr Glu Leu Ala Lys Glu Glu Gln Asp Ile Gln Phe Gln Leu
            20                  25                  30

Glu Val Gly Asp Leu Arg Ser Gly Val Ala Ile Ala Glu Gln Ala Val
        35                  40                  45

Ser Gln Gly Ile Asp Ile Met Met Ser Arg Gly Gly Thr Ala Ser Leu
    50                  55                  60
```

-continued

Ile Gln Lys His Val Arg Ile Pro Val Val Asp Ile Pro Val Ser Gly
65                  70                  75                  80

Tyr Asp Leu Leu Arg Ala Leu Thr Leu Ile Lys Asp Tyr Gln Gly Lys
                85                  90                  95

Ala Ala Val Val Gly Phe Glu Asn Ile Thr Gln Gly Val Arg Thr Ile
            100                 105                 110

Ser Glu Leu Phe Gly Ile Glu Val Asp Leu Tyr Thr Ile Lys Glu Glu
        115                 120                 125

Met Glu Val Trp Asp Leu Leu Arg Asp Ile Gln Gln Gln Gly Thr Gln
    130                 135                 140

Ile Val Leu Gly Asp Val Ile Thr Asp Lys Ala Ala Lys Glu Leu Gly
145                 150                 155                 160

Met Gln Ser Met Leu Ile Thr Ser Gly Arg Glu Ser Val Lys Glu Ala
                165                 170                 175

Phe His Thr Ala Lys Gln Met Tyr Arg Leu Phe Lys Glu Ala Ser Glu
            180                 185                 190

Glu Gln Arg Met Phe Arg Asp Met Ile Asp Gln Glu Glu Lys Gly Met
        195                 200                 205

Leu Val Ile Asp Asp Asn Ser Arg Val Arg Phe Val Asn Lys Met Val
    210                 215                 220

Lys Lys Trp Met Lys Glu Gly Leu Leu Glu Pro Ile Ala Pro Ala Ala
225                 230                 235                 240

Ala Val Asn Glu Trp Asp Glu Leu Ala Phe Ala Val Gln Ser Ile
                245                 250                 255

Arg Glu Gly Lys Leu Ser Gly Tyr Phe Gln Leu Glu Thr Gly Glu Val
            260                 265                 270

Val Trp His Met Lys Gly Ser Phe Leu Ser Lys Gly Glu Leu Leu Ile
    275                 280                 285

Ala Ile Glu Gln Ser Ser Ser Arg Asp Asp Arg Asn His Pro Val
    290                 295                 300

Trp Ser Phe Ala Ala Pro Val His Ser Leu His Pro Phe Ser Ser Phe
305                 310                 315                 320

Thr Gln Gln Ser Ser Ser Met Arg Asp Thr Val Gln Gln Ala Gln Ala
                325                 330                 335

Phe Ser Gln Thr His Lys Pro Ile Leu Leu Tyr Gly Glu Glu Gly Thr
            340                 345                 350

Gly Lys Ser Asp Leu Ala Leu Ala Ile His Gln Met Ser Pro Arg Arg
        355                 360                 365

Gln His Thr Phe Met Thr Ile His Cys Ser Lys Val Lys Glu Thr Ser
    370                 375                 380

Leu Leu Lys Ala Leu Pro Ala Val Gln Asn Gly Thr Ile Phe Leu Arg
385                 390                 395                 400

Tyr Val Glu His Leu Pro Leu Glu Val Gln His Asp Leu Ala Leu Gln
                405                 410                 415

Trp Met Lys Pro Asp Gln Gln Ile Arg Trp Leu Ala Ser Ser Ser Ala
            420                 425                 430

Asp Leu Cys Glu Glu Met Lys Ala Gly Arg Phe Asp Pro Asp Leu Tyr
        435                 440                 445

Ser Cys Leu Gln Gly Leu Thr Leu Tyr Val Pro Ser Leu Ser Glu Arg
    450                 455                 460

Val Glu Asp Met Glu Asp Met Ser Arg Leu Phe Ile Ala Glu Phe Asn
465                 470                 475                 480

Ser Val Tyr Gly Thr Gln Val Val Gly Leu Ala Pro Glu Val Met Asp

```
                485             490             495
Ala Phe Arg Asn Arg Thr Phe Arg Glu Asn Val Arg Gln Phe Lys Arg
                500             505             510

Val Leu Glu Glu Leu Ala Leu Thr Val Lys Ser Gly Tyr Ile Thr Leu
            515             520             525

Ala Glu Ala Ala Pro Gln Leu Asp Arg Leu Ser Asn Glu Lys Lys Glu
        530             535             540

Glu Ser Leu Lys Gly Tyr Thr Glu Gly Thr Leu Glu Asp Ile Glu Arg
545             550             555             560

Arg Ile Ile Gln Ala Val Leu Gln Glu Asn Met Asn Gln Ser Lys
                565             570             575

Ala Ala Lys Arg Leu Asn Ile Asn Arg Thr Thr Leu Trp Arg Lys Leu
            580             585             590

Lys Glu
```

<210> SEQ ID NO 81
<211> LENGTH: 446
<212> TYPE: PRT
<213> ORGANISM: Bacillus subtilis
<220> FEATURE:
<223> OTHER INFORMATION: >ABP10987

<400> SEQUENCE: 81

```
Met Thr Asn Ile Arg Cys Lys Lys Gly Ala Asn Ile Ser Arg Lys Ile
1               5                   10                  15

Leu Ile Val Ala Asp Asp Leu Thr Gly Ala Asn Asp Thr Gly Val Gln
            20                  25                  30

Phe Val Lys Ala Gly Met Ser Ala Ala Val Leu Phe Asp Arg Ser Gly
        35                  40                  45

Ala Asn Pro Gly Asp Ile Lys Glu Asp Val Met Ile Leu Asp Thr Asp
    50                  55                  60

Thr Arg Gly Val Ser Pro Ser Glu Ala Tyr Lys Glu Val Ser Ser Ala
65                  70                  75                  80

Ser His Pro Phe Ala Arg Leu Glu Ser His Leu Phe Leu Lys Lys Ile
                85                  90                  95

Asp Ser Thr Leu Arg Gly Asn Ile Gly Ile Glu Ile Lys Ala Leu Met
            100                 105                 110

Asp Leu Gly Arg Phe Asp Val Ala Val Ile Ala Pro Ala Phe Pro Asp
        115                 120                 125

Ala Arg Arg Ile Thr Val Asp Gly Met His Tyr Val Asn Gly Leu Pro
    130                 135                 140

Val His Glu Thr Glu Ala Ala Val Asp Pro Lys Thr Pro Val Ala Glu
145                 150                 155                 160

Ser Arg Ile Ala Asp Leu Leu Phe Gly Gln Thr Asn Ile Gln Pro Lys
                165                 170                 175

Thr Ile Gly Thr Lys Gln Leu His Lys Pro Asp Glu Gln Ile Gln Gln
            180                 185                 190

Asp Leu Arg Ala Trp Lys Thr Gln Gly His Glu Trp Phe Val Cys Asp
        195                 200                 205

Ala Glu Thr Asn Glu Asp Leu Arg Arg Ile Val Gln Val Phe Met Asn
    210                 215                 220

Ser Gly Gln Ser Val Leu Trp Val Gly Ala Ala Gly Leu Ala Gly Ala
225                 230                 235                 240

Leu Ala Gln His Val Arg Lys Arg Ala Leu Gln Thr Gly Lys Arg Asn
                245                 250                 255
```

-continued

```
Glu Pro Val Met Ile Val Ser Gly Ser Ala Ser Asn Thr Thr Asn Arg
            260                 265                 270

Gln Leu Ala Tyr Val Arg Glu Gln Arg Asp Leu Leu Asp Val Arg Ile
        275                 280                 285

Asn Pro Leu Asn Val Leu Asn Gly Cys Glu Ala Trp Glu His Lys Arg
    290                 295                 300

Ala Ile Asp Gln Val Val His Gln Gly Lys Asp Val Leu Leu Tyr
305                 310                 315                 320

Thr Asp Ala Lys Pro Glu Thr Val Gln Arg Ile Ile Ala Phe Gly Arg
                325                 330                 335

Lys Gln Gly Leu Asp Arg Gln Ala Val Gly Lys Leu Ser Leu Phe
        340                 345                 350

Leu Gly Ala Val Thr Ser Glu Ile Val Lys Leu Thr Gly Leu Lys Arg
            355                 360                 365

Leu Val Leu Thr Gly Gly Asp Thr Ala Arg Ala Ile Cys Asn Glu Leu
        370                 375                 380

Gly Ala Asp Gly Ile Gln Leu Leu Gly Glu Ile Glu Ala Gly Ile Pro
385                 390                 395                 400

Leu Gly Lys Leu Leu Asn Ala Asp Ile Tyr Ala Val Thr Lys Ala Gly
                405                 410                 415

Ala Tyr Gly Gln Thr Asp Ser Val Leu Arg Ala Val Glu Val Leu Arg
            420                 425                 430

Asn Val Glu Glu Glu Asp Arg Trp Gln Asn Gln Ser Leu Arg
        435                 440                 445

<210> SEQ ID NO 82
<211> LENGTH: 335
<212> TYPE: PRT
<213> ORGANISM: Bacillus subtilis
<220> FEATURE:
<223> OTHER INFORMATION: >ABP10988

<400> SEQUENCE: 82

Met Ala Lys Pro Ile Ile Ala Leu Thr Met Gly Asp Ala Ala Gly Val
1               5                   10                  15

Gly Pro Glu Ile Ile Lys Ala Phe Glu Gln Thr Asn Leu His Glu
            20                  25                  30

Asn Gly Thr Leu Phe Val Ile Gly Asp Tyr Ser Ile Leu Asn Arg Ala
        35                  40                  45

Lys Thr Phe Ile Gly Ser Asp Val Asp Ile Val Lys Ile Asn Glu Pro
    50                  55                  60

Glu Glu Ala Ala Asp Val Lys Pro Gly Val Ile Pro Cys Leu Asp Leu
65                  70                  75                  80

Gln Leu Leu Thr Asp Glu Leu Arg Val Gly Glu Val Ser Ala Glu Ala
                85                  90                  95

Gly Asn Ala Ala Phe Arg Tyr Leu Glu Lys Ala Ile Ala Leu Ala Asn
            100                 105                 110

Glu Asn Gln Ile Asp Gly Ile Cys Thr Ala Pro Leu Asn Lys Glu Ala
        115                 120                 125

Leu His Lys Ala Gly His Met Tyr Pro Gly His Thr Glu Ile Leu Ala
    130                 135                 140

Glu Leu Thr Gln Thr Lys Asp Tyr Ala Met Met Leu Ala Ala Pro Asn
145                 150                 155                 160

Leu Lys Val Val His Val Thr Thr His Val Gly Leu Leu Asp Ala Ile
                165                 170                 175
```

-continued

His Leu Ile Asp Ala Lys Arg Val Tyr Thr Thr Ile Gln Leu Ala His
                180                 185                 190

Asp Thr Leu Ile Arg Ala Gly Ile Pro Gln Pro Lys Ile Ala Val Cys
            195                 200                 205

Gly Ile Asn Pro His Ala Gly Glu Asn Gly Leu Phe Gly His Gly Glu
210                 215                 220

Glu Glu Glu Lys Ile Val Pro Ala Val Glu Arg Ala Gln Ser Glu Gly
225                 230                 235                 240

Ile Gln Ala Phe Gly Pro Leu Pro Ala Asp Thr Leu Phe Phe Arg Ala
                245                 250                 255

Val Arg Gly Asp Phe Asp Met Val Val Ala Met Tyr His Asp Gln Gly
            260                 265                 270

His Gly Pro Ile Lys Val Leu Gly Leu Glu Ala Gly Val Asn Ile Thr
        275                 280                 285

Val Gly Leu Pro Ile Ile Arg Thr Ser Val Asp His Gly Thr Ala Phe
290                 295                 300

Asp Ile Ala Gly Thr Gly Lys Ala Asp Pro Ala Ser Leu Glu Glu Ala
305                 310                 315                 320

Val Arg Gln Ala Ile Met Leu Ser Gly Thr Arg Asn Arg His Ala
                325                 330                 335

<210> SEQ ID NO 83
<211> LENGTH: 248
<212> TYPE: PRT
<213> ORGANISM: Bacillus subtilis
<220> FEATURE:
<223> OTHER INFORMATION: >ABP10989

<400> SEQUENCE: 83

Met Glu Phe Tyr Lys Lys Thr Ala Ile Ile Thr Gly Ala Ser Arg Gly
1               5                   10                  15

Ile Gly Arg Ala Ile Ala Glu Thr Leu Ala Asp Lys Gly Ala Asn Val
            20                  25                  30

Val Ile Asn Gly Thr Asn Glu Glu Leu Leu Lys Ser Met Cys Thr Glu
        35                  40                  45

Leu Asn Thr Glu Arg Lys Cys Ala Ser Tyr Val Ala Gly Asp Ala Ser
    50                  55                  60

Leu Pro Glu Thr Ala Ser Leu Leu Ile Ala Glu Ala Lys Gln Gln Phe
65                  70                  75                  80

Gly Gln Ile Asp Ile Leu Val Asn Asn Ala Gly Ile Asn Leu Arg Lys
                85                  90                  95

Thr Thr Val Asp Thr Ser Leu Glu Glu Trp Lys Arg Val Ile Asp Leu
            100                 105                 110

Asn Leu Thr Gly Ile Phe Leu Met Cys Gln Ala Val Ile Pro Glu Met
        115                 120                 125

Thr Ala Gln Gly Gly Lys Ile Val Asn Met Ser Ser Thr Thr Ser
    130                 135                 140

Lys Thr Pro His His Asn Ala Ser Pro Ala Tyr Gly Ala Ser Lys Ala
145                 150                 155                 160

Gly Ile Asn Tyr Leu Thr Met His Leu Ala Lys Glu Leu Ala Ala His
                165                 170                 175

Arg Ile His Val Asn Ala Val Cys Pro Gly Pro Ile Glu Thr Asp Met
            180                 185                 190

Ser Lys Gln Trp Ser Glu Glu Tyr Arg Ala Ala Val Val Glu Arg Ile
        195                 200                 205

```
Pro Leu Lys Met Ile Gly Ser Pro Glu His Val Ala Asn Ile Val Ala
    210                 215                 220
Phe Leu Ala Ser Asp Lys Ser Asp Phe Met Thr Gly Glu Thr Ile Asn
225                 230                 235                 240
Ile Asn Gly Gly Thr Tyr Met Asn
                245
```

```
<210> SEQ ID NO 84
<211> LENGTH: 51
<212> TYPE: PRT
<213> ORGANISM: Bacillus subtilis
<220> FEATURE:
<223> OTHER INFORMATION: >ABP11306

<400> SEQUENCE: 84
```

```
Met Ser Pro Pro Asn Glu Ala Pro Ile Ile Pro Leu Asp Cys Gly Ser
1               5                   10                  15
Leu Val Thr Phe Gln Phe Ser Ser Ile Ser Gly Met Asn Trp Phe Val
                20                  25                  30
Cys Gln Thr His Ser Leu Met Glu Leu Ala Phe Tyr Tyr Leu Arg Asp
            35                  40                  45
Arg Ile Pro
    50
```

```
<210> SEQ ID NO 85
<211> LENGTH: 272
<212> TYPE: PRT
<213> ORGANISM: Bacillus subtilis
<220> FEATURE:
<223> OTHER INFORMATION: >ABP11307

<400> SEQUENCE: 85
```

```
Met Lys Lys Leu Ile Glu Asn Thr Glu Asn Pro Arg Thr Thr Gln Ser
1               5                   10                  15
Ile Lys Lys Asp Leu Glu Gly Leu Gly Leu Asn Lys Gly Met Thr Val
                20                  25                  30
Leu Val His Ser Ser Leu Ser Ser Ile Gly Trp Val Asn Gly Gly Ala
            35                  40                  45
Ile Ala Val Ile Gln Ala Leu Met Asp Ile Val Thr Glu Glu Gly Asn
        50                  55                  60
Ile Val Met Pro Ser Gln Ser Val Asp Leu Ser Asp Pro Ser Glu Trp
65                  70                  75                  80
His Tyr Pro Ser Val Pro Glu Lys Trp Trp Asp Thr Ile Arg Glu Ser
                85                  90                  95
Met Pro Ala Tyr Asn Ala Gln Tyr Thr Pro Thr Thr Gly Met Gly Lys
            100                 105                 110
Ile Val Glu Val Phe Arg Ser Tyr Pro Glu Val Lys Arg Ser Cys His
        115                 120                 125
Pro Asn Tyr Ser Phe Ile Ala Trp Gly Lys Asp Lys Asn Lys Ile Leu
    130                 135                 140
Asn Lys Gln Ser Leu Asn Phe Gly Leu Gly Glu Gln Ser Pro Leu Gly
145                 150                 155                 160
Asn Leu Tyr Met Asp Asn Ser Tyr Val Leu Leu Gly Thr Asp Phe
                165                 170                 175
Asp Ser Asn Thr Cys Phe His Leu Ala Glu Tyr Arg Ile Pro Phe Gln
            180                 185                 190
Lys Val Val Ile Lys Gly Ala Pro Val Leu Ile Asn Gly Lys Thr Val
```

```
            195                 200                 205
Trp Lys Lys Tyr Lys Asp Leu Glu Phe Arg Glu Asp Leu Phe Glu Glu
    210                 215                 220

Ile Gly Lys Ser Phe Glu Ile Glu Ser Asp Met Lys Ser Gly Lys Val
225                 230                 235                 240

Gly Ser Ala Asn Cys Arg Leu Phe Ser Leu Lys Glu Ala Val Asp Phe
                245                 250                 255

Ala Glu Lys Trp Phe Ile Glu Tyr Asp Cys Lys Met Asn Ser Arg Gly
            260                 265                 270

<210> SEQ ID NO 86
<211> LENGTH: 504
<212> TYPE: PRT
<213> ORGANISM: Bacillus subtilis
<220> FEATURE:
<223> OTHER INFORMATION: >ABP11308

<400> SEQUENCE: 86

Met Ser Asn Tyr Arg Asp Tyr Ile Leu Lys Gly Lys Asp Val Ala Val
1               5                   10                  15

Phe Glu Ile Asp Thr Asp Pro Ile Ser Leu Asp Pro Ala Lys Cys Asp
                20                  25                  30

Asp Tyr Ile Gly Gln Ile Ile Ser Gln Ala Met Phe Glu Pro Leu Phe
            35                  40                  45

Ile Arg Asp Ile Glu Thr Glu Gln Trp Val Cys Gly Ala Ala Glu Asn
        50                  55                  60

Phe Glu Val Ser Ser Asp Gly Leu Thr Tyr Ile Phe Asn Leu Arg Lys
65                  70                  75                  80

Asp Arg Phe Trp Ser Asp Gly Ile Ser Val Val Ala Gln Asp Phe Val
                85                  90                  95

Phe Ala Phe Gln Arg Leu Phe His Pro Lys Ile Asn Ser Pro Ile Gly
                100                 105                 110

Gln Ile Leu Ser Phe Ile Lys Asn Gly Glu Glu Ile Leu Asn Gly Val
            115                 120                 125

Leu Pro Val Thr Glu Leu Gly Val Glu Ala Leu Gly Pro Arg Lys Leu
        130                 135                 140

Lys Ile Ser Leu Thr Glu Cys Leu Pro Phe Leu Pro Ser Ile Leu Gly
145                 150                 155                 160

Ser Pro Asn Thr Ser Pro Phe Pro Tyr Arg Thr Glu Gln Val Ser Trp
                165                 170                 175

Thr Asp Glu Arg Leu Asn Ile Thr Asn Gly Ala Tyr Val Leu Lys Glu
            180                 185                 190

Tyr Lys Ser Gly Gln Phe Val Arg Leu Glu Arg Asn Pro Phe Tyr Pro
        195                 200                 205

Asn Ser Ser Asn His Val Lys Asp Val Leu Phe Val Ile Asn Arg
    210                 215                 220

Glu Leu Asp Tyr Ser Leu Gln Asn Tyr Lys Gly Asn Ile Asp Val
225                 230                 235                 240

Thr Cys Asn Thr Tyr Phe Pro Phe Glu Glu Ile Lys Arg Phe Lys Gln
                245                 250                 255

Arg Asp Asp Phe Tyr Met Phe Pro Ser Gly Ile Leu Phe Leu Gln
            260                 265                 270

Phe Gly Asn Arg Asn Asp Leu Phe Lys Lys Lys Gln Ala Arg Gln Ala
        275                 280                 285

Leu Tyr Tyr Ile Val Asn Lys Ser Gln Ile Ala Gln Thr Leu His Gly
```

```
                    290                 295                 300
Gly Ile Ile Pro Trp Asp His Phe Ala Ser Ile Gly Val Ser Glu Lys
305                 310                 315                 320

Leu Phe Asp Asp Gln Ser Asn Tyr Cys Tyr His Pro Glu Lys Ala Val
                325                 330                 335

Lys Leu Trp Lys Gln Glu Arg Glu Asn Gln Ala Leu Ser Ile Leu
            340                 345                 350

Tyr Ala Asp Phe Phe Pro Asn Gly Glu Ile Cys His Ser Ile Lys Ser
                355                 360                 365

Glu Met Glu Lys His Leu Gly Ile Thr Leu Thr Leu Glu Gly Cys Ser
370                 375                 380

Phe Glu Asp Phe Val Ile Arg His Glu Gln Arg Glu Tyr Asp Leu Cys
385                 390                 395                 400

Leu Ala Leu Leu Ser Pro Leu Tyr Asn Asp Pro Phe Asn Tyr Phe Gln
                405                 410                 415

Tyr Phe Leu Ser Glu Leu Ser Glu Glu Asp Glu Asp Glu Phe Ile Asp
                420                 425                 430

Ile Leu Gln Lys Ala Leu Gly Asp Glu Lys Glu Asn His Cys Thr Tyr
            435                 440                 445

Tyr Lys Lys Ala Asn Asp Tyr Leu Leu Glu Lys Leu Pro Ser Ile Pro
            450                 455                 460

Leu Phe Asn Gly Gln Ser Ile Phe Leu Lys Asn Pro Phe Leu Lys Gly
465                 470                 475                 480

Tyr Lys Ile Phe Lys Asp Gly Ser Ile Ser Ile Gln Asn Leu Ser Trp
                485                 490                 495

Gly Thr Glu Glu Lys Pro Lys Leu
            500

<210> SEQ ID NO 87
<211> LENGTH: 341
<212> TYPE: PRT
<213> ORGANISM: Bacillus subtilis
<220> FEATURE:
<223> OTHER INFORMATION: >ABP11309

<400> SEQUENCE: 87

Met Tyr Lys Leu Ala Asp Arg Ile Gln Ile Val Ser Leu His Asn Gly
1               5                   10                  15

Arg Ile Phe Leu Ile Asp Asp Glu Ile Thr Glu Leu Glu Gly Ser Pro
                20                  25                  30

Gln His Thr Glu Lys Ala Leu Lys Leu Leu Glu Lys Gly Cys Met Glu
            35                  40                  45

Glu Glu Leu Asn Arg Ile Met Pro Leu Glu Asp Thr Gln Lys Leu Leu
        50                  55                  60

Glu Phe Leu Lys Glu Glu Leu Leu Arg Glu Asn Trp Glu Asn Glu
65                  70                  75                  80

Tyr Leu Asp Thr Ile Val Glu Lys Gln Leu Tyr Tyr Leu Asp Asp Phe
                85                  90                  95

Ser Ile Asp Ser Asn Gln Leu Gln Ser Asn Leu Lys Ser Ala Lys Val
                100                 105                 110

Val Ile Leu Gly Val Gly Val Gly Ser Val Leu Ile Gln His Leu
            115                 120                 125

Ile Gly Ala Gly Ile Glu Asn Phe Ile Leu Ile Asp Asn Asp Val Val
        130                 135                 140

Asn Ile His Asn Leu Asn Arg Gln Phe Leu Tyr Thr Gln Glu Asp Phe
```

```
                145                 150                 155                 160
        Gly Lys Pro Lys Val Lys Ala Ala Glu Asn Phe Met Arg Lys Val Asn
                            165                 170                 175

Pro Ser Val Lys Val Thr Ser Tyr Gln Thr Thr Ile Asp Ser Ile Lys
                    180                 185                 190

Ser Leu Asp Phe Leu Ala Ser His Ser Ile Asp Ile Phe Ile Asn Ala
                        195                 200                 205

Ala Asp Tyr Pro Lys His Leu Asp Lys Ile Val Asp Glu Tyr Cys Phe
                    210                 215                 220

Glu Arg Lys Ile Pro Trp Val Gly Ser Val Gly Arg His Gln Gly
        225                 230                 235                 240

Phe Trp Gly Pro Leu Phe Val Pro Gly Lys Thr Cys Cys Leu Asn Cys
                            245                 250                 255

Phe Ile Ala Glu Glu Lys Glu Met Lys Glu Ile Glu Lys Ile Ile
                        260                 265                 270

Arg Glu Arg Ser Asn Ser Ile Ile Gln Ala Ser Phe Ala Pro Thr Asn
                    275                 280                 285

Thr Ile Val Ser Ala Phe Leu Ala Met Asp Val Ile His Phe Leu Ala
                    290                 295                 300

Gln Ile Asn Gln Ile His Ser Tyr Leu Thr Arg Cys Gln Ile Asp Phe
        305                 310                 315                 320

Thr Thr Leu Lys Leu Asn Arg Phe Thr Ile Asp Glu Pro Lys Leu Cys
                            325                 330                 335

Asn Cys Gly Gly Glu
                    340

<210> SEQ ID NO 88
<211> LENGTH: 464
<212> TYPE: PRT
<213> ORGANISM: Bacillus subtilis
<220> FEATURE:
<223> OTHER INFORMATION: >ABP11310

<400> SEQUENCE: 88

Met Leu Ser Lys Asn Tyr Ser Phe Ser Leu Ser Ile Ser His Leu Lys
        1               5                   10                  15

Ser Lys Ser Asp Asn His Gln Arg Val Gln Glu Ile Phe Gly Val Thr
                    20                  25                  30

Asp Thr Gln Leu Asn Asn Arg Leu Ile Phe Lys Asn Ile Thr Phe Leu
                        35                  40                  45

Met His Asp Val Thr Tyr Ile Thr Gly Phe Ser Gly Ser Gly Lys Ser
                50                  55                  60

Thr Leu Val Asn Leu Ile Lys Lys Asp Phe Pro Asp Ala Val Ile Pro
        65                  70                  75                  80

Thr Pro Pro Ala Lys Gln Asp Ile Pro Ile Ile Asp Leu Leu Asp Leu
                            85                  90                  95

Glu Leu Gln Glu Ser Met Lys Ile Leu Gly Trp Val Gly Leu Gly Glu
                        100                 105                 110

Ala Tyr Leu Tyr Leu Thr Pro Tyr Ser Ala Leu Ser Glu Gly Gln Lys
                    115                 120                 125

Thr Arg Phe Leu Leu Ala Met Ala Leu Ser Arg Asn Pro Ser Ile Ile
                    130                 135                 140

Ile Val Asp Glu Phe Leu Ser Asn Leu Asp Arg Ile Thr Ala Lys Val
        145                 150                 155                 160

Val Ala Tyr Ser Phe Gln Lys Ile Cys Arg Lys Gln Glu Ile His Leu
```

165                 170                 175
Ile Val Ala Ser Ala His Asn Asp Leu Ile Glu Ala Leu Ala Pro Asp
                180                 185                 190

Ile Leu Ile Asp Leu Asp Leu Asn Gly Thr His Arg Ile Thr Asn Arg
            195                 200                 205

Pro Ile Glu Lys Pro Phe Val Pro Asp Ile Ser Gly Val Gln Val Glu
    210                 215                 220

Ser Gly Thr Ile Lys Asp Tyr Glu Glu Leu Lys Arg Phe His Tyr Phe
225                 230                 235                 240

Gly Asp Glu Asp Leu Phe Val Asp Asn Glu Phe Glu Thr Glu Ile Phe
                245                 250                 255

Thr Ile Arg Leu Lys Glu Lys Cys Ile Gly Val Ser Val Met Lys Ser
            260                 265                 270

Pro Tyr Pro Lys Asp Trp Glu Glu Ile Asp Tyr Phe Lys Asp Ile Asn
    275                 280                 285

Asp Arg Ile Arg Cys Leu Val Arg Leu Ile Ile His Pro Ser Phe Arg
290                 295                 300

Thr Ile Gly Leu Ser Lys Leu Leu Met Arg Pro Lys Phe Leu Asp Val
305                 310                 315                 320

Pro Tyr Ile Glu Thr Arg Ser Ala Leu Gly Leu Tyr Met Pro Ile Tyr
                325                 330                 335

Leu Ser Gly Gly Tyr Ser Arg Thr Glu Leu Pro Asp Asn Lys Leu Ser
            340                 345                 350

Pro Leu Arg Gln Lys Leu Trp Asn Asn Leu Ser Phe Met Gly Leu Ser
    355                 360                 365

Asp Val His Leu Leu Arg Asp Asp Ile Tyr Cys Glu Asn Phe Val Gln
370                 375                 380

Asn Leu Ser Gly Lys Gln Lys Glu Ala Leu Arg Tyr Leu Ala Leu Asn
385                 390                 395                 400

Val Tyr Val Glu Met Met Val Asn Asn Tyr Ile Tyr Phe Arg Ser Ile
                405                 410                 415

Ser Lys Met Ile Pro Leu Leu Pro Lys Glu Met Asp Glu Leu Lys Glu
            420                 425                 430

Met Phe Leu Asp Val Ser Asp Glu Ile Pro Val Thr Val Leu Leu Gln
    435                 440                 445

Glu Thr Ser Leu Phe Lys Met Gln Gly Phe Val Gln His Lys Gln
450                 455                 460

<210> SEQ ID NO 89
<211> LENGTH: 404
<212> TYPE: PRT
<213> ORGANISM: Bacillus subtilis
<220> FEATURE:
<223> OTHER INFORMATION: >ABP11311

<400> SEQUENCE: 89

Met Pro Leu Phe Ser Thr Asn Lys Asn Val Ser Phe Ile Tyr Leu Thr
1               5                   10                  15

Ser Cys Phe Gly Asn Gly Phe Phe Glu Arg Gly Ile Trp Met Leu Phe
            20                  25                  30

Leu Ile Glu Lys Gly Phe Ser Leu Phe Gln Ile Gly Leu Leu Gln Ala
        35                  40                  45

Phe Val Asn Gly Thr Met Phe Leu Phe Glu Ile Pro Gly Gly Met Leu
    50                  55                  60

Ala Asp Arg Tyr Gly Arg Lys Val Ser Leu Leu Ile Gly Arg Phe Met

Ile Met Ser Tyr Leu Leu Ile Ile Met Ile Ala Asp Ser Phe Glu Ser
65                  70                  75                  80

Leu Ala Leu Ser Phe Cys Leu Leu Gly Leu Gly Met Thr Phe Ile Ser
                85                  90                  95

Gly Ser Glu Glu Ser Leu Leu Val Asp Ser Val Lys Glu Gln Thr Gly
            100                 105                 110

Glu Asn Asn Phe Ser Arg Phe Leu Gly Arg Tyr Met Ala Ile Ile Thr
        115                 120                 125

Val Ala Leu Ser Leu Ala Met Met Ile Gly Gly Phe Leu Lys Glu Ile
    130                 135                 140

Ser Trp Ser Leu Val Phe Ala Val Ser Phe Ile Phe Gln Met Val Ala
145                 150                 155                 160

Phe Phe Gly Cys Phe Phe Leu Lys Glu Thr Lys Tyr Lys Lys Gly Ser
                165                 170                 175

Gln Arg Glu Ser Phe Thr Leu Ile Phe Lys Asp Thr Phe Asn Phe Leu
            180                 185                 190

Lys Thr Asn Asn Thr Ser Arg Thr Leu Ile Phe Gly Ile Ala Leu Phe
        195                 200                 205

Thr Gly Ile Gly Ser Ile Phe Tyr Met Phe Ala Gln Glu Leu Phe Asn
    210                 215                 220

Gln Leu Gly Ile Lys Val Tyr Leu Ile Ser Ile Phe Phe Gly Leu Glu
225                 230                 235                 240

Ser Phe Leu Ala Ala Ile Leu Ala Asp Arg Ala Tyr Ile Leu Glu Lys
                245                 250                 255

Lys Phe Ser Ser Arg Gly Val Met Met Val Cys Val Tyr Leu Cys Gly
            260                 265                 270

Ile Ser Phe Leu Leu Ile Tyr Ile Asn Phe Asn Trp Leu Ile Leu Ser
        275                 280                 285

Phe Phe Ile Ile Ser Ala Phe Tyr Asn Leu Phe Thr Thr Ile Ser Tyr
    290                 295                 300

Ser Val Ile Asn Gln Asp Ile Pro Ser Lys Gln Arg Ala Thr Leu Leu
305                 310                 315                 320

Ser Ile Ile Ser Phe Ile Ser Ser Leu Val Met Phe Ile Ser Ile Pro
                325                 330                 335

Ile Phe Gly Tyr Leu Ser Asp Lys Phe Gly Thr Ala Tyr Leu Leu Ser
            340                 345                 350

Phe Thr Gly Val Ile Ser Met Val Leu Val Ala Leu Ser Ile Leu Ser
        355                 360                 365

Phe Tyr Lys Asn Arg Lys Asp Ser Val Glu Lys His Lys Leu Leu Lys
    370                 375                 380

Val Gln Glu Lys
385

<210> SEQ ID NO 90
<211> LENGTH: 269
<212> TYPE: PRT
<213> ORGANISM: Bacillus subtilis
<220> FEATURE:
<223> OTHER INFORMATION: >ABP11312

<400> SEQUENCE: 90

Met Glu Lys Lys Leu Ser His His Pro Ile Asp Arg Arg Val Asp Leu
1               5                   10                  15

Thr Tyr Asp Glu Phe Met Lys Glu Tyr Gly Leu Pro Gly Lys Pro Val
            20                  25                  30

```
Ile Ile Ser Asn Ala Ile Asn Asn Trp Glu Ala Lys Lys Leu Trp Thr
         35                  40                  45

Leu Asp Phe Phe Arg Glu Lys Tyr Gly His Ile Ile Val Pro Ile Phe
 50                  55                  60

Glu Ser Gly Lys Arg Tyr Glu Leu Tyr Glu Thr Thr Leu Gly Glu Tyr
 65                  70                  75                  80

Ile Asp Tyr Ile Leu Lys Glu Glu Gln Glu Asp Gly Ile Phe Asn Leu
                 85                  90                  95

Ala Asp Trp Glu Phe Ser Arg Asp Cys Pro Glu Leu Arg Glu His Tyr
            100                 105                 110

Gln Val Pro Asn Tyr Phe Gln Ser Trp Leu Glu Asp Ala Pro Ile Ser
            115                 120                 125

Leu Leu Pro Ala Leu Arg Trp Ile Tyr Ile Asn Gln Lys Asn Thr Gly
        130                 135                 140

Ser Gly Leu His Ile Asp Tyr Gly His Thr Ala Ser Trp Asn Ala Val
145                 150                 155                 160

Ile Ser Gly Lys Lys Trp Ile Leu Leu Asn Gln Asn Glu Ser Glu
                165                 170                 175

Asn Ile Tyr Asn Gly Ala Val Asp Ala Phe Asn Pro Asp Phe Lys Lys
            180                 185                 190

Phe Pro Leu Tyr Thr His Ser Gln Thr Phe Tyr Gly Glu Gln Ser Glu
        195                 200                 205

Gly Asp Ile Met Tyr Ile Pro Ser Gly Trp Trp His Gln Val His Asn
210                 215                 220

Glu Glu Leu Thr Ile Ala Val Thr Glu Asn Phe Ile Asn Glu Thr Asn
225                 230                 235                 240

Tyr Lys Asn Cys Leu Trp Pro Leu Val Ser Asn Ile Val Glu Tyr Gln
            245                 250                 255

Leu Glu Ile Ser Lys Thr Pro Glu Lys Val Gln Lys Val
            260                 265

<210> SEQ ID NO 91
<211> LENGTH: 388
<212> TYPE: PRT
<213> ORGANISM: Bacillus subtilis
<220> FEATURE:
<223> OTHER INFORMATION: >ABP11821

<400> SEQUENCE: 91

Met Gly Gly Gly Leu Tyr Gly His Arg Asn Ile Glu Asp Glu Arg Leu
 1               5                  10                  15

Lys Glu Trp Ile Lys Thr Trp Lys Ala Glu Asn Tyr Ile His Phe Phe
                20                  25                  30

Cys Asn Tyr Tyr Gly Val Gly Met Asn Ala Glu Phe Asn Asp Ser Leu
            35                  40                  45

Ala Lys Gln Val Glu Leu Val Ile Gln Glu Ser Ser Ile Thr Val
         50                  55                  60

Ser Lys Asp Arg Tyr Leu Phe Asp Glu Val Met Lys Tyr Met Thr Pro
 65                  70                  75                  80

Glu Met Phe Tyr Cys Tyr Phe Arg Tyr Asp Ser Ser Thr Ala Tyr Cys
                 85                  90                  95

Gly Asn Tyr Tyr Glu Val Leu Ile Glu Phe Ala Asp Glu Leu Thr Lys
            100                 105                 110

Lys Lys Leu Ile Lys Gly Tyr Asp Tyr Val Gln Thr Gly Gly Ile Thr
        115                 120                 125
```

```
Leu Glu Lys Asn Gly Glu Val Ile Gly His Ile Gly Gln Met Ser Asp
            130                 135                 140

Leu Phe Trp Gln Thr Phe Tyr Asp Gln Tyr Ile Val Glu Asp Tyr Gly
145                 150                 155                 160

Ala Ile Glu His Ala Arg Asn Asn Gly Lys Asp Ile Thr Leu Gln Ile
                165                 170                 175

Trp Asn Asp Lys Val Phe Glu Asn Thr Glu Gln Phe Tyr Lys Phe Ile
                180                 185                 190

Glu Gln Ile Leu Phe Glu Cys Asn Val Asn Leu Gly Phe Gly Phe Lys
            195                 200                 205

Met Ser Arg Phe Glu Asn Glu Ser Lys Leu Lys Gly His Thr Ser Asn
210                 215                 220

Thr Lys Leu Cys Leu Ser Asn Ile Glu Leu Glu Glu Thr Pro Leu Arg
225                 230                 235                 240

Tyr Phe Asn Phe Ala Asn Tyr Thr Lys Ile Pro Arg His Lys Tyr Leu
                245                 250                 255

Ala Tyr Tyr Gln Val Ile Glu Phe Phe Thr Arg Ala Val Arg Lys
            260                 265                 270

Ala Arg Phe Pro Gln Pro Asn Glu Leu Leu Ile Val Lys Tyr Ile Ala
            275                 280                 285

Thr Asn Ser Ile Thr Glu Leu Glu Val Val Thr Trp Leu Asp Asp Ile
290                 295                 300

Lys Ser Arg Gly Lys His Tyr Thr Lys Pro Ser Glu Lys Tyr Pro Ala
305                 310                 315                 320

Leu Phe Pro Leu Glu Ala Thr Glu Ile Val Glu Ser Val Ala Lys Arg
                325                 330                 335

Ile Tyr Leu Ile Arg Cys Ser Leu Val His Ser Lys Glu Ala Pro Asn
                340                 345                 350

Asp Val Asn Phe Ile Pro Asn Leu Asn Asp Glu Ile Ile Asp Lys Glu
                355                 360                 365

Ile Ser Leu Ile Lys Tyr Val Ala Glu Lys Val Leu Tyr Lys Trp Ser
            370                 375                 380

Asn Ala Pro Glu
385

<210> SEQ ID NO 92
<211> LENGTH: 130
<212> TYPE: PRT
<213> ORGANISM: Bacillus subtilis
<220> FEATURE:
<223> OTHER INFORMATION: >ABP11822

<400> SEQUENCE: 92

Met Leu Glu Ser Thr Tyr Leu Gln Ile Thr Asp Val Ile Gly Lys Ile
1               5                   10                  15

Ile Pro Ala Asp Trp Ser Lys Ile Val Leu Tyr Ala Glu Ile Leu Asp
                20                  25                  30

Gly Ser Arg Glu Val Tyr Phe Phe Gln Thr Pro Glu Asn Asp Glu
            35                  40                  45

Tyr Ile Tyr Ser His Asp Ile Pro Glu Gln Phe Gln Val Ser Lys Lys
        50                  55                  60

Ile Tyr Thr Glu Leu Leu Ile Asp Leu Gln Glu Leu Phe Lys Gln Leu
65                  70                  75                  80

His Asn Glu Phe Lys Glu Asn Asn Pro Glu Ala Trp Thr Asn Leu Thr
                85                  90                  95
```

Leu Asn Leu Glu Ser Asn Gly Thr Phe Ser Ile Asp Tyr Asn Tyr Asp
            100                 105                 110

Asp Val Leu Ser Ser Glu Leu Asp Leu Gln Arg Arg Asp Val Trp
        115                 120                 125

Lys Cys
    130

<210> SEQ ID NO 93
<211> LENGTH: 162
<212> TYPE: PRT
<213> ORGANISM: Bacillus subtilis
<220> FEATURE:
<223> OTHER INFORMATION: >ABP11823

<400> SEQUENCE: 93

Met Glu Asn Glu Leu Asn Ala Leu Tyr Arg Ser Ile Ala Glu Thr Val
1               5                   10                  15

Asn Glu Met Ile Pro Glu Pro Trp Glu Lys Phe Leu Phe Tyr Ala Gln
            20                  25                  30

Val Ser Glu Thr Gly Gly Gly Thr Tyr Phe Phe Tyr Asn Ser Gln Asn
        35                  40                  45

Glu Pro Asn His Phe Lys Tyr Ser Leu Glu Ile Pro Phe Glu Phe Asp
    50                  55                  60

Ile Asp Glu Asn Glu Phe Asp Gln Tyr Glu Met Glu Leu Phe Lys Leu
65                  70                  75                  80

Ser Glu Lys Met Arg Asp Val Phe Lys Asp His Asp Gln Glu Leu Phe
                85                  90                  95

Tyr Ser Phe Thr Leu Ser Leu Glu Arg Ser Gly Lys Leu Thr Val Asn
            100                 105                 110

Phe Asp Tyr Thr Asp Trp Phe Lys Thr Asp Tyr Ser Phe Ser Asp Gln
        115                 120                 125

Leu Ile Ile Trp Lys Phe Lys Tyr Leu Gly Glu Pro Lys Asp Pro
    130                 135                 140

Ser Leu Gln Lys Leu Ile Lys Lys Tyr Leu Glu Glu Tyr Pro Glu Asn
145                 150                 155                 160

Pro Ile

<210> SEQ ID NO 94
<211> LENGTH: 669
<212> TYPE: PRT
<213> ORGANISM: Bacillus subtilis
<220> FEATURE:
<223> OTHER INFORMATION: >ABP11824

<400> SEQUENCE: 94

Met Lys Val Phe Glu Ala Lys Thr Leu Leu Ser Glu Ala Thr Asp Arg
1               5                   10                  15

Ala Lys Glu Tyr Lys Glu Leu Arg Thr Gln Met Val Asn Leu Arg Lys
            20                  25                  30

Ala Leu Lys Ser Val Ala Asp Leu Ser Asp Ser Glu Phe Ser Gly Lys
        35                  40                  45

Gly Ala Ser Asn Ile Lys Ala Phe Tyr His Asp His Val Gly Val Thr
    50                  55                  60

Asp Gln Trp Ile Asp Tyr Ile Asp Met Lys Ile Ala Phe Phe Asn Ser
65                  70                  75                  80

Ile Ala Gly Ala Ala Glu Asp Lys Ala Leu Ser Asp Ala Tyr Ile Glu
                85                  90                  95

```
Glu Ser Phe Leu Glu His Glu Leu Ala Asn Ala Asn Lys Lys Ser Lys
                100                 105                 110

Ser Ile Met Ser Glu Gln Lys Lys Ala Met Lys Asp Ile Leu Asn Asp
                115                 120                 125

Ile Asp Asp Ile Leu Pro Leu Asp Leu Phe Ser Thr Glu Thr Phe Lys
            130                 135                 140

Asp Glu Leu Ala Asp Ala Asn Asp Lys Arg Lys Lys Thr Leu Glu Lys
145                 150                 155                 160

Leu Asp Ala Leu Asp Glu Asp Leu Lys Thr Glu Tyr Ala Leu Ser Glu
                165                 170                 175

Pro Asn Glu Gln Phe Ile Lys Ser Asp Phe Gln Lys Leu Gln Glu Ala
            180                 185                 190

Thr Gly Lys Gly Lys Asn Ala Thr Pro Ile His Tyr Asn Ala Lys Ala
            195                 200                 205

Tyr Arg Glu Ser Asp Ile His Lys Lys Gly Asp Ile Glu Thr Arg
210                 215                 220

Thr Glu Ala Tyr Leu Lys Ile Lys Lys Glu Glu Ala Lys Glu Arg Glu
225                 230                 235                 240

Ile Glu Lys Leu Lys Glu Arg Leu Lys Asn Tyr Asp Tyr Ala Asp Ala
                245                 250                 255

Asp Glu Phe Tyr Glu Met Ala Lys Thr Ile Gly Tyr Glu Asn Leu Thr
            260                 265                 270

Ala Glu Gln Gln Arg Tyr Phe Thr Gln Ile Glu Asn Thr Arg Glu Leu
            275                 280                 285

Glu Ala Gly Phe Lys Gly Val Ala Val Gly Leu Tyr Asp Ser Gly Lys
            290                 295                 300

Asp Ala Val Val Gly Leu Trp Asp Met Val Thr Asp Pro Gly Gly Thr
305                 310                 315                 320

Val Glu Ala Ile Thr Gly Ala Met Ala His Pro Ile Lys Thr Tyr Glu
                325                 330                 335

Ala Ile Ser Ala Ala Ile Glu Glu Ser Tyr Gln Lys Asp Met Val Asn
            340                 345                 350

Gly Asp Thr Tyr Ser Arg Ala Arg Trp Val Ser Tyr Ala Val Gly Thr
            355                 360                 365

Val Val Thr Ser Ile Val Gly Thr Lys Gly Val Gly Ala Val Ser Lys
            370                 375                 380

Thr Gly Thr Ala Ala Lys Val Thr Thr Lys Val Lys Thr Ala Ala Ser
385                 390                 395                 400

Lys Ser Ala Thr Ala Gln Lys Ala Ile Thr Val Ser Lys Gln Thr Val
                405                 410                 415

Asp His Ile Lys Gln Lys Val Asn Thr Gly Ile Glu Val Ser Lys Lys
            420                 425                 430

His Val Lys Thr Lys Leu Asn Gln Ile Gly Asp Leu Thr Leu Ala Asp
            435                 440                 445

Ile Leu Pro Tyr His Pro Arg His Asp Leu Val Pro Ala Gly Val Pro
            450                 455                 460

Tyr Asn Ala Val Asn Gly Val Thr Leu Lys Glu Gly Leu Gln Lys Phe
465                 470                 475                 480

Ala Lys Val Ile Leu Pro Lys Pro Tyr Gly Thr Ser Ser Gly Arg
                485                 490                 495

Arg Thr Pro Ala Pro His Val Pro Val Thr Val Lys Tyr Gly Glu
            500                 505                 510
```

```
His Tyr Ala Lys Trp Ser Arg Lys Lys Val Leu Lys Pro Asn Val Glu
            515                 520                 525

Tyr Lys Thr Lys Glu Gly Tyr Thr Tyr Asn Thr Asp Asn Tyr Gly Arg
        530                 535                 540

Ile Thr Lys Val Glu Ala Asp Leu Gln Leu Gly Glu Ala Lys Arg Asn
545                 550                 555                 560

Gln Tyr Ala Gln Ser Asn Ala Gly Lys Pro Gln Asp Arg Leu Pro Asp
                565                 570                 575

Asp Asp Gly Gly His Leu Ile Gly Ser Gln Phe Arg Gly Ser Gly Glu
            580                 585                 590

Leu Asp Asn Leu Val Ala Gln Asn Ser Gln Ile Asn Arg Ser Gly Gly
            595                 600                 605

Glu Trp Tyr Lys Met Glu Thr Glu Trp Ala Ala Leu Lys Glu Glu
            610                 615                 620

Pro Pro Arg Lys Val Ser Val Arg Ile Arg Pro Lys Tyr Leu Gly Asp
625                 630                 635                 640

Ser Leu Arg Pro Asp Ser Phe Glu Val Ile Tyr Arg Ile Glu Gly Lys
                645                 650                 655

Gly Leu Phe Lys Lys Phe Ile Lys Asn Gln Ala Gly Gly
            660                 665
```

<210> SEQ ID NO 95
<211> LENGTH: 112
<212> TYPE: PRT
<213> ORGANISM: Bacillus subtilis
<220> FEATURE:
<223> OTHER INFORMATION: >ABP11825

<400> SEQUENCE: 95

```
Met Asp Lys Asp Phe Leu Ile Ile Lys Ile Lys Asp Ile Gln Lys Gly
1               5                   10                  15

Asp Thr Leu Thr Asn Arg Ala Cys Gly Asn Trp Asp Met Lys Leu Ser
            20                  25                  30

Arg Ala Lys Glu Cys Lys Arg Ala Ile Val Val Arg Ser Gly Val Ile
        35                  40                  45

Leu Asn Val Tyr Lys Ile Val Asp Ala Trp Glu Ser Asp Glu Pro Ala
    50                  55                  60

Lys Ile Thr Lys Thr Asn Asn Arg Val Arg Phe Gln Leu Ala Glu Cys
65                  70                  75                  80

Arg Asp Tyr Ser Tyr Leu Ile Gly Gly Thr Leu Lys Thr Lys Thr Gln
                85                  90                  95

Asn Pro Val Ser Ser Leu Ser Leu Glu Thr Leu Met Glu Leu Val Lys
            100                 105                 110
```

<210> SEQ ID NO 96
<211> LENGTH: 306
<212> TYPE: PRT
<213> ORGANISM: Bacillus subtilis
<220> FEATURE:
<223> OTHER INFORMATION: >ABP11826

<400> SEQUENCE: 96

```
Met Tyr Leu Tyr Lys Val Asn Asn Gln Asn Ile Glu Asp Ile Arg
1               5                   10                  15

Glu Lys Pro Phe Lys Lys Glu Lys Glu Ile Gln Asp Leu Cys Glu Ala
            20                  25                  30

Asn Leu Gln Gln Met Leu Gly Leu Gly Phe Val Lys Ser Glu Phe Arg
        35                  40                  45
```

```
Ile Ser Asn Phe Arg Ile Asp Thr Leu Ala Phe Asp Ala Glu Thr Lys
 50                  55                  60

Ser Phe Val Ile Ile Glu Tyr Lys Asn Thr Lys Asn Phe Ser Val Val
 65                  70                  75                  80

Asp Gln Gly Tyr Ala Tyr Leu Ala Ala Met Leu Asn His Lys Ala Asp
                 85                  90                  95

Phe Ile Leu Glu Tyr Asn Glu Asn His Asp Leu Pro Leu Lys Arg Asp
                100                 105                 110

Asp Val Asp Trp Ser Gln Ser Lys Val Ile Phe Ile Ser Pro Val Phe
            115                 120                 125

Thr Val Tyr Gln Lys Gln Ser Ile His Phe Lys Asp Leu Pro Ile Glu
        130                 135                 140

Leu Trp Glu Val Lys Arg Tyr Glu Asn Asp Leu Ile Gln Leu Asn Gln
145                 150                 155                 160

Met Lys Ala Asp Gly Val Ser Glu Ser Ile Lys Thr Ile Ser Gln Gln
                165                 170                 175

Ser Glu Thr Ile Gln Glu Val Ser Lys Glu Ile Lys Val Phe Ser Glu
            180                 185                 190

Glu Asp His Leu Ala Asp Lys Pro Phe Asp Ile Ile Glu Leu Tyr Gln
        195                 200                 205

Gln Leu Lys Glu Phe Ile Phe Asn Leu Asp Asp His Ile Ser Ile Lys
210                 215                 220

Pro Thr Lys Leu Tyr Ile Ala Phe Thr Ser Asn Lys Arg Asn Phe Thr
225                 230                 235                 240

Asp Ile Leu Leu Leu Lys Ser Gly Leu Lys Leu Trp Val Asn Met Lys
                245                 250                 255

Lys Gly Glu Leu His Asp Pro Glu Glu Arg Met Arg Asp Val Ser Glu
            260                 265                 270

Thr Gly His Trp Gly Asn Gly Asp Tyr Glu Ile Phe Ile Lys Asp Glu
        275                 280                 285

Glu Asn Ile Glu Tyr Ile Met Gly Leu Ile Lys Gln Ser Tyr Glu Lys
290                 295                 300

Asn Lys
305

<210> SEQ ID NO 97
<211> LENGTH: 335
<212> TYPE: PRT
<213> ORGANISM: Bacillus subtilis
<220> FEATURE:
<223> OTHER INFORMATION: >ABP11827

<400> SEQUENCE: 97

Met Lys Lys Arg Phe Ile Leu Leu Gly Leu Phe Ala Ser Val Phe Met
 1               5                  10                  15

Leu Ala Val Tyr Ile Ser Phe Gln Asn Lys Asn Thr His Pro Val Gln
                 20                  25                  30

Ser Pro Val Ile His Pro Glu Glu Asp Arg Ile Phe Phe Ile Tyr Ser
             35                  40                  45

Asn Leu Phe Ile Lys Glu Ser Val Leu Leu Ser Thr Thr Gly Glu
         50                  55                  60

Arg Phe Asn Arg Arg Thr Phe Lys Val Ala Asp Val Pro Tyr Ile Gln
 65                  70                  75                  80

Met Lys Ser Tyr Lys Ser Thr Asp Leu Val Leu Leu Ala Glu His Glu
                 85                  90                  95
```

```
Pro Phe Tyr Tyr Thr Leu Glu Lys Asp Ala Ile Lys Glu His Pro Leu
            100                 105                 110

Ser Asp Pro Phe Ala Phe Trp His Glu Gly Lys Asp Val Ser Val Lys
            115                 120                 125

Ala Tyr Asn Val Asp Thr Thr Gly Asn Glu Ile Arg Ile Asn Asp Lys
130                 135                 140

Lys Met Lys Lys Glu Tyr Thr Leu Thr Leu Pro Ser Leu Val Thr Met
145                 150                 155                 160

Gly Ala Ser Asp Glu Asn Tyr Ile Tyr Ile Ile Gln Ser Met Ala Ile
                165                 170                 175

Tyr Val Ile Asp Arg Lys Thr Glu Glu Met Ile Glu Thr Leu Ser Leu
            180                 185                 190

Ala Ser Tyr Ala Asp Gln Phe Ala Asp Ser Lys Glu Phe Ile Val Ala
            195                 200                 205

Ser Ser Glu His Glu Leu Thr Val Ile Glu Lys Gly Thr Trp Lys Ala
210                 215                 220

Thr Tyr Ile Ala Tyr Pro Glu Asp Leu Glu Tyr Ala Asp Thr Val Tyr
225                 230                 235                 240

Tyr Asp Lys Glu Ser Gly Ser Phe Tyr Val Thr Tyr Glu Asp Lys Lys
                245                 250                 255

Gly Glu Ala Asn Leu Leu Glu Tyr Gly Lys Glu Phe Ser Phe His Thr
            260                 265                 270

Tyr Ser Leu Asn Phe Pro Tyr Met Glu Ala Lys Phe Lys Gly Asn Leu
            275                 280                 285

Leu Tyr Ile Val Ala Gln Glu His Lys Lys Gly Ile Gly Gly Tyr
290                 295                 300

Val Gly Val Phe Asp Ile His Ser Lys Lys Met Leu Tyr Gln Phe Asp
305                 310                 315                 320

Leu Pro Glu Glu Gln Val Lys Val Gln Asp Phe Val Val Val Asp
                325                 330                 335

<210> SEQ ID NO 98
<211> LENGTH: 284
<212> TYPE: PRT
<213> ORGANISM: Bacillus subtilis
<220> FEATURE:
<223> OTHER INFORMATION: >ABP11828

<400> SEQUENCE: 98

Met Gly Gly Ser Tyr Leu Ser Asp Leu Cys Ser Met Tyr Gln Lys Asp
1               5                   10                  15

Lys Phe Phe Thr Gly Phe Val Pro Asp Glu Leu Leu Thr Tyr Ala Cys
            20                  25                  30

Glu Leu Phe Pro Leu Ser Glu Lys Glu Thr Val Thr Ala Leu Leu Asn
        35                  40                  45

Cys Ser Met Gly Asn Lys Ala Lys Ser Phe Val Met Phe Thr Ser Lys
    50                  55                  60

Gly Leu Tyr Trp Lys Arg Phe Gly Glu Gln Glu Gly Cys Val Thr Trp
65                  70                  75                  80

Glu Ala Phe Thr Asp Ile Gln Ser Ile Lys Ser Thr Asp Asp Tyr Glu
                85                  90                  95

Ile Trp Phe Glu Gly Glu Glu Val Phe Asp Val Gly Phe Ser Ser Tyr
            100                 105                 110

Pro Ala Asp Leu Leu Ala Glu Leu Leu Arg Met Ile Gln Gln Phe Leu
            115                 120                 125
```

-continued

Ser Glu Asn Gly Ser Asp Leu Leu Thr Glu Ala Trp Arg Asp His Val
130                 135                 140

Ser Val Ser Ala Ser Glu Leu Lys Glu Ile Ser Thr Leu Phe Gln Asn
145                 150                 155                 160

Ser His Asp Lys Met Phe Gly Leu Thr Asn Gly Leu Leu Val Gly Asn
                165                 170                 175

Glu Ile Ser Glu Lys Arg Glu Val Arg Leu Arg Lys Arg Leu His Ile
                180                 185                 190

Pro Lys Asp Gln Glu Met Ile Ser Phe Trp Ser Thr Phe Pro Val Lys
            195                 200                 205

Gln Thr Asp Gly Ile Thr Leu Thr Asp Lys Gly Ile Tyr Phe Ser Asp
            210                 215                 220

Pro Phe Leu Arg Leu Phe Tyr Pro Trp His Val Phe Lys Glu Thr Pro
225                 230                 235                 240

Val Met Leu Lys Asp Gln Glu Leu Ile Val Gly Lys Glu Asn Val Ile
                245                 250                 255

Gln Leu Leu Glu Asn Leu Met Pro Ala Glu Asp Val Phe Ala Phe Ile
                260                 265                 270

Glu Gln Val Lys Arg Arg Ile Ser Ala Val Thr Ser
                275                 280

<210> SEQ ID NO 99
<211> LENGTH: 298
<212> TYPE: PRT
<213> ORGANISM: Bacillus subtilis
<220> FEATURE:
<223> OTHER INFORMATION: >ABP11889

<400> SEQUENCE: 99

Met Leu Arg Lys Lys Gly Gln Glu Thr Lys Asp Tyr Lys Thr Gln Gln
1               5                   10                  15

Val Glu Ser Trp Gly Leu Arg Leu Ile Gly Lys Asn Glu Lys Ile Glu
                20                  25                  30

Lys Lys Ser Asn Ile Ser Ile Ala Ile Leu Asp Ser Gly Ile Asp Ser
            35                  40                  45

Asn His Glu Asp Leu Lys Gly Val Val Lys Lys Glu Tyr Asn Ala Leu
50                  55                  60

Glu Pro Ser Lys Gly Val Ile Glu Asp Lys Phe Gly His Gly Thr Ala
65                  70                  75                  80

Val Ala Gly Ile Ile Ala Ser Asn Asp Asn Lys Ile Gly Thr Leu Gly
                85                  90                  95

Ile Ala Pro Tyr Ala Asp Ile Tyr Ser Val Lys Val Leu Asp Asp Lys
                100                 105                 110

Gly Arg Gly Ser Val Glu Ser Ile Val Lys Gly Ile Glu Trp Ser Ile
            115                 120                 125

Asp Asn Asn Val Asp Ile Val Asn Ile Ser Val Gly Leu Lys Lys Ser
130                 135                 140

Asp Gln Lys Leu Lys Arg Val Ile Asp Glu Ala Asn Glu Lys Gly Val
145                 150                 155                 160

Ile Val Val Ala Ala Gly Asn Asn Tyr Gly Leu Asn Ala Asp Tyr
                165                 170                 175

Pro Ala Arg Tyr Gln Asn Val Ile Ser Val Gly Ala Ile Asn Lys Lys
            180                 185                 190

Met Lys Arg Ala Lys Tyr Ser Ala Arg Gly Lys Ile Asp Phe Val Ala
            195                 200                 205

-continued

Pro Gly Glu Asp Ile Leu Thr Thr Ser Pro Lys Asp Asn Tyr Ile Asn
    210                 215                 220

Val Ser Gly Thr Ser Met Ala Thr Pro Phe Val Ser Gly Val Ile Ala
225                 230                 235                 240

Asn Ile Ile Met Gln Glu Pro Val Lys Tyr Ser Lys Thr Lys Ser Arg
                245                 250                 255

Phe Thr Ser Ile Tyr Lys Thr Leu Lys Lys Tyr Ser Thr Pro Tyr Leu
            260                 265                 270

Ser Glu Lys Ser Asp Met Lys Ser Leu Gly Asn Gly Leu Ile Ser Leu
        275                 280                 285

Lys Lys Glu Thr Asn Asn Glu Lys Ile Asn
290                 295

<210> SEQ ID NO 100
<211> LENGTH: 308
<212> TYPE: PRT
<213> ORGANISM: Bacillus subtilis
<220> FEATURE:
<223> OTHER INFORMATION: >ABP11890

<400> SEQUENCE: 100

Met Lys Lys Ser Ile Lys Phe Ile Ala Ile Ser Leu Ile Phe Ala Ile
1               5                   10                  15

Ile Val Ser Ile Ile Pro Glu Lys Asn Val Ala Ser Ala Gly Ala Glu
            20                  25                  30

Thr Pro Val Glu Ile Thr Asn Glu Asp Leu Gln Arg Ala Leu Val Glu
        35                  40                  45

Asn Gly Asp Ile Val Asp Pro Asp Ser Val Glu Ile Val Lys Asn Asn
50                  55                  60

Glu Asp Thr Ile Lys Ala Glu Val Asp Val Gln Thr Asp Asp Phe Gly
65                  70                  75                  80

Ile Asp Gln Asp Leu Asp Gly Ser Asp Ser Glu Ser Leu Ile Asp Glu
                85                  90                  95

Asp Leu Asp Glu Ser Ser Ser Glu Thr Val Thr Ala Glu Val Asp Lys
            100                 105                 110

Glu Asp Ala Thr Ala Ile Val Thr Ser Val Glu Lys Asp Glu Asp Gly
        115                 120                 125

Lys Asp Ile Glu Lys Lys Tyr Glu Val Asp Ile Glu Glu Ala Asp Gly
    130                 135                 140

Asp Asp Ile Val Ala Thr Phe Lys Asp Leu Asp Thr Asn Gln Val Tyr
145                 150                 155                 160

Asp Val Asn Thr Lys Glu Ala Gln Ala Ser Phe Ala Phe Leu Val Pro
                165                 170                 175

Ile Ala Val Val Val Gly Gly Ala Leu Val Glu His Leu Val Ala Ala
            180                 185                 190

Ser Leu Ala Ile Val Ile Ala Gly Val Thr Tyr Thr Val Ala Thr Lys
        195                 200                 205

Val Arg Ser Lys Leu Lys Lys Lys Lys Tyr Tyr Tyr Ala Ala
    210                 215                 220

Thr Leu Asn Lys Asn Lys Thr Asn Met Tyr Ile Gly Pro Ala Leu Ser
225                 230                 235                 240

Lys Lys Gln Ala Val Ser Arg Leu Arg Lys Gly Asp Val Trp Ser Val
                245                 250                 255

Ser Lys Ser Lys Ala Lys Asn Val Ala Gln Thr Ala Gly Gly Gly Arg
            260                 265                 270

-continued

Lys Pro Val Gly Pro Glu Ile His Asn Lys Asp Gly Lys Ile Lys
                275                 280                 285

Lys Gly Thr Tyr Tyr Tyr His Tyr His Thr Tyr Asn Arg Lys Gly Gly
            290                 295                 300

His Ser Phe Tyr
305

<210> SEQ ID NO 101
<211> LENGTH: 52
<212> TYPE: PRT
<213> ORGANISM: Bacillus subtilis
<220> FEATURE:
<223> OTHER INFORMATION: >ABP11891

<400> SEQUENCE: 101

Met Trp Glu Ser Ile Gln Asn Gly Lys Arg Val Asn Lys Ile Phe Glu
1               5                   10                  15

Ser Lys Asp Gly Asn Tyr Ile Ser Asn Phe Thr Val Gln Gly Asn Val
            20                  25                  30

Glu Lys Ile Glu Lys Glu Leu Val Phe Ile Arg Gly Ile Leu Glu Lys
        35                  40                  45

Glu Lys Asn Asn
    50

<210> SEQ ID NO 102
<211> LENGTH: 153
<212> TYPE: PRT
<213> ORGANISM: Bacillus subtilis
<220> FEATURE:
<223> OTHER INFORMATION: >ABP12521

<400> SEQUENCE: 102

Met Lys Leu Ile Tyr Pro Tyr Gly Ala Asp Lys Ile Tyr Leu Gly Asn
1               5                   10                  15

Pro Val Glu Leu Phe Arg Asp Gln Asp Thr Gly Asp Tyr Ile Ile Pro
            20                  25                  30

Lys Asn Ala Thr Asp Ile Pro Pro Glu Leu Asn Gly Glu Gly Met Trp
        35                  40                  45

Arg Pro Met Phe Asn Glu Glu Lys Gln Thr Trp Ile Glu Thr Ala Asp
    50                  55                  60

Gln Ala Tyr Lys Lys Ser Leu Leu Glu Asp Val Pro Ser Glu Ser Asn
65                  70                  75                  80

Pro Thr Asn Asp Gln Leu Ser Ala Leu Gly Lys Gln Leu Thr Glu Glu
                85                  90                  95

Lys Leu Ala Arg Ile Gln Ala Asp Gln Ala Gln Lys Ala Leu Gly Met
            100                 105                 110

Gln Leu Thr Glu Glu Val Ile Ala Arg Lys Glu Ala Glu Ala Leu Ser
        115                 120                 125

Gln Ser Leu Gly Lys Gln Ile Ala Ala Leu Lys Leu Asp Leu Leu Asn
    130                 135                 140

Leu Lys Gly Gly Met Thr Ser Glu Ser
145                 150

<210> SEQ ID NO 103
<211> LENGTH: 63
<212> TYPE: PRT
<213> ORGANISM: Bacillus subtilis
<220> FEATURE:
<223> OTHER INFORMATION: >ABP12522

<400> SEQUENCE: 103

Met Ser Leu Asn Phe Trp Val Tyr Ala Leu Phe Tyr Lys Trp Ala Thr
1               5                   10                  15

Thr Ser Met Val Arg Glu Ala Met Met Phe His Asp Cys Ser Val Asp
                20                  25                  30

Asp Leu Lys Glu Gly Val Ser Glu Lys Tyr Val Thr Leu Ala Gln Phe
            35                  40                  45

Lys Glu Ile Thr Asp Gln Thr Tyr Glu Glu Thr Met Lys Ala Asn
    50                  55                  60

<210> SEQ ID NO 104
<211> LENGTH: 92
<212> TYPE: PRT
<213> ORGANISM: Bacillus subtilis
<220> FEATURE:
<223> OTHER INFORMATION: >ABP12523

<400> SEQUENCE: 104

Met Ser Glu Leu Ser Glu Val Pro Asp Met Asn Leu Leu Glu Lys Glu
1               5                   10                  15

Ile Thr Glu Ile Lys Thr Glu Gln Lys Thr Leu Glu Gln Arg Val Ser
                20                  25                  30

Val Leu Glu Arg Ser Ser Asp Arg Gln Asp Gln Gln Ile Met Thr Leu
            35                  40                  45

Asn Glu Lys Leu Asn Lys Ile Glu Glu Asn Thr Thr Trp Ile Lys Arg
    50                  55                  60

Thr Ile Thr Gly Ala Ile Ile Thr Ala Val Ser Thr Gly Ile Ile Gly
65                  70                  75                  80

Gly Ala Ile Ala Ile Met Tyr Ser Leu Leu Gln His
                85                  90

<210> SEQ ID NO 105
<211> LENGTH: 250
<212> TYPE: PRT
<213> ORGANISM: Bacillus subtilis
<220> FEATURE:
<223> OTHER INFORMATION: >ABP12651

<400> SEQUENCE: 105

Met Lys Leu Glu Gln Gln Glu Ile Asn Ile Leu His Ser Asp Ser Gly
1               5                   10                  15

Pro Tyr Gly Ile Ala Ile Ser Pro Glu Gly Lys Val Trp Phe Thr Gln
                20                  25                  30

His Lys Ala Asn Lys Ile Ser Cys Leu Asp Arg Thr Gly Gln Ile Gln
            35                  40                  45

Glu Tyr Ile Val Pro Thr Pro Asp Ala Gly Val Met Cys Leu Thr Val
    50                  55                  60

Ser Ser Glu Gly Asp Ile Trp Phe Thr Glu Asn Arg Ala Asn Lys Ile
65                  70                  75                  80

Gly Lys Leu Thr Ala Lys Arg Gln Phe Ile Glu Tyr Pro Leu Pro His
                85                  90                  95

Gln His Ser Ala Pro Tyr Gly Ile Thr Glu Gly Pro Asp Gly Asp Ile
            100                 105                 110

Trp Phe Thr Glu Met Asn Gly Asn Arg Ile Gly Lys Leu Thr Ser Glu
    115                 120                 125

Gly Lys Ile His Glu Tyr Glu Leu Pro Asn Glu Gly Ser Tyr Pro Ser
130                 135                 140

```
Phe Ile Thr Leu Gly Ser Asp His Ser Leu Trp Phe Thr Glu Asn Gln
145                 150                 155                 160

Asn Asn Ala Ile Gly Lys Ile Thr Glu Ser Gly Glu Leu Thr Glu Phe
            165                 170                 175

Pro Ile Pro Thr Pro Ala Ala Gly Pro Val Gly Ile Thr Lys Gly His
        180                 185                 190

Asp Asp Ala Leu Trp Phe Val Glu Ile Val Gly Asn Lys Ile Gly Lys
            195                 200                 205

Ile Thr Val Ser Gly Asp Ile Thr Glu Tyr Asp Ile Pro Thr Pro Asn
        210                 215                 220

Ala Arg Pro His Ala Ile Ala Ala Gly Val Lys Ser Asp Leu Trp Phe
225                 230                 235                 240

Thr Glu Trp Gly Gly Ile Lys Ser Glu Gly
                245                 250
```

<210> SEQ ID NO 106
<211> LENGTH: 58
<212> TYPE: PRT
<213> ORGANISM: Bacillus subtilis
<220> FEATURE:
<223> OTHER INFORMATION: >ABP12652

<400> SEQUENCE: 106

```
Met Val Tyr Arg Met Gly Gly Asn Lys Ile Gly Arg Leu Thr Ser Asp
1               5                   10                  15

Gln Thr Ile Glu Glu Tyr Thr Ile Asn Thr Pro His Ala Glu Pro His
            20                  25                  30

Gly Ile Gly Cys Asp Asn Asp Gly Thr Val Trp Phe Ala Leu Glu Cys
        35                  40                  45

Asn Lys Ile Gly Lys Leu Lys Leu Thr Lys
    50                  55
```

<210> SEQ ID NO 107
<211> LENGTH: 43
<212> TYPE: PRT
<213> ORGANISM: Bacillus subtilis
<220> FEATURE:
<223> OTHER INFORMATION: >ABP12653

<400> SEQUENCE: 107

```
Met Lys Val Lys Glu Lys Arg Ile Val Val Asn Lys Phe Pro Ser Gln
1               5                   10                  15

Pro Asp Glu Glu Asp Cys Arg Asn Leu Thr Leu Leu Gly Trp Gly Ser
            20                  25                  30

Gly Gly Phe Phe Leu Phe Leu His Thr Phe Arg
        35                  40
```

<210> SEQ ID NO 108
<211> LENGTH: 49
<212> TYPE: PRT
<213> ORGANISM: Bacillus subtilis
<220> FEATURE:
<223> OTHER INFORMATION: >ABP13703

<400> SEQUENCE: 108

```
Met Lys Gln Arg Lys Arg Ile Ile Gln Lys Asp Arg Arg Lys Leu Leu
1               5                   10                  15

Lys Tyr Phe Asn Ala Lys Phe Thr Ala Glu Glu Arg Ala Met Glu Ser
            20                  25                  30
```

```
Leu Phe Cys Glu Lys Thr Ser Gln Ser Ser Asn Val Leu Leu Asn
            35                  40                  45

Asp

<210> SEQ ID NO 109
<211> LENGTH: 185
<212> TYPE: PRT
<213> ORGANISM: Bacillus subtilis
<220> FEATURE:
<223> OTHER INFORMATION: >ABP13704

<400> SEQUENCE: 109

Met Lys Thr Lys Ser Glu Pro Lys Val Ile Leu Glu Pro Ala Lys Glu
1               5                   10                  15

Ser Asp Leu Pro Glu Phe Gln Lys Lys Leu Gln Glu Ala Phe Ala Ile
            20                  25                  30

Ala Val Ile Glu Thr Phe Gly Asp Cys Glu Asp Gly Pro Ile Pro Ser
        35                  40                  45

Asp Asn Asp Val Gln Glu Ser Phe Asn Ala Pro Gly Ala Val Val Tyr
    50                  55                  60

His Ile Leu Gln Asp Gly Lys Asn Val Gly Gly Ala Val Val Arg Ile
65                  70                  75                  80

Asn Ser Gln Thr Asn His Asn Ser Leu Asp Leu Phe Tyr Val Ser Pro
                85                  90                  95

Glu Tyr His Ser Gln Gly Ile Gly Leu Ser Ala Trp Lys Ala Ile Glu
            100                 105                 110

Ala Gln Tyr Pro Asp Thr Val Leu Trp Glu Thr Val Thr Pro Tyr Phe
        115                 120                 125

Glu Lys Arg Asn Ile Asn Phe Tyr Val Asn Lys Cys Gly Phe His Ile
    130                 135                 140

Val Glu Phe Tyr Asn Glu His His Ser Asp Pro His Ile His Arg Asn
145                 150                 155                 160

Gly Arg Val Asp Asp Lys Pro Leu Pro Asp Asn Asp Asp Phe Phe Arg
                165                 170                 175

Phe Val Lys Ile Met Lys Lys Lys Asp
            180                 185

<210> SEQ ID NO 110
<211> LENGTH: 44
<212> TYPE: PRT
<213> ORGANISM: Bacillus subtilis
<220> FEATURE:
<223> OTHER INFORMATION: >ABP13705

<400> SEQUENCE: 110

Met Pro Leu Thr Leu Ile Trp Arg Asn Phe Glu Phe Ser Glu Lys Phe
1               5                   10                  15

Leu Gly Thr Tyr Ala Asp Asn Val Leu Lys Val Leu Gln Glu Ala Gln
            20                  25                  30

Glu Glu Leu Glu Asp Glu Phe Lys Ile Ile Val Glu
        35                  40

<210> SEQ ID NO 111
<211> LENGTH: 303
<212> TYPE: PRT
<213> ORGANISM: Bacillus subtilis
<220> FEATURE:
<223> OTHER INFORMATION: >ABP13706

<400> SEQUENCE: 111
```

```
Met Ser Leu Glu Glu Gln Leu Gln Ser Lys Glu Glu Leu Thr Lys
1               5                   10                  15

Leu Val Ser Thr Phe Ala Ala Lys Glu Gly Thr Asn Glu Thr Ser Ile
            20                  25                  30

Ser Gly Leu Glu Phe Ile Arg Ser Ala Lys Pro Leu Met Pro Val His
            35                  40                  45

Thr Met His Glu Pro Ala Leu Cys Ile Val Leu Gln Gly Arg Lys Val
        50                  55                  60

Ile Ser Ile Ile Gly Glu Asp Phe Phe Tyr Gly Lys Gly Glu Tyr Leu
65                  70                  75                  80

Val Val Ala Val Asp Leu Pro Val Ile Gly Glu Ile Leu Lys Ala Ser
                85                  90                  95

Glu Arg Glu Pro Tyr Leu Cys Leu Arg Leu Asn Phe Asn Leu Met Gln
                100                 105                 110

Ile Ala Glu Val Ser Lys Glu Tyr Gln Gln His Ser Thr Asn His Asn
            115                 120                 125

Ala Ala Gly Arg Gly Ile Phe Val Asp Gln Thr Asp Gly Val Ile Leu
        130                 135                 140

Asp Ala Leu Ile Arg Leu Val Lys Leu Leu His Thr Pro Glu Asp Thr
145                 150                 155                 160

Glu Ile Leu Ala Pro Leu Ile Ile Lys Glu Ile Leu Tyr Arg Ile Met
                165                 170                 175

Gln Gly Lys His Gly His Thr Val Lys Ser Leu Val Ala Lys Gly Ser
                180                 185                 190

Lys Leu Ser Glu Val Ala Ala Ala Leu Asp Tyr Leu Arg Asn His Phe
            195                 200                 205

Ser Gln Glu Ile Lys Ile Asp Ala Leu Ala Lys Lys Val Asn Leu Ser
        210                 215                 220

Pro Ser Ala Leu Tyr His His Phe Lys Gln Val Thr Met Met Thr Pro
225                 230                 235                 240

Ile Gln Tyr Gln Arg Ala Leu Arg Leu His Glu Ala Arg Arg Leu Ile
                245                 250                 255

Phe Gly Lys Asp Met Arg Val Ala Asp Ala Ala Phe Gln Val Gly Tyr
                260                 265                 270

Glu Ser Pro Ser Tyr Phe Asn Arg Glu Tyr Arg Lys Met Phe Gly Lys
            275                 280                 285

Pro Pro Gly Lys Asp Arg Lys Glu Asn Leu Asn Leu Tyr Tyr Val
        290                 295                 300

<210> SEQ ID NO 112
<211> LENGTH: 82
<212> TYPE: PRT
<213> ORGANISM: Bacillus subtilis
<220> FEATURE:
<223> OTHER INFORMATION: >ABP13707

<400> SEQUENCE: 112

Met Glu Lys Asn Asn His Ser Tyr Gly Gly Leu Trp Val Thr Lys Asp
1               5                   10                  15

Arg Tyr Ile Arg His Glu Leu Leu Ser Asn Gly Arg Tyr Val Glu Ala
            20                  25                  30

Arg Gly Asn Val Glu Cys Ala Tyr Thr Gly Asn Tyr Gln Ile Thr Gly
        35                  40                  45

Asp Arg Ile Glu Tyr Gln Asp Asp Ala Gly Phe Thr Ala Asp Gly Asp
    50                  55                  60
```

Phe Ile Asn Gly Ile Leu Tyr His Ala Gly Met Val Leu His Arg Asp
 65                  70                  75                  80

Arg Ser

<210> SEQ ID NO 113
<211> LENGTH: 243
<212> TYPE: PRT
<213> ORGANISM: Bacillus subtilis
<220> FEATURE:
<223> OTHER INFORMATION: >ABP13708

<400> SEQUENCE: 113

Met Ser Ile Lys Asn Lys Val Val Leu Val Thr Gly Gly Ser Ser Gly
  1               5                  10                  15

Ile Gly Ala Ala Thr Val Asp Leu Leu Ala Glu Asn Gly Ala Thr Val
                 20                  25                  30

Ile Ala Ala Ala Arg Arg Thr Asp Arg Leu Glu Thr Leu Val Thr Thr
             35                  40                  45

Leu Gln Gln Lys Gly Tyr His Ala Asp Tyr Lys Gln Leu Asp Val Thr
         50                  55                  60

Asp Phe Gly Gln Met Gln Gln Thr Val Gln Glu Val Thr Asp Ala Tyr
 65                  70                  75                  80

Gly Lys Ile Asp Val Ile Val Asn Asn Ala Gly Val Met Pro Leu Ser
                 85                  90                  95

Lys Leu Asp Ser Leu Lys Ile Ala Glu Trp Asn Arg Met Ile Asp Val
            100                 105                 110

Asn Ile Arg Gly Val Leu His Gly Ile Gly Ala Val Leu Pro Val Met
        115                 120                 125

Lys Glu Gln Asn Ser Gly His Ile Val Asn Ile Ala Ser Ile Gly Ala
    130                 135                 140

Tyr Glu Val Thr Pro Thr Ala Ala Val Tyr Cys Ala Thr Lys Tyr Ala
145                 150                 155                 160

Val Arg Ala Ile Thr Glu Gly Leu Arg Gln Glu Ala Thr His Asn Ile
                165                 170                 175

Arg Thr Thr Leu Ile Ala Pro Gly Val Thr Glu Ser Glu Leu Ala Asp
            180                 185                 190

His Ile Thr Asp Lys Gln Ala Ser Glu Ala Met Ile Glu Tyr Arg Arg
        195                 200                 205

Gln Ala Leu Pro Ala Ser Ala Ile His Ala Ile Leu Tyr Ala Ile
    210                 215                 220

Ser Gln Pro Ile Glu Ile Asp Val Ser Glu Leu Ile Val Arg Pro Thr
225                 230                 235                 240

Leu Ser Leu

<210> SEQ ID NO 114
<211> LENGTH: 260
<212> TYPE: PRT
<213> ORGANISM: Bacillus subtilis
<220> FEATURE:
<223> OTHER INFORMATION: >ABP13709

<400> SEQUENCE: 114

Met Arg Arg Ile Asp Phe Gly Leu Thr Phe Leu Ile Cys Thr Leu Ile
  1               5                  10                  15

Met Leu Phe Asn Glu Ile Trp Lys Leu Leu Gly Asn Arg Pro Glu Ala
                 20                  25                  30

```
Phe Lys Tyr Gly Ser Ile Ile Tyr Gln Val Ile Ala Val Phe Ser Ser
            35                  40                  45

Ile Ile Thr Asn Val Ala Ile Gly Val Ala Gly Ala Ile Ser Phe Tyr
        50                  55                  60

Tyr Ile Ala Gln Leu Ile Asp Lys Lys Asn Arg Glu Leu Tyr Thr
65                  70                  75                  80

Asp Leu Arg Lys His Leu Leu Phe Met Phe Tyr Asn His Leu Lys Leu
                85                  90                  95

Leu Thr Arg Leu Asp Gln Phe Arg Glu Val Asn Asn Arg Glu Arg Arg
            100                 105                 110

Val Ala Asp Phe Tyr Asp Ile Phe Asp Ile Pro Val Phe Tyr Asp Asn
        115                 120                 125

Phe Lys Lys Ile Asn Ser Lys Glu Val Thr Arg Phe Lys Lys Asn
130                 135                 140

Leu Tyr Asp Tyr Phe Ala Thr Gln Ser Glu Gln Gln Ile Lys Val Phe
145                 150                 155                 160

Thr Glu Ala Phe Glu Lys Asp Ile Lys Lys Leu Lys Glu Lys Ser Asn
                165                 170                 175

Ile Arg Phe Phe Lys Glu Ser Lys Asp Leu Ile Asp Thr Val Cys Ile
            180                 185                 190

Ile Tyr Asp Asp Asp Phe Ser Met Ile Ser Ser Ile Tyr Leu Ser Asn
        195                 200                 205

Phe Glu Asp Thr Gln Asn Lys Ser Asn Tyr Ile Glu Glu Leu Val Lys
210                 215                 220

Asp Tyr Tyr Asp Phe Leu Asn Ala Thr Val Ile Leu Tyr Glu Glu Leu
225                 230                 235                 240

Glu Glu Phe Leu Glu Ser Met Asp Lys Asn Arg Trp Val Val Phe Ile
                245                 250                 255

Lys Met Leu Asp
            260

<210> SEQ ID NO 115
<211> LENGTH: 48
<212> TYPE: PRT
<213> ORGANISM: Bacillus subtilis
<220> FEATURE:
<223> OTHER INFORMATION: >ABP13710

<400> SEQUENCE: 115

Met Glu Asn Ala Gln Glu Ile Tyr Glu Leu Val Lys Glu Met Ser Lys
1               5                   10                  15

Thr Val Lys Glu Ile Asp Glu Thr Thr Lys Arg Ile Glu Asn Thr Thr
            20                  25                  30

Lys Arg Ile Ala Lys Gly Tyr Glu Leu Ile Thr Glu Glu Leu Ala Glu
        35                  40                  45

<210> SEQ ID NO 116
<211> LENGTH: 339
<212> TYPE: PRT
<213> ORGANISM: Bacillus subtilis
<220> FEATURE:
<223> OTHER INFORMATION: >ABP13711

<400> SEQUENCE: 116

Met Thr Tyr Arg Val Gly Ser Met Phe Ala Gly Ile Gly Gly Thr Cys
1               5                   10                  15

Leu Gly Phe Ile Gln Ala Gly Ala Glu Ile Val Trp Ala Asn Glu Ile
            20                  25                  30
```

-continued

Asp Ala Asn Ala Cys Ile Thr Tyr Arg Asn Tyr Phe Gly Asp Thr Tyr
            35                  40                  45

Leu Gln Glu Gly Asp Ile Thr Gln Ile Asp Lys Ser Thr Ile Pro Glu
 50                  55                  60

Leu Asp Ile Leu Ile Gly Gly Phe Pro Cys Gln Ala Phe Ser Ile Ala
 65                  70                  75                  80

Gly Tyr Arg Lys Gly Phe Glu Asp Arg Gly Asn Val Phe Phe Gln
            85                  90                  95

Ile Leu Glu Val Leu Glu Ala Gln Arg Asn Val Tyr Gly Arg Leu Pro
                100                 105                 110

Gln Ala Ile Met Leu Glu Asn Val Lys Asn Leu Phe Thr His Asp Lys
            115                 120                 125

Gly Asn Thr Phe Arg Val Ile Lys Glu Ala Leu Glu Ala Tyr Gly Tyr
            130                 135                 140

Thr Val Lys Ala Glu Val Leu Asn Ser Met Glu Tyr Gly Asn Val Pro
145                 150                 155                 160

Gln Asn Arg Glu Arg Ile Tyr Ile Val Gly Phe Gln Asp Glu Asn Gln
                165                 170                 175

Ala Glu Met Phe Arg Phe Pro Glu Pro Ile Pro Leu Thr Asn Gln Leu
            180                 185                 190

Asn Asp Val Val Asp Arg Thr Arg Arg Tyr Asp Glu Arg Tyr Tyr Tyr
                195                 200                 205

Asp Glu Thr Ser Gln Tyr Tyr Glu Met Leu Arg Glu Ala Met Val Ser
            210                 215                 220

Thr Asp Thr Thr Tyr Gln Leu Arg Arg Ile Tyr Val Arg Glu Asn Arg
225                 230                 235                 240

Ser Asn Val Cys Pro Thr Leu Thr Ala Asn Met Gly Thr Gly Gly His
                245                 250                 255

Asn Val Pro Leu Val Leu Asp Tyr Glu Asn Asn Ile Arg Lys Leu Thr
            260                 265                 270

Pro Glu Glu Cys Leu Leu Leu Gln Gly Phe Pro Ala Asp Tyr His Tyr
            275                 280                 285

Pro Glu Gly Met Ala Asn Ser His Lys Tyr Lys Gln Ala Gly Asn Ser
            290                 295                 300

Val Thr Val Pro Val Ile Arg Arg Ile Ala Thr Asn Ile Ile Asn Val
305                 310                 315                 320

Leu Asn Gly Glu Thr Asn Ala Asn Asp Glu Gln Glu His Gln Tyr Ala
                325                 330                 335

Ile Thr Gln

<210> SEQ ID NO 117
<211> LENGTH: 78
<212> TYPE: PRT
<213> ORGANISM: Bacillus subtilis
<220> FEATURE:
<223> OTHER INFORMATION: >ABP13712

<400> SEQUENCE: 117

Met Ile Pro Phe Leu Gly Asn Arg Ile Gln Asn Ala Arg Glu Ala Arg
1               5                   10                  15

Gly Leu Lys Pro Ser Gln Val Ala Asp Lys Val Lys Val Thr Arg Ser
            20                  25                  30

Thr Tyr Ser Leu Tyr Glu Ser Glu Asn Arg Thr Pro Ser Leu Glu Thr
            35                  40                  45

Phe Ile Arg Ile Ala Glu Thr Leu Asn Val Ser Ala Asp Tyr Leu Leu
 50                  55                  60

Gly Leu Lys Glu Glu Met Thr Ser Leu Asn Glu Glu Asn
 65                  70                  75

<210> SEQ ID NO 118
<211> LENGTH: 382
<212> TYPE: PRT
<213> ORGANISM: Bacillus subtilis
<220> FEATURE:
<223> OTHER INFORMATION: >ABP13713

<400> SEQUENCE: 118

Met Phe Phe Thr Asn Gln Pro Ala Ser Asn Arg Thr Thr Tyr Lys Gln
 1               5                   10                  15

Met Leu Ser Ser Thr Gly Ser Leu Ser Asn Leu Phe Ser Glu Ser Asp
             20                  25                  30

Ser Pro Tyr Leu Val Ser Arg Asn Val Glu Asn Ala Phe Cys Glu Ala
         35                  40                  45

Leu Gly Ala Glu Asn Leu Gly Arg Ser Asp Cys Ser Ala Asp Ala Ser
     50                  55                  60

Lys Asp Arg Val Gly Ile Gly Ile Lys Thr Phe Leu His Gly Asn Gly
 65                  70                  75                  80

His Thr Leu Gln Lys Val Ala Glu Phe Asn Arg Asp Ser Asp Leu Tyr
                 85                  90                  95

Arg Gly Lys Ser Pro Lys Glu Leu Ile Asn Ile Val Ala Thr Leu Arg
            100                 105                 110

Asn Glu Arg Ile Glu Phe Thr Lys Arg Thr Tyr Gly Ile Asp Thr Met
        115                 120                 125

Ile Tyr His Cys Val Thr Arg Lys Pro Gly Lys Ile Leu Ile Phe Glu
130                 135                 140

Glu Pro Met Asp Leu Val Gln Ile Ser Ser Ile Thr Asn Ile Lys Val
145                 150                 155                 160

Ser Asn Asn Arg Asn Thr Ile Thr Phe Glu Asp Gly Leu His Glu Tyr
                165                 170                 175

Ser Phe Asn Val Thr Lys Ser Thr Leu Tyr Lys Arg Phe Ile Thr Asp
            180                 185                 190

Glu Pro Ile Glu Ile Asp Val Glu Ile Leu Glu Asn Pro Tyr Gln
        195                 200                 205

Glu Leu Ala Lys Leu Phe Gly Phe Glu Ile Ala Pro Ile Gln Val Pro
    210                 215                 220

Glu Val Ser Ser Pro Ile Glu Asn Phe Glu Tyr Val Ile Leu Pro Leu
225                 230                 235                 240

Phe Ser Asp Arg Gly Asn Lys Arg His Val Pro Glu Lys Ser Gly Leu
                245                 250                 255

Asn Gln Trp Asn Ala Ala Gly Arg Pro Arg Asn Ala Asn Glu Ile Tyr
            260                 265                 270

Ile Pro Ile Pro Met Trp Ile His Arg Lys Phe Pro Glu Phe Pro
        275                 280                 285

Ala Arg Asp Lys Pro Phe Gln Leu Arg Leu Pro Asp Lys Ser Leu Leu
    290                 295                 300

Ser Ala Lys Val Cys Gln Asp Asn Ser Lys Ala Leu Met Ser Asn Pro
305                 310                 315                 320

Asn Ser Ala Leu Gly Glu Trp Leu Leu Arg Gln Val Met Asn Leu Gly
                325                 330                 335

```
Glu Arg Glu Leu Leu Thr Tyr Glu Met Leu Glu Arg Leu Ser Ile Asp
            340                 345                 350

Ser Val Ile Val Tyr Lys His Ser Glu Gln His Tyr Ser Ile Asp Phe
        355                 360                 365

Arg Glu Ile Gly Ser Tyr Asp Glu Phe Glu Asn Glu Asn Asn
    370                 375                 380

<210> SEQ ID NO 119
<211> LENGTH: 141
<212> TYPE: PRT
<213> ORGANISM: Bacillus subtilis
<220> FEATURE:
<223> OTHER INFORMATION: >ABP13714

<400> SEQUENCE: 119

Met Thr Asp Thr Phe Ser Lys Glu Gln Arg Arg Lys Asn Met Gln Ala
1               5                   10                  15

Ile Lys Ser Arg Ser Lys Leu Glu Asp Lys Val Thr Lys Glu Leu Trp
            20                  25                  30

Asn Arg Gly Ile Arg Phe Arg Lys Asn Val Lys Gly Leu Phe Gly Lys
        35                  40                  45

Pro Asp Ile Ala Ile Lys Lys His Lys Ile Val Ile Phe Ile Asp Ser
    50                  55                  60

Cys Phe Trp His Ala Cys Glu Lys His Gly Asn Lys Pro Lys Ser Asn
65                  70                  75                  80

Thr Glu Tyr Trp Glu Lys Lys Leu Gln Arg Asn Lys Glu Arg Asp Arg
                85                  90                  95

Glu Val Asn Lys Tyr Tyr Glu Glu Lys Gly Trp Asn Ile Lys Arg Ile
            100                 105                 110

Trp Glu His Glu Leu Lys Glu Asp Phe Asp Glu Thr Ile Asn Arg Ile
        115                 120                 125

Ile Ala Phe Ile Glu Ala Val Lys His Glu Gln Arg Lys
    130                 135                 140

<210> SEQ ID NO 120
<211> LENGTH: 49
<212> TYPE: PRT
<213> ORGANISM: Bacillus subtilis
<220> FEATURE:
<223> OTHER INFORMATION: >ABP13715

<400> SEQUENCE: 120

Met Leu Lys Ile Lys Lys Leu Asp Phe Met Pro Phe Phe Asn Arg Met
1               5                   10                  15

Ile Cys Phe Val Asp Val Lys Asn Pro Asp Glu Ala Asp Lys Lys Ala
            20                  25                  30

Leu Ala Lys Asp Ile Leu Glu Asn Asn Lys Asp Gln Tyr Gln Gly Tyr
        35                  40                  45

Asp

<210> SEQ ID NO 121
<211> LENGTH: 224
<212> TYPE: PRT
<213> ORGANISM: Bacillus subtilis
<220> FEATURE:
<223> OTHER INFORMATION: >ABP13716

<400> SEQUENCE: 121

Met Lys Phe Ile Glu Leu Asp Pro Ala Leu Gln Ile Lys Val Arg Gln
1               5                   10                  15
```

-continued

```
Leu Glu Ala Asn Ala Glu Glu His Gln Asp Lys Ser His Pro Asp Val
         20                  25                  30

Arg Ala Leu Trp Leu Glu Leu Gln Lys Glu Asp Ser Ile Cys Gly Ala
         35                  40                  45

Leu Ser Glu Lys Asp Gly Ser Tyr Lys Val Cys Leu Arg Ala Pro Val
 50                  55                  60

Glu Glu Arg Asn Arg Cys Ser Leu His Gly Lys Thr Leu Lys Gly
 65                  70                  75                  80

Glu Gln Met Thr Pro Ala Gln Lys Leu Asn Met Met Lys Asn Leu Arg
                 85                  90                  95

Pro Arg Val Val Glu His Cys Trp Tyr Ala Glu Glu Ser Asn Phe Leu
                100                 105                 110

Ala Ser Leu Thr Glu Ser Glu Ile Lys Tyr Met Ser Phe Leu Glu Lys
            115                 120                 125

Ser Val Lys Asp Gln Tyr His Val Asn Asp Gly Leu Glu Glu Leu Leu
130                 135                 140

Leu Glu Asp Ile Leu Gln Ser Ala Ile Ile His Met Arg Met Val Asn
145                 150                 155                 160

Arg Gly Val Phe Glu Lys Gly Ser Arg His Thr Ala Arg Pro Leu Gln
                165                 170                 175

Glu Val Leu Lys Thr Ile Lys Glu Leu Gly Trp Thr Cys Lys Glu Lys
            180                 185                 190

Gly Gly Lys Val Gln Phe Val Ser Val Arg Asn Asp Phe Met Ala Ser
        195                 200                 205

Ile Phe Gly Asn Asn Thr Glu Glu Glu Glu Asp Lys Lys Leu Asn
    210                 215                 220

<210> SEQ ID NO 122
<211> LENGTH: 58
<212> TYPE: PRT
<213> ORGANISM: Bacillus subtilis
<220> FEATURE:
<223> OTHER INFORMATION: >ABP13717

<400> SEQUENCE: 122

Met Ser Leu Lys Glu Lys Leu Ala Glu Leu Asn Lys Arg Ala Gly Lys
1               5                   10                  15

Leu Glu Gly Ser Leu Lys Lys Ala Ser Lys Lys Ala Ser Ser Glu Ala
            20                  25                  30

Asp Arg Leu Lys Lys Lys Arg Gln Glu Arg Glu Tyr Tyr Asp Ala Tyr
        35                  40                  45

Glu Lys Lys Phe Pro Ile Asp Lys Asn Phe
    50                  55

<210> SEQ ID NO 123
<211> LENGTH: 50
<212> TYPE: PRT
<213> ORGANISM: Bacillus subtilis
<220> FEATURE:
<223> OTHER INFORMATION: >ABP13718

<400> SEQUENCE: 123

Met Lys Lys Asp Trp Phe Ser Gln Arg Leu Glu Leu Ile Asn Lys Glu
1               5                   10                  15

Gln Lys Leu Asn Glu Glu Phe Asn Leu Trp Lys Leu Gln Gln Ile Thr
            20                  25                  30

Lys Arg Met Lys Glu Val Thr Lys Lys Leu Asp Glu Leu Glu Thr Glu
```

```
                35                  40                  45
Arg Val
    50

<210> SEQ ID NO 124
<211> LENGTH: 192
<212> TYPE: PRT
<213> ORGANISM: Bacillus subtilis
<220> FEATURE:
<223> OTHER INFORMATION: >ABP13719

<400> SEQUENCE: 124

Met Gly Leu Phe Asn Lys Lys Ser Glu Met Val Lys Phe Glu Glu Glu
1               5                   10                  15

Leu Asn Val Val Gln Gly Ser Ile Arg Glu Val Glu Ala Glu Leu Arg
            20                  25                  30

Asp Phe Asp Thr Ser Lys Lys Gly Ile Glu Leu Glu Leu Lys Leu Gly
        35                  40                  45

Ala Asp Ser Ser Leu Thr Lys Arg Leu Lys Val Ser Glu Lys Val
    50                  55                  60

Ala Glu Thr Glu Lys Cys Leu Ala Glu Leu Arg Gln Arg Glu Gly Glu
65                  70                  75                  80

Ile Asn Ala Glu Lys Arg Thr Ala Tyr Leu Asn Glu Leu Ala Asp Lys
                85                  90                  95

Asp Leu Ala Ser Ile Asp Lys Gly Arg Arg Ala Thr Val Ile Lys Tyr
            100                 105                 110

Glu Leu Gln Ala Leu Met Arg Val Val Asp Glu Arg Asp Gly Arg Trp
        115                 120                 125

Gly Tyr Ser Lys Pro Glu Asn Leu Leu Lys Glu Tyr Gly Ile Glu Ile
    130                 135                 140

Gly His Ile Pro Ala Glu His Leu Arg Arg Glu Glu Phe Asp Ser Phe
145                 150                 155                 160

Trp Lys Thr Arg Lys Asn Asp Ala Glu Lys Arg Ile Gln Asn Glu Cys
                165                 170                 175

Gln Glu Ala Ile Glu Thr Leu Lys Lys Tyr Leu Gly Gly Phe Asp Lys
            180                 185                 190

<210> SEQ ID NO 125
<211> LENGTH: 209
<212> TYPE: PRT
<213> ORGANISM: Bacillus subtilis
<220> FEATURE:
<223> OTHER INFORMATION: >ABP13720

<400> SEQUENCE: 125

Met Glu Ser Lys Val Asn Met Leu Arg Ile Leu Glu Phe Tyr Met Gly
1               5                   10                  15

Glu Thr Gly Asn Phe Lys Lys Leu Val Val Ile Gln Glu Ile Tyr Arg
            20                  25                  30

Asn Asn Pro Ser Lys Met Lys Gly Cys Glu Leu Ser Phe Leu Lys Asp
        35                  40                  45

Asn Lys Phe Val Ala Lys Gly Phe Phe Glu Ala Glu Thr Ile Met Val
    50                  55                  60

Arg Asn Ser Phe His Ser Tyr Asn Ser Glu Leu Pro Glu Leu Lys Glu
65                  70                  75                  80

His His Phe Lys Lys Met Glu Lys Arg Asp Gln Asp Ser His Tyr Pro
                85                  90                  95
```

```
Val Ser Glu Thr Thr Val Leu Tyr Leu Ser Gly Tyr Val Phe Ala Glu
            100                 105                 110

Phe Lys Phe His Lys Ile Ala Asn Asp Lys Lys Ile Gly Asp Lys Val
        115                 120                 125

Tyr Leu Pro Ile Lys Leu Asp Asp Lys Gln Lys Pro Asp Ser Asn Glu
    130                 135                 140

Phe Cys Lys Leu Leu Val Leu Glu Glu Tyr Arg Asp Gly Thr Phe Glu
145                 150                 155                 160

Leu Pro Glu Leu Pro Lys Arg Ala Glu Met Phe Thr Cys Trp Val Arg
                165                 170                 175

Leu Glu Leu Ala Pro Asp Ser Lys Asn Asp Ser Gly Val Lys Val Ser
            180                 185                 190

Glu Arg Glu Phe Asn Lys Ala Arg Met Gly Glu Ile Lys Gly Asn Ile
        195                 200                 205

Ala

<210> SEQ ID NO 126
<211> LENGTH: 273
<212> TYPE: PRT
<213> ORGANISM: Bacillus subtilis
<220> FEATURE:
<223> OTHER INFORMATION: >ABP13721

<400> SEQUENCE: 126

Met Ser Glu Asp Val Lys Lys Tyr Phe Thr Thr Gly Glu Phe Ser Lys
1               5                   10                  15

Leu Cys Arg Val Lys Lys Gln Thr Leu Phe His Tyr Asp Glu Ile Gly
            20                  25                  30

Leu Phe Ser Pro Glu Ile Lys Lys Glu Asn Gly Tyr Arg Tyr Tyr Ser
        35                  40                  45

Tyr His Gln Phe Glu Ile Phe Gln Val Ile Ser Leu Phe Lys Glu Leu
    50                  55                  60

Gly Val Pro Leu Lys Glu Ile Lys Cys Leu Ile Lys Gly Lys Thr Pro
65                  70                  75                  80

Asp Lys Ile Leu His Val Leu Lys Glu Lys Ser Ile Glu Ile Asp Lys
                85                  90                  95

Lys Ile Asn Glu Leu Lys Gln Leu Gln Thr Ile Leu Gln Thr Lys Val
            100                 105                 110

Thr Leu Thr Glu Gln Ala Leu Glu Thr Asp Phe Ser Ser Ile Ser Phe
        115                 120                 125

Glu Tyr Leu Asn Glu Glu Thr Phe Met Leu Ser Arg Lys Thr Leu Asn
    130                 135                 140

Leu Pro Glu Arg Lys Tyr Val Ala Ala Ile Ser Glu Leu Ile His Glu
145                 150                 155                 160

Val Gln Gln Tyr Glu Leu Asp Glu Gly Tyr Pro Ile Gly Gly Ile Phe
                165                 170                 175

Ala Arg Glu Gln Ile Leu Glu Lys Asp Phe Tyr Asn Tyr Ser Tyr Phe
            180                 185                 190

Tyr Ile Lys Val Lys Asp Gly Ala Glu Asn Ile Asn Tyr His Val Arg
        195                 200                 205

Pro Lys Gly Leu Tyr Ala Val Gly Tyr Glu Ile Gly Gly Lys Thr Glu
    210                 215                 220

Glu Ala Tyr Arg Arg Ile Ile Glu Phe Ile Glu Arg Asn Gly Met Gln
225                 230                 235                 240

Ile Gly Glu Asn Ala Tyr Glu Glu Tyr Met Leu Asp Glu Met Val Val
```

Asp Gly Tyr Glu Asn Thr Tyr Ala Lys Ile Leu Leu Gln Val Lys Glu
                    245                 250                 255

Val
    260                 265                 270

<210> SEQ ID NO 127
<211> LENGTH: 419
<212> TYPE: PRT
<213> ORGANISM: Bacillus subtilis
<220> FEATURE:
<223> OTHER INFORMATION: >ABP22957

<400> SEQUENCE: 127

Met Arg Glu Lys Lys Leu Gly Pro Val Leu Ser Gly Leu Ile Val
1               5                   10                  15

Gly Pro Ile Leu Gly Ser Gly Ile Ile Leu Pro Pro Ile Ile Tyr
            20                  25                  30

Gly Lys Thr Gly Asp Tyr Ala Ile Leu Ala Trp Phe Ile Met Met Ile
            35                  40                  45

Ile Ser Phe Leu Phe Ala Ser Leu Phe Gly Lys Leu Ser Val Leu Phe
50                  55                  60

Pro Asn Glu Ser Gly Val Ala His Thr Val Glu Leu Ala Phe Gly Gln
65                  70                  75                  80

His Ile Lys Gln Leu Thr Ser Val Phe Phe Ile Ile Ala Gly Ser Val
                85                  90                  95

Gly Pro Val Ala Val Leu Met Thr Ala Ser Gln Tyr Leu Lys Ala Leu
            100                 105                 110

Phe Lys Ser Asn Gly Trp Ser Leu Glu Thr Tyr Gly Ile Ile Leu Met
        115                 120                 125

Met Ile Cys Leu Phe Val Leu Leu Ser Asn Ile Ser Ser Val Gly Lys
130                 135                 140

Val Ser Phe Met Phe Ser Thr Val Ser Thr Val Val Leu Leu Ser Gly
145                 150                 155                 160

Gly Ile Ser Ser Ile Pro Phe Met Arg Asp Lys Ala Phe Ile Lys Thr
                165                 170                 175

Pro Phe His Leu Asp Asp Phe Gly Tyr Ser Ile Leu Leu Leu Phe Trp
            180                 185                 190

Ala Leu Val Gly Trp Glu Ile Ile Gly Asn Tyr Ser Leu Asp Val Lys
        195                 200                 205

Asn Arg Lys Arg Thr Ile Pro Gln Ala Ile Val Ile Ser Ser Val Val
210                 215                 220

Ile Thr Thr Val Cys Ile Val Val Ala Ala Tyr Gln Trp Ile Asp
225                 230                 235                 240

Leu His His Thr His Thr Leu Thr Ile Ile Leu Ile Pro Leu Leu Gly
                245                 250                 255

Thr Ser Phe Ala Ser Pro Thr Met Ala Phe Ile Thr Thr Ile Leu Cys
            260                 265                 270

Met Ser Thr Tyr Leu Leu Val Thr Gly Gly Val Ser Arg Leu Ile Ala
        275                 280                 285

Ser Glu Asn Lys Lys Ile Thr Leu Ile Ser Tyr Arg Ser Lys Thr Asn
290                 295                 300

Ile Pro Ile Gly Ala Ile Ser Ile Leu Thr Leu Val His Ala Ile Val
305                 310                 315                 320

Phe Ile Leu Leu Phe Ile Asn Ile Ile Asn Val Glu Gln Ile Val Gly
                325                 330                 335

Met Ala Asn Ala Phe Phe Ile Ser Asn Ala Ile Cys Gly Ile Leu Ser
            340                 345                 350

Ala Tyr Lys Leu Leu Pro Gly Lys Phe Ser Lys Ser Leu Ser Leu Met
            355                 360                 365

Leu Ile Ile Ser Phe Leu Ile Ile Leu Ser Phe Ser Ser Ile Trp Ile
370                 375                 380

Leu Leu Met Ile Ala Leu Ile Thr Thr Phe Tyr Leu Ile Arg His Phe
385                 390                 395                 400

Ile Trp Ile Arg Gln Leu Lys Lys Ser Ala Thr Asn Ser Gln Asp Lys
                405                 410                 415

Leu Arg Phe

<210> SEQ ID NO 128
<211> LENGTH: 299
<212> TYPE: PRT
<213> ORGANISM: Bacillus subtilis
<220> FEATURE:
<223> OTHER INFORMATION: >ABP22958

<400> SEQUENCE: 128

Met Glu Ile Arg His Leu Lys Thr Phe Ile Thr Ile Val Glu Lys Gly
1               5                   10                  15

Gly Phe Thr Lys Ala Ala Glu Tyr Leu Gly Tyr Ala Gln Ser Thr Ile
            20                  25                  30

Thr Ser His Ile Lys Asp Ile Glu Gln Glu Ile Gly Gly Pro Leu Phe
            35                  40                  45

Asn Arg Phe Gly Lys Lys Met Leu Leu Thr Glu Val Gly Glu Tyr Leu
50                  55                  60

Leu Pro Tyr Ala Asn Glu Met Ile Arg Ile Ser Glu Lys Val Lys Gln
65                  70                  75                  80

Ile Gln Ser Asn Asp Glu Pro Met Gly Asn Leu Val Ile Gly Ala Pro
                85                  90                  95

Glu Ser Leu Thr Val Tyr Arg Leu Pro Pro Ile Ile His Glu Phe Lys
            100                 105                 110

Lys Leu Phe Pro Lys Val Lys Ile Thr Leu Lys Ser Ser Thr Cys Trp
            115                 120                 125

Glu Leu Lys Asp Asp Leu Arg Asn Gly Lys Val Asp Leu Ala Phe Leu
130                 135                 140

Leu Glu Tyr Glu Gln Glu Glu Ala Asp Leu Tyr Ile Glu Lys Leu Ile
145                 150                 155                 160

Thr Glu Pro Met Ile Leu Val Phe Pro Lys Gln His Lys Leu Gln Asn
                165                 170                 175

Thr Pro Phe Asp Asp Phe Tyr Phe Ser Ser Asp Glu Val Ile Leu Tyr
            180                 185                 190

Thr Glu His Gly Cys Ser Tyr Arg Thr Tyr Phe Glu Glu Tyr Met Lys
            195                 200                 205

His Gln Gly Leu Val Ser Glu Asn Thr Phe Glu Phe Trp Ser Val Glu
        210                 215                 220

Ala Ile Lys Gln Cys Val Met Cys Gly Leu Gly Ile Ser Leu Leu Pro
225                 230                 235                 240

Leu Ile Thr Val Gln Lys Glu Leu Lys Glu Asn Lys Leu Ser Gly Leu
                245                 250                 255

Ile Met Asp Glu Thr Arg Ile Ile Thr Gln Val Ala Tyr His Lys Lys
            260                 265                 270

Arg Trp Asn Ser Leu Ala Met Ala Glu Phe Ile Asn Ile Val Lys Lys
            275                 280                 285

His Ala Glu Leu Trp Lys Arg Thr Gln Thr Leu
            290                 295

<210> SEQ ID NO 129
<211> LENGTH: 187
<212> TYPE: PRT
<213> ORGANISM: Bacillus subtilis
<220> FEATURE:
<223> OTHER INFORMATION: >ABP22959

<400> SEQUENCE: 129

Met Asn Pro Leu Leu Asp Val Pro Leu Gln Leu Glu Thr Glu Arg
1               5                   10                  15

Leu Ile Leu Arg Ala Pro His Gln Thr Gly Asp Gly Lys Ile Val Asn
            20                  25                  30

Gln Ala Ile Arg Asp Ser Phe Ser Glu Leu Lys Ala Trp Leu Pro Phe
        35                  40                  45

Ala Gln Glu Leu Pro Thr Val Glu Glu Thr Glu Ile Asn Leu Arg Asn
    50                  55                  60

Ala His Ile Asn Phe Leu Lys Arg Glu Ser Phe Arg Phe Leu Ile Phe
65                  70                  75                  80

Asp Lys Asp Ser Asn Asp Phe Ile Gly Ile Thr Ser Leu Gln Arg Ile
                85                  90                  95

Asp Trp Asn Ile Pro Lys Cys Glu Ile Gly Tyr Trp Val Asn Thr Lys
            100                 105                 110

Tyr Ser Gly Asn Gly Tyr Met Thr Glu Ala Val Lys Lys Leu Ala Asn
        115                 120                 125

Phe Gly Leu His Asn Ile Lys Phe Arg Arg Ile Glu Ile Arg Cys Asp
    130                 135                 140

Ser Thr Asn Leu Lys Ser Arg Ala Ile Pro Glu Lys Leu Gly Phe Val
145                 150                 155                 160

Phe Glu Gly Thr Leu Arg Asn Asp Asp Leu Ser Ala Asp Gly Ser Lys
                165                 170                 175

Leu Thr Asp Thr Cys Phe Tyr Ser Ile Val Lys
            180                 185

<210> SEQ ID NO 130
<211> LENGTH: 102
<212> TYPE: PRT
<213> ORGANISM: Bacillus subtilis
<220> FEATURE:
<223> OTHER INFORMATION: >ABP22960

<400> SEQUENCE: 130

Met Val Asp Gln Leu Trp Ala Tyr Phe Leu Asn Leu Ile Glu Glu Ala
1               5                   10                  15

Ile Glu Thr Gly Lys Ser Glu Thr Tyr Phe Pro Asp Gln Pro Leu Leu
            20                  25                  30

Leu Lys Met Lys Ser Ile Ser Asn Asp Met Leu Leu Phe Glu Ile Asp
        35                  40                  45

Gln Lys Gln Lys Val Leu Leu Pro Lys Leu Asp Phe Phe Glu Ser Leu
    50                  55                  60

Leu Lys Asn Ala Lys Ser Phe Phe Glu Thr Met Asn Phe Val Leu Glu
65                  70                  75                  80

Gly Asn Cys Asp Tyr Glu Tyr Glu Leu Asn Lys Ile Asp Glu Leu Gln
                85                  90                  95

Thr Lys Ile Lys Cys Met
            100

<210> SEQ ID NO 131
<211> LENGTH: 573
<212> TYPE: PRT
<213> ORGANISM: Bacillus subtilis
<220> FEATURE:
<223> OTHER INFORMATION: >ABP22961

<400> SEQUENCE: 131

Met Lys Val Phe Glu Ala Lys Ser Leu Leu Ser Glu Ala Glu Asn Arg
1               5                   10                  15

Ala Lys Asp Tyr Lys Glu Leu Lys Asn Gln Met Ile Lys Leu Arg Lys
            20                  25                  30

Ala Phe Lys Ala Val Ala Asp Leu Asp Asp Ser Glu Phe Ser Gly Lys
        35                  40                  45

Gly Ala Asn Asn Ile Lys Ala Phe Tyr His Asp His Val Gly Val Thr
    50                  55                  60

Asp Gln Trp Ile Asp Leu Ile Glu Met Lys Ile Ala Phe Leu Thr Ser
65                  70                  75                  80

Ile Ser Gly Val Leu Glu Asp Ala Ser Leu Ser Asp Ala Tyr Ile Glu
                85                  90                  95

Glu Ser Phe Leu Glu His Glu Leu Thr Asn Ala Tyr Lys Lys Ser Lys
            100                 105                 110

Ser Ile Met Ser Glu Gln Lys Lys Ala Met Lys Asp Ile Leu Asn Asp
        115                 120                 125

Ile Asp Asp Ile Leu Thr Leu Asp Leu Phe Ser Thr Glu Thr Phe Lys
    130                 135                 140

Asp Glu Leu Ser Ser Ala Glu Asn Lys Arg Lys Thr Val Asp Lys
145                 150                 155                 160

Ile Gly Asp Val Asp Glu Asn Leu Lys Thr Glu Tyr Ala Ile Thr Glu
                165                 170                 175

Pro Asn Glu Gln Phe Ile Lys Ala Asp Phe Gln Lys Leu Gln Glu Ser
            180                 185                 190

Thr Gly Lys Gly Lys Asn Ala Thr Pro Leu His Tyr Asn Ala Lys Ala
        195                 200                 205

Tyr Arg Glu Ser Asp Ile His Lys Lys Gly Asp Ile Glu Lys Gln
    210                 215                 220

Ser Glu Ala Tyr Leu Lys Ile Lys Lys Glu Ala Asn Lys Cys Glu
225                 230                 235                 240

Ile Lys Asp Leu Lys Lys Gln Leu Val Lys Val Thr Asp Pro Asp Glu
                245                 250                 255

Tyr Leu Lys Ile Ala Lys Lys Ile Gly Tyr Glu Asn Leu Glu Pro Glu
            260                 265                 270

Gln Gln Val Tyr Phe Arg Gln Leu Glu Glu Leu Gln Gln Lys Ala Glu
        275                 280                 285

Ile Gly Lys Gly Ile Ala Met Gly Met Tyr Glu Ala Gly Lys Asp Thr
    290                 295                 300

Val Met Gly Leu Tyr Gln Leu Ala Arg His Pro Ile Glu Ser Leu Ser
305                 310                 315                 320

Gly Thr Val Asn Ala Ala Leu His Pro Ile Asp Thr Tyr Lys Ile Ile
                325                 330                 335

Ala Lys Asp Ile Glu Asp Thr Phe Gln Arg Glu Met Ile Asn Gly Asp
            340                 345                 350

```
Ser His Ser Arg Ala Lys Trp Val Ser Tyr Val Gly Ser Thr Val Val
        355                 360                 365

Leu Ala Ile Val Gly Pro Lys Gly Ile Asp Lys Val Ser Lys Val Ala
370                 375                 380

Lys Ala Gly Ser Lys Val Ala Ala Leu Lys Thr Leu Glu Val Ser Lys
385                 390                 395                 400

Thr Gly Ile Lys Lys Gly Ile Glu Tyr Val Lys Ile Pro Ser Val Phe
                405                 410                 415

Glu Gln Gln Phe Ala Met Ala Gly Gly Ser Gly Thr Phe Pro Phe Asn
            420                 425                 430

Val Leu Asp Gly Glu Asn Tyr Lys Asn Ser Ala Leu Gly Ile Phe Lys
        435                 440                 445

Asn Ser Ser Thr Val Gln Gly Leu Lys Lys Ala Lys Pro His Glu Val
    450                 455                 460

Val Asn Glu Leu Lys Thr Phe Gln Ser Arg Lys Tyr Thr Phe Gly Gly
465                 470                 475                 480

Gln Ser Phe Leu Ile Asp Lys Arg Gly Met Lys His Ile Leu Glu Arg
                485                 490                 495

His His Pro Asn Leu Trp Asp Gly Ser Ile Lys Ser Gln Gln Ser Phe
            500                 505                 510

Leu Asn Lys Glu Met Thr Val Asn Asp Val Ala Asp Ala Ile Glu Ser
        515                 520                 525

Ile Met Lys Gln Asn Arg Glu Glu Leu Thr Lys Lys Gly Thr Lys Phe
    530                 535                 540

Ser Tyr Gln Ile Arg Gly Ser Tyr Glu Gly Gln Gly Tyr Val Val Gly
545                 550                 555                 560

Phe Gln Lys Gly Arg Val Gly Gln Phe Tyr Pro Glu Lys
                565                 570

<210> SEQ ID NO 132
<211> LENGTH: 84
<212> TYPE: PRT
<213> ORGANISM: Bacillus subtilis
<220> FEATURE:
<223> OTHER INFORMATION: >ABP22962

<400> SEQUENCE: 132

Met Val Gln Glu Val Met Val Met Lys Lys Asp Phe Gly Asp Ser Ile
1               5                   10                  15

Ser Asn Lys Val Tyr Glu Tyr Arg Val Leu Ala Arg Leu Ser Gln Gln
            20                  25                  30

Glu Leu Ala Lys Lys Val Gly Val Ser Lys Gln Thr Ile Phe Val Met
        35                  40                  45

Glu Lys Gly Asn Tyr Val Pro Thr Leu Leu Leu Ala Phe Arg Ile Ala
    50                  55                  60

Glu Phe Phe Lys Val Asp Val Asn Glu Ile Phe Thr Tyr Glu Lys Gly
65                  70                  75                  80

Asn Asp Gln Lys

<210> SEQ ID NO 133
<211> LENGTH: 58
<212> TYPE: PRT
<213> ORGANISM: Bacillus subtilis
<220> FEATURE:
<223> OTHER INFORMATION: >ABP22963

<400> SEQUENCE: 133
```

```
Met Asn Asn Lys Lys Asn Ile Phe Asp Ile Val Met Tyr Ile Ile Phe
1               5                   10                  15

Gly Val Leu Ser Leu Phe Leu Val Ala Lys Thr Asp Tyr Gly Thr Gly
                20                  25                  30

Val Leu Val Phe Val Ala Ile Leu Tyr Leu Ala Val Ile Ala Tyr Lys
            35                  40                  45

Ile Lys Gln Val Phe Ser Asn Ser Asp Ser
    50                  55
```

<210> SEQ ID NO 134
<211> LENGTH: 222
<212> TYPE: PRT
<213> ORGANISM: Bacillus subtilis
<220> FEATURE:
<223> OTHER INFORMATION: >ABP22964

<400> SEQUENCE: 134

```
Met Arg Lys Lys Arg Val Ile Thr Cys Val Met Ala Ala Ser Leu Thr
1               5                   10                  15

Leu Gly Ser Leu Leu Pro Ala Gly Tyr Ala Ser Ala Lys Glu Asp Ser
                20                  25                  30

Lys Thr Thr Pro Ser Tyr Glu Glu Leu Ala Leu His Tyr Lys Met Lys
            35                  40                  45

Ser Glu Lys Ile Ser Ser Asn Gly Lys Leu Val Glu Ile Glu Tyr Val
    50                  55                  60

Ser Gly Asn Glu Thr His Lys Val Gln Met Asn Gly Asn Asn His Thr
65                  70                  75                  80

Val Lys Val Asp Gly Ile Glu Gln Lys Gly Leu Asn Phe Glu Tyr Asp
                85                  90                  95

Glu Asn Val Ala Lys Arg Thr Asn Tyr Glu Asn Asn Leu Lys Ser
            100                 105                 110

Asn Glu Phe Thr Thr Gln Ala Ala Lys Pro Lys Lys Gly Tyr His Tyr
        115                 120                 125

Val Gly Thr Leu Ser Gly His Thr Lys Ala Ala Lys Asn Ala Leu Ser
    130                 135                 140

Val Thr Met Ser Leu Val Gly Ile Val Pro Gly Leu Gly Trp Gly Ser
145                 150                 155                 160

Lys Ala Ala Thr Ile Leu Phe Ser Tyr Trp Ala Lys Glu Gln Ile Pro
                165                 170                 175

Asp Ala Tyr Tyr Lys Tyr Asp Leu Tyr Glu Lys Gly Ala Met Thr Asp
            180                 185                 190

Ser Trp Tyr Gln Tyr Ala Thr Val Gln Phe Leu Lys Ile Lys Leu Ile
        195                 200                 205

Lys Arg Lys Trp Ala Asn Leu Gly Gln Val Leu Leu Gln Lys
    210                 215                 220
```

<210> SEQ ID NO 135
<211> LENGTH: 87
<212> TYPE: PRT
<213> ORGANISM: Bacillus subtilis
<220> FEATURE:
<223> OTHER INFORMATION: >ABP23145

<400> SEQUENCE: 135

```
Met Lys Asn Phe Asp Lys Gly Thr Val Arg Thr Val Leu Leu Leu
1               5                   10                  15

Ile Ala Leu Ile Asn Gln Thr Met Leu Met Phe Gly Lys Ser Pro Leu
```

```
                20                  25                  30
Asp Ile Thr Asp Val Gln Val Asn Gln Leu Ala Asp Ala Leu Tyr Thr
            35                  40                  45
Ala Gly Ser Leu Ile Phe Thr Ile Gly Thr Thr Leu Ala Ala Trp Phe
 50                  55                  60
Lys Asn Asn Tyr Val Thr Ala Lys Gly His Lys Gln Lys Ala Ile Leu
 65                  70                  75                  80
Lys Gln Asn Asn Leu Thr Lys
                85

<210> SEQ ID NO 136
<211> LENGTH: 273
<212> TYPE: PRT
<213> ORGANISM: Bacillus subtilis
<220> FEATURE:
<223> OTHER INFORMATION: >ABP23146

<400> SEQUENCE: 136

Met Thr Ile Ala Val Lys Lys Asn Leu Val Ser Glu Ala Lys Tyr Ala
 1               5                  10                  15
Leu Lys Cys Pro Asn Pro Met Thr Ala Glu Tyr Ile Thr Ile His Asn
            20                  25                  30
Thr Tyr Asn Asp Ala Ser Ala Ala Asn Glu Val Ser Tyr Met Ile Gly
            35                  40                  45
Asn Thr Ser Ser Thr Ser Phe His Phe Ala Val Asp Asp Lys Glu Val
 50                  55                  60
Arg Gln Gly Ile Pro Thr Asp Arg Asn Ala Trp His Thr Gly Asp Gly
 65                  70                  75                  80
Thr Asn Gly Pro Gly Asn Arg Lys Ser Ile Gly Val Glu Ile Cys Tyr
                85                  90                  95
Ser Lys Ser Gly Gly Ala Lys Tyr Tyr Ala Ala Glu Lys Leu Ala Ile
            100                 105                 110
Lys Phe Val Ala Gln Leu Leu Lys Glu Arg Gly Trp Gly Ile Asp Arg
            115                 120                 125
Val Arg Lys His Gln Asp Trp Ser Gly Lys Tyr Cys Pro His Arg Ile
130                 135                 140
Leu Ser Glu Gly Arg Trp Asn Glu Val Lys Ala Ala Ile Asp Ala Glu
145                 150                 155                 160
Leu Lys Ala Leu Gly Gly Lys Ser Ser Lys Lys Thr Thr Ser Ser
                165                 170                 175
Lys Ala Val Lys Lys Pro Ser Ser Lys Lys Ser Ser Phe Asn
            180                 185                 190
Leu Pro Ser Gly Ile Phe Lys Val Lys Ser Pro Leu Met His Ser Ala
            195                 200                 205
Ala Val Glu Gln Ile Gln Thr Ala Leu Ala Ala Leu His Phe Tyr Pro
210                 215                 220
Asp Lys Lys Ala Lys Asn Phe Gly Ile Asp Ser Tyr Tyr Gly Pro Lys
225                 230                 235                 240
Thr Ala Asp Ala Val Arg Arg Phe Gln Leu Met Asn Gly Leu Lys Ala
                245                 250                 255
Asp Gly Ile Tyr Gly Pro Ala Thr Lys Ala Lys Leu Glu Ala Leu Leu
            260                 265                 270
Lys

<210> SEQ ID NO 137
```

```
<211> LENGTH: 52
<212> TYPE: PRT
<213> ORGANISM: Bacillus subtilis
<220> FEATURE:
<223> OTHER INFORMATION: >ABP23147

<400> SEQUENCE: 137
```

Met Lys Arg Lys Gln Thr Phe Ile Phe Ser Met Ile Leu Leu Ser Val
1               5                   10                  15

Ala Ser Ile Gly Leu Arg Ser Phe Trp Thr Asn Pro Phe Thr Thr Gly
            20                  25                  30

Val Met Ile Phe Val Leu Ala Leu Thr Ile Tyr Ala Ile Ile Lys Asp
        35                  40                  45

Leu Arg Arg Arg
    50

```
<210> SEQ ID NO 138
<211> LENGTH: 81
<212> TYPE: PRT
<213> ORGANISM: Bacillus subtilis
<220> FEATURE:
<223> OTHER INFORMATION: >ABP23148

<400> SEQUENCE: 138
```

Met Glu Tyr His Leu Lys Ser Arg Gln Glu Val Glu Asp Phe Ile Arg
1               5                   10                  15

His Glu Val Leu Thr Thr Lys Glu Ala Ala Glu Leu Leu Gly Val Asn
            20                  25                  30

Arg Gln Arg Val Ser Gln Leu Ile Ser Ser Gly Lys Leu Asn Pro Ile
            35                  40                  45

Lys Lys Leu Ser Gly Ile Ser Leu Phe Leu Arg Thr Asp Leu Glu Glu
    50                  55                  60

Lys Lys Lys Glu Leu Glu Ala Gly Arg Lys Lys Tyr Arg Pro Tyr Asp
65                  70                  75                  80

Glu

```
<210> SEQ ID NO 139
<211> LENGTH: 306
<212> TYPE: PRT
<213> ORGANISM: Bacillus subtilis
<220> FEATURE:
<223> OTHER INFORMATION: >ABP23149

<400> SEQUENCE: 139
```

Met Asp Glu Gly Thr Tyr Asn Ile Asp Ile Val Gly Phe His Gly Thr
1               5                   10                  15

Ser Leu Glu Ser Ala Gln Lys Ile Ile Thr Glu Gln Asn Phe Thr Ser
            20                  25                  30

Gly Asp Ile Arg Asn Asp His Trp Leu Gly Gln Gly Ala Tyr Phe Phe
        35                  40                  45

Arg Glu Asp Pro Glu Gln Ala Lys Ile Trp Ala Lys Asn Lys Ile Lys
    50                  55                  60

Gly Ser Glu Thr Ala Val Ile Lys Thr Ile Val Ser Leu Asp Asn Asn
65                  70                  75                  80

Ser Phe Leu Asn Leu Asp Thr Arg Ser Gly Leu Asn Tyr Phe Asn Arg
            85                  90                  95

Tyr Ile Lys Thr Glu Val Lys Arg Lys Ile Leu Glu Glu Lys Ala Glu
            100                 105                 110

Ile Glu Leu Thr Thr Asp Asp His Ser Lys Ile Lys His Ile Tyr Arg

```
              115                 120                 125
Cys Phe Phe Cys Asn Glu Leu Pro Thr Asn Ile Lys Ala Ile Gln Arg
        130                 135                 140

Thr Phe Phe Val Gln Ser Thr Leu Asn Glu Asp Glu Thr Phe Lys Lys
145                 150                 155                 160

Met Asp Val Phe Val Gln Gly Val Gln Val Cys Ile Arg Asp Leu Ser
                165                 170                 175

Val Ile Asp Phe Thr Lys Thr Gly Ile Asn Asn Val Ile Asn Met His
            180                 185                 190

Thr Phe Arg Arg Arg Lys Lys Thr Lys Gln Lys Glu Asn Tyr Arg Lys
        195                 200                 205

Asp Val Met Lys Met Arg Arg Glu Phe Asn Asn Pro Glu Leu Ile Lys
    210                 215                 220

Asp Ala Glu Asn Leu Gly Ile Lys Ile Thr Leu Asn Ser Ser Glu Pro
225                 230                 235                 240

Gly Val Phe Ala Asn Val Asn Gly Glu Arg Tyr Arg Ile Asn Ile Asp
                245                 250                 255

Asp Leu Phe Ser Glu Cys Asp Asp Leu Tyr Tyr His Glu Asp Phe
            260                 265                 270

Lys Leu Asp Asp Phe Ser Ile Thr Arg Asp Ser Asn Gln His Lys Val
        275                 280                 285

Glu Ile Ile Lys Glu Glu Lys Asn Phe Tyr Lys Asn Glu Leu Val Glu
    290                 295                 300

Ala Ala
305

<210> SEQ ID NO 140
<211> LENGTH: 60
<212> TYPE: PRT
<213> ORGANISM: Bacillus subtilis
<220> FEATURE:
<223> OTHER INFORMATION: >ABP23150

<400> SEQUENCE: 140

Met Lys Ser Phe Phe Gln Phe Asp Asp Tyr Asn Ile Ile Asp Val Asn
1               5                  10                  15

Tyr Lys Phe Asn Asn Asn Phe Glu Gly Asp Glu Ala Val Leu Ser Pro
            20                  25                  30

Ile Phe Asp Phe Glu Leu Glu Phe Glu Asp Glu Thr Lys Asp Glu Ala
        35                  40                  45

Asp Leu Ile Leu Gly Ile Glu Leu Gly Ile Arg Ile
    50                  55                  60

<210> SEQ ID NO 141
<211> LENGTH: 62
<212> TYPE: PRT
<213> ORGANISM: Bacillus subtilis
<220> FEATURE:
<223> OTHER INFORMATION: >ABP23151

<400> SEQUENCE: 141

Met Thr Asp Phe Glu Arg Lys Val Tyr Gln Ile Ile Val Asn Met His
1               5                  10                  15

Leu Tyr Gly Lys Asn Pro Thr Leu Asp Asp Leu Lys Arg Lys Thr Gly
            20                  25                  30

Lys Ser Lys Glu Asp Ile Arg Thr Ala Val Lys Ser Leu Leu Met Glu
        35                  40                  45
```

Gly Glu Leu Lys Trp Asp Lys Gln Gln Lys Lys Trp Ile Ile
          50                  55                  60

<210> SEQ ID NO 142
<211> LENGTH: 973
<212> TYPE: PRT
<213> ORGANISM: Bacillus subtilis
<220> FEATURE:
<223> OTHER INFORMATION: >ABP23223

<400> SEQUENCE: 142

Met Thr Asp Ser Trp Gln Asn Gly Phe Ile Glu Lys Ile Asn Arg Asn
1               5                   10                  15

Gly Asn Asn Gly Gly Leu Arg Lys Pro Gln Tyr Gly Ala Leu Ser Ala
            20                  25                  30

Ile Arg Ala His Trp Thr Ile Ser Ser Lys Pro Ala Thr Ile Val Leu
        35                  40                  45

Pro Thr Gly Thr Gly Lys Thr Glu Thr Met Leu Ala Thr Ile Leu Ser
    50                  55                  60

Glu Gln Ile Glu Ser Val Leu Ile Ile Val Pro Ser Asn Leu Leu Arg
65                  70                  75                  80

Asp Gln Thr Phe Glu Lys Ala Lys Ser Phe Gly Ile Leu Pro Asp Leu
                85                  90                  95

Lys Met Val Gly Lys Asn Ile Leu Tyr Pro Asn Thr Val Leu Tyr Lys
            100                 105                 110

Thr Arg Ile Lys Asp Glu Thr Glu Val Trp Glu Trp Phe Ser Glu Ala
        115                 120                 125

Asn Val Ile Val Ser Thr Val Asn Ala Val Asn Gly Leu Ser Thr Ser
130                 135                 140

Ile Leu Asn Lys Leu Val Glu Lys Val Asp Val Leu Met Ile Asp Glu
145                 150                 155                 160

Ala His His Ile Ala Ala Gly Gly Trp Ser Ser Leu Arg Glu Lys Phe
                165                 170                 175

Leu Asn Lys Arg Ile Leu Gln Phe Thr Ala Thr Pro Phe Arg Ala Asp
            180                 185                 190

Gly Lys Lys Ile Asp Gly Asp Ile Ile Tyr Asn Tyr Ser Leu Ser Leu
        195                 200                 205

Ala Gln Lys Asp Gly Tyr Phe Lys Pro Ile Asp Phe Tyr Pro Ile Glu
    210                 215                 220

Glu Phe Asn Glu Glu Leu Gly Asp Ile Gln Ile Ala Glu Lys Ala Val
225                 230                 235                 240

Glu Leu Leu Asn Lys Asp Leu Glu Asp Lys Tyr Met His Gln Leu Leu
                245                 250                 255

Val Arg Ala Asn Ser Lys Lys Arg Ala Glu Glu Leu Tyr Asn Lys Ile
            260                 265                 270

Tyr Ser Ile Tyr Lys Lys Phe Asn Pro Val Leu Ile Ile Ser Gly Gln
        275                 280                 285

Ser Lys Lys Asn Lys Glu Asn Leu Lys Lys Leu Arg Glu Gly Ile Ala
    290                 295                 300

Lys Ile Val Val Cys Val Asp Met Phe Gly Glu Gly Ile Asp Ile Pro
305                 310                 315                 320

Asn Leu Lys Ile Ala Ala Ile His Asp Lys Tyr Lys Ser Leu Pro Ile
                325                 330                 335

Thr Leu Gln Phe Ile Gly Arg Phe Ala Arg Ser Lys Ser Gly Ile Gly
            340                 345                 350

```
Asn Ala Arg Ile Val Thr Asn Ile Ala Asn Asp Asp Leu Lys Asp Ala
        355                 360                 365
Leu Gln Ser Leu Tyr Ser Gln Asp Ala Asp Trp Asn Gln Leu Leu Ser
        370                 375                 380
Met His Ser Ser Asp Ala Ile Gln Thr Glu Ile Ser His Arg Lys Phe
385                 390                 395                 400
Ile Asn Gln Phe Tyr Ser Asn Asp Asn Ile Asn Ile Asp Ile Ser Gln
                405                 410                 415
Ile Lys Met Arg Ile Ser Thr Arg Val Phe Tyr Leu Gly Gly Val His
                420                 425                 430
Trp Asn Arg Lys Gly Trp Arg Ser Val Leu Asn Val Asp Lys Thr Glu
        435                 440                 445
Phe Phe Ile Asn Glu Glu Ser Ser Val Met Ile Leu Ile Glu Ser Ile
        450                 455                 460
Glu Ser Gln Val Asp Trp Ser Asp Gln Lys Asp Ile Ser Lys Tyr Asn
465                 470                 475                 480
Tyr Asp Val Phe Ile Ile Tyr Val Asp Lys Lys Asn Lys Leu Ile Phe
                485                 490                 495
Ile Asn Glu Thr Asn Ala Ser Lys Gly Asn Gln Leu Ile Lys Tyr Met
                500                 505                 510
Phe Ser Glu Ala Asn Gln Ile Ser Gly Glu Arg Val Phe Arg Val Leu
        515                 520                 525
Asp Gly Ile Asn Gln Leu Met Ile Gly Thr Leu Gly Leu Lys Glu Gln
        530                 535                 540
Pro Ser Gly Arg Ile Ser Phe Arg Met Phe Ala Gly Thr Asn Ile Lys
545                 550                 555                 560
Asp Gly Ile Asn Gln Val Ala Arg Ala Ser Thr Thr Lys Ser Asn Leu
                565                 570                 575
Phe Ala Thr Gly Tyr Lys Asp Asn Asn Lys Ile Ser Ile Gly Cys Ser
                580                 585                 590
Tyr Lys Gly Lys Val Trp Met Arg Trp Val Asp Ser Val Val Phe Trp
        595                 600                 605
Arg Lys Trp Cys Gln Lys Ile Gly Ser Gln Ile Leu Asp Ser Ser Ile
        610                 615                 620
Asn Thr Asp Tyr Ile Leu Glu Asn Ser Leu Gln Ser Glu Glu Ile Thr
625                 630                 635                 640
Glu Tyr Pro Arg Gly Ile Pro Tyr Lys Ile Gln Met Pro Val Glu Phe
                645                 650                 655
Glu Leu Ser Asn Ser Glu Leu Lys Ala Phe Tyr Ile Pro Asn Glu Asp
                660                 665                 670
Lys Glu Ile Pro Phe Tyr Leu Cys Glu Phe Asn Asn Pro Arg Leu Asp
        675                 680                 685
Gly Lys Gln Leu Leu Phe Glu Leu Trp Ile Asn Glu Arg Lys Tyr Thr
        690                 695                 700
Phe Ser Gln Thr Leu Lys Glu Arg Gly Phe Val Ile Asn Arg Ile Leu
705                 710                 715                 720
Gly Lys Asp Ile Lys Ile Lys Lys Ser Arg Asn Met Ile Thr Val Glu
                725                 730                 735
Glu Tyr Leu Gln Asp Asn Leu Pro Gln Val Thr Phe Phe Asn Glu Asp
                740                 745                 750
Gly Ser Leu Ser Ile Val Glu Gly Asn Leu Val Asn Lys Lys Pro
        755                 760                 765
Leu Ala Glu Val Leu Phe Pro Lys Glu Lys Leu His Ile Val Asp Trp
```

```
                770                 775                 780
Lys Lys Leu Lys Val Asp Ile Thr Ile Glu Ser Gln Gly Leu Thr Lys
785                 790                 795                 800

Leu Asn Asn Ser Ile Gln Tyr Ala Ser Ile Lys Asn Ile Val Pro Val
                805                 810                 815

Asp Ser Leu Ile Ile Phe Asp Asp Asn Ser Gly Glu Ile Ala Asp
        820                 825                 830

Ile Val Cys Ile Ser Thr Asn Glu Glu His Arg Lys Ile Thr Val Gln
            835                 840                 845

Leu Tyr His Cys Lys Tyr Ser His Gly Thr Asn Pro Gly Ala Arg Leu
            850                 855                 860

Leu Asp Leu Tyr Glu Val Cys Gly Gln Ala Glu Arg Ser Ile Thr Trp
865                 870                 875                 880

Asn Asp Ser Met Val Glu Leu Leu Lys Arg Met Arg Phe Arg Glu Asn
                885                 890                 895

Lys Arg Ile Asn Glu Asn Lys Thr Ser Arg Phe Glu Lys Gly Asn Leu
                900                 905                 910

Ser Asp Leu Lys Thr Ile Glu Asn Gln Ile Arg Ser Gly Phe Glu Thr
            915                 920                 925

Glu Met Lys Ile Ser Ile Val Gln Pro Gly Val Ser Ile Ser Asn Ile
            930                 935                 940

Ser Gln Gln Met Asn Gln Leu Leu Leu Ala Thr Asp Thr Tyr Leu Lys
945                 950                 955                 960

Glu Thr Tyr Gly Ile Asp Leu Asn Cys Tyr Phe Ser Lys
                965                 970

<210> SEQ ID NO 143
<211> LENGTH: 376
<212> TYPE: PRT
<213> ORGANISM: Bacillus subtilis
<220> FEATURE:
<223> OTHER INFORMATION: >ABP23238

<400> SEQUENCE: 143

Met Ser Gln Ala Ile Pro Ser Ser Arg Val Gly Val Lys Ile Asn Glu
1               5                   10                  15

Trp Tyr Lys Met Ile Arg Gln Phe Ser Val Pro Asp Ala Glu Ile Leu
                20                  25                  30

Lys Ala Glu Val Glu Gln Asp Ile Gln Gln Met Glu Glu Asp Gln Asp
            35                  40                  45

Leu Leu Ile Tyr Tyr Ser Leu Met Cys Phe Arg His Gln Leu Met Leu
        50                  55                  60

Asp Tyr Leu Glu Pro Gly Lys Thr Tyr Gly Asn Arg Pro Thr Val Thr
65                  70                  75                  80

Glu Leu Leu Glu Thr Ile Glu Thr Pro Gln Lys Lys Leu Thr Gly Leu
                85                  90                  95

Leu Lys Tyr Tyr Ser Leu Phe Phe Arg Gly Met Tyr Glu Phe Asp Gln
            100                 105                 110

Lys Glu Tyr Val Glu Ala Ile Gly Tyr Tyr Arg Glu Ala Glu Lys Glu
            115                 120                 125

Leu Pro Phe Val Ser Asp Asp Ile Glu Lys Ala Glu Phe His Phe Lys
        130                 135                 140

Val Ala Glu Ala Tyr Tyr His Met Lys Gln Thr His Val Ser Met Tyr
145                 150                 155                 160

His Ile Leu Gln Ala Leu Asp Ile Tyr Gln Asn His Pro Leu Tyr Ser
```

```
                165                 170                 175
Ile Arg Thr Ile Gln Ser Leu Phe Val Ile Ala Gly Asn Tyr Asp Asp
            180                 185                 190
Phe Lys His Tyr Asp Lys Ala Leu Pro His Leu Glu Ala Ala Leu Glu
            195                 200                 205
Leu Ala Met Asp Ile Gln Asn Asp Arg Phe Ile Ala Ile Ser Leu Leu
            210                 215                 220
Asn Ile Ala Asn Ser Tyr Asp Arg Ser Gly Asp Asp Gln Met Ala Val
225                 230                 235                 240
Glu His Phe Gln Lys Ala Ala Lys Val Ser Arg Glu Lys Val Pro Asp
                245                 250                 255
Leu Leu Pro Lys Val Leu Phe Gly Leu Cys Trp Thr Leu Cys Lys Ala
                260                 265                 270
Gly Gln Thr Gln Lys Ala Phe Gln Phe Ile Glu Glu Gly Leu Asp His
                275                 280                 285
Ile Thr Ala Arg Ser His Lys Phe Tyr Lys Glu Leu Phe Leu Phe Leu
                290                 295                 300
Gln Ala Val Tyr Lys Glu Thr Val Asp Glu Arg Lys Ile His Asp Leu
305                 310                 315                 320
Leu Ser Tyr Phe Glu Lys Lys Asn Leu His Ala Tyr Ile Glu Ala Cys
                325                 330                 335
Ala Arg Ser Ala Ala Val Phe Glu Ser Ser Cys His Phe Glu Gln
                340                 345                 350
Ala Ala Ala Phe Tyr Arg Lys Val Leu Lys Ala Gln Glu Asp Ile Leu
                355                 360                 365
Lys Gly Glu Cys Leu Tyr Ala Tyr
                370                 375

<210> SEQ ID NO 144
<211> LENGTH: 200
<212> TYPE: PRT
<213> ORGANISM: Bacillus subtilis
<220> FEATURE:
<223> OTHER INFORMATION: >ABP23224

<400> SEQUENCE: 144

Met Ser Lys Ile Pro Pro Glu Lys Tyr Tyr Glu Ala Cys Ile Thr Tyr
1               5                   10                  15
His Leu Val Asn Tyr Phe Glu Phe Thr Leu Glu Lys Lys Ile Tyr Pro
            20                  25                  30
Phe Ser Ile Ser Gln Ile Glu Glu Lys Lys Gly Tyr Asp Phe Gly
            35                  40                  45
Tyr Lys Met Ser Glu Lys Ser Phe Phe Ile Gln Tyr Lys Arg Pro Tyr
50                  55                  60
Lys Val Ile Pro Lys Asp Thr Tyr His Trp Lys Ile Glu Ile Glu Gln
65                  70                  75                  80
Leu Lys Thr Ile Asn Arg Lys Ala Asn Asn Ile Asn Thr Tyr Tyr Ala
                85                  90                  95
Leu Pro Ser Phe Gly Asp Ser Met Gly Trp Tyr Glu Ala Leu Asp Asn
            100                 105                 110
Thr Phe Phe Val Asn Ser Arg Ser Leu Glu Tyr Gln Ile Lys Gln Ile
            115                 120                 125
Asn Arg Gly Arg Asn Ile Lys Thr Thr Phe Ile Ser Pro Glu Lys Ile
            130                 135                 140
Leu Leu Asp Lys Phe Tyr Arg Ile Ser Cys Asn Ile Val Gly Asp Leu
```

```
                145                 150                 155                 160
His Ser Val Ala Val Ser Gln Lys Asn Ile Asn Ser Lys Ile Gly Asn
                    165                 170                 175

Ile Thr Asn Tyr Ile Lys Gly Leu Asn Glu Asp Val Lys Ser Ser Thr
                    180                 185                 190

Trp Leu Tyr Ile Leu Glu Glu Asp
                    195                 200

<210> SEQ ID NO 145
<211> LENGTH: 623
<212> TYPE: PRT
<213> ORGANISM: Bacillus subtilis
<220> FEATURE:
<223> OTHER INFORMATION: >ABP23225

<400> SEQUENCE: 145

Met Lys Tyr Glu Asn Val Glu Val Leu Gly Ser Tyr Ser Val Arg Glu
1               5                   10                  15

Gly Gly Ser Ile Asn Phe Ser Met Gly Lys Asn Leu Glu Leu Gly Thr
                20                  25                  30

Glu Ile Asn Thr Tyr Ile His Glu Leu Phe His Met His Leu Thr Asn
            35                  40                  45

Tyr Ser Ser Leu Gly Phe Leu Leu Leu Phe Glu Lys Glu Cys Asn
        50                  55                  60

Leu Ser Leu Glu Tyr Gln Asp Glu Leu His Tyr Asn Gln Ile Lys Glu
65                  70                  75                  80

Leu Ser Thr Ile Ile Phe Asn Arg Thr Val Asp Val Gln Glu Val Tyr
                85                  90                  95

Ala Asn Asn Gln Glu Leu Leu Trp Leu Glu Asn Asn Ile Asn Ser Glu
            100                 105                 110

Phe Lys Glu Lys Ser Phe Lys Leu Lys Pro Lys Lys Tyr Gln Glu Tyr
        115                 120                 125

Cys Asn Lys Leu Asn Ile Ile Thr Asn Asp Met Arg Leu Asn Asn Glu
    130                 135                 140

Glu Lys Arg Tyr Trp Ile Asp Arg Val Cys Phe Tyr Ala Leu Asn Ile
145                 150                 155                 160

Gln Ile Phe Ser Asp Lys Phe Ile Glu Ala Leu Lys Ser Arg Gln Lys
                165                 170                 175

Leu Ser Glu Tyr Leu Ser Arg Asn His Pro Asn Lys Arg Leu Asp Glu
            180                 185                 190

Ala Leu Val Lys Tyr Ser Lys Asn Glu Lys Phe Asp Gly Val Val Glu
        195                 200                 205

Ile Arg Ile Gln Asp Ile Leu Ser Lys Ile Lys Lys Ile Asn Ile Ile
    210                 215                 220

Lys Tyr Phe Asn Glu Ile Leu Ser Gln Leu Glu Pro Asn Ala Thr Asn
225                 230                 235                 240

Phe Lys Ile Gly Asp Tyr Leu Cys Glu Asn Asp Ile Lys Lys Phe Ile
                245                 250                 255

Glu Leu Asn Gln Lys Arg Met Asp Glu Arg Val Lys Leu Phe Asp Phe
            260                 265                 270

Tyr Asn Leu Asp Val Ile Lys Val Asp Asp Ile Ser Asn His Leu Asn
        275                 280                 285

Phe Gly Ile Phe Ala Ile Lys Asn Tyr Glu Ser Thr Ile Asn Lys Glu
    290                 295                 300

Asn Phe Tyr Tyr Ile Thr Glu Ala Leu Ile Asn Leu Thr Pro Ser Tyr
```

```
              305                 310                 315                 320
        Ile Ser Glu Glu Val Ser Tyr Asp Phe Leu Asn Asn Pro Lys Ile Lys
                        325                 330                 335

Val Ile Gly Ile Pro Ser Gln Glu Phe Asp Ile Ala Lys Met Lys Pro
                        340                 345                 350

Asn Tyr Ile Glu Val Lys Asp Thr Pro Ile Val Leu Ile Asp Ser
                        355                 360                 365

Tyr Asn Thr Ala Lys Lys Ile Leu Lys Val Leu Leu Asn Gly Glu Leu
        370                 375                 380

Tyr Val Gly Asp Leu Tyr Glu Gln Thr Val Lys Asn Phe Ser Thr Ile
        385                 390                 395                 400

Leu Phe Phe Arg Glu Arg Thr Glu Pro Lys Ile Ile Tyr Ile Phe Pro
                        405                 410                 415

Thr Leu Lys Lys Met Ser Ile Arg Leu Val Lys Glu Leu Gly Ile Glu
                        420                 425                 430

Asp Ile Leu Val Tyr Ser Lys Asp Thr Arg Phe Lys Lys Ile Leu Ser
                        435                 440                 445

Ile Phe Asn Cys Glu Val Glu Met Leu Lys Phe Ile Lys Trp Ile Phe
                        450                 455                 460

Ser Phe Ile Met Lys Ser Ser Cys Ile Phe Thr Ser Ile Gly Asp Pro
        465                 470                 475                 480

Ala Thr Lys Met Ser Phe Asn Leu Thr Arg Ser Leu Phe Asp Asp Val
                        485                 490                 495

Met Lys Ile Lys Ile Pro Asn Tyr Tyr Ile His Trp Ala Ala Leu Pro
                        500                 505                 510

Thr Lys Lys Thr Ile Gly Glu Pro Phe Tyr Ser Leu Met Glu Phe Glu
                        515                 520                 525

Asn Gly Glu Asn Ile Gly Ser Phe Lys Ala Thr Asn Gln Asn Thr Ile
                        530                 535                 540

Ile Phe Phe Leu Asn Lys Asn Asp Ala Val Asn Tyr Arg Lys Lys Ile
        545                 550                 555                 560

Phe Thr Thr Asp Ser Met Ala His Lys Leu Glu Val Val Gly Ile Asp
                        565                 570                 575

Arg His Tyr Trp Asn Ile Ile Glu Lys Tyr Ile Leu Glu Thr Gly Ile
                        580                 585                 590

Asn Ile Cys Ile Cys Thr Asp Val Asn Asn Ile Gly Lys Ile Met
                        595                 600                 605

Lys Leu Lys Glu Val Asp Asn Ile Ile Thr Gln Phe Ser Lys Val
                        610                 615                 620

<210> SEQ ID NO 146
<211> LENGTH: 65
<212> TYPE: PRT
<213> ORGANISM: Bacillus subtilis
<220> FEATURE:
<223> OTHER INFORMATION: >ABP23226

<400> SEQUENCE: 146

Met Lys Phe Lys Leu Thr Leu Cys Ala Val Ile Ala Leu Ile Gly Val
1               5                   10                  15

Ser Phe Ile Ser Ser Ser Leu Gly Asn Glu Val Asn Val Ala Ser Arg
                20                  25                  30

Asn Met Thr Ser Lys Ala Ala Asn Asp Ser Thr Asn Ser Leu Ala Asp
                35                  40                  45

Lys Ala Ile Phe Asp Lys Glu Met Thr Ile Ala Glu Asn Gly Thr Leu
```

```
                    50                  55                  60
Gly
 65

<210> SEQ ID NO 147
<211> LENGTH: 378
<212> TYPE: PRT
<213> ORGANISM: Bacillus subtilis
<220> FEATURE:
<223> OTHER INFORMATION: >ABP23227

<400> SEQUENCE: 147

Met Arg Ser Leu Gly Thr Ile Ser Ser Pro His Val Gly Met Lys Ile
 1               5                  10                  15

Asn Glu Trp Asn Arg His Ile Gln Lys Phe Asn Val Thr Asp Ala Glu
                20                  25                  30

Met Leu Lys Ala Glu Ile Glu Arg Asp Ile Asp Ile Met Glu Glu Asp
             35                  40                  45

Gln Asp Leu Leu Ile Tyr Tyr Gln Leu Ile Ala Phe Arg His Gln Leu
         50                  55                  60

Met Ile Asp Tyr Val Ile Pro Thr Glu Gly Asn Gln Met Glu Leu Ser
 65                  70                  75                  80

Glu Tyr Leu Lys Arg Ile Glu Gly Ser Asn Arg Lys Met Glu Lys Leu
                 85                  90                  95

Val Glu Tyr Tyr Tyr Phe Phe Gln Gly Met Tyr Glu Phe Lys Glu
                100                 105                 110

Gly Asn Phe Leu Ser Ala Ile Thr Phe Tyr Gln Lys Ala Glu Asn Thr
            115                 120                 125

Ile Pro Tyr Ile Ser Asp Glu Ile Glu Arg Ala Glu Phe Tyr Phe Lys
        130                 135                 140

Met Ala Glu Val Phe Tyr His Met Lys Gln Thr His Val Ser Met His
145                 150                 155                 160

Tyr Ser Ser Gln Ala Tyr Asn Ile Tyr Lys Thr His Asp Leu Tyr Ser
                165                 170                 175

Val Arg Arg Ile Gln Cys His Phe Val Ile Ala Gly Asn Tyr Asp Asp
            180                 185                 190

Leu Glu Ser His Glu Lys Ala Leu Pro His Leu Glu Gln Ala Leu Lys
        195                 200                 205

Gly Ala Arg Leu Leu Glu Ser Lys Asn Lys Arg Ile Tyr Gly Gln Ala
    210                 215                 220

Leu Phe Asn Ile Gly Asn Cys Tyr Leu Lys Met Gly Glu Leu Thr Lys
225                 230                 235                 240

Ala Ala Lys Tyr Met Glu Lys Ser Ile Phe Gln Phe Lys Lys Ser Asn
                245                 250                 255

Phe Asn Asn Leu Thr Gln Ala Tyr His Asp Leu Ala Leu Ile Tyr Phe
            260                 265                 270

Leu Gln His Lys Gln Glu Gln Ala Met Asp Cys Phe Arg Lys Gly Val
        275                 280                 285

Arg Phe Ala Cys Lys Phe Asp Asp Leu Phe Lys Ile Met Phe Glu
    290                 295                 300

Gly Leu Gln Thr Leu Phe Ile Lys Lys Gly Ala Ser Ile Leu Leu
305                 310                 315                 320

Asn Val Phe Asn Lys Leu Glu Thr Ser Gln Gly Tyr Pro Tyr Met Glu
                325                 330                 335

Glu Leu Ala Leu Leu Ala Ala Lys Phe Tyr Thr Glu Ile Gly Gln Met
```

```
                340             345             350
Asp Asp Ser Val Ile Cys Phe Lys Lys Met Val His Ala Arg Lys Gln
            355                 360             365

Ile Gln Arg Gly Asp Cys Leu Tyr Glu Ile
    370                 375

<210> SEQ ID NO 148
<211> LENGTH: 107
<212> TYPE: PRT
<213> ORGANISM: Bacillus subtilis
<220> FEATURE:
<223> OTHER INFORMATION: >ABP23228

<400> SEQUENCE: 148

Met Thr Val Arg Glu Glu Leu Ile Lys Arg Asn Pro Thr Pro Ile Met
1               5                   10                  15

Lys Asn Ile Leu Lys Arg Tyr Glu Glu Ala Lys Glu Phe Ile Gln His
            20                  25                  30

Ser Thr Lys Glu Gln Phe Glu Glu Asp Leu Ser Arg Val Lys Asn Lys
        35                  40                  45

Leu Asp Thr Leu Thr Arg Ala Tyr Leu Glu Ser Ala Asn Asp Tyr Met
50                  55                  60

Asn Pro Met Leu Arg Glu Met Tyr Lys Thr Glu Lys Leu Leu Lys Glu
65                  70                  75                  80

Tyr Asp Glu Thr Ala Ser Val Val Ile Thr Ala Ile Gln Ser Ser Lys
                85                  90                  95

Val Glu Ile Val Leu Pro Ser Gln Asn Gln Ile
            100                 105

<210> SEQ ID NO 149
<211> LENGTH: 130
<212> TYPE: PRT
<213> ORGANISM: Bacillus subtilis
<220> FEATURE:
<223> OTHER INFORMATION: >ABP23229

<400> SEQUENCE: 149

Met Asp Leu Phe Glu Glu Cys Ile Glu Ala Leu Lys Asp Pro Lys Glu
1               5                   10                  15

Ile Leu Ser Asp Glu Leu Thr Glu Gln Tyr Phe Glu Thr Leu Asn Asn
            20                  25                  30

Lys Phe Pro Ile Thr Ser Trp Ala Arg Ile Asp Trp Asp Lys Val Pro
        35                  40                  45

Gln Lys Glu Ser Ile Glu Thr Tyr Asp Asp Leu Tyr Asn Trp Leu Lys
    50                  55                  60

Phe Gln Gly Ile Val Asp Thr Thr Ile Asn Leu Leu Trp Asn Pro Ser
65                  70                  75                  80

Asp Val Pro Val Val Arg Thr Thr Leu Glu Asn Ala Leu Glu Val Leu
                85                  90                  95

Asp Asp Val Leu Ala Val Gly Ser Asp Thr Phe Met Tyr Ser Asp His
            100                 105                 110

Gly Phe Val Ile Glu Phe Phe His Asp Gly Glu Val Thr Ile Gly Arg
        115                 120                 125

Ser Glu
    130

<210> SEQ ID NO 150
<211> LENGTH: 51
```

```
<212> TYPE: PRT
<213> ORGANISM: Bacillus subtilis
<220> FEATURE:
<223> OTHER INFORMATION: >ABP23230

<400> SEQUENCE: 150

Met Ala Gln Leu Phe Thr Ala Gly Leu Phe Leu Phe Gln Ile Gly Leu
1               5                   10                  15

Ala Ile Met Glu Thr Glu Lys Gly Leu Leu Tyr Lys Lys Ser Ala Glu
                20                  25                  30

Gln Phe Asn Asn Leu Leu Leu Leu Asn Glu Ile Arg Leu Thr Tyr Thr
            35                  40                  45

Leu Lys Phe
    50

<210> SEQ ID NO 151
<211> LENGTH: 156
<212> TYPE: PRT
<213> ORGANISM: Bacillus subtilis
<220> FEATURE:
<223> OTHER INFORMATION: >ABP23231

<400> SEQUENCE: 151

Met Glu Thr Glu Lys Met Gly Gln Leu Tyr Gln Gln Ile Ala Glu Gln
1               5                   10                  15

Leu Asn Glu Met Ile Pro Ser Glu Trp Thr Lys Ile Val Leu Tyr Ala
                20                  25                  30

Glu Ile Leu Asp Asp Ser Ser Glu Val Tyr Phe Phe Phe Asn Thr Pro
            35                  40                  45

Gln Ser Glu Glu Tyr Ile Tyr Ser His Asp Ile Pro Lys Gln Phe Asp
    50                  55                  60

Val Ser Lys Lys Ile Tyr Val Ser Leu Leu Ile Glu Leu Gln Glu Leu
65                  70                  75                  80

Phe Glu Glu Leu Arg Glu Glu Phe Lys Ala Asn Asn Gln Asp Thr Trp
                85                  90                  95

Thr Asn Leu Thr Leu Lys Leu Glu Asn Thr Gly Lys Phe Ser Ile Asp
            100                 105                 110

Tyr Asp Tyr Thr Asp Val Ile Ala Ser Asp Leu Asn Gly Thr Gln Arg
        115                 120                 125

Gln Val Val Trp Glu Tyr Lys Asn Leu Gly Ile Leu Pro Glu Asp Lys
    130                 135                 140

Glu Asp Lys Asp Phe Val Ile Asn Tyr Phe Ser Leu
145                 150                 155

<210> SEQ ID NO 152
<211> LENGTH: 670
<212> TYPE: PRT
<213> ORGANISM: Bacillus subtilis
<220> FEATURE:
<223> OTHER INFORMATION: >ABP23232

<400> SEQUENCE: 152

Met Val Met Lys Val Phe Glu Ala Lys Thr Leu Leu Ser Glu Ala Thr
1               5                   10                  15

Asp Arg Ala Lys Glu Tyr Lys Glu Leu Arg Thr Gln Met Val Asn Leu
                20                  25                  30

Arg Lys Ala Leu Lys Gly Val Ala Asp Leu Ser Asp Ser Glu Phe Ser
            35                  40                  45

Gly Lys Gly Ala Ser Asn Ile Lys Ala Phe Tyr His Asp His Val Gly
```

```
              50                  55                  60
Val Ala Asp Gln Trp Ile Asp Tyr Ile Asp Met Lys Ile Ala Phe Phe
 65                  70                  75                  80

Asn Ser Ile Ala Gly Ala Ala Glu Asp Lys Gly Leu Ser Asp Ala Tyr
                 85                  90                  95

Ile Glu Glu Ser Phe Leu Glu His Glu Leu Ala Asn Ala Asn Lys Lys
            100                 105                 110

Ser Lys Ser Ile Met Ser Glu Gln Lys Lys Ala Met Lys Asp Ile Leu
        115                 120                 125

Asn Asp Ile Asp Asp Ile Leu Pro Leu Asp Leu Phe Ser Thr Glu Thr
130                 135                 140

Phe Lys Asp Glu Leu Ala Asp Ala Asn Asp Lys Arg Lys Lys Thr Leu
145                 150                 155                 160

Glu Lys Leu Asp Ala Leu Asp Glu Asp Leu Lys Thr Glu Tyr Ala Leu
                165                 170                 175

Ser Glu Pro Asn Glu Gln Phe Ile Lys Ser Asp Phe Gln Lys Leu Gln
            180                 185                 190

Glu Ala Thr Gly Lys Gly Lys Asn Ala Thr Pro Ile His Tyr Asn Ala
        195                 200                 205

Lys Ala Tyr Arg Glu Ser Asp Ile His Lys Lys Gly Asp Ile Glu
210                 215                 220

Lys Arg Thr Glu Ala Tyr Leu Lys Ile Lys Glu Glu Ala Lys Glu
225                 230                 235                 240

Arg Glu Ile Glu Lys Leu Lys Glu Arg Leu Lys Asn Tyr Asp Tyr Ala
                245                 250                 255

Asp Ala Asp Glu Phe Tyr Glu Met Ala Lys Thr Ile Gly Tyr Glu Asn
            260                 265                 270

Leu Thr Ala Glu Gln Gln Arg Tyr Phe Thr Gln Ile Glu Asn Thr Arg
        275                 280                 285

Glu Leu Glu Ala Gly Phe Lys Gly Val Ala Val Gly Leu Tyr Asp Ser
290                 295                 300

Gly Lys Asp Ala Val Val Gly Leu Trp Asp Met Val Thr Asp Pro Gly
305                 310                 315                 320

Gly Thr Val Glu Ala Ile Thr Gly Ala Met Ala His Pro Ile Lys Thr
                325                 330                 335

Tyr Glu Ala Ile Ser Ala Ala Ile Glu Glu Ser Tyr Gln Lys Asp Met
            340                 345                 350

Val Asn Gly Asp Thr Tyr Ser Arg Ala Arg Trp Val Ser Tyr Ala Val
        355                 360                 365

Gly Thr Val Val Thr Ser Ile Val Gly Thr Lys Gly Val Gly Ala Val
370                 375                 380

Ser Lys Thr Gly Thr Ala Ala Lys Val Thr Lys Val Lys Thr Ala
385                 390                 395                 400

Ala Ser Lys Ser Ala Thr Ala Gln Lys Ala Ile Thr Val Ser Lys Gln
                405                 410                 415

Thr Val Asp His Ile Lys Gln Lys Val Asn Thr Gly Ile Glu Val Ser
            420                 425                 430

Lys Lys His Val Lys Thr Lys Leu Asn Gln Ile Gly Asp Leu Thr Leu
        435                 440                 445

Ala Asp Ile Leu Pro Tyr His Pro Arg His Asp Leu Val Pro Ala Gly
450                 455                 460

Val Pro Tyr Asn Ala Val Asn Gly Val Thr Leu Lys Glu Gly Leu Gln
465                 470                 475                 480
```

```
Lys Phe Ala Lys Val Ile Leu Pro Lys Pro Tyr Gly Thr Ser Ser Ser
                485                 490                 495

Gly Arg Arg Thr Pro Ala Pro His Val Pro Pro Val Thr Val Lys Tyr
            500                 505                 510

Gly Glu His Phe Ala Arg Trp Ser Arg Lys Val Leu Lys Pro Asn
        515                 520                 525

Ile Ile Tyr Lys Thr Lys Glu Gly Tyr Thr Thr Thr Asp Asn Tyr
    530                 535                 540

Gly Arg Ile Thr Ser Val Lys Ala Asp Leu Gln Leu Gly Glu Ala Lys
545                 550                 555                 560

Arg Asn Gln Tyr Ala Gln Thr Asn Ala Gly Lys Pro Gln Asp Arg Lys
                565                 570                 575

Pro Asp Asp Gly His Leu Ile Ala Thr Gln Phe Lys Gly Ser
            580                 585                 590

Gly Gln Phe Asp Asn Ile Val Pro Met Asn Ser Gln Ile Asn Arg Ser
            595                 600                 605

Gly Gly Lys Trp Tyr Glu Met Glu Gln Glu Trp Ala Lys Ala Leu Lys
            610                 615                 620

Glu Glu Pro Pro Lys Arg Val Asn Val Asn Ile Glu Ser Ile Tyr Lys
625                 630                 635                 640

Gly Asp Ser Leu Arg Pro Thr Lys Phe Ile Ile Glu Tyr Thr Ile Gly
                645                 650                 655

Asn Lys Thr Lys Phe Val Thr Ile Lys Asn Gln Ala Gly Gly
                660                 665                 670

<210> SEQ ID NO 153
<211> LENGTH: 112
<212> TYPE: PRT
<213> ORGANISM: Bacillus subtilis
<220> FEATURE:
<223> OTHER INFORMATION: >ABP23233

<400> SEQUENCE: 153

Met Asp Lys Asp Phe Leu Ile Ile Lys Ile Asp Ile Gln Lys Gly
1               5                   10                  15

Asp Thr Leu Thr Asn Arg Ala Cys Gly Asn Trp Asp Met Lys Leu Ser
                20                  25                  30

Arg Ala Lys Glu Cys Lys Arg Ala Ile Val Val Arg Ser Gly Val Ile
            35                  40                  45

Leu Asn Val Tyr Lys Ile Val Asp Ala Trp Glu Ser Asp Glu Pro Ala
    50                  55                  60

Lys Ile Thr Lys Thr Asn Asn Arg Val Arg Phe Gln Leu Ala Glu Cys
65                  70                  75                  80

Arg Asp Tyr Ser Tyr Leu Ile Gly Gly Thr Leu Lys Thr Lys Thr Gln
                85                  90                  95

Asn Pro Val Ser Ser Leu Ser Leu Glu Thr Leu Met Glu Leu Val Lys
            100                 105                 110

<210> SEQ ID NO 154
<211> LENGTH: 306
<212> TYPE: PRT
<213> ORGANISM: Bacillus subtilis
<220> FEATURE:
<223> OTHER INFORMATION: >ABP23234

<400> SEQUENCE: 154

Met Tyr Leu Tyr Lys Val Asn Asn Gln Asn Gln Ile Glu Asp Ile Arg
```

```
              1               5                  10                 15
           Glu Lys Pro Phe Lys Glu Lys Glu Ile Gln Asp Leu Cys Glu Ala
                            20                 25                 30

Asn Leu Gln Gln Met Leu Gly Leu Gly Phe Val Lys Ser Glu Phe Arg
                            35                 40                 45

Ile Ser Asn Phe Arg Ile Asp Thr Leu Ala Phe Asp Ala Glu Thr Lys
                50                     55                 60

Ser Phe Val Ile Ile Glu Tyr Lys Asn Thr Lys Asn Phe Ser Val Val
            65                     70                 75                 80

Asp Gln Gly Tyr Ala Tyr Leu Ala Ala Met Leu Asn His Lys Ala Asp
                                85                 90                 95

Phe Ile Leu Glu Tyr Asn Glu Asn His Asp Leu Pro Leu Lys Arg Asp
                           100                105                110

Asp Val Asp Trp Ser Gln Ser Lys Val Ile Phe Ile Ser Pro Val Phe
                           115                120                125

Thr Val Tyr Gln Lys Gln Ser Ile His Phe Lys Asp Leu Pro Ile Glu
                           130                135                140

Leu Trp Glu Ile Lys Arg Tyr Glu Asn Asp Leu Ile Gln Leu Asn Gln
           145                150                155                160

Met Lys Ala Asp Gly Val Ser Glu Ser Ile Lys Thr Ile Ser Arg Gln
                           165                170                175

Ser Glu Thr Ile Gln Glu Val Ser Lys Glu Ile Lys Val Phe Ser Glu
                           180                185                190

Glu Asp His Leu Ala Asp Lys Pro Phe Asp Ile Ile Glu Leu Tyr Gln
                           195                200                205

Gln Leu Lys Glu Phe Ile Phe Asn Leu Asp Asp His Ile Ser Ile Lys
                           210                215                220

Pro Thr Lys Leu Tyr Ile Ala Phe Thr Ser Ser Lys Arg Asn Phe Val
           225                230                235                240

Asp Ile Leu Leu Leu Lys Ser Gly Leu Lys Val Trp Val Asn Met Lys
                           245                250                255

Lys Gly Glu Leu His Asp Pro Glu Glu Lys Met Arg Asp Val Ser Glu
                           260                265                270

Thr Gly His Trp Gly Asn Gly Asp Tyr Glu Ile Phe Ile Lys Asp Asp
                           275                280                285

Glu His Ile Glu Tyr Ile Met Gly Leu Ile Lys Gln Ser Tyr Glu Lys
                           290                295                300

Asn Lys
           305

<210> SEQ ID NO 155
<211> LENGTH: 273
<212> TYPE: PRT
<213> ORGANISM: Bacillus subtilis
<220> FEATURE:
<223> OTHER INFORMATION: >ABP23235

<400> SEQUENCE: 155

Met Lys Lys Arg Phe Ile Leu Leu Gly Leu Phe Ala Ser Val Phe Met
            1                5                 10                 15

Leu Ala Val Tyr Ile Ser Phe Gln Asn Lys Asn Thr His Pro Val Gln
                            20                 25                 30

Ser Pro Val Ile His Pro Glu Glu Asp Arg Ile Phe Phe Ile Tyr Ser
                            35                 40                 45

Asn Pro Phe Ile Lys Glu Ser Thr Leu Leu Ser Thr Ser Thr Gly Glu
```

```
                50                  55                  60
Arg Phe Asn Arg Arg Thr Phe Lys Val Ala Asp Val Pro Phe Ile Gln
 65                  70                  75                  80

Thr Lys Ser Tyr Lys Ser Thr Asp Ile Val Leu Leu Ala Glu His Glu
                 85                  90                  95

Pro Phe Tyr Tyr Thr Leu Lys Lys Asp Val Ile Lys Glu His Pro Leu
                100                 105                 110

Ser Asp Pro Phe Ala Phe Trp Tyr Glu Gly Lys Asp Val Ser Val Lys
            115                 120                 125

Ala Tyr Asn Val Asp Thr Thr Gly Asn Glu Ile Arg Ile Asn Asp Lys
            130                 135                 140

Lys Met Lys Lys Glu Tyr Thr Leu Thr Leu Pro Ser Leu Val Thr Met
145                 150                 155                 160

Gly Ala Ser Asp Glu Asn Tyr Ile Tyr Ile Ile Gln Ser Met Ser Ile
                165                 170                 175

Tyr Val Ile Asp Arg Lys Thr Glu Glu Met Ile Glu Thr Leu Ser Leu
            180                 185                 190

Ala Ser Tyr Ala Asp Gln Phe Ala Asp Ser Lys Glu Phe Ile Val Ala
            195                 200                 205

Ser Ser Glu His Glu Leu Thr Val Ile Glu Lys Glu Thr Trp Lys Ala
210                 215                 220

Thr Tyr Ile Ala Tyr Pro Glu Asp Leu Glu Tyr Ala Asp Thr Val Tyr
225                 230                 235                 240

Tyr Asp Lys Glu Ser Gly Ser Phe Tyr Val Thr Tyr Glu Asp Lys Glu
                245                 250                 255

Gly Glu Ala Asn Leu Leu Glu Tyr Gly Lys Glu Phe Phe Ile His Ile
            260                 265                 270

Val

<210> SEQ ID NO 156
<211> LENGTH: 47
<212> TYPE: PRT
<213> ORGANISM: Bacillus subtilis
<220> FEATURE:
<223> OTHER INFORMATION: >ABP23236

<400> SEQUENCE: 156

Met Tyr Ile Val Ala Gln Glu Glu His Lys Gln Gly Ile Gly Gly Tyr
 1               5                  10                  15

Val Gly Val Phe Asp Ile His Ser Lys Lys Met Leu Tyr Gln Phe Asp
                20                  25                  30

Leu Pro Glu Glu Gln Val Lys Val Gln Asp Phe Val Val Asp
            35                  40                  45

<210> SEQ ID NO 157
<211> LENGTH: 285
<212> TYPE: PRT
<213> ORGANISM: Bacillus subtilis
<220> FEATURE:
<223> OTHER INFORMATION: >ABP23237

<400> SEQUENCE: 157

Met Gly Gly Leu Tyr Leu Ser Asp Leu Cys Ser Met Tyr Gln Lys Asp
 1               5                  10                  15

Lys Phe Phe Thr Gly Phe Val Pro Glu Glu Leu Leu Thr Tyr Ala Tyr
                20                  25                  30

Glu Leu Phe Pro Ser Ser Glu Lys Glu Thr Val Thr Ala Leu Leu Asn
```

```
                  35                  40                  45
        Cys Ser Met Gly Ser Lys Ala Lys Ser Phe Val Met Phe Thr Ser Lys
         50                  55                  60

Gly Leu Tyr Trp Lys Arg Phe Gly Glu Gln Glu Gly Cys Val Thr Trp
         65                  70                  75                  80

Glu Ala Phe Thr Asp Ile Gln Ser Ile Lys Ser Thr Asp Asp Tyr Glu
                         85                  90                  95

Ile Trp Phe Asp Gly Val Glu Val Phe Asp Val Gly Phe Ser Ser Tyr
                        100                 105                 110

Pro Ala Asp Leu Leu Ala Glu Leu Leu Arg Ile Ile Gln Gln Ser Leu
                        115                 120                 125

Ser Glu Asn Gly Leu Asp Leu Leu Thr Glu Pro Arg Ile Asp His Val
        130                 135                 140

Ser Val Ser Ala Ser Glu Leu Arg Glu Ile Ser Ile Leu Phe Gln Asn
        145                 150                 155                 160

Lys His Asp Lys Met Phe Gly Leu Thr Asn Gly Leu Val Gly Asn
                        165                 170                 175

Glu Ile Ser Glu Lys Arg Glu Val Arg Leu Arg Lys Arg Leu His Ile
                        180                 185                 190

Pro Lys Asp Gln Glu Met Ile Ser Phe Trp Ser Thr Phe Pro Val Lys
                        195                 200                 205

Gln Thr Asp Gly Ile Thr Leu Thr Asp Lys Gly Ile Tyr Phe Ser Asp
        210                 215                 220

Pro Phe Leu Arg Leu Phe Tyr Pro Trp His Val Phe Lys Glu Thr Pro
        225                 230                 235                 240

Val Met Leu Lys Asp Gln Glu Leu Ile Val Gly Lys Lys Asn Val Ile
                        245                 250                 255

Gln Leu Leu Glu Asn Leu Met Pro Ala Lys Asp Val Phe Ala Phe Leu
                        260                 265                 270

Glu Gln Val Lys Arg Arg Ile Ser Ala Val Thr Ser Ser
                        275                 280                 285

<210> SEQ ID NO 158
<211> LENGTH: 37
<212> TYPE: PRT
<213> ORGANISM: Bacillus subtilis
<220> FEATURE:
<223> OTHER INFORMATION: >ABP23502

<400> SEQUENCE: 158

Met Phe Val Leu Leu Leu Tyr Pro Lys Gln Ser Leu Leu Ile His Tyr
 1               5                  10                  15

Ser Ser Lys Ala Glu Lys Gly Arg Thr Leu Phe Ile Leu Phe Leu Ala
                20                  25                  30

Ser Thr Leu Asn Ile
         35

<210> SEQ ID NO 159
<211> LENGTH: 41
<212> TYPE: PRT
<213> ORGANISM: Bacillus subtilis
<220> FEATURE:
<223> OTHER INFORMATION: >ABP24563

<400> SEQUENCE: 159

Met Phe Asn Gly Lys His Leu Lys Val Lys Ala Cys Phe Lys Ser Asn
 1               5                  10                  15
```

Ala Phe Leu Ile Ile Lys Glu Ser Val Tyr Ile Phe Ile Ser Pro
                20                  25                  30

Leu Pro Asp Asp Ala Phe Arg Thr Pro
            35                  40

<210> SEQ ID NO 160
<211> LENGTH: 484
<212> TYPE: PRT
<213> ORGANISM: Bacillus subtilis
<220> FEATURE:
<223> OTHER INFORMATION: >ABP24564

<400> SEQUENCE: 160

Met Asp Gln Arg Glu Lys Met Asp Thr Ala Gly Gly Asn Thr Ser Cys
1               5                   10                  15

Lys His Lys Lys Phe Phe Arg Lys Ile Thr Ile Ile Ser Thr Phe Gly
                20                  25                  30

Gly Leu Leu Phe Gly Tyr Asp Thr Gly Val Ile Asn Gly Ala Leu Pro
            35                  40                  45

Phe Met Ala Gln Arg Asp Gln Leu Asp Leu Thr Pro Phe Thr Glu Gly
        50                  55                  60

Leu Ile Thr Ser Ser Leu Leu Phe Gly Ala Ala Phe Gly Ser Leu Ala
65                  70                  75                  80

Gly Gly Arg Leu Ala Asp Arg Ile Gly Arg Arg Lys Thr Ile Leu Asn
                85                  90                  95

Leu Ala Phe Leu Phe Phe Ile Ala Thr Ile Gly Cys Ser Phe Ala Pro
            100                 105                 110

Asn Thr Ser Val Met Ile Ile Cys Arg Ser Leu Leu Gly Leu Ala Val
        115                 120                 125

Gly Ala Ala Ser Val Thr Val Pro Ala Phe Leu Ala Glu Met Ser Pro
130                 135                 140

Ala Glu Gln Arg Gly Lys Thr Ile Thr Gln Asn Asp Leu Met Ile Ile
145                 150                 155                 160

Leu Gly Gln Leu Leu Ala Phe Thr Cys Asn Ala Val Ile Gly Thr Ser
                165                 170                 175

Met Gly Glu Tyr Ala His Val Trp Arg Phe Met Leu Ile Leu Ala Thr
            180                 185                 190

Leu Pro Ala Ile Phe Leu Trp Phe Gly Met Leu Ile Val Pro Glu Ser
        195                 200                 205

Pro Arg Trp Leu Ala Ser Lys Gly Lys Val Gly Glu Ala Phe Arg Val
    210                 215                 220

Leu Lys His Val Arg Glu Glu Asn Cys Ala Lys Ala Glu Leu Thr Glu
225                 230                 235                 240

Ile Lys Ala Ser Ile Asn Arg Glu Thr Glu Ile Asn Arg Ala Thr Leu
                245                 250                 255

Lys Asp Leu Ser Val Pro Trp Ile Arg Arg Leu Val Gly Leu Gly Ile
            260                 265                 270

Gly Ile Ala Val Val Gln Gln Ile Thr Gly Val Asn Ser Ile Met Phe
        275                 280                 285

Tyr Gly Thr Gln Ile Leu Gln Lys Ala Gly Phe Ala Arg Asp Ala Ala
    290                 295                 300

Leu Val Ala Asn Ile Gly Asn Gly Val Ile Ser Val Ile Ala Cys Thr
305                 310                 315                 320

Phe Gly Ile Trp Ile Val Gly Lys Val Gly Arg Arg Pro Leu Leu Leu
                325                 330                 335

```
Thr Gly Leu Ala Gly Thr Thr Ala Ser Ile Leu Leu Ile Ala Ile Cys
                340                 345                 350

Ser Ile Thr Leu Gln Gly Thr Pro Val Leu Pro Phe Ile Val Ile Gly
            355                 360                 365

Leu Thr Ile Thr Phe Leu Ala Phe Gln Gln Ser Ala Val Ser Val Val
        370                 375                 380

Thr Trp Leu Met Ile Ser Glu Ile Phe Pro Leu Arg Leu Arg Gly Leu
385                 390                 395                 400

Gly Met Gly Ile Ser Val Phe Phe Leu Trp Met Met Asn Phe Leu Ile
                405                 410                 415

Gly Leu Thr Phe Pro Val Leu Leu Asp Gln Leu Gly Met Ser Ser Thr
            420                 425                 430

Phe Phe Val Phe Val Val Leu Gly Ala Ser Ala Ile Leu Tyr Val Lys
        435                 440                 445

Lys Tyr Leu Pro Glu Thr Lys Gly Arg Thr Leu Glu Glu Leu Glu Asn
    450                 455                 460

Asp Phe Arg Ser Asn Gln Gly Val Arg Lys Ala Ser Ser Gly Lys Gly
465                 470                 475                 480

Glu Ile Asn Met

<210> SEQ ID NO 161
<211> LENGTH: 388
<212> TYPE: PRT
<213> ORGANISM: Bacillus subtilis
<220> FEATURE:
<223> OTHER INFORMATION: >ABP24565

<400> SEQUENCE: 161

Met Ile Asn Gly Glu Lys Lys Val Asp Arg Pro Ile Arg Trp Ala Met
1               5                   10                  15

Val Gly Gly Gly Arg Gly Ser Gln Ile Gly Tyr Ile His Arg Ser Ala
                20                  25                  30

Ala Leu Arg Asp His His Phe Gln Leu Val Ala Gly Ala Phe Asp Ile
            35                  40                  45

Asn Pro Glu Arg Gly Lys Asp Phe Gly Met Asn Leu His Val Thr Pro
        50                  55                  60

Glu Arg Cys Tyr Leu Asp Phe Gln Gln Met Phe Glu Glu Ala Lys
65                  70                  75                  80

Arg Glu Asp Gly Ile Glu Ala Val Ser Ile Ala Thr Pro Asn Gly Thr
                85                  90                  95

His Tyr Glu Ile Cys Lys Ala Ala Leu Asn Val Gly Leu His Val Val
            100                 105                 110

Cys Glu Lys Pro Leu Cys Phe Thr Phe Glu Glu Ala Lys Glu Leu Glu
        115                 120                 125

Asn Leu Ala Lys Lys Lys Asn Arg Val Val Gly Ile Thr Tyr Gly Tyr
    130                 135                 140

Ser Gly His Gln Met Ile Glu Gln Ala Arg Gln Met Ile Ala Asn Gly
145                 150                 155                 160

Glu Leu Gly Asp Ile Arg Ile Ile Asn Met Gln Phe Ala His Gly Phe
                165                 170                 175

His Ser Asp Pro Val Glu Met Asn Asn Pro Ser Thr Lys Trp Arg Val
            180                 185                 190

Asp Pro Lys Phe Ala Gly Pro Ser Tyr Val Leu Gly Asp Leu Gly Thr
        195                 200                 205

His Pro Leu Phe Leu Ser Glu Ile Met Ile Pro Glu Leu Lys Ile Asn
```

|     |     |     |     |     | 210 |     |     |     |     | 215 |     |     |     |     | 220 |     |

Lys Leu Leu Cys Thr Arg Gln Ser Phe Val Lys Ser Arg Ala Pro Leu
225                 230                 235                 240

Glu Asp Asn Ala Tyr Thr Ile Met Glu Tyr Asp Asn Gly Ala Val Gly
                245                 250                 255

Thr Val Trp Ser Ser Cys Val Asn Ala Gly Ser Met His Gly Gln Lys
            260                 265                 270

Ile Arg Val Ile Gly Ser Lys Ala Ser Ile Glu Trp Trp Asp Glu Gln
            275                 280                 285

Pro Asn Gln Leu Arg Phe Glu Ile Gln Gly Lys Pro Val Gln Ile Leu
290                 295                 300

Glu Arg Gly Met Gly Tyr Leu Tyr Pro Glu Ala Leu Gln Asp Asp Arg
305                 310                 315                 320

Ile Gly Gly Gly His Pro Glu Gly Leu Phe Glu Ala Trp Ser Asn Leu
                325                 330                 335

Tyr Ser Arg Phe Ala Val Ala Met Glu Ala Ala Asp Arg Gly Lys Glu
                340                 345                 350

Leu Glu His Met Trp Tyr Pro Gly Ile Glu Ala Gly Val Gly Gly Val
            355                 360                 365

Arg Trp Val Glu Asn Cys Val Arg Ser Ala Asp Lys Gly Ala Val Trp
370                 375                 380

Val Asp Tyr Gln
385

<210> SEQ ID NO 162
<211> LENGTH: 309
<212> TYPE: PRT
<213> ORGANISM: Bacillus subtilis
<220> FEATURE:
<223> OTHER INFORMATION: >ABP24566

<400> SEQUENCE: 162

Met Ser Ile His Ile Ala Gly Ala Pro Cys Cys Trp Gly Val Asp Asp
1               5                   10                  15

Pro Lys Asn Pro Tyr Leu Pro Pro Trp Glu Arg Val Leu Gln Glu Ala
            20                  25                  30

Ser Gln Ala Gly Tyr Lys Gly Ile Glu Leu Gly Pro Tyr Gly Tyr Ile
        35                  40                  45

Pro Met Asp Ile Glu Arg Val Gln Ala Glu Leu Leu Lys Asn Asn Leu
    50                  55                  60

Ser Ile Ile Ala Gly Thr Ile Phe Asp Asp Leu Val Ser Glu Ser His
65                  70                  75                  80

Leu Gly Asn Leu Leu Glu Gln Val Asp Glu Ile Cys Ser Leu Ile Thr
                85                  90                  95

Lys Leu Pro Phe Ser Phe Gln Asp Lys Glu Glu Arg Phe Arg Phe Ser
            100                 105                 110

Pro Pro Tyr Leu Val Leu Ile Asp Trp Gly His Asp Glu Arg Asp Tyr
        115                 120                 125

Lys Ala Gly Arg Pro Asp Gln Ala Lys Arg Leu Ser Lys Lys Glu Trp
    130                 135                 140

Asn Arg Met Met Ser His Ile Arg Thr Ile Ala Glu Arg Ala Trp Lys
145                 150                 155                 160

Gln Tyr Gly Val Arg Ala Val Ile His Pro His Ala Gly Gly Tyr Ile
                165                 170                 175

Glu Phe Glu Asp Glu Ile Gln Gln Leu Leu Lys Asp Ile Pro Tyr Asp

```
                   180                 185                 190
Ile Ala Gly Leu Cys Leu Asp Thr Gly His Leu Tyr Tyr Ser Lys Met
                195                 200                 205

Asp Pro Glu Gln Trp Leu Arg Asp Tyr Ala Asp Arg Val Asp Tyr Ile
            210                 215                 220

His Phe Lys Asp Ile Asp Glu His Val Tyr Gln Gln Val Met Gly Glu
225                 230                 235                 240

His Ile Arg Phe Phe Asp Ala Cys Ala Lys Gly Val Met Cys Pro Ile
                245                 250                 255

Gly Gln Gly Ile Ile Asp Tyr Glu Ala Ile Tyr Lys Leu Leu Lys Asp
                260                 265                 270

Ile His Tyr His Gly Tyr Ile Thr Ile Glu Gln Glu Arg Asp Pro Arg
            275                 280                 285

Asn Ser Asp Thr Ser Leu Arg Asp Val Ser Gln Ser Leu Ala Tyr Leu
            290                 295                 300

Lys Asn Val Gly Tyr
305

<210> SEQ ID NO 163
<211> LENGTH: 339
<212> TYPE: PRT
<213> ORGANISM: Bacillus subtilis
<220> FEATURE:
<223> OTHER INFORMATION: >ABP24567

<400> SEQUENCE: 163

Met Glu Lys Glu Val Phe Ser Lys Met Lys Thr Thr Ile Tyr Asp Val
1               5                   10                  15

Ala Glu Lys Ala Gly Val Ser Ile Ser Thr Val Ser Lys Val Ile Asn
            20                  25                  30

His Gln Pro Val Gly Met Lys Ser Lys Gln Lys Val Leu Asp Ala Met
        35                  40                  45

Gln Glu Leu Asn Tyr Lys Pro Ser Val Leu Ala Ser Ala Leu Thr Gly
    50                  55                  60

Lys Arg Thr Ser Thr Ile Gly Phe Leu Leu Pro Asp Ile Ala Asn Pro
65                  70                  75                  80

Leu Ile Ala Glu Met Ala Arg Arg Val Glu Asp Arg Ala His Glu Tyr
                85                  90                  95

Gly Phe Asn Val Val Ile Cys Ser Thr Asp Phe Lys Ser Glu Lys Glu
            100                 105                 110

Glu Arg Tyr Val Ser Leu Leu Arg Gln Lys Arg Val Asp Gly Phe Ile
        115                 120                 125

Leu Ala Gly Gly Phe Arg Asn Lys Gln Val Ile His Glu Leu Ile Ser
    130                 135                 140

Asp Asn Ile Pro Val Ile Leu Leu Ser Glu Ser Gln Pro Tyr Ser Ser
145                 150                 155                 160

Leu Thr Thr Val Thr Val Asp Asn Phe Leu Gly Gly Tyr Glu Leu Thr
                165                 170                 175

Ala Tyr Leu Ile Ser Leu Gly His Ser Arg Ile Ala Val Ile Ala Glu
            180                 185                 190

Asp Asn Ala Ser Ser Arg Glu Arg Ile Arg Gly Tyr Ser Gln Ala Leu
        195                 200                 205

Gln Glu Ser Asp Leu Asp Ile His Glu Asp Leu Ile Val Val Thr Asp
    210                 215                 220

Ser Thr Ala Glu Ser Ala Gln Ser Leu Ala Ser Ser Leu Leu Gln Ser
```

```
                225                 230                 235                 240

Ser Asn Pro Pro Thr Ala Met Ile Cys Cys Asn Asp Ile Leu Ala Ile
                245                 250                 255

Gly Ala Leu Leu Ala Ala Arg Glu Glu His Val Leu Val Pro Glu Glu
                260                 265                 270

Leu Ser Ile Thr Gly Phe Asp Asn Thr Leu Ile Ser Lys Ser Ser Asp
                275                 280                 285

Pro Pro Leu Thr Thr Val Glu Val Pro Val Gln Ser Met Cys Ser Gln
                290                 295                 300

Ala Val Asp Leu Leu Ile Asp Glu Ile Glu Gly Lys Ala Ser Glu Lys
305                 310                 315                 320

Gln Lys Ile Leu Val Leu Pro Lys Leu Ile Val Arg Lys Ser Thr Ser
                325                 330                 335

Arg Phe His

<210> SEQ ID NO 164
<211> LENGTH: 41
<212> TYPE: PRT
<213> ORGANISM: Bacillus subtilis
<220> FEATURE:
<223> OTHER INFORMATION: >ABP24568

<400> SEQUENCE: 164

Met Ser Leu Val Lys Asn Gly Asp Ser Ile Lys Val Val Phe Val Phe
1               5                   10                  15

Gln Lys Asn Glu Gln Ile Glu Glu Val Glu Leu Asn Ser Ala Gln Leu
                20                  25                  30

Ser Ala Leu Leu His Ser Lys Gln Val
            35                  40

<210> SEQ ID NO 165
<211> LENGTH: 52
<212> TYPE: PRT
<213> ORGANISM: Bacillus subtilis
<220> FEATURE:
<223> OTHER INFORMATION: >ABP24598

<400> SEQUENCE: 165

Met Asp Ile Asn Asp Ala Ser Glu His Leu Ile Gln Leu Lys Gln Asp
1               5                   10                  15

Leu Ile Asp Arg Ser Lys Ile Glu Met Ile Asn Lys Leu Lys Arg Trp
                20                  25                  30

Ala Phe Ser Phe Leu Lys His Leu Asn Phe Glu Ile Gln Thr Phe Asn
            35                  40                  45

Tyr Gly Phe Val
    50

<210> SEQ ID NO 166
<211> LENGTH: 111
<212> TYPE: PRT
<213> ORGANISM: Bacillus subtilis
<220> FEATURE:
<223> OTHER INFORMATION: >ABP24599

<400> SEQUENCE: 166

Met Lys Lys Arg Leu Ile Gly Phe Leu Val Leu Val Pro Ala Leu Ile
1               5                   10                  15

Met Ser Gly Ile Ile Leu Ile Glu Ala Asn Lys Lys Ala Pro Val Glu
                20                  25                  30
```

```
Val Leu Glu Ser Ala Trp Asp Glu Phe Gly Leu Ser Phe Gln Ile
         35                  40                  45

Gly Lys Thr Asp Pro Ser Ile Thr Ile Gly Met Asp His Thr Lys Ser
 50                  55                  60

Glu Ala Lys Leu Arg Glu Tyr Leu Glu His Asn Leu Ser Arg Glu Ala
 65                  70                  75                  80

Lys Glu Lys Tyr Lys Ile Tyr Ile Phe Lys Asp Asp Ile Asp Lys Leu
                 85                  90                  95

Glu Lys Glu His Arg Glu Tyr Leu Lys Ala Asn Asn Pro Asn Lys
            100                 105                 110

<210> SEQ ID NO 167
<211> LENGTH: 48
<212> TYPE: PRT
<213> ORGANISM: Bacillus subtilis
<220> FEATURE:
<223> OTHER INFORMATION: >ABP24600

<400> SEQUENCE: 167

Met Arg Phe Thr Ala Gly Gly Asn Leu Ser Thr Met Asp Ser Gln Val
 1               5                  10                  15

Leu Asp Val Ile Lys Lys Ala Tyr Asn Leu Gly Met Val Asn Lys Asp
             20                  25                  30

Asn Met Leu Leu Arg Asn Glu Ala Ile Asn Ala Tyr Arg Asn Ser Ile
         35                  40                  45

<210> SEQ ID NO 168
<211> LENGTH: 384
<212> TYPE: PRT
<213> ORGANISM: Bacillus subtilis
<220> FEATURE:
<223> OTHER INFORMATION: >ABP24601

<400> SEQUENCE: 168

Met Leu Pro Glu Tyr Arg Lys Lys Thr Pro Glu Glu Ile Leu Glu Glu
 1               5                  10                  15

Ile Glu Arg Leu Lys Arg Gly Arg Leu Lys Val Tyr Ile Gly Ser Ala
             20                  25                  30

Pro Gly Val Gly Lys Thr Tyr Arg Met Leu Gln Glu Ala His Glu Leu
         35                  40                  45

Lys Ala Glu Gly Leu Asp Val Val Ile Gly Leu Ile Glu Thr His Asn
 50                  55                  60

Arg Lys Glu Thr Glu Asp Leu Ile Gly Asp Leu Glu Ile Val Pro Lys
 65                  70                  75                  80

Lys Asn Ile Asp Tyr Lys Gly Arg Leu Leu Glu Glu Met Asp Thr Glu
                 85                  90                  95

Ala Ile Ile Lys Arg Ala Pro Asp Leu Val Leu Ile Asp Glu Leu Ala
            100                 105                 110

His Thr Asn Val Pro Phe Ser Gln Arg Asn Lys Arg Tyr Met Asp Val
            115                 120                 125

Glu Glu Ile Leu Lys Ser Gly Ile Asn Val Leu Ser Ala Val Asn Ile
        130                 135                 140

Gln His Leu Glu Ser Leu His Asp Ile Val Gln Ile Thr Gly Val
145                 150                 155             160

Gln Val Arg Glu Arg Ile Pro Asp Ser Phe Leu His Met Ala His Glu
                165                 170                 175

Ile Ile Leu Val Asp Val Thr Pro Glu Ile Leu Arg Lys Arg Leu Ser
            180                 185                 190
```

```
Glu Gly Lys Ile Tyr His Pro Ser Lys Ile Glu Gln Ala Leu Asn Asn
            195                 200                 205

Phe Phe Thr Ala Ser Asn Leu Gly Ala Leu Arg Glu Leu Ser Leu Arg
210                 215                 220

Glu Val Ala Asn Asp Val Asp Glu Arg Val Glu Lys Ala Asn Glu Lys
225                 230                 235                 240

Asn Gly Lys Asn Lys Pro Ser Gly Ile Asn Glu Lys Ile Met Val Cys
            245                 250                 255

Val Gln His Gly Ser Asn Ala Glu Arg Leu Ile Arg Arg Gly Trp Arg
            260                 265                 270

Ile Ala Asn Arg Leu Lys Thr Glu Leu Ile Ile Leu His Val Thr Asn
            275                 280                 285

Glu Val Ser Met Lys Arg Ser Thr Glu Asn Arg Lys Lys Ile Gln Asp
290                 295                 300

Trp Lys Arg Leu Ala Ile Gln Phe Asn Ala Arg Phe Ile Ile Glu Gln
305                 310                 315                 320

Ile Lys Lys Arg His Ile Ala Lys Ala Ile Thr Asp Val Ala Lys Glu
            325                 330                 335

His Asp Val Thr Gln Ile Ile Leu Gly Gln Ser Ala Arg Ser Arg Trp
            340                 345                 350

Glu Glu Ile Arg Lys Gly Ser Ile Val Asn Met Ile Met Arg Tyr Thr
            355                 360                 365

Thr Gly Val Asp Ile His Ile Val Ser Asp Gln Gln Pro Arg Arg Lys
            370                 375                 380

<210> SEQ ID NO 169
<211> LENGTH: 189
<212> TYPE: PRT
<213> ORGANISM: Bacillus subtilis
<220> FEATURE:
<223> OTHER INFORMATION: >ABP24602

<400> SEQUENCE: 169

Met Leu Lys Ile Ile Arg Leu Ala Leu Leu Met Ile Ile Ile Cys Gly
1               5                   10                  15

Ile Leu Tyr Pro Leu Leu Met Thr Gly Leu Ala Gln Ala Ile Phe Pro
            20                  25                  30

Asp Gln Ala Asn Gly Ser Ile Leu Lys Asn Lys Asp Gly Gln Ile Val
        35                  40                  45

Gly Ser Glu Leu Ile Gly Gln Gln Phe Thr Lys Ser Asn Tyr Phe Gln
50                  55                  60

Gly Arg Ile Ser Ser Ile Lys Tyr Asn Ala Val Gly Ser Gly Ser Asn
65                  70                  75                  80

Asn Tyr Gly Pro Thr Asn Gln Glu Met Leu Glu Arg Thr Lys Ser Phe
            85                  90                  95

Ile Arg Val Leu Glu Glu Gly Asn Pro Asp Leu Lys Thr Lys Glu Leu
            100                 105                 110

Pro Ile Asp Leu Ile Thr Asn Ser Gly Ser Gly Leu Asp Pro Asp Ile
        115                 120                 125

Ser Val Lys Ala Ala Lys Phe Gln Val Asn Arg Val Ser Asn Ala Thr
130                 135                 140

Gly Val Ser Glu Ser Thr Leu Asn Lys Leu Ile Asp Asn Thr Ile Asp
145                 150                 155                 160

Gly Arg Ser Leu Gly Ile Phe Gly Glu Pro Arg Val Asn Val Leu Lys
            165                 170                 175
```

```
                Leu Asn Met Lys Val Gln Glu Ile Ile Ser Lys Gly Asn
                            180                 185

<210> SEQ ID NO 170
<211> LENGTH: 674
<212> TYPE: PRT
<213> ORGANISM: Bacillus subtilis
<220> FEATURE:
<223> OTHER INFORMATION: >ABP24603

<400> SEQUENCE: 170

Met Asn Lys Ser Asn Glu Asn Ser Glu Met Ile Lys Glu Ala Ile Thr
1               5                   10                  15

Gln Ser Phe Ile Lys Leu Asn Pro Leu Ser Met Met Lys Asn Pro Val
            20                  25                  30

Met Phe Val Val Glu Val Gly Thr Phe Leu Val Leu Leu Met Leu Ile
        35                  40                  45

Met Pro Ser Ala Phe His Ser Glu Gly Tyr Val Tyr Asn Leu Ile
    50                  55                  60

Val Phe Leu Ile Leu Leu Phe Thr Ile Leu Phe Ala Asn Phe Ala Glu
65                  70                  75                  80

Ala Leu Ala Glu Gly Arg Gly Lys Ala Gln Ala Asp Ser Leu Lys Lys
                85                  90                  95

Thr Lys Lys Asp Thr Val Ala Arg Arg Ile Asn Lys Asn Gly Thr Val
            100                 105                 110

Thr Asp Ile Ser Ser Ala Asp Leu Lys Lys Gly Asp Ile Val Leu Val
        115                 120                 125

Glu Thr Gly Asp Phe Ile Pro Gly Asp Gly Glu Ile Ile Glu Gly Leu
    130                 135                 140

Ala Ser Ile Asp Glu Ser Ala Ile Thr Gly Glu Ser Ala Pro Val Ile
145                 150                 155                 160

Lys Glu Ala Gly Gly Asp Phe Ser Ser Val Thr Gly Thr Lys Val
                165                 170                 175

Val Ser Asp Ser Ile Lys Val Arg Ile Thr Ala Asp Pro Gly Glu Ser
            180                 185                 190

Phe Leu Asp Lys Met Ile Ser Leu Val Glu Gly Ala Lys Arg Gln Lys
        195                 200                 205

Thr Pro Asn Glu Ile Ala Leu Thr Ile Leu Val Thr Leu Thr Ile
    210                 215                 220

Ile Phe Leu Leu Val Val Thr Leu Leu Pro Ile Ala Asn Tyr Val
225                 230                 235                 240

Gly Val His Ile Glu Leu Ser Thr Leu Ile Ala Leu Val Cys Leu
                245                 250                 255

Ile Pro Thr Thr Ile Gly Ala Leu Leu Ser Ala Ile Gly Ile Ala Gly
            260                 265                 270

Met Asp Arg Val Thr Gln Phe Asn Val Leu Ala Met Ser Gly Lys Ala
        275                 280                 285

Val Glu Val Ala Gly Asp Ile Asn Thr Ile Ile Leu Asp Lys Thr Gly
    290                 295                 300

Thr Ile Thr Phe Gly Asn Arg Leu Ala Ala Glu Phe Ile Pro Val Ser
305                 310                 315                 320

Ser Thr Thr Gln Glu Glu Leu Met Gln Ala Val Ile Thr Ser Leu
                325                 330                 335

Phe Asp Glu Thr Pro Glu Gly Arg Ser Val Leu Glu Leu Ala Lys Asn
        340                 345                 350
```

```
Asn Gly Ala Ser Trp Glu Ala Ser Ala Tyr Glu Ser Ala Glu Ile Ile
            355                 360                 365

Pro Phe Thr Ala Glu Glu Arg Met Ser Gly Leu Ile Lys Asp Gly His
    370                 375                 380

His Tyr Arg Lys Gly Ala Val Asp Ser Ile Lys Ala Phe Val Gln Glu
385                 390                 395                 400

Met Gly Gly Pro Leu Pro Leu Asp Leu Gln Ser Lys Ser Glu Glu Val
                405                 410                 415

Ala Arg Gln Gly Gly Thr Pro Leu Ala Val Ser Tyr Asn Asn Arg Ile
            420                 425                 430

Leu Gly Leu Ile Tyr Leu Lys Asp Thr Val Lys Pro Gly Met Arg Glu
            435                 440                 445

Arg Phe Asp Glu Leu Arg Lys Met Gly Ile Lys Thr Ile Met Cys Thr
    450                 455                 460

Gly Asp Asn Pro Leu Thr Ala Ser Thr Ile Ala Lys Glu Ala Gly Val
465                 470                 475                 480

Asp Asp Phe Ile Ala Glu Ala Lys Pro Glu Asp Lys Ile Arg Val Ile
                485                 490                 495

Arg Glu Glu Gln Glu Lys Gly Lys Leu Val Ala Met Thr Gly Asp Gly
            500                 505                 510

Thr Asn Asp Ala Pro Ala Leu Ala Gln Ala Asp Val Gly Leu Ala Met
            515                 520                 525

Asn Ser Gly Thr Ile Ala Ala Lys Glu Ala Ala Asn Met Val Asp Leu
            530                 535                 540

Asp Ser Asp Pro Thr Lys Ile Ile Glu Val Val Ala Ile Gly Lys Gln
545                 550                 555                 560

Leu Leu Met Thr Arg Gly Ser Leu Thr Thr Phe Ser Ile Ala Asn Asp
                565                 570                 575

Ile Ala Lys Tyr Phe Ala Ile Ile Pro Ala Met Phe Thr Val Ala Ile
            580                 585                 590

Pro Gly Met Gln Val Leu Asn Ile Met Arg Leu His Ser Pro Thr Thr
            595                 600                 605

Ala Ile Leu Ser Ala Leu Ile Phe Asn Ala Ile Ile Pro Leu Leu
            610                 615                 620

Ile Pro Leu Ala Met Lys Gly Val Lys Tyr Val Pro Met Ser Ala Ser
625                 630                 635                 640

Lys Leu Leu Ser Arg Asn Ile Leu Ile Tyr Gly Leu Gly Ile Val
                645                 650                 655

Val Pro Phe Ile Gly Ile Lys Leu Ile Asp Ile Leu Val Ser Val Phe
                660                 665                 670

Met Ser

<210> SEQ ID NO 171
<211> LENGTH: 389
<212> TYPE: PRT
<213> ORGANISM: Bacillus subtilis
<220> FEATURE:
<223> OTHER INFORMATION: >ABP24604

<400> SEQUENCE: 171

Met Lys Gly His Thr Arg Leu Leu Ile Pro Met Ser Ile Ile Leu Thr
1               5                   10                  15

Ile Ile Leu Val Ser Leu Lys Val Pro Gln Thr Leu Ser Pro Ser Ile
            20                  25                  30
```

Glu Val Thr Thr Leu Glu Gly Val Lys Gln Val Ile Ser Ile Gly Pro
35                  40                  45

Val Ala Ser Leu Glu Ser Ile Lys His Leu Gly Thr Asn Gly Gly Gly
50                  55                  60

Phe Phe Gly Ala Asn Ser Ala His Pro Phe Glu Asn Pro Ser Pro Leu
65                  70                  75                  80

Thr Asn Val Ile Glu Ile Leu Ser Met Trp Cys Ile Pro Ala Ser Leu
                85                  90                  95

Thr Tyr Thr Tyr Gly Arg Phe Ala Lys Lys Gln Lys Gln Gly Trp Val
                100                 105                 110

Ile Phe Gly Ala Met Phe Ile Leu Phe Ile Ala Phe Leu Ser Leu Ile
                115                 120                 125

Tyr Val Ser Glu Ser His Gly Asn Pro Ala Leu Thr Ala Leu Gly Leu
130                 135                 140

Asp Pro Ser Gln Gly Ser Met Glu Gly Lys Glu Val Arg Phe Gly Ile
145                 150                 155                 160

Ala Gln Ser Ala Leu Phe Ser Ser Val Thr Thr Ala Ala Thr Thr Gly
                165                 170                 175

Thr Val Asn Asn Met His Asp Thr Leu Thr Pro Leu Gly Gln Ile Thr
                180                 185                 190

Pro Leu Ser Leu Met Met Leu Asn Thr Val Phe Gly Gly Asp Gly Val
                195                 200                 205

Gly Leu Val Asn Met Leu Met Tyr Ala Ile Ile Gly Val Phe Ile Cys
                210                 215                 220

Gly Leu Met Val Gly Arg Thr Pro Glu Phe Leu Gly Arg Lys Ile Glu
225                 230                 235                 240

Pro Lys Glu Met Lys Leu Ile Thr Val Ala Leu Leu Ala His Pro Leu
                245                 250                 255

Ile Ile Leu Ala Pro Thr Ala Leu Ala Phe Leu Ala Asp Ile Gly Lys
                260                 265                 270

Gly Ser Ile Ser Asn Pro Gly Phe His Gly Val Ser Gln Val Leu Tyr
                275                 280                 285

Glu Phe Ala Ser Ser Ala Ala Asn Asn Gly Ser Gly Phe Glu Gly Leu
290                 295                 300

Ala Asp Asn Thr Pro Phe Trp Asn Ile Ser Thr Gly Leu Val Met Leu
305                 310                 315                 320

Val Gly Arg Tyr Ile Ser Ile Ala Leu Leu Ala Val Ala Gly Ser
                325                 330                 335

Leu Val Gln Lys Gln Pro Val Pro Glu Thr Ile Gly Thr Phe Lys Thr
                340                 345                 350

Asp Asn Leu Leu Phe Ile Gly Ile Leu Val Gly Val Leu Ile Val
                355                 360                 365

Gly Ala Leu Thr Phe Phe Pro Val Ile Ala Leu Gly Pro Ile Ala Glu
370                 375                 380

Tyr Leu Ser Ile Arg
385

<210> SEQ ID NO 172
<211> LENGTH: 170
<212> TYPE: PRT
<213> ORGANISM: Bacillus subtilis
<220> FEATURE:
<223> OTHER INFORMATION: >ABP24605

<400> SEQUENCE: 172

```
Met Gly Ile Leu Gln Ile Val Val Ile Met Leu Met Leu Phe Met
1               5                   10                  15

Ile Lys Pro Leu Gly Thr Tyr Ile Tyr His Val Phe Ser Asn Glu Pro
            20                  25                  30

Asn Lys Thr Asp Lys Ile Phe Asn Pro Ile Glu Lys Ile Ile Tyr Lys
        35                  40                  45

Ile Cys Gly Met Lys Asn Arg Leu Ser Met Thr Trp Lys Gln Tyr Ala
    50                  55                  60

Gly Ser Leu Leu Leu Thr Asn Met Val Phe Ala Val Gly Tyr Val
65                  70                  75                  80

Ile Leu Arg Phe Gln Tyr Ile Leu Pro Leu Asn Pro Asn Gly Ile Glu
                85                  90                  95

Asn Met Asn Ser Met Leu Ser Phe Asn Thr Ile Ile Ser Phe Met Thr
                100                 105                 110

Asn Thr Asn Leu Gln His Tyr Ser Gly Glu Thr Gly Leu Ser Tyr Phe
            115                 120                 125

Ser Gln Met Ala Val Ile Met Met Met Phe Thr Ser Ala Ala Thr
            130                 135                 140

Gly Ile Ala Ala Ile Ala Phe Ile Arg Gly Ile Thr Ser Lys Gly
145                 150                 155                 160

Lys Thr Ile Gly Asn Phe Leu Lys Ile Leu
                165                 170
```

<210> SEQ ID NO 173
<211> LENGTH: 43
<212> TYPE: PRT
<213> ORGANISM: Bacillus subtilis
<220> FEATURE:
<223> OTHER INFORMATION: >ABP24606

<400> SEQUENCE: 173

```
Met Asn Asn Asn Leu Gly Gly Ile Thr Leu Asp Asp Val Cys Met Leu
1               5                   10                  15

Ala Val Ile Ala Val Ile Phe Ala Val Phe Trp Ala Phe Val Lys Trp
            20                  25                  30

Cys Asp Phe Thr Ile Gly Gly Gly Glu Lys Gln
            35                  40
```

<210> SEQ ID NO 174
<211> LENGTH: 155
<212> TYPE: PRT
<213> ORGANISM: Bacillus subtilis
<220> FEATURE:
<223> OTHER INFORMATION: >ABP20078

<400> SEQUENCE: 174

```
Met Pro Lys Gln Gln Thr Ala Glu Leu Lys Pro Phe Phe His Asn Lys
1               5                   10                  15

Thr Val Leu Val Thr Gly Gly Thr Gly Ser Ile Gly Ser Gln Ile Val
            20                  25                  30

Lys Arg Leu Leu Met Leu Thr Pro Lys Gln Val Ile Val Phe Ser Lys
            35                  40                  45

Asp Asp Ser Lys Gln Tyr Val Met Ser Gln Lys Tyr Ala Glu Asp Lys
        50                  55                  60

Arg Leu Leu Phe Val Leu Gly Asp Val Arg Asp His Arg Arg Val Asn
65                  70                  75                  80

Gln Val Met Lys Gly Val Asp Ile Val Phe His Ala Ala Ala Leu Lys
            85                  90                  95
```

```
Gln Val Pro Thr Cys Glu Asp His Pro Phe Glu Ala Ile Gln Thr Asn
            100                 105                 110

Leu Ile Gly Gly Gln Asn Val Glu Ala Ala Leu Ser His Arg Val
        115                 120                 125

Gln His Val Ile Asn Ile Ser Thr Asp Lys Ala Val Phe Lys Asp Thr
130                 135                 140

Asp Tyr Lys Leu Ile Lys Lys Gly Leu Phe
145                 150                 155

<210> SEQ ID NO 175
<211> LENGTH: 56
<212> TYPE: PRT
<213> ORGANISM: Bacillus subtilis
<220> FEATURE:
<223> OTHER INFORMATION: >ABP20079

<400> SEQUENCE: 175

Met Pro Tyr Glu Glu Tyr Glu Glu Leu Lys Lys Thr Ile Lys Val
1               5                   10                  15

Ile Gln Arg Lys Asn Tyr Ser Ile Arg Ile Ile Asp Gln Lys Phe Glu
                20                  25                  30

Asn Asp Asn Leu Asp Gln Leu Tyr Lys Glu Val Ala Arg Leu Leu Phe
            35                  40                  45

Glu Arg Ala Leu Lys Ser Ser Glu
    50                  55

<210> SEQ ID NO 176
<211> LENGTH: 196
<212> TYPE: PRT
<213> ORGANISM: Bacillus subtilis
<220> FEATURE:
<223> OTHER INFORMATION: >ABP20080

<400> SEQUENCE: 176

Met Gly Ala Asn Asn Gln Gly Lys Val Phe Glu Ala Asn Ile Glu Lys
1               5                   10                  15

Ser Ala Ala Asp Gln Lys Leu Phe Phe Tyr Arg Ile Lys Asp Val Asn
                20                  25                  30

Pro Met Phe Leu Lys Arg Gly Ala Ala Val Ser Lys Asn Lys Tyr Asp
            35                  40                  45

Cys Phe Leu His Phe Asn Gly Tyr Leu Phe Pro Phe Glu Leu Lys Ser
    50                  55                  60

Thr Lys Asp Lys Ser Ile Ala Phe Arg Glu Lys Ile Ile Lys Pro Gln
65                  70                  75                  80

Gln Ile Lys Tyr Leu Lys Glu Ala Thr Gln Tyr Pro Asn Ile Ile Pro
                85                  90                  95

Gly Phe Leu Phe Gln Phe Arg Glu Pro Glu Asn Lys Val Tyr Phe Val
            100                 105                 110

His Ile Asp Glu Phe Leu Lys Tyr Lys Asn Ile Ala Glu Lys Gln Leu
        115                 120                 125

Lys His Thr Tyr Lys Asn Lys Val Asn Lys Ala Ser Ile Pro Ile Ala
130                 135                 140

Ile Cys Glu Glu Ile Gly Thr Glu Val Arg Trp Met Lys Lys Val
145                 150                 155                 160

Asn Tyr Thr Tyr Tyr Leu Asn Lys Leu Cys Val Glu Leu Ile Lys Lys
                165                 170                 175

Glu Gln Ser Arg Asp Lys Pro Leu His Thr Tyr Asn Thr Pro Val Lys
```

```
                 180                 185                 190

Thr Gly Val Arg
        195

<210> SEQ ID NO 177
<211> LENGTH: 93
<212> TYPE: PRT
<213> ORGANISM: Bacillus subtilis
<220> FEATURE:
<223> OTHER INFORMATION: >ABP20081

<400> SEQUENCE: 177

Met Tyr Val Leu Lys Ser Leu Leu Lys Glu Val Tyr Ile Val Lys Lys
1               5                   10                  15

Gln Trp Lys Pro Val Asp Ser Arg Leu Asn Glu Leu Met His Glu Tyr
            20                  25                  30

Ser Val Ser Ile Glu Asp Leu Val Glu Arg Thr Gly Leu Pro Lys Gln
        35                  40                  45

Arg Ile Asn Asp Tyr Val Ser Gly Phe Lys Ser Asn Met Asn Ile Gly
    50                  55                  60

Thr Ala Met Thr Phe Ala Asp Ala Ile Gly Cys Ser Ile Glu Glu Leu
65                  70                  75                  80

Tyr Val Trp Asn Phe Lys Glu Arg Arg Gln Leu Ile Lys
                85                  90

<210> SEQ ID NO 178
<211> LENGTH: 43
<212> TYPE: PRT
<213> ORGANISM: Bacillus subtilis
<220> FEATURE:
<223> OTHER INFORMATION: >ABP20082

<400> SEQUENCE: 178

Met Lys Thr Val Lys Glu Ala Ile Asp Glu Lys Asp Leu Gln Arg Ala
1               5                   10                  15

His Arg Asn Leu Ile Asn Leu Ala Asp Asn Asn Glu Glu Leu Met Gln
            20                  25                  30

Glu Ile Arg Trp Ile Lys Lys Gly Thr Thr Leu
        35                  40

<210> SEQ ID NO 179
<211> LENGTH: 109
<212> TYPE: PRT
<213> ORGANISM: Bacillus subtilis
<220> FEATURE:
<223> OTHER INFORMATION: >ABP20083

<400> SEQUENCE: 179

Met Asn Leu Lys Asn Ile Asp Glu Asn Arg Tyr Lys Lys Thr Tyr Ser
1               5                   10                  15

Val Gln Pro Asn Asp Ile Phe Phe Val Val Arg Lys Asn Gly Asn Gln
            20                  25                  30

Thr Pro Tyr Leu Ile Tyr Lys Asp Lys Asn Lys Met Leu Lys Leu Ile
        35                  40                  45

Asn Leu Gln Ser Gly Ala Ser Asn Tyr Cys Ala Asp Thr Ile Asp Ser
    50                  55                  60

Leu Val Gly Ile Tyr Ile Lys Glu Asn Gln Glu Ser Pro Ala Asn Lys
65                  70                  75                  80

Val Asn Pro Ile Lys Glu Tyr Phe Phe Ala Lys Ser His Glu Thr Ser
                85                  90                  95
```

Ile Arg Val His Asn Thr Phe Asn Tyr Asn Pro Ile Lys
            100                 105

<210> SEQ ID NO 180
<211> LENGTH: 144
<212> TYPE: PRT
<213> ORGANISM: Bacillus subtilis
<220> FEATURE:
<223> OTHER INFORMATION: >ABP20084

<400> SEQUENCE: 180

Met Lys Thr Ile Lys Leu Tyr Glu Leu Val Ser Glu Gly Lys Lys Pro
1               5                   10                  15

Ile Ile Lys Phe Asn Asp Asn Val Tyr Glu Trp Ile Glu Glu Ser Val
            20                  25                  30

Asp Thr Met Met Met Gly Lys Ile Ile Gly Ala Ser Ile Glu Tyr Glu
        35                  40                  45

Asp Ser Val Arg Phe Leu Ile Asp Leu Asn Pro Phe Glu Ala Tyr Asn
50                  55                  60

Arg Ser Val Ala Arg His Asp Trp Arg Asp Asp Gly Gly Asn Cys Val
65                  70                  75                  80

Leu Thr Trp Phe Asp Thr Ser Phe Tyr Pro Lys Asn Gly Ile Glu Ala
                85                  90                  95

Ile Tyr Leu Pro Ile Asn Gly Arg Thr Glu Ile Ala Phe Asp Phe Thr
            100                 105                 110

Glu Glu Asp Ser Leu Leu Asn Glu Tyr Ala Lys Val Pro Gln Glu Ile
        115                 120                 125

Ser Tyr Val Glu Trp Leu Glu Asn Glu Val Lys Gln Leu Ile Ser Lys
    130                 135                 140

<210> SEQ ID NO 181
<211> LENGTH: 51
<212> TYPE: PRT
<213> ORGANISM: Bacillus subtilis
<220> FEATURE:
<223> OTHER INFORMATION: >ABP20085

<400> SEQUENCE: 181

Met Ile Val Thr Ala Trp Ile Leu Leu Ile Met Phe Gly Leu Phe Ala
1               5                   10                  15

Leu Ser Asp Leu Asn Leu Thr Glu Asp Glu Thr Lys His Ile Lys Phe
            20                  25                  30

Phe Met Leu Met Lys Phe Phe Ser Val Phe Ile Ala Ala Ile Ala Ala
        35                  40                  45

Gly Val Ile
    50

<210> SEQ ID NO 182
<211> LENGTH: 182
<212> TYPE: PRT
<213> ORGANISM: Bacillus subtilis
<220> FEATURE:
<223> OTHER INFORMATION: >ABP20086

<400> SEQUENCE: 182

Met Lys Asn Thr Glu Phe Lys Lys Thr Ser Phe Leu Glu Glu Tyr Lys
1               5                   10                  15

Arg Gly Asp Glu Met Arg Arg Asp Phe Ile Ile His Glu Gly Tyr Thr
            20                  25                  30

```
Ala Ile Glu Glu Ile Ile Lys Glu Val Asn Gln Arg Gly Ser Leu Asn
        35                  40                  45

Glu Ala Asp Ile Tyr Tyr Gly Thr Pro Lys Pro Gln Leu Ser Phe Ser
 50                  55                  60

Asp Val Glu Leu Gly Tyr Met Leu Thr Ser Met Met Glu Tyr Ala Thr
 65                  70                  75                  80

Asn His Val Gly Asn Pro Val Asp Glu Glu Cys Glu Phe Glu Asn Lys
                 85                  90                  95

Leu Ala Tyr Phe Glu Tyr Lys Asp Glu Ile Val Gln Ile Phe Glu Val
            100                 105                 110

Tyr Gly Gln Gly Thr Glu Ser Trp Phe Ser Lys Pro Ser Asp Asp Thr
        115                 120                 125

Ile Asp Lys Leu Asn Asn Thr Ala Tyr Gly Val Tyr Leu Ile Gln Phe
130                 135                 140

Asp Asp Phe Ile Asn Tyr Thr Lys Asn Lys Asp Ser Glu Ser Glu Lys
145                 150                 155                 160

Leu Ser Pro Ser Ser Thr Ile Leu Asn Asp Ile Thr Gly Gly Tyr Thr
                165                 170                 175

Val Gly Arg Gly Ser Lys
            180

<210> SEQ ID NO 183
<211> LENGTH: 49
<212> TYPE: PRT
<213> ORGANISM: Bacillus subtilis
<220> FEATURE:
<223> OTHER INFORMATION: >ABP20087

<400> SEQUENCE: 183

Met Leu Glu Leu Asp Glu Tyr Ile Leu Lys Ser Glu Met Asp Phe Ala
 1               5                  10                  15

Asp Pro Glu Glu Ile Arg Ser Cys Ile Ile Ser Phe Val Ser Ser Leu
             20                  25                  30

Gln Gln Tyr Ile Asp Leu Cys Lys Glu Leu Asn Glu Glu Tyr Arg
         35                  40                  45

Val

<210> SEQ ID NO 184
<211> LENGTH: 53
<212> TYPE: PRT
<213> ORGANISM: Bacillus subtilis
<220> FEATURE:
<223> OTHER INFORMATION: >ABP20088

<400> SEQUENCE: 184

Met Val Glu Leu Ala Lys Glu Glu Asn Met Leu Phe Phe Asp His Tyr
 1               5                  10                  15

Pro Thr Glu Tyr Gly Gly Trp Gln Thr Gly Asn Arg Asp Val Trp Gly
             20                  25                  30

Ile Trp Gly Gln Arg Tyr Leu Leu Lys Lys Val Ser Asp Gly Cys Cys
         35                  40                  45

Glu Tyr Val Ser Arg
     50

<210> SEQ ID NO 185
<211> LENGTH: 73
<212> TYPE: PRT
<213> ORGANISM: Bacillus subtilis
<220> FEATURE:
```

```
<223> OTHER INFORMATION: >ABP20089

<400> SEQUENCE: 185

Met Tyr Gly Glu Asp Val Glu Val Thr Leu Asp Gly Asn Ile Lys Val
1               5                   10                  15

Lys Val Phe Val Phe Cys Leu Pro Thr Thr Cys Lys Glu Glu Lys Glu
            20                  25                  30

Lys Arg Ala Leu Leu Thr Leu Lys Asn Leu Ile Asp Lys Arg Leu Lys
        35                  40                  45

Asn Glu Asp Leu Lys Tyr Leu Asp Val Gln Ser Asp Phe Val Leu Ile
    50                  55                  60

Pro Lys Met Ile Glu Asn Gly Glu Phe
65                  70

<210> SEQ ID NO 186
<211> LENGTH: 67
<212> TYPE: PRT
<213> ORGANISM: Bacillus subtilis
<220> FEATURE:
<223> OTHER INFORMATION: >ABP20090

<400> SEQUENCE: 186

Met Arg Val Ser Ser Glu Ala Leu Lys Ile Val Ile Val Gln His Leu
1               5                   10                  15

Glu Arg Asp Asn Asp Leu Met Ser Glu Gly Lys Ile Ile Val Leu Pro
            20                  25                  30

Cys Arg Asp Glu Lys Thr Ala Lys Glu Phe Glu Asp Phe Tyr Arg Lys
        35                  40                  45

Lys Phe Pro Ser Thr Gln Leu Met Ser Ile Glu Ile Val Asp Ser Asn
    50                  55                  60

Ile Tyr Gly
65

<210> SEQ ID NO 187
<211> LENGTH: 216
<212> TYPE: PRT
<213> ORGANISM: Bacillus subtilis
<220> FEATURE:
<223> OTHER INFORMATION: >ABP20091

<400> SEQUENCE: 187

Met Glu Thr Lys Lys Tyr Val Arg Ile Ile Arg Asn Ala Ser Lys Tyr
1               5                   10                  15

Gly Asp Met Thr Gly Gln Ile Phe Pro Leu Phe Gly Thr Trp Glu Asp
            20                  25                  30

Ser Tyr Lys Ile Asp Gly Ser Asp Gly Val Val Tyr Val Arg Lys Lys
        35                  40                  45

Asp Val Glu Val Ile Val Thr Glu Asn Arg Arg Pro Lys Val Asp Glu
    50                  55                  60

Arg Val Leu Ile Thr Glu Val Leu Leu Ser Ser Gly His Tyr Lys Ile
65                  70                  75                  80

Gly Asp Ile Tyr Thr Val Leu Ser Val Asp Ile Tyr Gly Thr Ile
                85                  90                  95

Thr Val Lys Glu His Ser Asn Cys Val Ile Ser Arg Glu Tyr Glu Val
            100                 105                 110

Ile Val Asp Glu Val Lys Lys Glu Glu Ala Asp Gly Met Glu Asn Val
        115                 120                 125

Asn Gln Thr Val Ile Asn Asn Ala Asn Thr Val Phe Glu Lys Lys Asp
```

```
              130                 135                 140
Asp Lys Tyr Phe Gly Tyr Lys Ser Arg Phe Gly Asp Ile Val Ile Gly
145                 150                 155                 160

Gly Ala Tyr Ser Tyr Arg Phe Val Val Gln Tyr Ala Lys Thr Asn Gln
                165                 170                 175

Asp Val Val Val Ile Pro Gly Asp Glu Asn Thr Val Thr Thr Pro Val
            180                 185                 190

Cys Thr Thr Leu Glu Glu Arg Leu Trp Gln Pro Glu Lys Ala Val Lys
        195                 200                 205

Ser Ser Pro Arg Asn Leu His Tyr
    210                 215

<210> SEQ ID NO 188
<211> LENGTH: 117
<212> TYPE: PRT
<213> ORGANISM: Bacillus subtilis
<220> FEATURE:
<223> OTHER INFORMATION: >ABP20092

<400> SEQUENCE: 188

Met Glu Val Gly Asp Lys Ile His Asn Thr Asn Glu Gln Ile Thr Ala
1               5                   10                  15

Leu Glu Lys Lys Lys Tyr Gln Ile Glu Thr Leu Leu Glu Lys Gln
                20                  25                  30

Arg Asp Leu Leu Lys Leu Glu Thr Gln Gln Asn Lys Glu Lys Leu Glu
            35                  40                  45

Leu Leu Phe Glu Leu Ser Glu Val Leu Thr Gln Leu Gln Asp Glu Glu
        50                  55                  60

Trp Val Ser Cys Met Ile Ala Leu Arg Ile Ile Arg Arg Asn Lys Arg
65                  70                  75                  80

Lys Tyr Leu Asn Leu Phe Glu Leu Val Asn Glu Lys Ala Tyr Ile Asn
                85                  90                  95

Lys Asp Lys Phe Lys Val Leu His Asp Glu Phe Phe Asp Leu Lys Gln
            100                 105                 110

Gln Leu Asn Glu Ile
        115

<210> SEQ ID NO 189
<211> LENGTH: 66
<212> TYPE: PRT
<213> ORGANISM: Bacillus subtilis
<220> FEATURE:
<223> OTHER INFORMATION: >ABP20093

<400> SEQUENCE: 189

Met Ile Tyr Lys Thr Phe Leu Pro Tyr Ala Asp Lys Val Tyr Leu Thr
1               5                   10                  15

Ile Val Asp Ser Ala Gln Arg Glu Ala Asp Ser Tyr Phe Pro Met Leu
                20                  25                  30

Asp Asp Arg Trp Lys Leu Thr Asp Lys Arg His Asn Lys Ala Asp Glu
            35                  40                  45

Lys Asn Lys Tyr Asn Tyr Ser Phe Ile Thr Phe Glu Asn Asn Tyr Arg
        50                  55                  60

Gln Lys
65

<210> SEQ ID NO 190
<211> LENGTH: 279
```

<212> TYPE: PRT
<213> ORGANISM: Bacillus subtilis
<220> FEATURE:
<223> OTHER INFORMATION: >ABP20094

<400> SEQUENCE: 190

```
Met Thr Gln Phe Asp Lys Gln Tyr Asn Ser Ile Ile Lys Asp Ile Ile
1               5                   10                  15

Asn Asn Gly Ile Ser Asn Glu Glu Phe Asp Val Arg Thr Lys Trp Asp
            20                  25                  30

Ser Asp Gly Thr Pro Ala His Thr Leu Ser Val Met Ser Lys Gln Met
        35                  40                  45

Arg Phe Asp Asn Ser Glu Val Pro Ile Leu Thr Thr Lys Lys Val Ala
    50                  55                  60

Trp Lys Thr Ala Ile Lys Glu Leu Leu Trp Ile Trp Gln Leu Lys Ser
65                  70                  75                  80

Asn Asp Val Asn Asp Leu Asn Lys Met Gly Val His Ile Trp Asp Gln
                85                  90                  95

Trp Lys Gln Glu Asp Gly Thr Ile Gly His Ala Tyr Gly Phe Gln Leu
            100                 105                 110

Gly Lys Lys Asn Arg Asn Leu Asn Gly Glu Lys Val Asp Gln Val Asp
        115                 120                 125

Tyr Leu Leu His Gln Leu Lys Asn Asn Pro Ser Ser Arg Arg His Ile
    130                 135                 140

Thr Met Leu Trp Asn Pro Asp Glu Leu Asp Ala Met Ala Leu Thr Pro
145                 150                 155                 160

Cys Val Tyr Glu Thr Gln Trp Tyr Val Lys His Gly Lys Leu His Leu
                165                 170                 175

Glu Val Arg Ala Arg Ser Asn Asp Met Ala Leu Gly Asn Pro Phe Asn
            180                 185                 190

Val Phe Gln Tyr Asn Val Leu Gln Arg Met Ile Ala Gln Val Thr Gly
        195                 200                 205

Tyr Glu Leu Gly Glu Tyr Ile Phe Asn Ile Gly Asp Cys His Val Tyr
    210                 215                 220

Thr Arg His Ile Asp Asn Leu Lys Ile Gln Met Glu Arg Glu Gln Phe
225                 230                 235                 240

Glu Ala Pro Glu Leu Trp Ile Asn Pro Glu Val Lys Asp Phe Tyr Asp
                245                 250                 255

Phe Thr Ile Asp Asp Phe Lys Leu Ile Asn Tyr Lys His Gly Asp Lys
            260                 265                 270

Leu Phe Phe Glu Val Ala Val
        275
```

<210> SEQ ID NO 191
<211> LENGTH: 40
<212> TYPE: PRT
<213> ORGANISM: Bacillus subtilis
<220> FEATURE:
<223> OTHER INFORMATION: >ABP20095

<400> SEQUENCE: 191

```
Met Phe Lys Val Leu Asp Val Leu Asp Gly Glu Lys Thr Lys Gln Asn
1               5                   10                  15

Thr Tyr Ile Tyr Trp Leu Phe Val Cys Gly Asn Phe Leu Phe Val Val
            20                  25                  30

Phe Tyr Leu Ala Asp Val Phe Leu
        35                  40
```

```
<210> SEQ ID NO 192
<211> LENGTH: 101
<212> TYPE: PRT
<213> ORGANISM: Bacillus subtilis
<220> FEATURE:
<223> OTHER INFORMATION: >ABP20096

<400> SEQUENCE: 192
```

Met Leu Lys Asp Lys Asn Lys Ile Thr Lys Ser Ile Glu Lys Ile Asn
1               5                   10                  15

Lys Leu Glu Glu Gly Leu Ala Leu Phe Glu Gly Asp Glu Glu Tyr
            20                  25                  30

Leu Ser Val Leu Val Lys Ile Gln Gly Leu Tyr Asp Glu Ile Ala Asp
        35                  40                  45

Thr Ala Leu Glu Cys Phe Lys Glu Met Thr Thr Lys Ile Arg Lys Thr
50                  55                  60

Gly Gln Lys Arg Ile Gly Lys Gly Ile Asp Gln Leu Pro Tyr Thr Ile
65                  70                  75                  80

Lys Glu Asn Ile Ala Asp Gln Val Asn Glu Leu Lys Gly Ser Phe Leu
                85                  90                  95

Asp Glu Ser Lys Tyr
            100

```
<210> SEQ ID NO 193
<211> LENGTH: 72
<212> TYPE: PRT
<213> ORGANISM: Bacillus subtilis
<220> FEATURE:
<223> OTHER INFORMATION: >ABP20119

<400> SEQUENCE: 193
```

Met Asp Ser Tyr Pro Glu Ser Leu Lys Lys Glu Thr Glu Glu Ile Lys
1               5                   10                  15

Glu Arg Val Arg Asn Gly Asn Ile Lys Glu Asp Arg Ile Lys Glu Ile
            20                  25                  30

Ala Glu Thr Thr Val Glu Phe Leu Lys Ser Glu Glu Lys Arg His Lys
        35                  40                  45

Tyr Phe Ser Glu Val Ala Ala Met Ala Asp Asn Leu Ser Glu Phe
    50                  55                  60

Phe Lys Ser Tyr Leu Lys Gly Glu
65                  70

```
<210> SEQ ID NO 194
<211> LENGTH: 503
<212> TYPE: PRT
<213> ORGANISM: Bacillus subtilis
<220> FEATURE:
<223> OTHER INFORMATION: >ABP20120

<400> SEQUENCE: 194
```

Met Lys Lys Leu Arg Val Met Ser Leu Phe Ser Gly Ile Gly Ala Phe
1               5                   10                  15

Glu Ala Ala Leu Arg Asn Ile Gly Val Glu Tyr Glu Leu Val Gly Phe
            20                  25                  30

Ser Glu Ile Asp Lys Tyr Ala Ile Lys Ser Tyr Cys Ala Ile His Asn
        35                  40                  45

Val Asp Glu Gln Leu Asn Tyr Gly Asp Val Ser Lys Ile Asp Lys Lys
50                  55                  60

```
Lys Leu Pro Glu Phe Asp Leu Leu Val Gly Gly Ser Pro Cys Gln Ser
 65                  70                  75                  80

Phe Ser Val Ala Gly Tyr Arg Lys Gly Phe Glu Asp Thr Arg Gly Thr
             85                  90                  95

Leu Phe Phe Gln Tyr Ile Asp Thr Leu Lys Glu Lys Gln Pro Arg Tyr
            100                 105                 110

Phe Val Phe Glu Asn Val Lys Gly Leu Ile Asn His Asp Lys Gly Asn
            115                 120                 125

Thr Leu Asn Ile Met Ala Glu Ser Phe Ser Glu Val Gly Tyr Arg Ile
130                 135                 140

Asp Leu Glu Leu Leu Asn Ser Lys Phe Phe Asn Val Pro Gln Asn Arg
145                 150                 155                 160

Glu Arg Ile Tyr Ile Ile Gly Val Arg Glu Asp Leu Ile Glu Asn Asp
                165                 170                 175

Glu Trp Val Val Glu Lys Gly Arg Asn Asp Val Leu Ser Lys Gly Lys
            180                 185                 190

Lys Arg Leu Lys Glu Leu Asn Ile Lys Ser Phe Asn Phe Lys Trp Ser
            195                 200                 205

Ala Gln Asp Ile Val Gly Arg Arg Leu Arg Glu Ile Leu Glu Glu Tyr
210                 215                 220

Val Asp Glu Lys Tyr Tyr Leu Ser Glu Glu Lys Thr Ser Lys Leu Ile
225                 230                 235                 240

Glu Gln Ile Glu Lys Pro Lys Glu Lys Asp Val Val Phe Val Gly Gly
                245                 250                 255

Ile Asn Val Gly Lys Arg Trp Leu Asn Asn Gly Lys Thr Tyr Ser Arg
            260                 265                 270

Asn Phe Lys Gln Gly Asn Arg Val Tyr Asp Ser Asn Gly Ile Ala Thr
            275                 280                 285

Thr Leu Thr Ser Gln Ser Val Gly Gly Leu Gly Gly Gln Thr Ser Leu
290                 295                 300

Tyr Lys Val Glu Asp Pro Ile Met Ile Gly His Ile Asp Leu Lys Gly
305                 310                 315                 320

His Asp Ala Ile Lys Arg Val Tyr Ser Pro Asp Gly Val Ser Pro Thr
                325                 330                 335

Leu Thr Thr Met Gly Gly Gly His Arg Glu Pro Lys Ile Ala Val Glu
            340                 345                 350

Tyr Val Gly Asn Ile Asn Pro Ser Gly Lys Gly Met Asn Asp Gln Val
            355                 360                 365

Tyr Asn Ser Asn Gly Leu Ser Pro Thr Leu Thr Thr Asn Lys Gly Glu
370                 375                 380

Gly Val Lys Ile Ser Val Pro Asn Pro Glu Ile Arg Pro Val Leu Thr
385                 390                 395                 400

Pro Glu Arg Glu Glu Lys Arg Gln Asn Gly Arg Arg Phe Lys Glu Asp
                405                 410                 415

Asp Glu Pro Ala Phe Thr Val Asn Thr Ile Asp Arg His Gly Val Ala
            420                 425                 430

Ile Gly Glu Tyr Pro Lys Tyr Arg Ile Arg Lys Leu Thr Pro Leu Glu
            435                 440                 445

Cys Trp Arg Leu Gln Ala Phe Asp Glu Glu Asp Phe Glu Lys Ala Leu
450                 455                 460

Ser Val Gly Ile Ser Asn Ser Gln Leu Tyr Lys Gln Ala Gly Asn Ser
465                 470                 475                 480

Ile Thr Val Thr Val Leu Glu Ser Ile Phe Lys Glu Leu Ile His Thr
```

```
                485                 490                 495

Tyr Val Asn Glu Glu Ser Glu
            500

<210> SEQ ID NO 195
<211> LENGTH: 269
<212> TYPE: PRT
<213> ORGANISM: Bacillus subtilis
<220> FEATURE:
<223> OTHER INFORMATION: >ABP20121

<400> SEQUENCE: 195

Met Asp Ile Asn Gly Lys Asp Leu Asn Lys Ile His Asn Ile Asp Cys
1               5                  10                  15

Val Gln Phe Met Arg Glu Asn Met Gly Asp Cys Ser Ile Asp Leu Thr
            20                  25                  30

Val Thr Ser Pro Pro Tyr Asp Asp Leu Arg Lys Tyr Asn Gly Tyr Ser
        35                  40                  45

Phe Asn Phe Glu Ala Thr Ala Arg Glu Leu Tyr Arg Val Thr Lys Asp
    50                  55                  60

Gly Val Val Val Trp Val Ile Gly Asp Lys Thr His Asn Gly Ser
65                  70                  75                  80

Glu Ser Gly Thr Ser Phe Lys Gln Ala Leu Tyr Phe Lys Glu Ile Gly
                85                  90                  95

Phe Asn Leu His Asp Thr Met Ile Tyr Glu Lys Asp Ser Ile Ser Phe
            100                 105                 110

Pro Asp Lys Asn Arg Tyr Tyr Gln Ile Phe Glu Tyr Met Phe Val Phe
        115                 120                 125

Ser Lys Gly Lys Pro Lys Thr Ile Asn Leu Ile Ser Asp Arg Lys Asn
    130                 135                 140

Lys Trp Tyr Asn Gly Lys Lys His Ile Lys Gly His Tyr Arg Lys Met
145                 150                 155                 160

Asp Gly Glu Lys Val Arg His Asn Lys Gln Asn Leu Leu Lys Glu Phe
                165                 170                 175

Gly Val Arg Phe Asn Ile Trp Arg Ile Pro Asn Gly His Gln Lys Ser
            180                 185                 190

Thr Leu Asp Lys Val Ala Phe Glu His Pro Ala Ile Phe Pro Glu Arg
        195                 200                 205

Leu Ala Glu Asp His Ile Leu Ser Trp Ser Asn Glu Gly Asp Ile Val
    210                 215                 220

Leu Asp Pro Phe Met Gly Ser Gly Thr Thr Ala Lys Met Ala Ala Leu
225                 230                 235                 240

Asn Asn Arg Lys Tyr Ile Gly Thr Glu Ile Ser Lys Glu Tyr Cys Asp
                245                 250                 255

Ile Ala Asn Glu Arg Leu Arg Asn Tyr Ile Gly Thr Ile
            260                 265

<210> SEQ ID NO 196
<211> LENGTH: 172
<212> TYPE: PRT
<213> ORGANISM: Bacillus subtilis
<220> FEATURE:
<223> OTHER INFORMATION: >ABP20122

<400> SEQUENCE: 196

Met Lys Lys Val Ile Ala Ile Asp Met Asp Gln Val Leu Ala Asp Leu
1               5                  10                  15
```

Leu Ser Asp Trp Val Ala Tyr Ile Asn Thr His Asp Pro Phe Leu
            20                  25                  30

Lys Glu Glu Ile Leu Cys Trp Asp Ile Lys Lys Tyr Thr Asn Thr
        35                  40                  45

Asn Asn Asn Val Tyr Arg His Leu Asp Tyr Asp Leu Phe Arg Asn Leu
 50                  55                  60

Asp Val Ile Glu Gly Ser Gln Arg Val Val Lys Glu Leu Met Lys Lys
 65                  70                  75                  80

Tyr Glu Val Tyr Val Thr Thr Ala Thr Asn His Pro Glu Ser Leu
                85                  90                  95

Lys Ala Lys Leu Glu Trp Leu Thr Glu His Phe Ser Phe Ile Pro His
            100                 105                 110

Ser Asn Val Val Leu Cys Gly Asn Lys Ser Ile Ile Lys Ala Asp Ile
            115                 120                 125

Met Ile Asp Asp Gly Ile His Asn Leu Glu Ser Phe Glu Gly Met Lys
130                 135                 140

Ile Leu Phe Asp Ala Pro His Asn Arg Asn Asp Asn Arg Phe Ile Arg
145                 150                 155                 160

Val Met Asn Trp Glu Glu Ile Glu Arg Lys Leu Leu
                165                 170

<210> SEQ ID NO 197
<211> LENGTH: 165
<212> TYPE: PRT
<213> ORGANISM: Bacillus subtilis
<220> FEATURE:
<223> OTHER INFORMATION: >ABP20123

<400> SEQUENCE: 197

Met Ala Leu Ile Ile Leu Glu Gly Pro Asp Cys Cys Phe Lys Ser Thr
1               5                   10                  15

Val Ala Ala Lys Leu Ser Lys Ala Met Lys Tyr Pro Ile Ile Lys Gly
            20                  25                  30

Ser Ser Phe Glu Leu Ala Thr Ser Gly Asn Gln Lys Leu Phe Glu His
        35                  40                  45

Phe Asn Arg Leu Ala Asp Glu Asp Ser Val Ile Ile Asp Arg Phe Val
 50                  55                  60

Tyr Ser Asn Leu Val Tyr Ala Lys Lys Phe Lys Asp Tyr Ser Ile Leu
65                  70                  75                  80

Thr Glu Gln Gln Leu Arg Ile Ile Glu Asp Lys Ile Lys Leu Lys Ala
                85                  90                  95

Lys Val Val Tyr Leu His Ala Asp Pro Ser Val Ile Lys Glu Arg Leu
            100                 105                 110

Ser Ile Arg Gly Asp Glu Tyr Ile Glu Gly Lys Asp Ile Asp Ser Ile
            115                 120                 125

Leu Glu Leu Tyr Arg Glu Val Met Ser Asn Ala Gly Leu His Thr Tyr
130                 135                 140

Ser Trp Asp Thr Gly Gln Trp Ser Ser Asp Glu Ile Ala Lys Asp Thr
145                 150                 155                 160

Ile Phe Leu Val Glu
                165

<210> SEQ ID NO 198
<211> LENGTH: 227
<212> TYPE: PRT
<213> ORGANISM: Bacillus subtilis
<220> FEATURE:

<223> OTHER INFORMATION: >ABP20226

<400> SEQUENCE: 198

```
Met Gly Tyr Lys Leu Met Ala Tyr Gly Gly Tyr Phe Leu Phe Cys Leu
1               5                   10                  15

Phe Phe Leu Leu Met Asp Gly Trp Arg Gly Met Gly Ile Cys Leu Ile
            20                  25                  30

Ile Ala Gly Leu Ala Leu Leu Ala Leu Glu Pro Tyr Lys Ile Lys Ala
        35                  40                  45

Gln Lys Asn Ile Asp Lys Leu Lys Glu Asn Ala Glu Thr Leu Lys His
    50                  55                  60

Tyr Glu Ser Gly Phe Asn Pro Asp Asn Phe Phe Asn Thr Tyr Lys Thr
65                  70                  75                  80

Lys Ile Ala Phe Lys Glu Ser Asp Ser Leu Val Lys Ile Tyr Gln Leu
                85                  90                  95

Asn Arg Asn Glu His Ile Glu Glu Tyr Thr Ile Pro Phe Ser Asn Ile
            100                 105                 110

Ile Glu Ser Glu Ile Thr Leu Asp Asn Gln Ile Ile Ser Lys Val Ser
        115                 120                 125

Lys Ser Gly Ile Val Ala Gly Leu Leu Ala Gly Ile Gly Ala
130                 135                 140

Ala Leu Gly Gly Leu Ser Ala Ser Ser Ile Gln Asn Glu Met Val Lys
145                 150                 155                 160

Ser Val Thr Leu Lys Ile Thr Val Glu Asp Leu Gly Lys Pro Ile His
                165                 170                 175

Tyr Ile Asp Phe Leu Pro Thr Gln Glu Val Gly Tyr Asn Thr Gln
            180                 185                 190

Gly Tyr Lys Lys Asp Ser Asn Ile Ile Gln Gln Ala Leu Lys Asn Ala
        195                 200                 205

Glu Tyr Trp His Gly Val Met Asp Val Ile Lys Lys Ala Ser Lys
    210                 215                 220

Val Ala Gln
225
```

<210> SEQ ID NO 199
<211> LENGTH: 2296
<212> TYPE: PRT
<213> ORGANISM: Bacillus subtilis
<220> FEATURE:
<223> OTHER INFORMATION: >ABP20227

<400> SEQUENCE: 199

```
Met Ser Gln Asn Leu Lys Ile Ile Leu Thr Pro Gln Ala Asp Thr Ser
1               5                   10                  15

Ser Lys Thr Val Glu Gln Leu Asn Gln Gln Ile Lys Ser Leu Glu Lys
            20                  25                  30

Lys Leu Asn Ser Leu Lys Leu Asn Thr Asn Ile Asp Ser Thr Thr Leu
        35                  40                  45

Lys Ala Leu Gln Glu Phe Ser Ser Ala Val Asp Ala Tyr Gln Lys Asn
    50                  55                  60

Leu Lys Ser Tyr Asn Gln Thr Val Arg Glu Thr Ser Val Ile Lys
65                  70                  75                  80

Asn Ala Asp Gly Ser Val Glu Lys Leu Thr Gln Gln Tyr Lys Lys Asn
                85                  90                  95

Gly Glu Ile Leu Gln Arg Glu Thr Lys Ile Ile Asn Asn Arg Asn Thr
            100                 105                 110
```

```
Ala Leu Lys Gln Glu Thr Gln Glu Val Asn Lys Leu Thr Gln Ala Thr
    115                 120                 125

Glu Lys Leu Gly Gln Val Gln Lys Lys Thr Val Gln Arg Asn Leu Gln
130                 135                 140

Gly Gln Pro Thr Lys Ile Val Gln Lys Asn Arg Gln Gly Phe Asp Asp
145                 150                 155                 160

Ile Val Tyr Thr Thr Asp Pro Lys Thr Asn Ser Thr Ser Ser Lys Thr
                165                 170                 175

Thr Thr Asn Tyr Asp Gln Gln Arg Arg Ala Ile Glu Gln Leu Lys Gln
            180                 185                 190

Asp Leu Glu Lys Leu Arg Gln Gln Gly Ile Val Thr Asp Thr Thr Ile
        195                 200                 205

Ser Ser Leu Gly Arg Lys Ile Asn Thr Ala Gln Ser Ala Gln Gln Ile
    210                 215                 220

Glu Ala Leu Gln Asn Arg Ile Arg Met Leu Asp Asp Lys Ser Ala Ala
225                 230                 235                 240

Val Ala Lys Asn Asn Glu Leu Lys Lys Thr Ile Glu Leu Tyr Gln Arg
                245                 250                 255

Gln Ala Gln Val Asn Val Gln Asn Leu Asn Thr Arg Tyr Gly Ser Ser
            260                 265                 270

Met Gly Ser Ser Asn Arg Gln Ala Val Gln Asp Tyr Leu Asn Ala Val
        275                 280                 285

Asn Ser Leu Asn Val Ser Thr Gly Ser Asn Asn Ile Arg Ser Gln Ile
    290                 295                 300

Gln Ser Leu Asn Met Gln Phe Arg Glu Leu Ala Ser Ser Ala Gln Ala
305                 310                 315                 320

Ala Ala Asn Gln Ala Ser Ser Phe Gly Ala Glu Leu Thr Gln Thr Phe
                325                 330                 335

Lys Ser Met Ser Thr Tyr Leu Ile Ser Gly Ser Leu Phe Tyr Gly Ala
            340                 345                 350

Ile Ser Gly Leu Lys Glu Met Val Ser Gln Ala Val Glu Ile Asp Thr
        355                 360                 365

Leu Met Thr Asn Ile Arg Arg Val Met Asn Glu Pro Asp Tyr Lys Tyr
    370                 375                 380

Asn Glu Leu Leu Gln Glu Ser Ile Asp Leu Gly Asp Thr Leu Ser Asn
385                 390                 395                 400

Lys Ile Thr Asp Ile Leu Gln Met Thr Gly Asp Phe Gly Arg Met Gly
                405                 410                 415

Phe Asp Glu Ser Glu Leu Ser Thr Leu Thr Lys Thr Ala Gln Val Leu
            420                 425                 430

Gln Asn Val Ser Asp Leu Thr Pro Asp Asp Thr Val Asn Thr Leu Thr
        435                 440                 445

Ala Ala Met Leu Asn Phe Asn Ile Ala Ala Asn Asp Ser Ile Ser Ile
    450                 455                 460

Ala Asp Lys Leu Asn Glu Val Asp Asn Asn Tyr Ala Val Thr Thr Leu
465                 470                 475                 480

Asp Leu Ala Asn Ser Ile Arg Lys Ala Gly Ser Thr Ala Ser Thr Phe
                485                 490                 495

Gly Val Glu Leu Asn Asp Leu Ile Gly Tyr Thr Thr Ala Ile Ala Ser
            500                 505                 510

Thr Thr Arg Glu Ser Gly Asn Ile Val Gly Asn Ser Leu Lys Thr Ile
        515                 520                 525
```

```
Phe Ala Arg Ile Gly Asn Asn Gln Ser Ser Ile Lys Ala Leu Asp Glu
            530                 535                 540
Ile Gly Ile Ser Val Lys Thr Ala Ser Gly Glu Ala Lys Ser Ala Ser
545                 550                 555                 560
Asp Leu Ile Ser Glu Val Ala Gly Lys Trp Asp Thr Leu Thr Asp Ala
                565                 570                 575
Gln Lys Gln Asn Thr Ser Ile Gly Val Ala Gly Ile Tyr Gln Leu Ser
            580                 585                 590
Arg Phe Asn Ala Met Met Asn Asn Phe Ser Ile Ala Gln Asn Ala Ala
        595                 600                 605
Lys Thr Ala Ala Asn Ser Thr Gly Ser Ala Trp Ser Glu Gln Gln Lys
610                 615                 620
Tyr Ala Asp Ser Leu Gln Ala Arg Val Asn Lys Leu Gln Asn Asn Phe
625                 630                 635                 640
Thr Glu Phe Ala Ile Ala Ala Ser Asp Ala Phe Ile Ser Asp Gly Leu
                645                 650                 655
Ile Glu Phe Thr Gln Ala Ala Gly Ser Leu Leu Asn Ala Ser Thr Gly
            660                 665                 670
Val Ile Lys Ser Val Gly Phe Leu Pro Pro Leu Leu Ala Ala Val Ser
        675                 680                 685
Thr Ala Thr Leu Leu Leu Ser Lys Asn Thr Arg Thr Leu Ala Thr Thr
690                 695                 700
Leu Ile Leu Gly Thr Arg Ala Met Gly Gln Glu Thr Leu Ala Thr Ala
705                 710                 715                 720
Gly Leu Glu Ala Gly Met Thr Arg Ala Ala Val Ala Ser Arg Val Leu
                725                 730                 735
Lys Thr Ala Leu Arg Gly Leu Leu Val Ser Thr Leu Val Gly Gly Ala
            740                 745                 750
Phe Ala Ala Leu Gly Trp Ala Leu Glu Ser Leu Ile Ser Ser Phe Ala
        755                 760                 765
Glu Ala Lys Lys Ala Lys Asp Asp Phe Glu Gln Ser Gln Gln Thr Asn
770                 775                 780
Val Glu Ala Ile Thr Thr Asn Lys Asp Ser Thr Asp Lys Leu Ile Gln
785                 790                 795                 800
Gln Tyr Lys Glu Leu Gln Lys Val Lys Glu Ser Arg Ser Leu Thr Ser
                805                 810                 815
Asp Glu Glu Gln Glu Tyr Leu Gln Val Thr Gln Gln Leu Ala Gln Thr
            820                 825                 830
Phe Pro Ser Leu Val Lys Gly Tyr Asp Ser Gln Gly Asn Ala Ile Leu
        835                 840                 845
Lys Thr Asn Lys Glu Leu Glu Lys Ala Ile Glu Asn Thr Lys Glu Tyr
850                 855                 860
Leu Ala Leu Lys Lys Gln Glu Thr Arg Asp Ser Ala Lys Lys Thr Phe
865                 870                 875                 880
Glu Asp Ala Ser Lys Glu Ile Lys Lys Ser Lys Asp Glu Leu Lys Gln
                885                 890                 895
Tyr Lys Gln Ile Ala Asp Tyr Asn Asp Lys Gly Arg Pro Lys Trp Asp
            900                 905                 910
Leu Ile Ala Asp Asp Asp Tyr Lys Val Ala Ala Asp Lys Ala Lys
        915                 920                 925
Gln Ser Met Leu Lys Ala Gln Ser Asp Ile Glu Ser Gly Asn Ala Lys
930                 935                 940
Val Lys Asp Ser Val Leu Ser Ile Ala Asn Ala Tyr Ser Ser Ile Asp
```

```
                945                 950                 955                 960
Ile Ser Asn Thr Leu Lys Ala Ser Ile Ser Asp Val Val Asn Lys Leu
                    965                 970                 975
Asn Leu Lys Asp Asn Leu Asp Pro Glu Glu Leu Glu Lys Phe Ser Ser
                    980                 985                 990
Ser Leu Gly Lys Leu Gln Glu Lys Met Gln Lys Ala Leu Asp Ser Gly
                    995                 1000                1005
Asp Glu Lys Ala Phe Asp Asn Ala Lys Lys Asp Ile Gln Ser Leu Leu
                    1010                1015                1020
Glu Thr Tyr Ser Lys Ser Asp Ser Ser Ile Asp Val Phe Lys Met Ser
1025                1030                1035                1040
Phe Asp Lys Ala Gln Lys Asn Ile Lys Asp Gly Asp Lys Ser Leu Ser
                    1045                1050                1055
Ser Val Lys Ser Glu Val Gly Asp Leu Gly Glu Thr Leu Ala Glu Ala
                    1060                1065                1070
Gly Asn Glu Ala Glu Asp Phe Gly Lys Lys Leu Lys Glu Ala Leu Asp
                    1075                1080                1085
Ala Asn Ser Val Asp Asp Ile Lys Ala Ala Ile Lys Glu Met Ser Asp
                    1090                1095                1100
Ala Met Gln Phe Asp Ser Val Gln Asp Ala Leu Asn Gly Asp Ile Phe
1105                1110                1115                1120
Asn Asn Thr Lys Asp Gln Val Ala Pro Leu Asn Asp Leu Leu Glu Lys
                    1125                1130                1135
Met Ala Glu Gly Lys Ser Ile Ser Ala Asn Glu Ala Asn Thr Leu Ile
                    1140                1145                1150
Gln Lys Asp Lys Glu Leu Ala Lys Ala Ile Ser Ile Glu Asn Gly Val
                    1155                1160                1165
Val Lys Ile Asn Arg Asp Glu Val Ile Lys Gln Arg Lys Val Lys Leu
                    1170                1175                1180
Asp Ala Tyr Asn Asp Met Val Thr Tyr Ser Asn Lys Leu Met Lys Thr
1185                1190                1195                1200
Glu Val Asn Asn Ala Ile Lys Thr Leu Asn Ala Asp Thr Leu Arg Ile
                    1205                1210                1215
Asp Ser Leu Arg Lys Leu Arg Lys Glu Arg Lys Leu Asp Met Ser Glu
                    1220                1225                1230
Ala Glu Leu Ser Asp Leu Glu Val Lys Ser Ile Asn Asn Val Ala Asp
                    1235                1240                1245
Ala Lys Lys Glu Leu Lys Lys Leu Glu Glu Lys Met Leu Gln Pro Gly
                    1250                1255                1260
Gly Tyr Ser Asn Ser Gln Ile Glu Ala Met Gln Ser Val Lys Ser Ala
1265                1270                1275                1280
Leu Glu Ser Tyr Ile Ser Ala Ser Glu Ala Ala Ser Thr Gln Glu
                    1285                1290                1295
Met Asn Lys Gln Ala Leu Val Glu Ala Gly Thr Ser Leu Glu Asn Trp
                    1300                1305                1310
Thr Asp Gln Gln Glu Lys Ala Asn Glu Glu Thr Lys Thr Ser Met Tyr
                    1315                1320                1325
Val Val Asp Lys Tyr Lys Glu Ala Leu Glu Lys Val Asn Ala Glu Ile
                    1330                1335                1340
Asp Lys Tyr Asn Lys Gln Val Asn Asp Tyr Pro Lys Tyr Ser Gln Lys
1345                1350                1355                1360
Tyr Arg Asp Ala Ile Lys Lys Glu Ile Lys Ala Leu Gln Gln Lys Lys
                    1365                1370                1375
```

Lys Leu Met Gln Glu Gln Ala Lys Leu Leu Lys Asp Gln Ile Lys Ser
            1380                1385                1390

Gly Asn Ile Ala Gln Tyr Gly Ile Val Thr Thr Ser Ser Pro Gly
        1395                1400                1405

Gly Thr Ser Thr Ser Thr Gly Gly Ser Tyr Ser Gly Lys Tyr Ser Ser
    1410                1415                1420

Tyr Ile Asn Ser Ala Ala Ser Lys Tyr Asn Val Asp Pro Ala Leu Ile
1425                1430                1435                1440

Ala Ala Val Ile Gln Gln Glu Ser Gly Phe Asn Ala Lys Ala Arg Ser
                1445                1450                1455

Gly Val Gly Ala Met Gly Leu Met Gln Leu Met Pro Ala Thr Ala Lys
            1460                1465                1470

Ser Leu Gly Val Asn Asn Ala Tyr Asp Pro Tyr Gln Asn Val Met Gly
        1475                1480                1485

Gly Thr Lys Tyr Leu Ala Gln Gln Leu Glu Lys Phe Gly Gly Asn Val
    1490                1495                1500

Glu Lys Ala Leu Ala Ala Tyr Asn Ala Gly Pro Gly Asn Val Ile Lys
1505                1510                1515                1520

Tyr Gly Gly Ile Pro Pro Phe Lys Glu Thr Gln Asn Tyr Val Lys Lys
                1525                1530                1535

Ile Met Ala Asn Tyr Ser Lys Ser Leu Ser Ser Ala Thr Ser Ser Ile
            1540                1545                1550

Ala Ser Tyr Tyr Thr Asn Asn Ser Ala Phe Arg Val Ser Ser Lys Tyr
        1555                1560                1565

Gly Gln Gln Glu Ser Gly Leu Arg Ser Ser Pro His Lys Gly Thr Asp
    1570                1575                1580

Phe Ala Ala Lys Ala Gly Thr Ala Ile Lys Ser Leu Gln Ser Gly Lys
1585                1590                1595                1600

Val Gln Ile Ala Gly Tyr Ser Lys Thr Ala Gly Asn Trp Val Val Ile
                1605                1610                1615

Lys Gln Asp Asp Gly Thr Val Ala Lys Tyr Met His Met Leu Asn Thr
            1620                1625                1630

Pro Ser Val Lys Thr Gly Gln Ser Val Lys Ala Gly Gln Thr Ile Gly
        1635                1640                1645

Lys Val Gly Ser Thr Gly Asn Ser Thr Gly Asn His Leu His Leu Gln
    1650                1655                1660

Ile Glu Gln Asn Gly Lys Thr Ile Asp Pro Glu Lys Tyr Met Gln Gly
1665                1670                1675                1680

Ile Gly Thr Ser Ile Ser Asp Ala Ser Gln Ala Glu Ala Glu Arg Gln
            1685                1690                1695

Gln Gly Ile Ala Gln Ala Lys Ser Asp Leu Leu Ser Leu Gln Gly Asp
        1700                1705                1710

Ile Asp Ser Val Asn Asp Gln Ile Gln Glu Leu Gln Tyr Glu Leu Val
    1715                1720                1725

Gln Ser Lys Leu Asp Glu Phe Asp Lys Arg Ile Gly Asp Phe Asp Ile
        1730                1735                1740

Arg Ile Ala Lys Asp Glu Ser Met Ala Asn Arg Tyr Thr Ser Asp Ser
1745                1750                1755                1760

Lys Glu Phe Arg Lys Tyr Thr Ser Asp Gln Lys Lys Ala Val Ala Glu
                1765                1770                1775

Gln Ala Lys Ile Gln Gln Gln Lys Val Asn Trp Ile Gln Lys Glu Ile
            1780                1785                1790

```
Lys Thr Asn Lys Ala Leu Asn Ser Ala Gln Arg Ala Gln Leu Gln Glu
        1795                1800                1805

Glu Leu Lys Gln Ala Lys Leu Asp Leu Ile Ser Val Gln Asp Gln Val
    1810                1815                1820

Arg Glu Leu Gln Lys Gln Leu Val Gln Ser Lys Val Asp Glu Thr Leu
1825                1830                1835                1840

Lys Ser Ile Glu Lys Ser Ser Ser Lys Thr Gln Gly Lys Ile Lys Asp
            1845                1850                1855

Val Asp Asn Lys Ile Ser Met Thr Glu Asp Glu Asp Lys Val Lys
        1860                1865                1870

Tyr Tyr Ser Lys Gln Ile Lys Leu Ile Gln Gln Gln Lys Glu Ala
        1875                1880                1885

Lys Lys Tyr Ile Lys Gln Leu Glu Glu Gln Lys Lys Ala Ala Lys Gly
    1890                1895                1900

Phe Pro Asp Ile Gln Glu Gln Ile Thr Glu Glu Ile Glu Asn Trp Lys
1905                1910                1915                1920

Asp Lys Gln Lys Asp Phe Asn Leu Glu Leu Tyr Asn Thr Lys Lys Ser
            1925                1930                1935

Ile Lys Asp Ile Tyr Lys Ser Leu Ala Asp Glu Val Val Ser Ile Tyr
            1940                1945                1950

Lys Glu Met Tyr Glu Lys Met Arg Asp Ile Glu Leu Glu Ala His Gln
        1955                1960                1965

Lys Ala Thr Gln Asp Lys Ile Asp Glu Ile Asp Lys Glu Asp Glu Glu
        1970                1975                1980

Ala Lys Tyr Gln Lys Glu Leu Lys Glu Lys Asn Gln Ala Ile Gln Glu
1985                1990                1995                2000

Thr Lys Asp Lys Ile Ser Lys Leu Ser Met Asp Asp Ser Ser Glu Ala
            2005                2010                2015

Lys Ser Gln Val Lys Asp Leu Glu Lys Gln Leu Gln Glu Gln Gln Glu
        2020                2025                2030

Ala Leu Asp Glu Tyr Ile Lys Asp Arg Ser Asn Thr Lys Arg Lys Glu
        2035                2040                2045

Ala Leu Gln Asp Gln Leu Asp Lys Asp Glu Glu Ser Ile Asn Asn Lys
    2050                2055                2060

Tyr Asp Asp Leu Val Asn Asp Glu Arg Ala Phe Lys Lys Leu Glu Asp
2065                2070                2075                2080

Lys Leu Met Asp Gly Lys Ile Thr Asp Ile Ala Lys Gln Leu Asn Glu
            2085                2090                2095

Phe Thr Lys Phe Ile Asn Glu Asn Met Lys Ser Ile Gly Lys Ser Ile
            2100                2105                2110

Ser Asn Asn Leu Ile Asp Lys Leu Lys Asp Ala Ala Ser Ala Leu Asn
        2115                2120                2125

Thr Val Thr Thr Gly Asn Thr Thr Gly Lys Lys Val Ser Ser Phe Ala
    2130                2135                2140

Ser Gly Gly Tyr Thr Gly Thr Gly Leu Gly Ala Gly Lys Leu Ala Phe
2145                2150                2155                2160

Leu His Asp Lys Glu Leu Ile Leu Asn Lys Thr Asp Thr Glu Asn Met
            2165                2170                2175

Leu Glu Ala Val Lys Gln Val Arg Gln Thr Ser Thr Asp Asn Ser Val
        2180                2185                2190

Lys Thr Thr Ser Lys Trp Gly Gln Pro Gly Lys Ile Ser Asp Val Leu
        2195                2200                2205

Ser Lys Ser Ile Ser Leu Val Thr Pro Ala Met Asn Ala Ala Val Ala
```

-continued

```
                2210                2215                2220
Ser Gln Thr Ser Leu Thr Lys Gly Leu Ile Pro Thr Leu Lys Asn Phe
2225                2230                2235                2240

Ser Thr Pro Thr Val Thr Pro Ser Thr Pro Gln Gly Asn Thr Ser Asn
                2245                2250                2255

Asn Gln Asn Ser Phe Thr Ile Asn Val Thr Glu Ala Ser Asn Ala Lys
                2260                2265                2270

Glu Thr Ala Ser Leu Val Tyr Lys Gln Leu Ala Asn Gly Leu Lys Asn
                2275                2280                2285

Thr Gly Leu Asn Phe Asn Ile Thr
                2290                2295

<210> SEQ ID NO 200
<211> LENGTH: 253
<212> TYPE: PRT
<213> ORGANISM: Bacillus subtilis
<220> FEATURE:
<223> OTHER INFORMATION: >ABP20228

<400> SEQUENCE: 200

Met Ile Arg Gln Ser Gln Tyr Phe Leu Phe Asp Asn Glu Lys Ser Ile
1               5                   10                  15

Asp Tyr Gly Val Glu Asn Val Asn Thr Glu Ser Gly Leu Val Glu Glu
                20                  25                  30

Ser Phe Leu Gly Ser Arg Ser Val Asn Glu Thr Tyr Val Lys Gly Arg
            35                  40                  45

Ser Glu Pro Tyr Thr Glu Gly Val Lys Arg Glu Ala Lys Gln Phe Pro
        50                  55                  60

Leu Asn Phe Tyr Val Gly Glu Asn Tyr Asp Glu Lys Lys Ile Arg Ala
65                  70                  75                  80

Ile Lys Arg Trp Leu Asp Val Asp Asp Tyr Lys Pro Leu Ala Phe Ser
                85                  90                  95

Glu Asn Leu Asp Ile Val Tyr Tyr Ala Met Pro Val Asp Thr Ser Asp
                100                 105                 110

Leu Val His Asn Ala Ala Arg His Gly Tyr Val Arg Leu Thr Met Lys
            115                 120                 125

Cys Asn Ser Pro Tyr Ala Tyr Ser Arg Asn Thr Ser Thr His Ser Phe
        130                 135                 140

Asp Ile Ser Ser Gly Met Lys Thr Ile Glu Leu His Asn Lys Gly Asp
145                 150                 155                 160

Val Ala Ile Tyr Pro Thr Val Glu Ile Leu Lys Ile Gly Asp Gly Asp
                165                 170                 175

Val Lys Ile Glu Asn Leu Ser Asp Tyr Thr Asp Pro Phe Ile Phe Ser
                180                 185                 190

Asn Leu Lys Asp Arg Glu Ile Val Lys Val Asn Gly Asp Lys Glu Ile
            195                 200                 205

Ile Glu Ser Ser Leu Tyr Gly Asn Glu Arg Tyr Asp Asp Phe Asn Asp
        210                 215                 220

Asn Tyr Ile Arg Leu Asp Tyr Gly Lys Asn Arg Leu Lys Val Thr Gly
225                 230                 235                 240

Lys Cys Lys Leu Arg Leu Thr Phe Arg Phe Lys Tyr Arg
                245                 250

<210> SEQ ID NO 201
<211> LENGTH: 880
<212> TYPE: PRT
```

<213> ORGANISM: Bacillus subtilis
<220> FEATURE:
<223> OTHER INFORMATION: >ABP20229

<400> SEQUENCE: 201

```
Met Ile Thr Ile Arg Lys Asp Thr Glu Ile Lys Asn Ile Arg Leu Ser
1               5                   10                  15

Leu Ala Lys Pro Asp Lys Thr Lys Ile Ala Asn Ile Asp Glu Val Leu
            20                  25                  30

Asn Pro Thr Val Thr Leu Asn His Gly Ser Ser Val His Glu Leu Ser
        35                  40                  45

Phe Ser Ile Pro Leu Lys Ala Thr Tyr Asp Gly Val Ile Lys Arg Asn
    50                  55                  60

His Val Asp Leu Leu Lys Pro Trp Tyr Leu Ile Lys Thr Glu Phe
65                  70                  75                  80

Tyr Gly Leu Ala Ile Trp Phe Ile Ile Thr Lys Arg Thr Lys Ser Phe
                85                  90                  95

Ser Ser Glu Met Asp Thr Val Gln Val Glu Cys Arg Ser Leu Gln His
            100                 105                 110

Glu Leu Ser Arg Ile Ser Val Leu Lys Tyr Glu Glu Thr Ser Lys Asn
        115                 120                 125

Leu Gln Glu Val Val Thr Asp Cys Leu Lys Asn Thr Ser Trp Thr Val
130                 135                 140

Gly Tyr Ile Asp Thr Leu Phe Asn Val Lys Arg Arg Gln Phe Asp Val
145                 150                 155                 160

Ser Ser Thr Asn Lys Leu Asp Phe Leu Tyr Ser Ile Cys Glu Lys Phe
                165                 170                 175

Asp Ala Val Pro Val Phe Asp Thr Val Lys Glu Thr Val Ser Phe Tyr
            180                 185                 190

Lys Glu Ser Asp Ile Ser Lys Tyr Lys Gly Leu Lys Leu Asn Pro Arg
        195                 200                 205

Gln Tyr Met Ile Ser Met Asp Asp Ser Asp Ala Asp Glu Leu Val
    210                 215                 220

Thr Arg Leu Tyr Ala Thr Gly Lys Asp Gly Ile Ser Ile Asn Ser Val
225                 230                 235                 240

Asn Pro Thr Gly Gln Ser Tyr Ile Asp Asp Phe Ser Tyr Phe Leu Phe
                245                 250                 255

Pro Phe Gln Arg Asp Glu Gln Arg Asn Val Ile Ser His Ser Ala Tyr
            260                 265                 270

Met Pro Asp Glu Leu Cys His Ala Ile Leu Asp Tyr Asn Asp Leu Val
        275                 280                 285

Asn Ser Glu Gly Asn Ala Phe Asn Lys Leu Leu Thr Gln Lys Asn Glu
    290                 295                 300

Ala Glu Thr Gly Leu Thr Glu Leu Asn Asn Glu Leu Tyr Thr Leu Asp
305                 310                 315                 320

Leu Glu Val Gln Lys Leu Leu Asp Arg Ile Glu Val Ala Lys Lys Ala
                325                 330                 335

Gly Asp Asp Thr Ser Gln Leu Lys Ala Gln Leu Ala Val Lys Gln Lys
            340                 345                 350

Ala Val Ala Leu Lys Lys Asn Gln Ile Ala Thr Ile Glu Ser Thr Ile
        355                 360                 365

Ser Gln Ile Ser Ala Ser Ile Ser Lys Leu Lys Glu Lys Leu Ser Phe
    370                 375                 380

Glu Asn Asn Phe Ser Glu Asn Gln Gln Lys Leu Leu Ser Arg Phe Ile
```

```
                385                 390                 395                 400
Ser Thr Thr Glu Trp Ser Asn Asp Ser Ile Tyr Asp Glu Asn Glu Leu
                    405                 410                 415

Tyr Asp Asp Ala Asn Glu Glu Leu Glu Ser Arg Asn Thr Pro Pro Val
                420                 425                 430

Asn Val Thr Leu Asp Ile Val Asn Phe Phe Asn Cys Ile Ser Glu Lys
            435                 440                 445

His Asn Trp Asp Arg Phe Ser Leu Gly Asp Ile Val Arg Val Gln Gln
        450                 455                 460

Ser Asp Leu Asn Thr Asp Ile Lys Ala Ile Leu Ser Ala Ile Thr Ile
465                 470                 475                 480

Asp Phe Glu Gln Ser Asn Ile Ser Val Thr Val Thr Asn Gly Lys Arg
                485                 490                 495

Val Gln Ser Asp Phe Glu Lys Val Ile Lys Thr Val Tyr Arg Thr Asn
                500                 505                 510

Lys Ile Ser Thr Glu Leu Asn Lys Arg Lys Ile Glu Trp Asp Lys Val
            515                 520                 525

Thr Glu Asn Phe Asn Ile Arg Asn Asp Arg Ile Ser Val Gln Pro Ala
    530                 535                 540

Pro Pro Val Ile Ala Ser Asp Gly Thr Ala Ile Thr His Lys Val Asn
545                 550                 555                 560

Asp Asn Gly Ser Val Asp Ile Thr Ile Gln Trp Asn Tyr Val Asp Ser
                565                 570                 575

Asn Glu Asp Lys Tyr Asn Ile Asp Gly Phe Glu Val Tyr Leu His Gly
                580                 585                 590

Ser Asp Asp Asn Glu Glu Tyr Thr Phe Gly Ser Val Gln Ala Ser Glu
            595                 600                 605

Asn Leu Gln Asn Val Lys Tyr Asp Arg Arg Thr Ala Thr Phe Thr Gly
        610                 615                 620

Leu Pro Ser Asn Met Tyr Tyr Thr Ile Gly Val Gln Ala Tyr Arg Arg
625                 630                 635                 640

Val Asp Ala Asp Ile Asp Ile Asn Gln Ile Leu Leu Ser Asp Ile Val
                645                 650                 655

Lys Ser Asn His Pro Ser Glu Asn Pro Tyr Leu Pro Thr Pro Ser Ile
                660                 665                 670

Glu Val Lys Gly Ser Leu Ser Gly Lys Val Asn Gly Leu Tyr Thr Ile
            675                 680                 685

Ser Thr Glu Ser Lys Pro Glu Glu Pro Glu Thr Gly Thr Ile Trp Ile
    690                 695                 700

Asp Pro Lys Thr Asn Lys Gln Glu Leu Phe Asn Gly Glu Glu Trp Ile
705                 710                 715                 720

Val Ser Ser Ala Gly Ser Ala Asp Ser Leu Asn Gly Phe Thr Ala Ser
                725                 730                 735

Leu Thr Thr Ser Pro Asn Ser Ile Pro Val Arg Asp Gln Ser Gly Val
                740                 745                 750

Ile Ser Gly Ser Ile Asp Gly Asn Ala Glu Met Leu Gly Gly Arg Ala
            755                 760                 765

Ala Ser Asp Tyr Ala Leu Thr Glu Asn Ile Pro Val Pro Pro Lys Phe
    770                 775                 780

Ala Lys Gly Val Tyr Thr Gly Asp Gly Thr Leu Ser Lys Gln Ile Pro
785                 790                 795                 800

Leu Ala Phe Thr Pro Asp Leu Val Lys Ile Thr Pro Ile Ser Pro Glu
                805                 810                 815
```

-continued

Asp Ser Gln Leu Val Ile Glu Ser Gln Leu Gly Gly Tyr Ala Tyr Gln
            820                 825                 830

Val Thr Ser Thr Gly Leu Ser Leu Ile Gly Gly Asp Leu Ser Tyr Gly
            835                 840                 845

Ala Leu Gly Asn Asn Leu Phe Ile Thr Gly Ser Asp Ser Asn Cys Arg
850                 855                 860

Gly Asn Lys Leu Asn Val Lys Tyr Ile Trp Glu Ala Tyr Gln Gln Asn
865                 870                 875                 880

<210> SEQ ID NO 202
<211> LENGTH: 285
<212> TYPE: PRT
<213> ORGANISM: Bacillus subtilis
<220> FEATURE:
<223> OTHER INFORMATION: >ABP20230

<400> SEQUENCE: 202

Met Gly Ser Leu Pro Thr Lys Leu Thr Glu Val Ile Lys Leu Ala Asp
1               5                   10                  15

Phe Ala Glu Leu Tyr Asn Asp Pro Ile Leu Ser Lys Lys Arg Ile Gly
            20                  25                  30

Ser Val Glu Asp Pro Tyr Leu Thr Tyr Ser Glu Thr Leu Thr Val Tyr
        35                  40                  45

Asn Gly Arg Ala Leu Leu Thr Glu Ile Pro Asn Arg Glu Phe Arg Val
    50                  55                  60

Glu Val Ile Gly Asp Lys Lys Glu Trp Arg Glu Ile Glu Asp Gly Glu
65                  70                  75                  80

Leu Glu Asp Asn Tyr Phe Lys Val Asp Tyr Leu Met Gly Val Val Phe
                85                  90                  95

Phe Asn Ala Ser Asn Glu Gly Lys Ser Leu Thr Phe Asn Tyr Ser Gly
            100                 105                 110

Glu Gly Ala Ser Phe Phe Pro Ala Ser Arg Ile Trp Ile Lys Arg Gln
        115                 120                 125

Gly Asn Met Val Ile Glu Thr Leu Gln Gly Leu Ile Asp Asp Ala Glu
    130                 135                 140

Asp Thr Ile Ile Arg Met Asn Glu Arg Ile Ala Glu Cys Glu Arg Val
145                 150                 155                 160

Thr Lys Arg Cys Ile Glu Ile Thr Asn Trp Cys Arg Gln Ala Thr Ser
                165                 170                 175

Asp Tyr Glu Tyr Val Val Glu Asn Thr Arg Lys Ile Tyr Leu Pro Met
            180                 185                 190

Val Tyr Thr Tyr Gln Asp Leu Met Asp Thr Tyr Pro Asn Pro Gln Ile
        195                 200                 205

Gly Trp Val Val Thr Ile Arg Asp Thr Gly Ile Glu Tyr Arg Trp Asp
    210                 215                 220

Gly Phe Asp Trp Ile Asn Ile Ser Ile Ser Asp Gln Phe Asp Gly Tyr
225                 230                 235                 240

Asn Val Val Ser Ser Tyr Ile Glu Pro Tyr Asn Ile Arg Thr Val Trp
                245                 250                 255

Leu Arg Thr Asn Ser Pro Pro Ser Lys Lys Arg Val Lys Pro Ser Lys
            260                 265                 270

Asp Ala Pro Asp Gly Ser Met Val Trp Ile Arg Lys Gly
        275                 280                 285

<210> SEQ ID NO 203

<211> LENGTH: 744
<212> TYPE: PRT
<213> ORGANISM: Bacillus subtilis
<220> FEATURE:
<223> OTHER INFORMATION: >ABP20231

<400> SEQUENCE: 203

```
Met Ser Asp Asn Leu Ile Pro Val Asn Thr Met Gly Tyr Tyr Asp Glu
1               5                   10                  15

Glu Thr Lys Gln Trp Val Pro Ile Asp Ala Val Ala Leu Lys Ser Glu
            20                  25                  30

Asn Tyr Arg Phe Thr Ala Asp Asp Ile Ser Gln Lys Phe Asn Lys Ile
        35                  40                  45

Gly Asp Ile Asp Ala Ile Lys Ala Thr Gly Asn Thr Leu Ser Glu Lys
    50                  55                  60

Ile Ile Asn Glu Phe Asn Tyr Arg Gly Ile Asn Ile Ser Trp Leu Gly
65                  70                  75                  80

Ala Lys Gly Asp Gly Thr Thr Asp Asp Ser Ser Val Phe Ser Ser Ile
                85                  90                  95

Glu Ser Thr Tyr Gln Asp Lys Val Phe Asp Leu Ala Gly Lys Thr Tyr
            100                 105                 110

Val Val Asn Ser Phe Pro Asn Lys Asn Lys Tyr Leu Asn Gly Tyr Phe
        115                 120                 125

Ile Ile Asp Gly Asn Lys Tyr Phe Ser Gly Tyr Val Ser Ser Phe Gln
    130                 135                 140

Thr Gly Asn Ser Asn Ile Ile Gly Asn Asn Ala Ala Lys Asn Phe
145                 150                 155                 160

Arg Pro Gly Asp Gln Tyr Lys Gly Ile Ala Gly His Asn Ile Ile Ala
                165                 170                 175

Ile Gly Glu Asn Ala Leu Ser Asn Ala Ser Glu Tyr Thr Lys Asn Thr
            180                 185                 190

Thr Ala Ile Gly Ala Gly Ala Leu Phe Asn Asn Lys Tyr Gly Val Tyr
        195                 200                 205

Asn Leu Ala Ile Gly Leu Gln Ser Gln Tyr Tyr Val Thr Gly Val Gln
    210                 215                 220

Gly Asp Ala Phe Lys Gly Thr Arg Asn Thr Ser Val Gly Asp Asn Ser
225                 230                 235                 240

Met Arg Phe Asn Lys Asp Gly Tyr Ser Asn Val Ala Met Gly Arg Asn
                245                 250                 255

Ala Leu Gln Thr Asn Glu Lys Ser Leu Trp Asn Thr Ala Leu Gly Ala
            260                 265                 270

Ala Ala Met Ser Gly Tyr Ala Pro Leu Asn Leu Asp Ser Lys Thr Ile
        275                 280                 285

Ile Asn Asn Ser Pro Gln Thr Ala Gly Tyr Gln Val Ala Val Gly Thr
    290                 295                 300

Asn Ser Leu Tyr Trp Ser Asn Gly Ile Gly Asn Val Gly Val Gly Val
305                 310                 315                 320

Asn Ala Gly Arg Glu Ile Lys Asn Ser Gln Arg Asn Val Ala Met Gly
                325                 330                 335

Tyr Tyr Ala Met Ser Gln Leu Ser Asp Val Ser Phe Glu Gly Lys
            340                 345                 350

Gln Arg Phe Phe Pro Ser Ile Gln Ala Gly Tyr Thr Trp Ile Gly Gln
        355                 360                 365

Asp Ile Thr Leu Thr His Ile Gly His Thr Phe Ile Val Gly Gln Asn
    370                 375                 380
```

```
Leu Ser Leu Ala Leu Asp Gly Gly Glu Lys Phe Ser Thr Thr Val Lys
385                 390                 395                 400

Ser Ile Thr Val Asp Thr Phe Thr Val Ser Thr Thr Gln Ile Ala Gln
            405                 410                 415

Asn Glu Ile Ser Gly Met Ala Gln Val Ser Glu Tyr Tyr Thr Thr Thr
        420                 425                 430

Gly Thr Tyr Val Trp Lys Asp Asn Asn Ile Gln Val Ser Met Gly Asn
            435                 440                 445

His Pro Phe Gln Asn Gly Tyr Lys Val Leu Met Ser Val Gly Gly Arg
        450                 455                 460

Glu Ala Ile Tyr Phe Thr Val Ala Asn Ser Thr Ser Ser Gly Phe Thr
465                 470                 475                 480

Val Ser Thr Asp Ile Ile Gly Asp Glu Ser Gly Ala Val Lys Ile Thr
            485                 490                 495

Glu Tyr Ser Asp Thr Thr Pro Met Ala Val Asn Tyr Asp Asn Thr Ala
        500                 505                 510

Ile Gly Val Lys Ala Ala Trp Lys Met Lys Lys Gly Ser Phe Asn Thr
            515                 520                 525

Ala Ile Gly Gly Leu Ser Leu Glu Asn Asn Lys Gly Asp Tyr Asn Thr
        530                 535                 540

Ala Leu Gly Tyr Met Ala Leu Lys Asn Asn Thr Thr Gly Asn Gln Asn
545                 550                 555                 560

Thr Ala Leu Gly Tyr Gly Ala Leu Arg Phe Thr Thr Gly Gly Asp Glu
            565                 570                 575

Met Lys Asp Ile Ser Asn Ser Thr Gly Val Gly Phe Asn Ser Arg Val
        580                 585                 590

Ser Gly Ser Asn Gln Ile Gln Leu Gly Asp Gly Asn Ser Thr Pro Tyr
            595                 600                 605

Ser Phe Asn Ala Leu Gln Asn Arg Ser Asp Leu Arg Asp Lys Ala Asp
        610                 615                 620

Ile Arg Asp Thr Val Leu Gly Leu Asp Phe Ile Asn Lys Val Arg Pro
625                 630                 635                 640

Val Asp Tyr Lys Trp Asp Ile Arg Asp Glu Tyr Val Glu Ile Lys Glu
            645                 650                 655

Asp Gly Thr Val Ile Thr His Glu Arg Asp Gly Ser Lys Lys Lys Asn
        660                 665                 670

Arg Tyr His His Gly Val Ile Ala Gln Glu Ile Gln Lys Val Ile Glu
            675                 680                 685

Ala Glu Gly Ile Asp Phe Gly Gly Phe Gln His His Glu Leu Ser Gly
        690                 695                 700

Gly Glu Asp Val Met Ser Ile Gly Tyr Thr Glu Phe Ile Ala Pro Leu
705                 710                 715                 720

Ile Lys Ala Val Gln Glu Leu Ser Ala Lys Val Glu Glu Gln Ala Lys
            725                 730                 735

Glu Ile Ala Ala Leu Lys Lys Ala
            740

<210> SEQ ID NO 204
<211> LENGTH: 355
<212> TYPE: PRT
<213> ORGANISM: Bacillus subtilis
<220> FEATURE:
<223> OTHER INFORMATION: >ABP20232
```

<400> SEQUENCE: 204

```
Met Thr Ile Gln Ala Arg Gln Met Leu Val Ser Pro Gly Lys Tyr Pro
1               5                   10                  15
Ile Lys Gly Arg Tyr Ala Met Thr Ala Glu Tyr Ile Thr Phe His Asn
            20                  25                  30
Thr Ala Asn Asp Ala Ser Ala Asn Glu Ile Ser Tyr Met Arg Asn
        35                  40                  45
Asn Asn Glu Thr Val Ser Tyr His Phe Ala Val Asp Asp Lys Glu Val
    50                  55                  60
Val Gln Gly Leu Pro Thr Asn Arg Ser Ala Phe His Cys Gly Asp Gly
65                  70                  75                  80
Glu Tyr Gly Thr Gly Asn Arg Lys Ser Ile Gly Val Glu Val Cys Tyr
                85                  90                  95
Ser Lys Ser Gly Gly Glu Arg Tyr Arg Lys Ala Glu Ala Leu Ala Ile
            100                 105                 110
Lys Phe Ile Ala Gln Leu Leu Lys Glu Arg Gly Trp Gly Val Glu Arg
        115                 120                 125
Val Lys Lys His Gln Glu Trp Ser Gly Lys Tyr Cys Pro His Arg Val
130                 135                 140
Leu Asp Glu Gly Arg Trp Asn Glu Val Lys Ala Ala Ile Ala Ala Glu
145                 150                 155                 160
Leu Lys Ser Leu Gly Gly Lys Ser Thr Thr Pro Thr Lys Thr Ser Thr
                165                 170                 175
Lys Pro Thr Thr Ser Ser Pro Ser Ser Ser Ala Ala Ser Gly Ser
            180                 185                 190
Leu Lys Ser Lys Val Asp Gly Leu Arg Phe Tyr Ser Lys Pro Ser Trp
        195                 200                 205
Glu Asp Lys Asn Val Val Gly Thr Val Asn Lys Gly Ile Gly Phe Pro
210                 215                 220
Thr Val Val Glu Lys Val Lys Val Gly Ser Ala Tyr Gln Tyr Lys Val
225                 230                 235                 240
Lys Asn Ser Lys Gly Ala Thr Tyr Tyr Ile Thr Ala Ser Asp Lys Tyr
                245                 250                 255
Val Asp Val Thr Gly Ser Val Lys Ala Ser Ser Pro Thr Pro Lys Thr
            260                 265                 270
Thr Ser Thr Ser Ser Ser Ser Ser Ile Lys Ser Val Gly Lys Ile
        275                 280                 285
Lys Ile Val Gly Val Ser Ser Ala Ala Ile Val Met Asp Lys Pro Asp
290                 295                 300
Arg Asn Ser Ser Lys Asn Ile Gly Thr Val Lys Leu Gly Ser Thr Val
305                 310                 315                 320
Ser Ile Ser Gly Ser Val Lys Gly Lys Asn Asn Ser Lys Gly Tyr Trp
                325                 330                 335
Glu Val Ile Tyr Asn Gly Lys Arg Gly Tyr Ile Ser Gly Gln Phe Gly
            340                 345                 350
Ser Lys Ile
        355
```

<210> SEQ ID NO 205
<211> LENGTH: 83
<212> TYPE: PRT
<213> ORGANISM: Bacillus subtilis
<220> FEATURE:
<223> OTHER INFORMATION: >ABP20233

```
<400> SEQUENCE: 205

Met Thr Lys Ile Asn Trp Lys Val Arg Leu Lys Lys Thr Phe Leu
1               5                   10                  15

Val Ala Ile Phe Ser Ala Thr Leu Leu Phe Val Gln Ala Ile Ala Ser
            20                  25                  30

Ala Phe Gly Tyr Asp Leu Thr Val Phe Gly Asp Asn Leu Thr Glu Lys
        35                  40                  45

Phe Asn Ala Leu Leu Thr Phe Leu Thr Ala Met Gly Ile Ile Val Asp
    50                  55                  60

Pro Thr Thr Gln Gly Ile Ser Asp Ser Glu Gln Ala Met Asp Tyr Asp
65                  70                  75                  80

Ser Pro Arg

<210> SEQ ID NO 206
<211> LENGTH: 379
<212> TYPE: PRT
<213> ORGANISM: Bacillus subtilis
<220> FEATURE:
<223> OTHER INFORMATION: >ABP20234

<400> SEQUENCE: 206

Met Leu Glu Gln Met Ile Ser Ser Lys Val Gly Val Lys Ile Asn
1               5                   10                  15

Glu Trp Tyr Lys Tyr Ile Arg Leu Phe Ser Val Pro Asp Ser Glu Ile
            20                  25                  30

Leu Lys Ala Glu Val Glu Glu Ile Arg His Met Lys Glu Asp Gln
        35                  40                  45

Asp Leu Phe Leu Tyr Tyr Ser Leu Met Cys Phe Arg His Gln Leu Met
    50                  55                  60

Leu Asp Tyr Leu Glu Pro Lys Thr Leu Asn Glu Arg Pro Lys Val
65                  70                  75                  80

Ser Asp Leu Leu Glu Lys Ile Glu Ser Ser Gln Thr Asp Leu Lys Gly
            85                  90                  95

Ile Leu Glu Tyr Tyr Phe Asn Phe Phe Arg Gly Met Tyr Glu Phe Glu
            100                 105                 110

Gln Tyr Glu Tyr Leu Asn Ala Ile Ser Phe Tyr Lys Gln Ala Glu Arg
        115                 120                 125

Lys Leu Ser Leu Val Ala Asp Glu Ile Glu Arg Ala Glu Phe His Tyr
    130                 135                 140

Lys Val Ala Glu Ile Tyr Tyr His Met Lys Gln Thr His Met Ser Met
145                 150                 155                 160

His His Ile Val Gln Ala Ile Asp Ser Tyr Lys Ala His Glu Asn Tyr
                165                 170                 175

Thr Val Arg Val Ile Gln Cys Ser Phe Val Ile Gly Leu Asn Tyr Leu
            180                 185                 190

Asp Met Asp Tyr Pro Glu Lys Ala Ile Pro His Phe Lys Asp Ala Leu
        195                 200                 205

Asp Lys Ala Arg Glu Ile Asp Met Ser Arg Leu Ile Gly Ser Ser Leu
    210                 215                 220

Tyr Asn Leu Gly Leu Cys Ser Phe Ala Glu Ala Tyr Glu Lys Ala
225                 230                 235                 240

Ser Glu Tyr Phe Lys Glu Gly Ile Arg Val Tyr Gln Asp Asn Gly Tyr
                245                 250                 255

Glu His Ser Asn Arg Ile Leu Asp Ile Leu Leu Met Leu Thr Lys Thr
            260                 265                 270
```

-continued

```
Thr Phe Lys Met Arg Asn His Ser Glu Gly Ile Ser Trp Cys Ala His
        275                 280                 285

Gly Leu Ser Leu Ser Lys Asn Leu Asn Asp Glu Ile Met Ala Lys Met
        290                 295                 300

Phe Glu Phe Ile His Ala Leu Tyr Val Asp Asn Asp Asn Glu Lys Leu
305                 310                 315                 320

Asn Ser Ile Leu Asn Tyr Leu Glu Leu Lys Ser Met Leu Ser Asp Val
                325                 330                 335

Glu Asp Leu Ala Ser Asp Ala Ala Lys Tyr Tyr Asn Glu Lys Glu Asp
            340                 345                 350

His Lys Val Ala Val Ala Tyr Tyr Glu Lys Val Leu Tyr Ala Arg Lys
        355                 360                 365

Gln Ile Gln Arg Gly Asp Cys Leu Tyr Glu Thr
    370                 375

<210> SEQ ID NO 207
<211> LENGTH: 58
<212> TYPE: PRT
<213> ORGANISM: Bacillus subtilis
<220> FEATURE:
<223> OTHER INFORMATION: >ABP20235

<400> SEQUENCE: 207

Met Lys Leu Lys His Ala Ser Val Phe Ile Leu Ala Ile Val Leu Ile
1               5                   10                  15

Gly Phe Val Ser Thr Tyr Leu Thr Asn Thr Gln Lys Asp Val Gln Glu
            20                  25                  30

Ala Arg Arg Gly His Thr Ala Ser Ile Gly Phe Thr Asp Gly His Ser
        35                  40                  45

Tyr Glu Ile Ala Ser Arg Gly His Thr Ser
    50                  55
```

US 11,617,770 B2

SPOREFORMING PROBIOTIC STRAINS, METHODS AND USES THEREOF

CROSS-REFERENCE TO RELATED APPLICATIONS

This application is a U.S. National Stage Application under 35 U.S.C. § 371 of International Patent Application No. PCT/M2019/059131, filed Oct. 24, 2019, which claims priority to Portugal Patent Application No. 115101, filed Oct. 24, 2018, which are hereby incorporated by reference in their respective entireties.

TECHNICAL FIELD

The present disclosure relates to the isolation, identification and characterization of novel sporeforming probiotic strain(s) with NSPase (Non-Starch Polysaccharides-active hydrolases) activity isolated from fish gut microbiota, methods and uses thereof.

The sporeforming probiotic strain(s) with NSPase activity now disclosed are able of producing carbohydrate-active enzymes (CAZymes) that hydrolyse non-starch polysaccharides (NSPs) and accesses their potential as probiotics (PRO) for use in particular in aquafeeds.

BACKGROUND ART

The gastrointestinal microbial community plays a critical role on vertebrates' health and metabolism, impacting host metabolism, immune status and health/disease balance. In the last decade, this relationship has received increased attention particularly in humans, where it is known to control local (at the gut level) health status as well as systemic health. The gut microbiota of vertebrates, ranging from mammals to teleost fish, is involved in host appetite control and obesity development [1], protection against pathogens, immunity enhancement or inflammatory processes [2]. Additionally, gut microorganisms respond to a wide range of factors, including dietary composition, and harbor a relevant and diversified enzymatic repertoire that might interfere with host metabolism [3, 4]. This is particularly important in fish nutrition, because fish do not possess all of the necessary enzymes to cope with the current aquaculture dietary challenges [4].

A main difficulty within fish nutrition is its dependence on fish meal (FM), an unsustainable commodity and a source of organic pollutants. The most obvious sustainable alternatives to fish meal are plant feedstuffs, but their nutritive value is limited by the presence of high levels of non-starch polysaccharides (NSPs) which are not metabolized by fish.

These facts are disclosed to illustrate the technical problem addressed by the present disclosure.

GENERAL DESCRIPTION

Aquaculture output is growing rapidly and has already surpassed fisheries in terms of providing food to meet the growing human population [5]. Aquaculture is greatly dependent on FM, an unsustainable commodity and a source of organic pollutants, almost exclusively provided by fisheries. This is particularly obvious in carnivorous fish production due to their high dietary protein requirement (40-50%), which is mainly provided by FM. Plant feedstuffs (PF) are sustainable alternatives to FM, and among them, soybean meal (SBM), rapeseed meal (RSM), and sunflower meal (SFM), have been acknowledged as the most promising due to their high protein level, world-wide availability, and reasonable price. However, the nutritive value of PF is limited by the presence of several anti-nutritional factors, including high levels of non-starch polysaccharides (NSPs) which are not digested by fish [6]. NSPs content in SBM, RSM, and SFM averages 22-24% and the major NSPs components are pectic polysaccharides with arabinose, galactose, and xylose residues predominating. Yet, the proportion of these sugar residues varies between PF with galactose being predominant in SBM, arabinose in RSM, and xylose in SFM.

In fish, the carbohydrate-active enzymes (CAZymes) able to hydrolyze the β-glycosidic bonds of NSPs are scarce or non-existent. Thus, dietary NSPs remain indigestible and cannot be used as energy source. Moreover, indigestible NSPs might have detrimental effects on fish performance and nutrient digestibility and on fish health [7]. These adverse effects are associated with the viscous nature of NSPs and their interaction with gut epithelium, mucus, and microbiota, which ultimately result on physiological and inflammatory imbalances [7]. Additionally, and contrary to other animal species, such as pigs and poultry, the supplementation of PF based diets with exogenous carbohydrases does not necessarily translate into an effective strategy for improving NSPs utilization, as diverging results on their impact on fish growth performance and feed utilization have been reported. Therefore, gut microorganisms characterized by a rich secretome are a potential source of in loch carbohydrases that may help fish to overcome the mentioned constraints.

Live microorganisms that confer a health benefit to the host when administered in adequate amounts are denominated probiotics (PRO) [8]. In particular, PRO decrease the incidence of diseases by competing with pathogens for adhesion sites/nutrients; produce natural antimicrobial compounds that inhibit pathogens growth; contribute to a balanced gut microbiota; improve host growth; enhance host immune system and gastrointestinal histomorphology. PRO have also been implicated in bioremediation and water quality improvement by reducing antibiotic usage, contributing to aquaculture sustainability.

Among the bacterial species currently used as PRO, sporeformers show critical advantages: bacterial spores are remarkably resistant dormant structures [9], permitting good shelf-storage; spores are easily produced in large scale and can be dehydrated, facilitating feed incorporation without losing characteristics. Importantly, spores survive gut transit since they are acid and bile tolerant and become successfully established in the gut [10]. In particular, *Bacillus subtilis* spores, which enjoy GRAS (Generally Regarded As Safe) status from the U.S. Food and Drug Administration (FDA) and are included in the European Food Safety Authority (EFSA) list of Qualified Presumption of Safety (QPS) [11], experience exponentially growing applications in biomedicine and biotechnology (as oral vaccines, disinfectants, PRO or display systems) [12]. In fact, different sporeformers are nowadays used as human and animal PRO [12-13], but within European Union (EU) just one PRO has been authorised for use in aquaculture (Bactocell®, LALLEMAND Inc., Canada).

The role of gut microbiota in shaping human and animal health is well established, and the potential health benefit of manipulating the gut ecosystem using PRO is increasingly being accepted. In carnivorous fish, such as European sea bass, an ideal PRO should not only enhance resistance to pathogens, i.e. by competitive exclusion, the most common criteria for selection of PRO strains, but also help fish in their current dietary challenges, including the utilization of PF. In this disclosure, the application of a PF-based dietary pressure to modulate European sea bass gut microbiota composition and corresponding metabolic functions revealed to be a successful strategy to find carbohydrate-active bacteria with PRO potential. In particular, it was targeted and isolated spore-forming Bacilli, commonly used in PRO preparations, mainly due to their extreme resistance characteristics and indefinitely survival, advantageous for industrial applications [9-10, 12-13, 17].

The composition of the gut microbial communities of fish have been demonstrated to adapt when the host is fed different dietary ingredients [1, 3, 4]. Thus, a selective pressure of plant-based diets on fish gut microbiota, can be a beneficial strategy for an enrichment of bacteria with a secretome able to mobilize the dietary NSPs. By targeting bacterial sporulating isolates with diverse carbohydrase activities from the gut of European sea bass (*Dicentrarchus labrax*), isolates with high probiotic potential were obtained. By inferring the adaptive fitness to the fish gut and the amenability to industrial processing, the best two candidates were identified to become industrially valuable PRO for improvement of fish health and utilization of dietary NSPs, contributing for sustainable and more cost-effective aquaculture practices.

Thus, the present disclosure relates to screening fish gut microbiota for bacteria capable of producing extracellular digestive enzymes that hydrolyse NSPs present in PF, in particular mannans, glucans, xylans, arabinans, and galactans.

Gut microbiota isolates showing promising metabolic traits and absence of safety concerns can be used as PRO in cost-effective and environmental-friendly diets by allowing the host to obtain energy from otherwise indigestible dietary constituents. In fact, native bacteria with PRO potential will be more apt to become established and persist in the fish gut environment after withdrawal from the diet.

The present disclosure provides several advantages, namely: it solves the incapability of fish to efficiently digest and utilize PF as alternative protein source to FM; compared to exogenous purified enzymes (the only available technology, with poor results in fish), this disclosure has the added value of being also an autochthonous PRO that besides helping fish with the digestive challenges also contributes to fish health and welfare by antagonizing fish pathogens, having a dual positive effect on fish performance. Additionally, this product, by being a sporeformer, is more robust and resistant than the other PRO in EU market, allowing feed incorporation without losing characteristics and storage without refrigeration.

The present disclosure relates to ABP1 which was received on 8 Jun. 2018 and accepted for deposit for patent purposes at the Coleccion Espanola de Cultivos Tipo (CECT)—International Depositary Authority under the Budapest Treaty—under the accession number CECT 9675.

The present disclosure also relates to ABP2 which was received on 8 Jun. 2018 and accepted for deposit for patent purposes at the Coleccion Espanola de Cultivos Tipo (CECT)—International Depositary Authority under the Budapest Treaty—under the accession number CECT 9676.

The present disclosure therefore relates to a bacterial strain selected from ABP1 with a deposit under the accession number CECT 9675, of 8 Jun. 2018, at Coleccion Espanola de Cultivos Tipo, and/or from ABP2 with a deposit under the accession number CECT 9676, of 8 Jun. 2018, at Coleccion Espanola de Cultivos Tipo.

Furthermore, the present disclosure also relates to a composition for aquatic animal feed comprising a bacterial strain selected from ABP1 with a deposit under the accession number CECT 9675, of 8 Jun. 2018, at Coleccion Espanola de Cultivos Tipo, and/or from ABP2 with a deposit under the accession number CECT 9676, of 8 Jun. 2018, at Coleccion Espanola de Cultivos Tipo.

In an embodiment, said composition may comprise $1 \times 10^5$-$1 \times 10^{12}$ of colony forming units of the bacterial strain per gram of the composition, preferably said composition may comprise $1 \times 10^7$-$1 \times 10^{10}$ colony forming units of the bacterial strain per gram of the composition, more preferably said composition may comprise $2 \times 10^9$ colony forming units of the bacterial strain per gram of the composition.

In an embodiment, said composition may further comprise a preservative.

In an embodiment, said composition may be a granulate form; a powdered form or a pellet.

In an embodiment, said composition may be a granulate form wherein the granulate form is coated, in particular wherein the coating comprises a salt and/or wax and/or a flour.

The present disclosure also relates to a method for feeding an aquatic animal present in an aquaculture comprising the step of feeding the aquatic animal with the composition now disclosed.

In an embodiment, the step of feeding the aquatic animal may be carried out during the life span of the aquatic animal.

In an embodiment, the aquatic animal may be selected from the following list: a shellfish, fish, amberjack, arapaima, barb, bass, bluefish, bocachico, bream, bullhead, cachama, carp, catfish, catla, chanos, char, cichlid, cobia, cod, crappie, dorada, drum, eel, goby, goldfish, gourami, grouper, guapote, halibut, java, labeo, lai, loach, mackerel, milkfish, mojarra, mudfish, mullet, paco, pearlspot, pejerrey, perch, pike, pompano, roach, Atlantic salmon, salmon, sampa, sauger, sea bass, European sea bass, seabream, gilthead seabream, white seabream, shiner, sleeper, snakehead, snapper, snook, sole, spinefoot, sturgeon, sunfish, sweetfish, tench, terror, tilapia, trout, tuna, turbot, vendace, walleye, halibut, whitefish or shrimp.

This disclosure also relates to the use of a bacterial strain selected from ABP1 with a deposit under the accession number CECT 9675, of 8 Jun. 2018, at Coleccion Espanola de Cultivos Tipo, and/or from ABP2 with a deposit under the accession number CECT 9676, of 8 Jun. 2018, at Coleccion Espanola de Cultivos Tipo, as a probiotic.

This disclosure also relates to the use of a bacterial strain selected from ABP1 with a deposit under the accession number CECT 9675, of 8 Jun. 2018, at Coleccion Espanola de Cultivos Tipo, and/or from ABP2 with a deposit under the accession number CECT 9676, of 8 Jun. 2018, at Coleccion Espanola de Cultivos Tipo, as a supplement to feedstuff, preferably as a supplement to feedstuff for fish or shellfish.

Furthermore, the present disclosure also relates to an isolated polynucleotide or polypeptide from ABP1 with a deposit under the accession number CECT 9675, of 8 Jun. 2018, at Coleccion Espanola de Cultivos Tipo, wherein the isolated polynucleotide is selected from the following list: SEQ. ID. No. 19 (ABP10666), SEQ. ID. No. 20 (ABP10667), SEQ. ID. No. 7 (ABP10654), SEQ. ID. No. 24 (ABP10671), SEQ. ID. No. 36 (ABP10829), SEQ. ID. No. 37 (ABP10830), or combinations thereof, wherein the isolated polynucleotide encodes for a polypeptide that hydrolyses a non-starch polysaccharide, preferably non-starch polysaccharides present in plant feedstuffs, preferably wherein the non-starch polysaccharide is mannan, glucan, xylan, arabinan, and/or galactan.

The present disclosure also relates to an isolated polynucleotide or polypeptide from ABP2 with a deposit under the accession number CECT 9676, of 8 Jun. 2018, at Coleccion Espanola de Cultivos Tipo, wherein the isolated polynucleotide is selected from the following list: SEQ. ID. No. 160 (ABP24564), SEQ. ID. No. 161 (ABP24565), SEQ. ID. No. 162 (ABP24566), SEQ. ID. No. 163 (ABP24567) or combinations thereof, wherein the isolated polynucleotide encodes for a polypeptide that hydrolyses a non-starch polysaccharide, preferably non-starch polysaccharides present in plant feedstuffs, preferably wherein the non-starch polysaccharide is mannan, glucan, xylan, arabinan, and/or galactan.

BRIEF DESCRIPTION OF THE DRAWINGS

The following figures provide preferred embodiments for illustrating the description and should not be seen as limiting the scope of the present disclosure.

DETAILED DESCRIPTION

Figure 1:
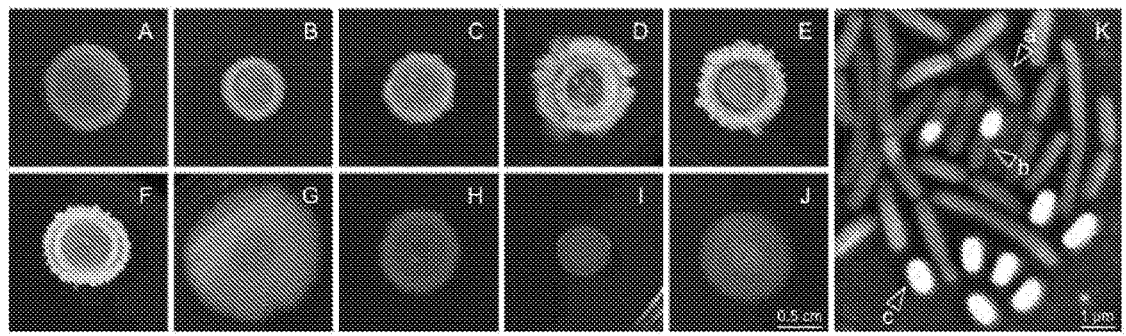
FIG. 1. Morphological diversity (Panels A-J) of representative sporeforming fish isolates obtained from European sea bass gut contents. Photographs of colonies grown 24 h in LB (Luria-Bertani) agar medium, are at the same scale defined in Panel J (0.5 cm). Panel K depicts a representative image of the different development stages of sporulation [(a) vegetative cell, (b) sporulating cell (forespore engulfed by the mother cell) and (c) free spore] that were observed in each sporeforming isolate by phase-contrast microscopy. Sporulation was induced by nutrient exhaustion in solid Difco Sporulation Medium (DSM).

The present disclosure relates to the isolation, identification and characterization of novel sporeforming probiotic strain(s) with NSPase (Non-Starch Polysaccharides-active hydrolases) activity isolated from fish gut microbiota, methods and uses thereof.

In an embodiment, sporeformers were isolated from the gut of European sea bass juveniles challenged with PF diets based on SBM, RSM or SFM, which have different NSPs profiles. European sea bass was the model species chosen due to its high commercial importance in European aquaculture and its carnivorous feeding habits, thus being more challenging to cope with PF-based diets. However, other models could be equally used such as gilthead seabream (*Sparus aurata*) or white seabream (*Diplodus sargus*) or Atlantic salmon (*Salmo salar*).

Providing fish with self-gut bacteria capable of producing carbohydrate-active extracellular enzymes that hydrolyse NSPs emerge as a strategy with enormous potential to overcome PF-diets limitations. The bacterial strains now disclosed were isolated with this purpose and their genome sequences support their view as potential NSPs-hydrolyzers that might help aquaculture fish on using high PF-diets.

Having in mind the enhanced adaptability of gut microbial communities, a selective pressure of plant-based diets on fish gut microbiota was carried out for an enrichment of bacteria with a secretome able to mobilize the dietary NSPs. By targeting bacterial spores, remarkably resistant dormant structures with increasing applications in animal health, namely as vaccines or PRO, it was possible to isolate carbohydrate-active gut bacterial strains, from European sea bass, with PRO potential. By inferring the adaptive fitness to the fish gut and the amenability to industrial processing, the best candidates were identified to become industrially valuable PRO for improvement of fish health and utilization of dietary NSPs, contributing for sustainable and more cost-effective aquaculture practices.

In an embodiment, the PRO were isolated and purified, identified to the species level, fully characterised, namely its safety following EFSA guidelines, NSPase activity, antimicrobial activity against important fish-pathogens, adaptive fitness to the fish gut and the amenability to industrial processing. The complete genome has been sequenced.

In an embodiment, there is a need for further research namely addressing the in vivo efficacy in improving PF utilization by fish and disease resistance in bacterial infection models. A preliminary assay using challenging plant-based diets (CTR−), revealed that supplementation with ABP1, or ABP1 and ABP2 (Mix) has a positive effect on the final body weight, the weight gain, the feed efficiency and the protein efficiency ratio of European sea bass juveniles, with a tendency to get closer to a FM-based diet (CTR+) (Table 1). Future analyses including digestive enzymes activity and gut microbiota modulation, might help explain the results obtained. Furthermore, a comprehensive screening of ABP1 and ABP2 genomes will potentially allow the identification of new carbohydrases or antimicrobial molecules.

In an embodiment, the fermentation of the strains can be easily reproduced by another practitioner. Furthermore, regarding commercial applications, companies within the aquaculture and feed industry may be potentially interested in acquiring these strains for the development of new PRO with digestive added-value.

In an embodiment, diet composition was formulated. Three experimental diets were formulated to be isonitrogenous (47% crude protein), isolipidic (17% crude lipid) and to contain 30% of soy bean meal (SBM diet), 30% of rapeseed meal (RSM diet) or 30% of sunflower meal (SFM diet). A FM-based diet was used as the control diet (CTR diet). Fish oil and pregelatinized maize starch were the main lipid and carbohydrate sources, respectively. Bicalcium phosphate was added to adjust dietary phosphorus level. All diet ingredients were thoroughly mixed and dry-pelleted in a laboratory pellet mill (California Pellet Mill, CPM Crawfordsville, Ind., USA), through a 3.0 mm die. Pellets were dried in an oven at 50° C. for 24 h, and then stored at −20° C. until used. Ingredients and proximate composition of the experimental diets are presented in Table 2.

TABLE 2

Ingredients composition and proximate analysis of experimental diets

| Diets[a] | CTR | SBM | RSM | SFM |
|---|---|---|---|---|
| Ingredients (% dry weight) | | | | |
| Fish meal[b] | 60.2 | 38.7 | 45.2 | 48.1 |
| Soy bean meal[c] | — | 30.0 | — | — |
| Rapeseed meal[d] | — | — | 30.0 | — |
| Sunflower meal[e] | — | — | — | 30.0 |
| Pregelatinized maize starch[f] | 23.2 | 11.6 | 8.0 | 4.8 |
| Fish oil | 12.1 | 13.6 | 12.4 | 13.0 |
| Bicalcium phosphate[g] | 1.0 | 2.6 | 1.0 | 0.6 |
| Choline chloride (50%) | 0.5 | 0.5 | 0.5 | 0.5 |
| Vitamin premix[h] | 1.0 | 1.0 | 1.0 | 1.0 |
| Mineral premix[i] | 1.0 | 1.0 | 1.0 | 1.0 |
| Binder[j] | 1.0 | 1.0 | 1.0 | 1.0 |
| Proximate analysis (% dry weight) | | | | |
| Dry matter | 91.5 | 92.4 | 92.7 | 93.5 |
| Crude protein | 46.9 | 46.5 | 46.3 | 46.4 |

TABLE 1

Growth performance and feed utilization efficiency of European sea bass fed the experimental diets[1].

| | Diets | | | | |
|---|---|---|---|---|---|
| | CTR− | ABP1 | ABP2 | Mix | CTR+ |
| Final body weight (g) | $74.0 \pm 4.8^{a}$ | $83.0 \pm 1.6^{ab}$ | $73.7 \pm 6.8^{a}$ | $80.0 \pm 12.0^{ab}$ | $97.0 \pm 2.0^{b}$ |
| Weight gain (% IBW[†]) | $155.4 \pm 16.6^{a}$ | $185.3 \pm 5.4^{ab}$ | $160.5 \pm 23.2^{a}$ | $176.0 \pm 41.3^{ab}$ | $233.8 \pm 6.7^{b}$ |
| Daily growth index[2] | $17.3 \pm 0.1$ | $19.8 \pm 0.0$ | $17.7 \pm 0.2$ | $18.9 \pm 0.3$ | $23.4 \pm 0.1$ |
| Feed intake (g kg ABW$^{-1\S}$ day$^{-1}$) | $15.4 \pm 1.4$ | $16.7 \pm 0.3$ | $15.6 \pm 0.2$ | $15.8 \pm 1.3$ | $17.5 \pm 0.1$ |
| Feed efficiency[3] | $0.82 \pm 0.03^{a}$ | $0.86 \pm 0.02^{ab}$ | $0.84 \pm 0.03^{ab}$ | $0.87 \pm 0.06^{ab}$ | $0.94 \pm 0.01^{b}$ |
| Protein efficiency ratio[4] | $1.82 \pm 0.08^{a}$ | $1.86 \pm 0.05^{ab}$ | $1.84 \pm 0.07^{a}$ | $1.88 \pm 0.12^{ab}$ | $2.09 \pm 0.02^{b}$ |

[†]IBW: initial body weight.
[§]ABW: average body weight (initial body weight + final body weight)/2.
[1]Mean values and standard deviation (±SD) are presented for each parameter (n = 3).
Significant differences within the diets are indicated by different letters (Tukey test, P < 0.05).
[2]DGI: ((final body weight$^{1/3}$ − initial body weight$^{1/3}$)/time in days) × 100.
[3]FE: (wet weight gain/dry feed intake).
[4]PER: (wet weight gain/crude protein intake).

TABLE 2-continued

Ingredients composition and proximate analysis of experimental diets

| Diets[a] | CTR | SBM | RSM | SFM |
|---|---|---|---|---|
| Crude lipids | 17.3 | 16.1 | 16.6 | 16.8 |
| Ash | 11.3 | 11.7 | 11.3 | 11.1 |

DM dry matter,
CP crude protein,
CL crude lipid
[a]CTR, control fishmeal-based diet; SBM, soybean meal-based diet; RSM, rapeseed meal-based diet; SFM, sunflower meal-based diet
[b]Steam Dried LT fish meal, Pesquera Diamante, Austral Group, S.A Perú (CP: 74.7% DM; GL: 9.8% DM)
[c]Sorgal, S.A. Ovar, Portugal (CP: 53.7% DM; GL: 2.1% DM)
[d]Sorgal, S.A. Ovar, Portugal (CP: 37.5% DM; GL: 4.0% DM)
[e]Sorgal, S.A. Ovar, Portugal (CP: 30.3% DM; GL: 1.0% DM)
[f]C-Gel Instant-12016, Cerestar, Mechelen, Belgium
[g]Premix, Portugal (Calcium: 24%; Total phosphorus: 18%)
[h]Vitamins (mg kg$^1$ diet): retinol acetate, 18,000 (IU kg$^{-1}$ diet); cholecalciferol, 2000 (IU kg$^{-1}$ diet); alfa tocopherol acetate, 35; sodium menadione bisulphate, 10; thiamine-HCl, 15; riboflavin, 25; calcium pantothenate, 50; nicotinic acid, 200; pyridoxine HCl, 5; folic acid, 10; cyanocobalamin, 0.02; biotin, 1.5; ascorbic acid, 50; inositol, 400
[i]Minerals (mg kg$^{-1}$ diet): cobalt sulphate, 1.91; copper sulphate, 19.6; iron sulphate, 200; sodium fluoride, 2.21; potassium iodide, 078; magnesium oxide, 830; manganese oxide, 26; sodium selenite, 0.66; zinc oxide, 37.5; dibasic calcium phosphate, 8.02 (g kg$^{-1}$ diet); potassium chloride, 1.15 (g kg$^{-1}$ diet); sodium chloride, 0.44 (g kg$^{-1}$ diet)
[j]Aquacube (guar gum, polymethyl carbamide, manioc starch blend, hydrate calcium sulphate) Agil, UK.

In an embodiment, the animal experiment was performed at the Marine Zoology Station, Porto University, Portugal, with European sea bass, juveniles obtained from a commercial fish farm (Maresa S. A., Ayamonte, Huelva, Spain). After transportation to the experimental facilities fish were first submitted to a quarantine period of 30 days before transfer to the experimental system where they were allowed to adapt for 15 days. Before the experimental period, fish were fed a commercial diet (48% protein, 11% lipids, 5% starch). The trial was performed in a recirculating water system equipped with 12 cylindrical fiberglass tanks of 100 l water capacity and thermo-regulated to 22.0±1.0° C. Tanks were supplied with continuous flow of filtered seawater (2.5-3.5 l min$^{-1}$) of 34.0±1.0 g l$^{-1}$ salinity and dissolved oxygen was kept near saturation (7 mg l$^{-1}$). Thereafter, 20 European sea bass with an initial mean body weight of 34.4 g were distributed to each tank and the experimental diets randomly assigned to triplicate groups. The trial lasted 45 days and fish were fed by hand, twice daily, 6 days a week, until apparent visual satiation. The experiment was performed by accredited scientists (following FELASA category C recommendations) and was conducted according to the EU directive 2010/63/EU on the protection of animals for scientific purposes.

In an embodiment, sampling was carried out as follows. Fish in each tank were bulk-weighed at the beginning and at the end of the trial, after 1 day of feed deprivation. For that purpose, fish were slightly anaesthetized with 0.3 ml l$^{-1}$ ethylene glycol monophenyl ether (Sigma-Aldrich, Steinheim, Germany). On the sampling days (at day 15 after the beginning of the trial and at the end of the trial or day 45), fish were fed several times over the day to guarantee that gut was full at sampling time. At 4 h after the first meal, 3 fish per tank were randomly sacrificed with an overdose of ethylene glycol monophenyl ether, for collection of biological samples under aseptic conditions. To overcome inter-fish variation, the resulting material was pooled into one sample per tank to assess differences between dietary groups. Whole-gut (without pyloric caeca) were aseptically excised and squeezed to collect the digesta contents.

In an embodiment, the isolation of sporeforming bacteria was performed as follows. Each sample of digesta (1 g) obtained from fish fed the different dietary treatments was homogenized in 9 ml of buffered saline solution (0.9%). Serial dilutions were prepared in Bott & Wilson (B&W) salts and 100 μl aliquots spread on the surface of LB agar medium, after 20 min heat treatment at 65° C., for sporeformers selection. Plates were incubated at 30° C. in aerobic conditions for up to 5 days. Following selection, sporeformers were isolated and characterized for morphology in DSM, to confirm spore production by phase-contrast microscopy. Colonies representing different morphologies were picked at random and purified by restreaking on agar plates of the same media, before storage at −80° C. in LB broth with 30% glycerol. Sporeformers isolates were routinely grown aerobically at 37° C. in LB or DSM. The laboratory strain B. subtilis 168 [14] was used as a control in most of the experiments described in the present disclosure.

In an embodiment, screening sporeforming bacteria for carbohydrates metabolization was carried out as follows. Each sporeformer isolate was cultured on solid M9 minimal medium [15] supplemented with 0.2% (w/v) of each of the following carbohydrates: D-glucose (G7528), D-fructose (F3510), D-xylose (X3877), L-arabinose (A3256), D-galactose (G0750), D-mannose (63580), all purchased from Sigma-Aldrich, Steinheim, Germany-Aldrich Co. LLC. The Xylooligosaccharides (XOS) and Galactooligosaccharides (GOS) are commercially available prebiotics from Qingdao FTZ United International Inc. (Quingdao, China) that were added at the same concentration (0.2%). Growth after 24 h at 37° C. was recorded by photographing colonies in a Gel Doc XR System (Bio-Rad) using the Image Lab software v.4.0.1 (Bio-Rad). Growth quantification was assessed by measuring the colony volume on fixed areas with local background subtraction (adjusted volume=[CNT*mm$^2$] data counts/mm$^2$) using the Quantity One software v.4.6.9 (Bio-Rad). Quantification of carbohydrates utilization in liquid M9 was performed after an overnight enrichment in liquid LB at 37° C. with agitation. Each isolate was diluted to an initial optical density (OD$_{600}$; absorbance measured at 600 nm) of 0.1 in liquid M9 minimal medium alone or supplemented with 0.2% of the different carbohydrates previously tested. Bacterial growth was followed during 48 h and quantified by measuring the OD$_{600}$. In both solid and liquid medium assays, results presented were corrected by subtracting the colony volume/OD$_{600}$ measured in M9 alone.

In an embodiment, the taxonomic identification of PRO isolates was performed as follows. Identification was carried out for all the isolates with promising extracellular carbohydrolytic activities. Total genomic DNA extraction was performed from overnight LB cultures, using the EZNA bacterial DNA purification kit (Omega Bio-Tek, USA), according to the manufacturer's instructions and quantified with the Qubit 2.0 Fluorometer (Invitrogen, Oregon, USA). PCR amplification of the small-subunit rRNA (16S rRNA) was carried at an annealing temperature of 55° C. using primers 27F and 1492R. Each 20 μl reaction contained 1× DreamTaq Buffer (Thermo Scientific, Vilnius, Lithuania), 0.2 mM of each dNTP (Thermo Scientific, Vilnius, Lithuania), 0.2 μM of each primer (STAB Vida, Lisboa, Portugal), 1 U of DreamTaq DNA Polymerase (Thermo Scientific, Vilnius, Lithuania) and 25 ng of DNA template. The Bioinformatics Resources Sequence Match package of the Ribosomal Database Project 11 (http://rdp.cme.msu.edu) and BLAST of the GenBank nonredundant (nr) nucleotide database (http://www.ncbi.nlm.nih.gov) were used to analyse the sequencing data.

In an embodiment, the screening of PRO isolates for NSPases was performed as follows: to tentatively obtain a set of primers specific for the genes encoding NSPs degrading enzymes (NSPases), an initial search was conducted at the Protein Knowledgebase—UniProtKB with terms "family:hydrolase AND annotation:(type:location AND secreted) AND taxonomy: "Bacteria". A file containing bacterial secreted glycosyl hydrolases (GH) was then created and the ones involved in the utilization of NSPs of interest were chosen for further analysis. Enzymes chosen included mannanases, mannosidases, arabinofuranosidases, arabinanases, glucosidases, glucanases, fructosidases (fructanases), fructafuranosidases, galactorunases, xylosidases, and xylanases. The protein sequence of each individual enzyme was used to search for similar proteins in the translated nucleotide database (tblastn) (http://www.ncbi.nlm.nih.gov) and to make nucleotide alignments between the sequences obtained with ClustalW algorithm using Geneious R7 v7.1.7 (Biomatters, Auckland, New Zealand). Regions of sequence conservation were chosen to design primer pairs (Table 4) with the Vector NTI 10 software (Invitrogen, Carlsbad, Calif.), with a calculated annealing temperature of approximately 55° C. and an amplicon size of 200 to 250 base pairs (bp). PCR amplification was done essentially as described for the 16S rRNA (previous section), adjusting the annealing temperature to 55° C. and the extension time to 30 s.

In an embodiment, biosafety issues in particular antibiotics susceptibility and hemolytic activity were also evaluated. Antimicrobial resistance was studied by testing susceptibility of sporeforming isolates to different classes of antibiotics, namely Macrolides (Erythromycin, EM), Aminoglycosides (Kanamycin, KM, Streptomycin, S M, and Gentamycin, GM), Tetracyclines (Tetracycline, TC), Glycopeptides (Vancomycin, VA) and Cloramphenicol (CL), following the recommendations of the EFSA Panel on Additives and Products or Substances used in Animal Feed [16]. Minimal inhibitory concentrations (MIC) were determined using Etest® (bioMérieux, inc.). Hemolysis was determined on Columbia 5% sheep blood agar plates streaked with colonies from fresh LB plates, after incubation at 37° C. for 24, 48 and 72 h.

In an embodiment, antimicrobial activity screening assays were performed as follows. The antimicrobial activity of selected sporeforming isolates was assessed by a colony overlay assay using as targets different fish pathogens. Zones of growth inhibition around the producer strains spots after 24 h incubation at 25° C. (for *Photobacterium damselae, Vibrio harveyi, Tenacibaculum maritimum* and *Aeromonas bivalvium*) or 37° C. (for *Staphylococcus aureus*) were considered as positives and the corresponding growth-inhibition halos diameter measured (mm). A cell-free supernatant screening assay was performed by inoculating BHI or Marine Agar (for *T. maritimum*) plates with overnight cultures of indicator strains, assuring a uniform and complete coverage of the agar plate. After 15 min rest to allow plates to dry, 1 cm holes where done in the agar and consequently filled with 200 µl of cell-free supernatant of each producer strain, previously centrifuged and filtered through a 0.2 µm cellulose filter, from stationary phase LB cultures (grown overnight at 37° C.). Zones of growth inhibition around the producer strains supernatant holes obtained after 24 h incubation at 25° C. or 37° C. (as before) were considered as positive. All observations were recorded by photographing in a Gel Doc XR System (Bio-Rad) using the Image Lab Software (Bio-Rad).

In an embodiment, sporulation, germination and resistance to gut environment were also carried out as follows. The kinetics of spore formation and germination was quantified using adaptations of well-established methods [15, 17]. Sporulation occurred in DSM for 24 h at 37° C. in an orbital shaker at 200 rpm, and its efficiency was determined by plating serial dilutions made in B&W isotonic buffer (Bott and Wilson salts: 1.24% $K_2HPO_4$, 0.76% $H_2PO_4$, 0.1% trisodium citrate, 0.6% $[NH_4]_2SO_4$, pH 6.7) on LB agar, before and after a 20 min heat treatment at 80° C. to eliminate vegetative cells. Following 24 h incubation at 37° C., visible colonies were counted, and sporulation efficiency calculated as the titre of colony forming units (CFU $ml^{-1}$) before and after the heat treatment.

Preparation of highly purified spores was done as follows: in brief, 48 h spores preparations (in liquid DSM) of each isolate were centrifuged for 10 min at 10000 g and 4° C. Cell pellets were suspended in 50 mM Tris-HCl (pH 7.2) containing 50 µg $ml^{-1}$ of lysozyme, and incubated for 1 h at 37° C. After a single wash with 1 volume of distilled water (10 min at 10000 g, 4° C.), cell pellets were suspended in 0.05% SDS, followed by three washes with distilled water and finally suspended in 1 volume of distilled water. Spores purity and recovery yields were determined by plating serial dilutions on LB agar, before and after a 20 min heat treatment at 80° C.

Spore germination in response to the addition of 100 mM L-alanine or to a mixture of 100 mM KCl, 56 mM glucose, 56 mM fructose and 33 mM L-asparagine (AGFK), was performed at 37° C. in 50 mM Tris-HCl, pH 7.5.

Potential resistance to gut transit was evaluated by determining the acid and bile tolerance of each selected isolate. For that purpose, 48 h DSM spores preparations were heat-treated for 20 min at 80° C. to eliminate vegetative cells and harvested by centrifugation. After a double wash with Phosphate-buffered saline (PBS), serial dilutions made in B&W salts were plated onto LB agar plates to determine the initial bacterial counts. Spores were then diluted in 1 volume of 0.85% NaCl, pH 2, containing 3 mg $ml^{-1}$ pepsin (Sigma-Aldrich, Steinheim, Germany), to mimic stomach conditions. Following 4 h incubation at 37° C. with agitation, serial dilutions made in B&W were again plated onto LB agar plates to determine bacterial counts, and, after a single wash with PBS, spores were resuspended in LB, pH 8 containing 1 mg $ml^{-1}$ pancreatin (Sigma-Aldrich, Steinheim, Germany) and 0.3% bile salts (Sigma-Aldrich, Steinheim, Germany). Bacterial incubation continued for 24 h at 37° C. with agitation to mimic passage through the gut. Finally, serial dilutions made in B&W were again plated onto LB agar plates to determine the final bacterial counts. All plates were incubated at 37° C. during 24 h prior to colonies count.

In an embodiment, shotgun genome sequencing was carried out at the Research and Testing Laboratory (Lubbock, Tex., USA) using the PacBio RSII sequencer (Pacific Biosciences, CA, USA). A total of 78,219 and 96,855 reads (with a mean read length of 13,383 and 15,478 base pairs) were obtained for ABP1 and ABP2, respectively, using as reference the *Bacillus subtilis* subsp. *subtilis* str. 168 (AL009126.3) [14]. The raw sequences were assembled using Pacific Biosciences SMRT Analysis v2.3.0. The total size of the assembly was around 4,068 Mb (2 final contigs) for ABP1 and 4,308 Mb (3 final contigs) for ABP2. A BLAST analysis against the RefSeq_genome database (NCBI) revealed that the best match for ABP1 is the *Bacillus subtilis* subsp. *subtilis* str. BSP1 (CP003695.1; (11)) while for ABP2 a best match is *Bacillus* sp. LM 4-2 (CP011101.1; (12)). The BLAST version used was the 2.7.1.

Both assemblies were analysed by using the Rapid Annotation Subsystem Technology (RAST) server. The amino acid sequences of each gene identified in RAST were processed using BLASTP+ against the RefSeq_Protein (NCBI), RefSeq_RNA (NCBI) and All-tRNA [4] (http://gtrnadb.ucsc.edu/) databases and then passed along the DAVID web service to determine other crucial annotation data such as GO Terms, PFAMs, TIGRFAMS, EC numbers or KEGG Pathways.

In an embodiment, statistical analysis was conducted by one-way ANOVA using the SPSS 21 software package for Windows (IBM® SPSS® Statistics, New York, USA). Data were tested for normality and homogeneity of variances by the Shapiro-Wilk and Levene's test, respectively. When normality was not verified, data were transformed prior to ANOVA. Significant differences among groups were determined by the Tukey's multiple range test. The probability level of 0.05 was used for rejection of the null hypothesis.

Figure 2:
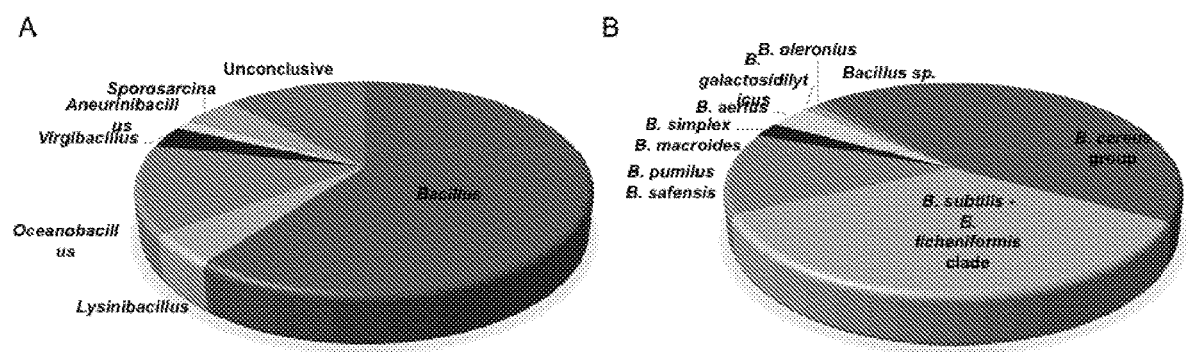
FIG. 2. (A) Diversity of sporeforming genera obtained from European sea bass digesta samples. (B) Distribution of bacterial species within the *Bacillus* genus depicted in panel A.

More than 200 bacterial isolates were obtained from the heat-treated gut contents of European sea bass fed each dietary situation (CTR, SBM, RSM and SFM). Following purification, 160 isolates representing different samples and colony morphologies (illustrated in FIG. 1, Panels A to J) were chosen for analysis. Spore production of each isolate, induced by nutrient exhaustion on Difco Sporulation medium, was confirmed by phase-contrast microscopy (FIG. 1, Panel K). All isolates were identified by partially sequencing the 16S rRNA gene revealing a predominance (60%) of Bacillus species among European sea bass gut contents (FIG. 2A). Oceanobacillus were also present, although to a lower extent (~10%), with the remaining isolates distributed between the genera Lysinibacillus and Sporosarcina (with 5% each), Aneurinibacillus and Virgibacillus (with less than 1% of the isolated population, each). Identification to the species level was in most cases inconclusive. Nevertheless, the great majority (>60%) of the isolates belonging to the Bacillus genus fall in the B. cereus group (B. cereus, B. anthracis, B. thuringiensis, B. mycoides, B. pseudomycoides, B. weihenstephanensis, and B. cytotoxicus) or in the B. subtilis-B. licheniformis clade (B. subtilis, B. vallismortis, B. mojavensis, B. atrophaeus, B. amyloliquefaciens, B. licheniformis, B. sonorensis, and B. tequilensis) (FIG. 28).

Figure 3:
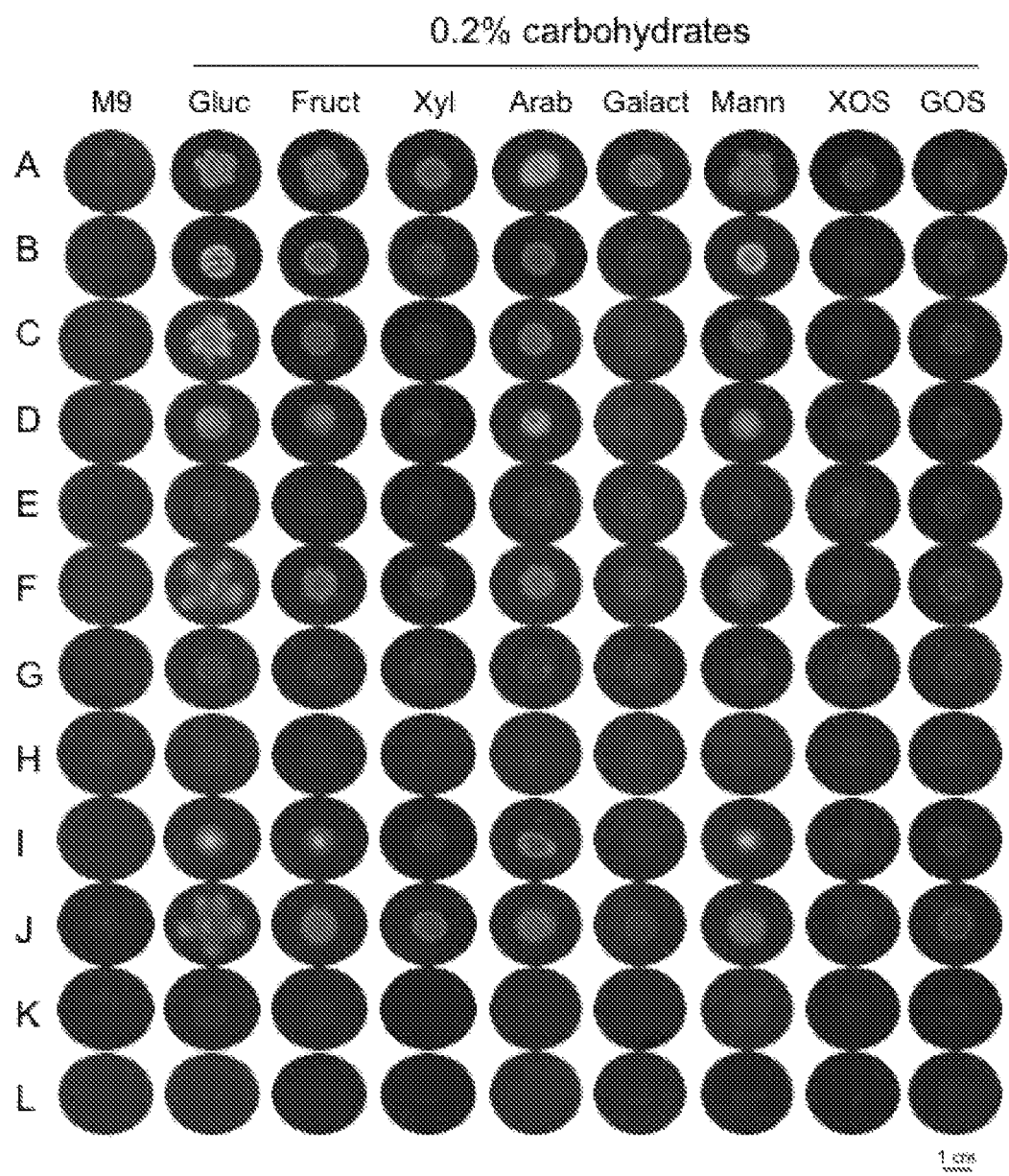
FIG. 3. Carbohydrolitic profile of representative sporeformers (A-L) isolated from the gut of European sea bass, when cultured on solid minimal medium (M9) alone or supplemented with D-glucose (Gluc), D-fructose (Fruct), D-xylose (Xyl), L-arabinose (Arab), D-galactose (Galact), D-mannose (Mann), Xylooligosaccharides (XOS) and Galactooligosaccharides (GOS).
Figure 8:
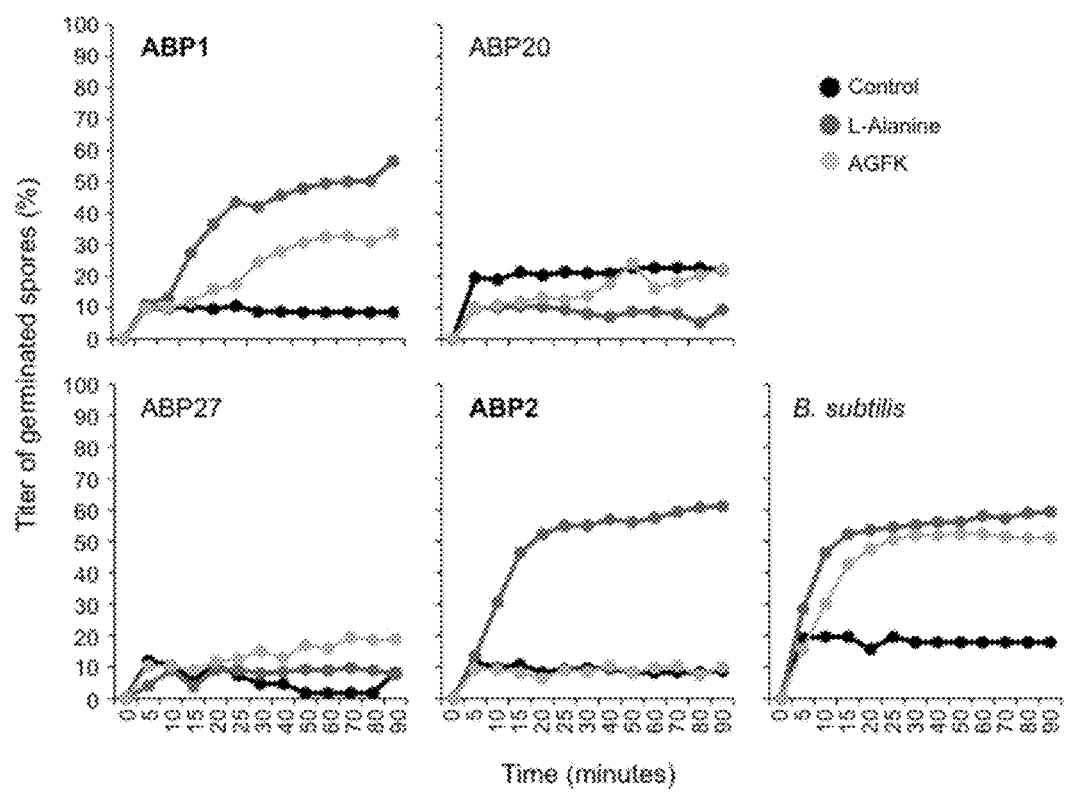
FIG. 8. Germination of populations of purified spores of sporeformers fish isolates ABP7, ABP1, ABP20, ABP27, ABP34 and ABP2 at 37° C. in 50 mM Tris-HCl, pH7.5 (control, black circles) or in response to the addition of 100 mM L-alanine (dark grey circles) or a mixture of 100 mM KCl, 56 mM glucose, 56 mM fructose and 33 mM L-asparagine (AGFK, light grey circles). *B. subtilis* 168 was used as control.

In an embodiment, the carbohydrolytic activity of gut sporeformes was evaluated. The entire collection of 160 isolates was screened for their carbohydrolytic potential by substrate specific culture-based methods, and different profiles of carbohydrate utilization could be assigned to different isolates, as illustrated in FIG. 3. The great majority of isolates grew well on glucose-supplemented medium, but not in the other carbohydrates tested. The quantification of each colony density or volume revealed the 43 isolates with higher and/or broader carbohydrolytic capacity (FIG. 8).

In an embodiment, the carbohydrate-active gut sporeformes were testes as PRO for aquaculture as follows. The selected 43 isolates were checked for minimal biosafety requirements to be considered as PRO, following the guidelines from the EFSA and the World Health Organization (WHO) [8, 17]. The majority (33) of the isolates exhibited some degree of hemolytic activity when cultivated on 5% sheep blood agar plates, with 14 isolates showing strong or β hemolysis (Table 3). Half of the isolates revealed to be resistant to at least 1 antimicrobial, and 10 isolates were resistant to 2 or more antimicrobials, defined as MR in Table 3 and detailed in Table 5. These tests allowed selecting a strict group of 11 isolates as good candidates to become a PRO for European sea bass (Table 3, highlighted in bold lettering), as isolates showing strong hemolytic activity or any antimicrobial resistance to the different classes of antibiotics tested were not further studied.

TABLE 3

Characterization and identification of the 43 isolates with broader carbohydrate-activity

| Isolate[a] | Diet[b] | Spores[c] | Catalase[d] | Hemolysis[e] | AbR[f] | 16S rRNA sequence analysis | |
|---|---|---|---|---|---|---|---|
| | | | | | | Closest known species[g] | % ID |
| ABP3 | CTR | + | + | β | — | B. thuringiensis; B. cereus | 100 |
| ABP4 | CTR | + | + | γ | — | Bacillus sp. | 99.2 |
| ABP5 | CTR | + | + | γ | — | B. subtilis | 98.2 |
| ABP6 | SFM | + | + | β | — | B. cereus | 100 |
| ABP7 | SFM | + | + | α | — | B. pumilus; B. safensis | 100 |
| ABP8 | SFM | + | + | α | MR | B. licheniformis | 100 |
| ABP9 | SFM | + | +\- | β | — | B. cereus | 100 |
| ABP10 | SFM | + | + | β | — | B. simplex; B. macroides | 100 |
| ABP1 | SFM | + | + | α | — | B. subtilis | 100 |
| ABP11 | SBM | + | + | β | R | B. sp | 99.2 |
| ABP12 | SBM | + | + | α | R | B. safensis | 99.8 |
| ABP13 | RSM | + | + | α | MR | B. licheniformis | 100 |
| ABP14 | RSM | + | + | α | R | B. pumilus | 99 |
| ABP15 | RSM | + | + | β | R | B. cereus; B. subtilis | 99.6 |
| ABP16 | RSM | + | + | α | R | B. safensis; B. pumilus | 100 |
| ABP17 | CTR | + | + | β | — | B. subtilis; B. mojavensis | 99.2 |
| ABP18 | CTR | + | + | α | MR | B. licheniformis; B. aerius | 100 |
| ABP19 | CTR | + | + | β | — | B. subtilis | 99.6 |
| ABP20 | SBM | + | + | α | — | B. subtilis; B. amyloliquefaciens | 100 |
| ABP21 | RSM | + | + | α | MR | B. licheniformis | 100 |
| ABP22 | RSM | + | + | γ | MR | B. licheniformis; B. aerius | 86.2 |
| ABP23 | RSM | + | + | α | MR | B. licheniformis | 100 |
| ABP24 | RSM | + | + | α | MR | B. licheniformis | 100 |
| ABP25 | RSM | + | + | α | R | B. pumilus | 99.9 |
| ABP26 | RSM | + | + | β | — | B. licheniformis | 100 |
| ABP27 | SFM | + | + | α | — | B. subtilis; B. amyloliquefaciens | 100 |
| ABP28 | SFM | + | + | β | R | B. cereus | 100 |
| ABP29 | SFM | + | + | α | MR | B. licheniformis; B. aerius | 100 |
| ABP30 | SFM | + | +\- | β | R | B. cereus | 100 |
| ABP31 | CTR | + | + | β | — | B. cytotoxicus | 97.8 |
| APB32 | SFM | + | + | γ | MR | B. licheniformis | 100 |
| ABP33 | SFM | + | + | α | R | B. safensis | 99.5 |

TABLE 3-continued

Characterization and identification of the 43 isolates with broader carbohydrate-activity

| | | | | | | 16S rRNA sequence analysis | |
|---|---|---|---|---|---|---|---|
| Isolate[a] | Diet[b] | Spores[c] | Catalase[d] | Hemolysis[e] | AbR[f] | Closest known species[g] | % ID |
| ABP34 | SFM | + | + | α | — | Bacillus sp. | 100 |
| ABP35 | SBM | + | + | γ | MR | B. licheniformis | 100 |
| ABP2 | SBM | + | + | α | — | B. subtilis | 100 |
| ABP36 | SBM | + | + | γ | — | B. simplex; B. macroides | 100 |
| ABP37 | SBM | + | + | β | — | B. subtilis | 76.1 |
| ABP38 | SFM | + | + | γ | — | Bacillus sp. | 99.5 |
| ABP39 | SFM | + | + | γ | R | Bacillus sp. | 100 |
| ABP40 | RSM | + | + | α | — | Bacillus sp. | 98.7 |
| ABP41 | SFM | + | + | γ | R | B. licheniformis | 100 |
| ABP42 | SBM | + | + | γ | R | B. licheniformis | 100 |
| ABP43 | RSM | + | + | β | — | B. thuringiensis; B. cereus | 100 |

[a]In underlined lettering are the isolates showing strong hemolytic activity or any antimicrobial resistance, discarded from the rest of the disclosure and in bold the 11 isolates used in subsequent tests.
[b]CTR, control fishmeal-based diet; SBM, soybean meal-based diet; RSM, rapeseed meal-based diet; SFM, sunflower meal-based diet.
[c]Spores detected by phase-contrast microscopy of 24 h cultures in DSM agar.
[d]Catalase activity tested by resuspending a colony in a 3% solution of hydrogen peroxide (Sigma).
[e]Hemolysis determined on Columbia 5% sheep blood agar plates after incubation at 37° C. for 24, 48 and 72 h (shown is the final reading at 72 h incubation). β-hemolysis, the bacterial hemolytic enzymes completely break down the blood cells; α-hemolysis, the bacterial hemolytic enzymes only partially break down the blood cells; γ-hemolysis corresponds to essentially no hemolytic activity detected.
[f]AbR-Antimicrobial resistance determined by the E-test method against several antibiotics (Table 5). R—resistance to one antimicrobial; MR—resistance to 2 or more antimicrobials; — no resistance phenotype detected.
[g]Closest known species found using RDP based on partial sequences (600 to 800 nt) of the 16S rRNA gene.

Figure 4:
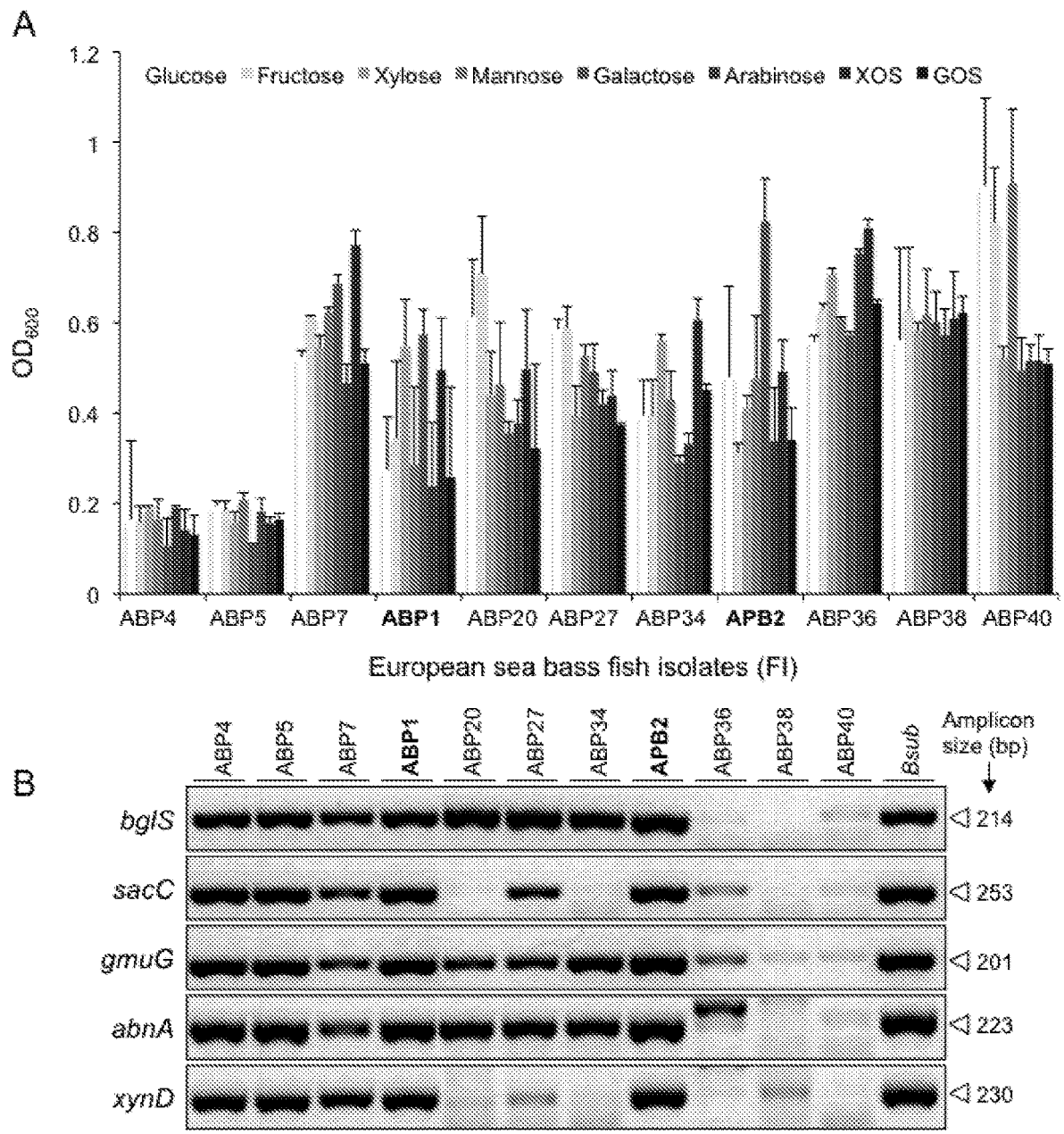
FIG. 4. (A) Carbohydrolitic profile of the best 11 sporeformers (codes in the x axis) isolated from European sea bass gut, when cultured in liquid minimal medium supplemented with D-glucose, D-fructose, D-xylose, L-arabinose, D-galactose, D-mannose, Xylooligosaccharides (XOS) and Galactooligosaccharides (GOS) for 24 h at 37° C. with agitation. Growth was quantified by measuring the optical density (OD) at an absorbance of 600 nm. The results presented are the average of three independent experiments with error bars representing the standard deviation. (B) PCR detection of genes coding for β-glucanase (bglS), levanase or β-D-fructofuranosidase (sacC), mannan endo-1,4-β-mannosidase (gmuG), endo-1,5-α-L-arabinanase (abnA) and arabinoxylan arabinofuranohydrolase (xynD) carbohydrases in the genome of fish isolates (FI numbers on top of the figure). The amplicon size, in base pairs (bp) is depicted on the right.

The selected 11 isolates were then simultaneously cultured in M9 liquid medium to quantify bacteria growth after 24 h in liquid M9 supplemented with the different carbohydrates (FIG. 4A). The results from 3 independent experiments (FIG. 4A) allowed to eliminate fish isolates ABP4 and ABP5 from the follow-up tests, after revealing the lowest capacity to metabolize the carbohydrates tested.

The presence of specific carbohydrases coding genes in these 11 isolates was investigated by using oligonucleotide primers specifically designed to target the genes coding for β-glucanase (bglS), levanase or β-D-fructofuranosidase (sacC), mannan endo-1,4-β-mannosidase (gmuG), endo-1,5-α-L-ara binanase (abnA), and arabinoxylan arabinofuranohydrolase (xynD) (Table 4). Their broad carbohydrolytic phenotype could not be correlated with the presence of the target genes, since no PCR amplification was obtained for the most promising isolates (ABP38 and ABP40) while all target genes seem to be present in the worst fish isolates ABP4 and ABP5 (FIG. 4B).

TABLE 4

Oligonucleotide primers used in the present disclosure

| Target enzyme[a]/gene[b] | Primer Name | Primer Sequence (5'-3') |
|---|---|---|
| β-glucanase (GH16-EC 3.2.1.73 /bglS | BglS-339F | AGGGATCGTTTCATCGTTCT |
| | BglS-553R | TAATAGAGTTTGGCTGCCAATC |
| Levanase (β-D-fructofuranosidase) (GH32 - EC 3.2.1.80)/sacC | SacC-106F | CCTCAATATCACTTCACACCGGAG |
| | SacC-336R | ATCTACAACTGCGCTTCCAGAAAA |
| Mannan endo-1,4-β-mannosidase (GH26-EC 3.2.1.78)/gmuG | GmuG-563F | TCAGGCCGCTGCATGAAATGAACG |
| | GmuG-786R | AATATCCACGTAAGACGCGCCCGG |
| Endo-1,5-α-L-arabinanase (GH43 - EC:3.2.1.99)/abnA | AbnA-311F | GGGCGCCGGACATCCAATACTATA |
| | AbnA-564R | AGTCAGCTTAATGCCGCTCCAAAA |
| Arabinoxylan arabinofuranohydrolase (GH43 - EC:3.2.1.55)/xynD | XynD-361F | AAATGGGCAGGTGCGTCATGGGC |
| | XynD-591R | GTCGTCATCTACAAATACTGCCGG |

[a]The enzyme Glycoside Hydrolase Family (GH) number and the EC number are providing in brackets
[b]gene name in B. subtilis strain 168 genome, whose sequence was used to design the oligonucleotide primers

TABLE 5

Susceptibility of selected isolates to various antimicrobial agents
MiC[a] (μg ml$^{-1}$)

| Isolate[b] | CL | TC | EM | KM | VA | GM | SM |
|---|---|---|---|---|---|---|---|
| ABP3 | 6 | 1.5 | 0.19 | 1.5 | 3 | 0.38 | 1.5-2 |
| ABP4 | 4 | 0.094 | 0.094 | 0.75 | 0.75 | 0.125 | 4.-6 |
| ABP5 | 4 | 0.125 | 0.094 | 0.75 | 1 | 0.125 | 4 |

TABLE 5-continued

Susceptibility of selected isolates to various antimicrobial agents
MIC$^a$ (µg ml$^{-1}$)

| Isolate$^b$ | CL | TC | EM | KM | VA | GM | SM |
|---|---|---|---|---|---|---|---|
| ABP6 | 4 | 0.75 | 0.125 | 3 | 2 | 0.75 | 0.75 |
| ABP7 | 5 | 0.75 | 0.142 | 0.625 | 0.375 | 0.094 | 0.75 |
| ABP8 | >256 | 4 | >256 | 3 | 8 | 0.75 | 24 |
| ABP9 | 4 | 0.38 | 0.125 | 2 | 2 | 0.28 | 0.38 |
| ABP10 | 1.5 | 0.047 | 0.032 | 0.25 | 0.094 | 0.094 | 0.75-1.0 |
| ABP1 | 3.5 | 0.22 | 0.0945 | 0.625 | 0.625 | 0.1095 | 1.875 |
| ABP11 | 4 | 0.75 | 0.125 | 3 | 8 | 0.75 | 1.5 |
| ABP12 | 8 | 0.5 | 0.094 | 1 | 0.25 | 0.38 | 1.5 |
| ABP13 | >256 | 4 | >256 | 2.-3 | 4 | 0.75 | 16-24 |
| ABP14 | 12 | 0.5 | 1 | 1.5 | 0.38 | 0.125 | 1.5 |
| ABP15 | 4 | 0.75 | 0.125 | 2 | 4 | 0.38 | 2 |
| ABP16 | 12 | 0.38 | 0.5 | 1.5 | 0.5 | 0.19 | 2,-3 |
| ABP17 | 6 | 4 | 0.19 | 1 | 1 | 0.064 | 4 |
| ABP18 | >256 | 4-6 | >256 | 3 | 4 | 0.5 | 24 |
| ABP19 | 6 | 3.-4 | 0.125 | 0.75 | 1 | 0.125 | 4 |
| ABP20 | 3.5 | 1.75 | 0.1095 | 0.875 | 0.875 | 0.1095 | 2.5 |
| ABP21 | >256 | 2 | >256 | 1.5-4 (?) | 6 | 0.75 | 32 |
| ABP22 | 14 | 0.315 | >256 | 1.75 | 2.75 | 0.565 | 3 |
| ABP23 | >256 | 2 | >256 | 4 | 6 | 0.75 | 32 |
| ABP24 | >256 | 2 | >256 | 12 | 4 | 0.5 | 19 |
| ABP25 | 16 | 0.5 | 0.75 | 1.5 | 0.5 | 0.125 | 3 |
| ABP26 | 6 | 1.5 | 0.125 | 0.75 | 1 | 0.125 | 2 |
| ABP27 | 3 | 1.5 | 0.125 | 0.875 | 1.125 | 0.172 | 2.5 |
| ABP28 | 6 | 0.5 | 0.19 | 2 | 4 | 0.38 | 0.75-2 |
| ABP29 | >256 | 4 | >256 | 3 | 6 | 0.5 | 16 |
| ABP30 | 6 | 0.75 | 0.125 | 2 | 6 | 0.38 | 1.5 |
| ABP31 | 3 | 0.094 | 0.125 | 0.75 | 1.5 | 0.25 | 0.5 |
| APB32 | 12 | 0.25 | 0.5 | 2 | 3 | 0.5 | 8 |
| ABP33 | 8 | 0.625 | 0.315 | 0.875 | 0.315 | 0.1095 | 0.625 |
| ABP34 | 3 | 4.5 | 0.1095 | 0.315 | 1 | 0.079 | 1.75 |
| ABP35 | 32 | 4.-6 | >256 | 2 | 2.-3 | 0.38 | 48 |
| ABP2 | 3.5 | 6 | 0.1095 | 0.75 | 1.125 | 0.094 | 7 |
| ABP36 | 5.5 | 20.625 | 2.032 | 0.3125 | 1 | 0.0585 | 4.25 |
| ABP37 | 4 | 0.094 | 0.094 | 0.38 | 0.75 | 0.094 | 1 |
| ABP38 | 4.5 | 0.1875 | 0.0705 | 0.875 | 0.22 | 0.094 | 2.5 |
| ABP39 | 8 | 0.047 | 0.064 | 0.38 | 0.125 | 0.016 | 0.75 |
| ABP40 | 2 | 0.625 | 0.1095 | 3 | 3 | 0.315 | 0.565 |
| ABP41 | 3 | 0.22 | 0.25 | 1.5 | 4 | 0.845 | 2.5 |
| ABP42 | 48 | 0.19 | 0.25 | 1.5 | 1.5 | 0.38 | 4 |
| ABP43 | 4 | 0.5 | 0.125 | 4 | 3 | 0.38 | 1.5 |

$^a$MICs were determined by the Etest® method and in bold numbering are the MIC values above the reference breakpoint (EFSA-FEEDAP, 2012).
CL, Chloramphenicol;
TC, Tetracyclin,
EM, Erythromycin;
KM, Kanamycin;
VA, Vancomycin;
GM, Gentamycin;
SM, Streptomycin.
$^b$Highlighted in underlined lettering are the isolates showing resistance to 2 or more antimicrobials. All isolates showing any antimicrobial resistance were discarded.

In an embodiment, sporeforming isolates ABP7, ABP1, ABP20, ABP27, ABP34, ABP2, ABP36, ABP38, and ABP40, that simultaneously met the minimal safety requirements to be eligible as PRO and were the most efficient isolates in metabolizing the carbohydrates tested, were further characterized to determine their sporulation efficiency, an important characteristic for future industrial production and feed incorporation.

Figure 5:
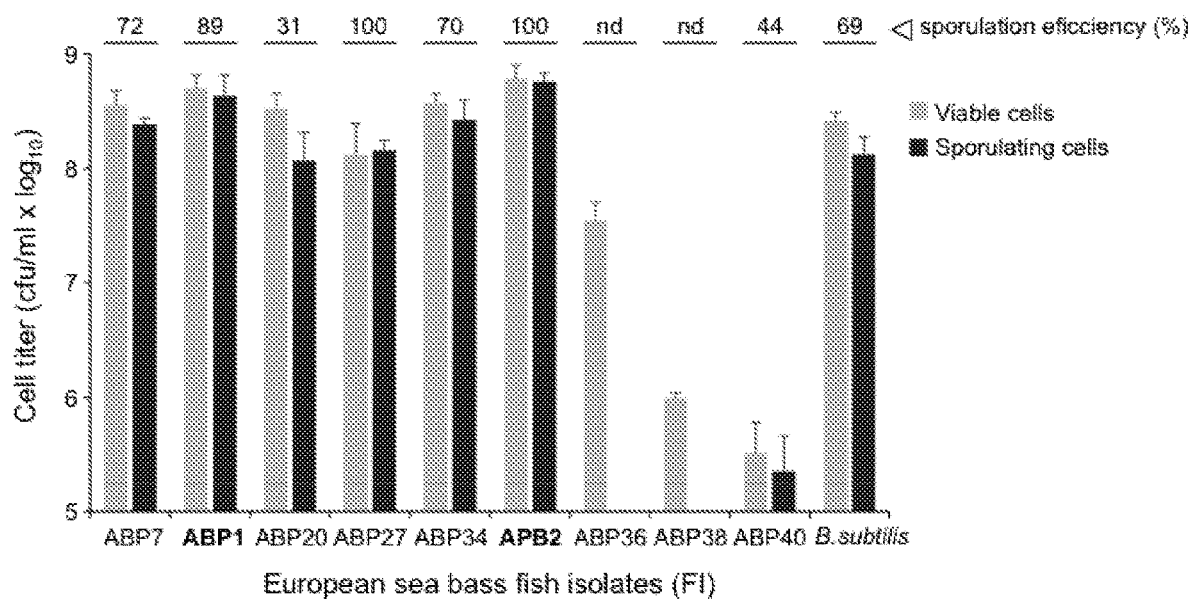
FIG. 5. Titer of viable cells present in 24 h DSM (Difco Sporulation Medium) cultures of each sporeformer fish isolate (codes in x axis) before (grey, total cells) and after (black, sporulating or heat resistant cells) a 20 min heat treatment at 80° C. Sporulation was induced by nutrient exhaustion in liquid DSM at 37° C., 150 rpm. Numbers on top of the panel correspond to the percentages (%) of sporulation calculated as the ratio between sporulating cells and total cells. *Bacillus subtilis* 168 was used as control and the results are the average of three independent experiments with error bars representing the standard deviation.

In an embodiment and by comparison with the well-studied standard strain *B. subtilis* 168 [14], isolates ABP36, ABP38, and ABP40 did not reach a minimum titer of 107 ml$^{-1}$ heat-resistant cells, after 24 h sporulation induction by nutrient exhaustion in DSM liquid medium (FIG. 5) and were discarded from the subsequent tests. Furthermore, ABP38, and ABP40 did not even reach that minimum level of total (viable) cells, revealing to be inadequate for future industrial applications. With the exception of ABP20, the remaining six isolates presented an efficiency of sporulation higher than 70%, which anticipates a high suitability for cost-effective spore production (FIG. 5).

Figure 6:
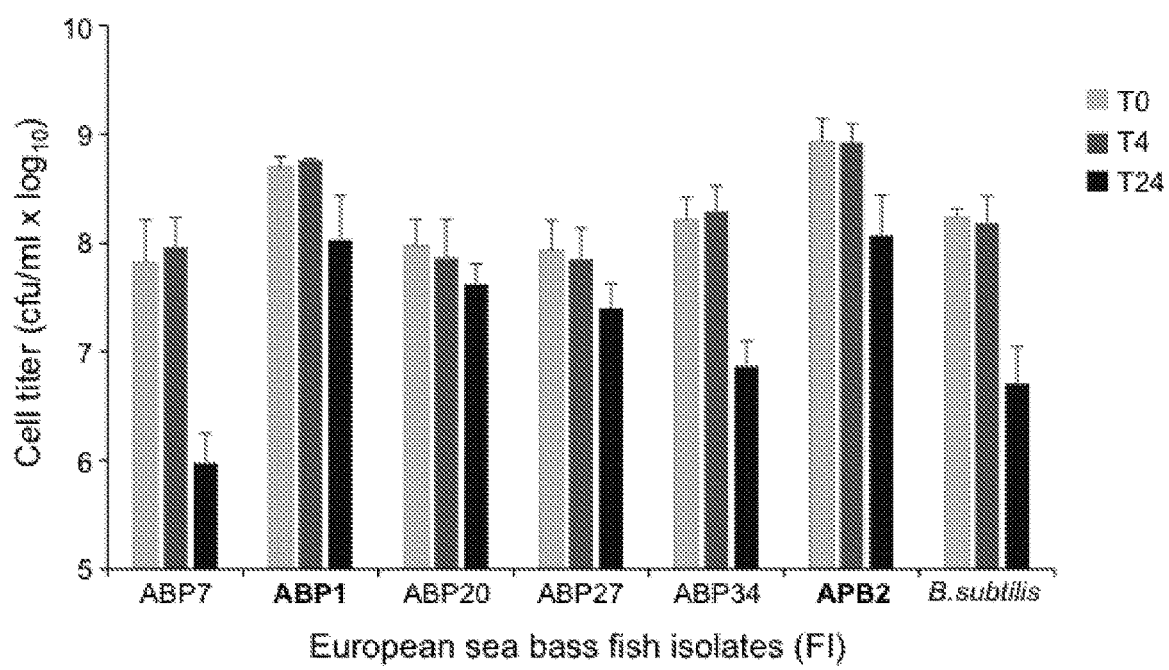
FIG. 6. Viability of spores from each sporeformer isolate (codes in x axis) when exposed for 4 h (T4, dark grey) to simulated stomach conditions (0.85% NaCl, pH 2, containing 3 mg ml$^{-1}$ pepsin) followed by 24 h (T24, black) exposition to simulated gut condition (Luria-Bertani, L B, pH 8 containing 1 mg ml$^{-1}$ pancreatin and 0.3% bile salts). The initial viable counts (time 0 or T0) are depicted in light grey. *B. subtilis* 168 was used as control and the results are the average of three independent experiments with error bars representing the standard deviation.

In an embodiment, the potential to survive passage through the gastrointestinal tract, important for in vivo efficacy, was determined by exposure to sequential simulated stomach and gut conditions. Purified spores of isolates ABP7, ABP1, ABP20, ABP27, ABP34 and ABP2 were first subjected during 4 h to acidified NaCl containing pepsin, to mimic stomach conditions, followed by 24 h exposure to alkalinized LB medium containing pancreatin and bile salts. While 4 h in simulated stomach conditions had nearly no effect on the isolates survival, the subsequent 24 h exposure to simulated gut conditions lead to a reduction in each bacterial population (FIG. 6). In particular, cell survival was dramatically decreased in isolates F192 and F1157, similarly to what was observed to the standard strain *B. subtilis* 168 (FIG. 6). Isolates ABP1 and ABP2, which showed higher sporulation efficiency, and consequently higher cell number at time 0, were the best fit to survive in the gut.

Figure 7:
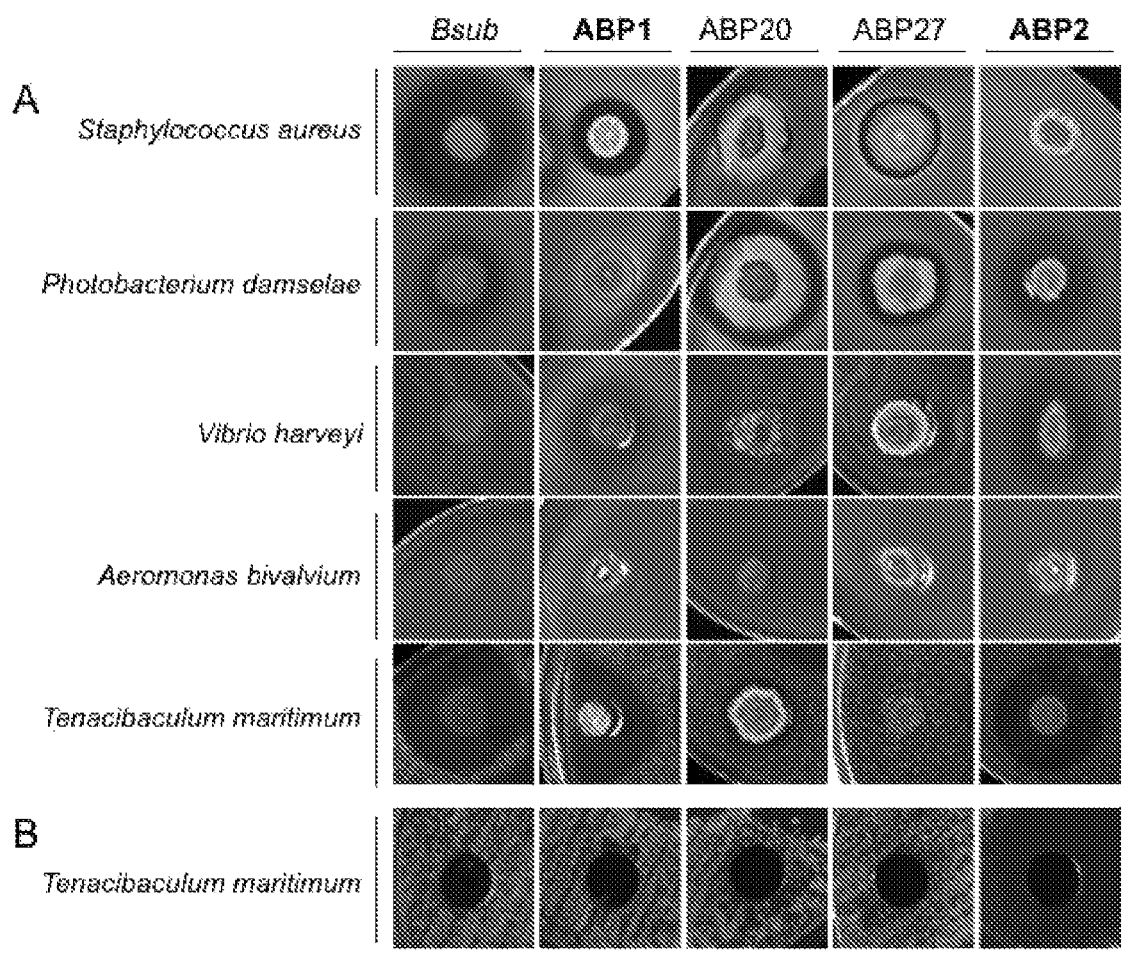
FIG. 7. Antimicrobial activity of sporeforming fish isolates ABP1, ABP20, ABP27 and ABP2 against different fish pathogens (*Staphylococcus aureus, Photobacterium damselae, Vibrio harveyi, Aeromonas bivalvium* and *Tenacibaculum maritimum*). (A) Growth inhibition screened by a colony overlay assay, where the producer strains were inoculated as spots on Luria-Bertani agar plates, grown for 24 h and then covered by Soft Marine Agar (for *Tenacibaculum maritimum*) or Soft Brain Heart Infusion Agar (for all the other) inoculated with indicator pathogenic strains. (B) Growth Inhibition screened by a cell-free supernatant assay in which a Marine Agar plate seeded with *Tenacibaculum maritimum* was perforated with 0.5 cm holes and filled with 100 μl of filtered culture medium from overnight grown sporeforming isolates. *B. subtilis* 168 (Bsub) was used as control. All photographs are to scale.

In an embodiment, the remaining four isolates, namely ABP1, ABP20, ABP27, ABP2, were characterized for their antimicrobial activity against several fish pathogenic strains, namely *P. damselae*, *V. harveyi*, *T. maritimum*, *A. bivalvium*, and *S. aureus*. As illustrated in FIG. 7A, all isolates showed some extent of antimicrobial activity. Strain ABP1 was successful in inhibiting the growth of *S. aureus*, *T. maritimum* and to a lower extent *V. harveyi*. ABP20 was only active against *Ph. damselae*. ABP27 inhibited the growth of *S. aureus* and of *Ph. damselae* while ABP2 was active against *Ph. damselae*, *V. harveyi* and *T. maritimum*. The control *B. subtilis* 168 could also effectively inhibit the growth of *S. aureus*, *Ph. damselae* and *T. maritimum*, but this last inhibitory activity was lost when using its cell-free supernatant (FIG. 7B) as opposing to the killing activity observed with the cell-free supernatant of ABP2, clearly indicating that this strain produces an extracellular inhibition molecule(s) capable of inhibiting *T. maritimum* growth (FIG. 7B).

In an embodiment, and in an attempt to infer the germination capacity of these strains inside the animal gut, spores of the same four isolates, ABP1, ABP20, ABP27 and ABP2, were subject to different germinants, namely L-alanine and a mixture of KCl, glucose, fructose and L-asparagine (AGFK). For the conditions tested, isolates ABP20 and ABP27 were unable to germinate (FIG. 9), leading to the selection of isolates ABP1 and ABP2 as the best PRO strains.

In an embodiment, the 4,068,058 bp genome of ABP1 was found to consist on 4,304 open reading frames (ORFs) with 4,184 genes identified (30 rRNAs genes and 86 tRNA genes).

In an embodiment, isolate ABP2 contained a slightly bigger genome, with 4,308,180 bp. A total of 4,643 genes (from 4,759 ORFs) were identified, including 28 rRNAs genes and 82 tRNA genes.

In an embodiment, the G+C content of ABP1 and ABP2 genomes was estimated to be 43.9% and 43.4% respectively.

In an embodiment, an exhaustive comparative analysis against the reference *B. subtilis* str. 168 [14] using Geneious R7 v7.1.7 software (Biomatters, Auckland, New Zealand) revealed the absence of more than 200 genes from ABP1 and ABP2 genomes. These are mostly associated with prophage like regions, namely Prophage3, SPB and the Skin element, or with mobile genetic elements such as the integrative and conjugative element ICEBs1. As previously described for other gut isolates including *B. subtilis* str. BSP1 [17], several negative regulators of sporulation (e.g. rapE, rapK) are also absent, resulting in a higher sporulation efficiency of these isolates when compared to the *B. subtilis* str. 168, with the advantage that this behaviour can have at the industrial and gut levels. Interestingly, both isolates lack the sdpABCIR operon of sporulation delaying proteins, which might result in even earlier trigger of sporulation.

In an embodiment, ABP1 and ABP2 genomes also accommodate new genes, some of which coding for NSPs-active hydrolases. For instance, additional genes that might be involved in xylose and mannose metabolism are found in ABP1, while ABP2 contains one myo-inositol catabolic operon, that might contribute to the cycling of inositol phosphates in the marine environment or to their bioavailability (from PF-diets) inside the fish-gut.

In an embodiment, by sequencing the 16S rRNA gene, all isolates could be assigned to a genus, being *Bacillus* the most prevalent (>60%). Affiliation to a species based on a single molecular marker (16S rRNA) was limited, as expected. This was the case for isolates belonging to the *B. cereus* group (*B. cereus*, *B. anthracis*, *B. thuringiensis*, *B. mycoides*, *B. pseudomycoides*, *B. weihenstephanensis*, and *B. cytotoxicus*) or to the *B. subtilis*-*B. licheniformis* clade (*B. subtilis*, *B. vallismortis*, *B. mojavensis*, *B. atrophaeus*, *B. amyloliquefaciens*, *B. licheniformis*, *B. sonorensis*, and *B. tequilensis*), whose 16S rRNA gene sequences obtained do not differ enough to distinguish them.

Although several *Bacillus* spp. are quite common in the gut of different animals, including the ones with high-fiber feeding habits, such as soil invertebrates or the giant panda [19], few studies have focused on their carbohydrolytic potential. For example, predominant *B. subtilis* strains from the gut microbial community of the giant panda, seem to have the capacity to growth in a higher fiber environment [20], opening the possibility that also in fish, *Bacillus* spp. may have a decisive role in shaping their host digestive capacity towards the efficient utilization of PF-diets. In fact, two recent studies, although limited to cellulase and xylanase activities, reported the isolation of carbohydrate-active *Bacillus* spp. from the gut of different fish species. The 160 isolates tested in the present disclosure showed different, and in some cases potent, hydrolytic capacities when using as sole carbon source selected carbohydrates including xylose, galactose, arabinose, or mannose. This observation was further sustained by the presence of genes coding for specific extracellular CAZymes that can help fish in obtaining the otherwise unavailable energy trapped in PF. The absence of amplification for these specific genes in some isolates, despite showing broad carbohydrolytic activities, is not surprising considering that some studies suggests that new or substantially different CAZymes involved the metabolization pathways are yet to be found in the Bacilli group of organisms. Furthermore, the lack of PCR amplification of these genes, observed with some isolates, may also be caused by mismatches of the primer pairs, due to the difficulty to design gene-specific primers regarding genomic regions poorly conserved.

In an embodiment, PRO approval within EU for incorporation into animal feed, including aquafeeds, is subject to strict and exhaustive exigencies following EFSA guidelines on quality, safety, and efficacy of the candidate(s) bacterial strain(s) [21]. Besides the obligation of strain deposition in an internationally recognised culture collection, candidate PRO isolates must be tested for the presence of any acquired antibiotic resistance genes [11, 16, 22]. PRO, which are given to animals in massive amounts, should not contribute to the escalation of antimicrobial resistance by acting as vehicles of transferable genetic determinants. Unfortunately, these rules do not apply worldwide, and very recently antimicrobial resistant strains were found in PRO products used in Vietnamese shrimp culture or in Chinese human commercial products, with all the risks those findings pose to the aquaculture production sector and to public health [23]. Although EFSA guidelines only require the absence of acquired (transmittable) resistance genes, allowing the use of bacterial strains whose antibiotic resistance is chromosomally encoded, the option of eliminating all the strains showing any antimicrobial resistance to the different classes of antibiotics tested. Adding to that criterion, strains showing strong hemolytic activity, indicative of virulence potential in several pathogenic bacterial species, including spore-forming ones, were also not further tested. These tests allowed to select a group of 11 PRO candidates that qualify with the minimal biosafety issues to be approved by EFSA.

In an embodiment, to demonstrate efficacy, EFSA requires three in vivo studies showing statistically-significant effects on each target animal species [21]. To conduct such follow-up in vivo studies in European sea bass growth and digestibility trials, it was necessary, for practical reasons, to narrow the group of interesting and potential PRO candidates. These were subjected to a series of consecutive tests to analyze some desired characteristics on a future PRO product. First the sporulation yield, an important parameter in industrial and economical terms, was determined by comparison with the well-studied standard laboratory strain *B. subtilis* 168 [14]. Six isolates demonstrated high yield spore formation, which anticipates a good suitability for cost-effective spores' production in industrial scale. Additionally, higher sporulation levels might also act as a form of propagation inside the animal gut, maximizing these strains beneficial effect [10, 17]. Second, exposure of purified spores to sequential simulated gastric and gut conditions, revealed the four isolates best equipped to survive passage through the gastrointestinal tract, important to guarantee their in vivo efficacy. In particular, isolates ABP1 and ABP2, which also showed higher sporulation efficiency, seem to be the best suited to reach, at higher numbers, the gut where their PRO action can take place. To take advantage of these isolates as PRO, upon passage through the stomach and anterior gut, spores must germinate to originate new vegetative cells that can produce the enzymes/molecules thought to benefit their host. In nature, spore germination is believed to occur in response to specific nutrients. For example, *B. subtilis* spores are known to germinate in response to L-alanine, L-valine and L-asparagine but not in response to their D-enantiomers. Taken this, and although the mechanisms of germination of spores of different Bacilli (independently of their specific species) are thought to be essentially the same, it cannot be ruled out that some of the isolates might respond efficiently to other germination molecules that might be abundant in vivo (inside the animal gut), explaining the germination failure of isolates ABP20 and ABP27 under the conditions assayed. Finally, and besides their carbohydrolytic potential, these PRO might also benefit the fish host by minimizing colonization with pathogenic species, known to be especially problematic in marine aquacultures. This is the case of *T. maritimum* whose growth was efficiently inhibited in vitro, when exposed to both cells and cell-free culture medium of isolate ABP2.

In an embodiment, sequencing ABP1 and ABP2 genomes allowed a comprehensive screening of their genomic potential to better meet the EFSA criteria for PRO. Both genomes accommodate new genes, some of which coding for NSPases (NSP-active hydrolases). For example, additional genes that might be involved in xylose (e.g. ABP10666, ABP10667), mannose (e.g. ABP10654, ABP10671) and sucrose (e.g. ABP10829, ABP10830) metabolism are found in ABP1, while ABP2 contains one myo-inositol catabolic operon (ABP24564 to ABP24567), that might contribute to the cycling of inositol phosphates in the marine environment or to their bioavailability (from PF-diets) inside the fish-gut.

In an embodiment, dissecting these genomes permitted to detail and further document their biotechnological value as PRO and/or as sources of carbohydrases or antimicrobial molecules. For instance, determining the number and type of CAZymes present in each genome provides deeper understanding on their carbohydrolytic potential also allows identification of genomic features responsible for adaptation to life within the gut that may support the role of *Bacillus* spp. as PRO [10, 12-13, 17-18]. The growing applications of spores in biomedicine and biotechnology (as oral vaccines, PRO or display systems) [12-13, 18], and the fact that there are approximately 30 PRO strains approved as feed additives in EU, but only one for aquaculture (Bactocell®, which is not a sporeformer formulation), underscore the importance of this disclosure.

Sequences

This disclosure relates to 2 PRO strains, ABP1 and ABP2, which genome comprises at least one polynucleotide encoding a protein which is involved in PRO behavior, and which polynucleotide is substantially identical to a polynucleotide sequence according to ABP10666, ABP10667, ABP10654, ABP10671, ABP10829, ABP10830 for ABP1 and ABP24564 to ABP24567 for ABP2.

In an embodiment, the polynucleotides as listed in Table 6 were isolated from *Bacillus subtilis* strain ABP1 or ABP2, and are absent or divergent in/from *B. subtilis* 168 [14], and at least in 5 out of 11 sequenced *Bacillus* isolates including:

TABLE 6

| Gene Name | Lenght (aa) | SED ID NR/Protein |
|---|---|---|
| ABP10118 | 202 | 1 |
| ABP10119 | 215 | 2 |
| ABP10120 | 286 | 3 |
| ABP10121 | 153 | 4 |
| ABP10181 | 604 | 5 |
| ABP10182 | 851 | 6 |
| ABP10654 | 316 | 7 |
| ABP10655 | 880 | 8 |
| ABP10656 | 37 | 9 |
| ABP10657 | 254 | 10 |
| ABP10658 | 422 | 11 |
| ABP10659 | 74 | 12 |
| ABP10660 | 771 | 13 |
| ABP10661 | 425 | 14 |
| ABP10662 | 710 | 15 |
| ABP10663 | 280 | 16 |
| ABP10664 | 623 | 17 |
| ABP10665 | 389 | 18 |
| ABP10666 | 163 | 19 |
| ABP10667 | 178 | 20 |
| ABP10668 | 237 | 21 |
| ABP10669 | 355 | 22 |
| ABP10670 | 65 | 23 |
| ABP10671 | 257 | 24 |
| ABP10672 | 130 | 25 |
| ABP10673 | 275 | 26 |
| ABP10674 | 527 | 27 |
| ABP10675 | 294 | 28 |
| ABP10676 | 509 | 29 |
| ABP10677 | 79 | 30 |
| ABP10678 | 61 | 31 |
| ABP10825 | 106 | 32 |
| ABP10826 | 111 | 33 |
| ABP10827 | 194 | 34 |
| ABP10828 | 520 | 35 |
| ABP10829 | 516 | 36 |
| ABP10830 | 473 | 37 |
| ABP10831 | 451 | 38 |
| ABP10832 | 227 | 39 |
| ABP10833 | 151 | 40 |
| ABP10834 | 161 | 41 |
| ABP10835 | 63 | 42 |
| ABP10836 | 489 | 43 |
| ABP10837 | 152 | 44 |
| ABP10838 | 234 | 45 |
| ABP10839 | 227 | 46 |
| ABP10840 | 598 | 47 |
| ABP10841 | 381 | 48 |
| ABP10842 | 278 | 49 |
| ABP10843 | 384 | 50 |
| ABP10844 | 367 | 51 |
| ABP10845 | 344 | 52 |
| ABP10846 | 358 | 53 |
| ABP10847 | 344 | 54 |
| ABP10848 | 482 | 55 |
| ABP10849 | 202 | 56 |
| ABP10850 | 216 | 57 |
| ABP10851 | 388 | 58 |

TABLE 6-continued

| Gene Name | Lenght (aa) | SED ID NR/Protein |
|---|---|---|
| ABP10852 | 322 | 59 |
| ABP10853 | 72 | 60 |
| ABP10854 | 39 | 61 |
| ABP10855 | 437 | 62 |
| ABP10856 | 563 | 63 |
| ABP10857 | 240 | 64 |
| ABP10858 | 332 | 65 |
| ABP10859 | 421 | 66 |
| ABP10860 | 418 | 67 |
| ABP10886 | 52 | 68 |
| ABP10887 | 1015 | 69 |
| ABP10888 | 66 | 70 |
| ABP10889 | 982 | 71 |
| ABP10890 | 715 | 72 |
| ABP10891 | 56 | 73 |
| ABP10892 | 84 | 74 |
| ABP10981 | 427 | 75 |
| ABP10982 | 300 | 76 |
| ABP10983 | 390 | 77 |
| ABP10984 | 467 | 78 |
| ABP10985 | 392 | 79 |
| ABP10986 | 594 | 80 |
| ABP10987 | 446 | 81 |
| ABP10988 | 335 | 82 |
| ABP10989 | 248 | 83 |
| ABP11306 | 51 | 84 |
| ABP11307 | 272 | 85 |
| ABP11308 | 504 | 86 |
| ABP11309 | 341 | 87 |
| ABP11310 | 464 | 88 |
| ABP11311 | 404 | 89 |
| ABP11312 | 269 | 90 |
| ABP11821 | 388 | 91 |
| ABP11822 | 130 | 92 |
| ABP11823 | 162 | 93 |
| ABP11824 | 669 | 94 |
| ABP11825 | 112 | 95 |
| ABP11826 | 306 | 96 |
| ABP11827 | 335 | 97 |
| ABP11828 | 284 | 98 |
| ABP11889 | 298 | 99 |
| ABP11890 | 308 | 100 |
| ABP11891 | 52 | 101 |
| ABP12521 | 153 | 102 |
| ABP12522 | 63 | 103 |
| ABP12523 | 92 | 104 |
| ABP12651 | 250 | 105 |
| ABP12652 | 58 | 106 |
| ABP12653 | 43 | 107 |
| ABP13703 | 49 | 108 |
| ABP13704 | 185 | 109 |
| ABP13705 | 44 | 110 |
| ABP13706 | 303 | 111 |
| ABP13707 | 82 | 112 |
| ABP13708 | 243 | 113 |
| ABP13709 | 260 | 114 |
| ABP13710 | 48 | 115 |
| ABP13711 | 339 | 116 |
| ABP13712 | 78 | 117 |
| ABP13713 | 382 | 118 |
| ABP13714 | 141 | 119 |
| ABP13715 | 49 | 120 |
| ABP13716 | 224 | 121 |
| ABP13717 | 58 | 122 |
| ABP13718 | 50 | 123 |
| ABP13719 | 192 | 124 |
| ABP13720 | 209 | 125 |
| ABP13721 | 273 | 126 |
| ABP22957 | 419 | 127 |
| ABP22958 | 299 | 128 |
| ABP22959 | 187 | 129 |
| ABP22960 | 102 | 130 |
| ABP22961 | 573 | 131 |
| ABP22962 | 84 | 132 |
| ABP22963 | 58 | 133 |
| ABP22964 | 222 | 134 |
| ABP23145 | 87 | 135 |
| ABP23146 | 273 | 136 |
| ABP23147 | 52 | 137 |
| ABP23148 | 81 | 138 |
| ABP23149 | 306 | 139 |
| ABP23150 | 60 | 140 |
| ABP23151 | 62 | 141 |
| ABP23223 | 973 | 142 |
| ABP23238 | 376 | 143 |
| ABP23224 | 200 | 144 |
| ABP23225 | 623 | 145 |
| ABP23226 | 65 | 146 |
| ABP23227 | 378 | 147 |
| ABP23228 | 107 | 148 |
| ABP23229 | 130 | 149 |
| ABP23230 | 51 | 150 |
| ABP23231 | 156 | 151 |
| ABP23232 | 670 | 152 |
| ABP23233 | 112 | 153 |
| ABP23234 | 306 | 154 |
| ABP23235 | 273 | 155 |
| ABP23236 | 47 | 156 |
| ABP23237 | 285 | 157 |
| ABP23502 | 37 | 158 |
| ABP24563 | 41 | 159 |
| ABP24564 | 484 | 160 |
| ABP24565 | 388 | 161 |
| ABP24566 | 309 | 162 |
| ABP24567 | 339 | 163 |
| ABP24568 | 41 | 164 |
| ABP24598 | 52 | 165 |
| ABP24599 | 111 | 166 |
| ABP24600 | 48 | 167 |
| ABP24601 | 384 | 168 |
| ABP24602 | 189 | 169 |
| ABP24603 | 674 | 170 |
| ABP24604 | 389 | 171 |
| ABP24605 | 170 | 172 |
| ABP24606 | 43 | 173 |
| ABP20078 | 155 | 174 |
| ABP20079 | 56 | 175 |
| ABP20080 | 196 | 176 |
| ABP20081 | 93 | 177 |
| ABP20082 | 43 | 178 |
| ABP20083 | 109 | 179 |
| ABP20084 | 144 | 180 |
| ABP20085 | 51 | 181 |
| ABP20086 | 182 | 182 |
| ABP20087 | 49 | 183 |
| ABP20088 | 53 | 184 |
| ABP20089 | 73 | 185 |
| ABP20090 | 67 | 186 |
| ABP20091 | 216 | 187 |
| ABP20092 | 117 | 188 |
| ABP20093 | 66 | 189 |
| ABP20094 | 279 | 190 |
| ABP20095 | 40 | 191 |
| ABP20096 | 101 | 192 |
| ABP20119 | 72 | 193 |
| ABP20120 | 503 | 194 |
| ABP20121 | 269 | 195 |
| ABP20122 | 172 | 196 |
| ABP20123 | 165 | 197 |
| ABP20226 | 227 | 198 |
| ABP20227 | 2296 | 199 |
| ABP20228 | 253 | 200 |
| ABP20229 | 880 | 201 |
| ABP20230 | 285 | 202 |
| ABP20231 | 744 | 203 |
| ABP20232 | 355 | 204 |
| ABP20233 | 83 | 205 |
| ABP20234 | 379 | 206 |
| ABP20235 | 58 | 207 |

Sequence Listing

| SEQ. ID No. | SEQ. Name | Amino acids sequence (one letter code) |
|---|---|---|
| SEQ. ID. NO. 1. | ABP10118 | MNLTGESKNFDDYLLELNEVDYSNPIICALANELFNPLQTEIEKVKIAYEFVRDEISHTWDTQSKRVTCNASE VLSFKEGICYAKSNLLAALLRSEGIPTGFCYQRLMLFNTPDKGYCIHALNAVFFHSLNKWIRLDSRGNKIGID AQFSLDKERLAFPIRQEFDEIDYPLIYVRPHPKTIAVLKEHKDAIEMYKYHLPERI |
| SEQ. ID. NO. 2. | ABP10119 | MIWLVGLDWSIQWGTVFTVAGTLTAAFLGQVFSHRYSQKREEIKQKKESFQNLYSPVVFKILNYLELEREK QNIMFIKGLDETEFTERYQDDELYNPSIEFKEILEIVGLNLKYGSLELIREYQETLSIAKRMEAFEGHCGTHLYF CGVFISDYINLSKDLGVYSQTMETSTEGSLLLSRLETLIPQLVVLECLWNFYLGFFMQYLVLIKKINIL |
| SEQ. ID. NO. 3. | ABP10120 | MELKNKIKRVAIYLRKSRNKEGEETEETLAKHRKRLLDIAHKNNWQYEIFQEVGSSMDEMRPECQRMINKL TDGIFDAVLSVNLARVTRDDAETPKFMNLLRQDDILFVTDSERVYDLEVQEDWQALKFTGFVNNWEYENI KAQLRKGKKDSAKMGRWSNGKPNYGYIYNRLERKLEIDEEKAKAVKLAFQMTIDGIGADNIAVKLNKLGY RTNKGKFFHGQSIVRMIRSEIYKGWIVANRLKGRNKTNGKIRPQDQWIVVKDAVKPCIIDEDTWDKANKA GHLIK |
| SEQ. ID. NO. 4. | ABP10121 | MYSYKLIDNEKVREKLEELIDEKREIHLKLTDNHLDKHLGITYDLLDVNDDGSYSGFFRTTPYIRRSDLILPGESI GIKLPSYFLIMINYLSRLEEQDCFPELELKITYNDTNFKTWETKFIIKVDQISKIEISSFYKLQTSLVYEFISKNKK |
| SEQ. ID. NO. 5. | ABP10181 | MAVVTTIKHPMISGYVKGFVDKYEISRRKAKNEHNIFEMFINDLILSSYNNDPNASYEDMETGTAFGIDGV AIFINDKLVEGVEDVDYICNSTRKIEVKPLFTQTKTSEKFDRSEVRDFLQGVNRFFNFEFCEITELKNSWETAK YIYDLSTKFKNDPALKMYYTALAPKKISVKDEDIDLHLKSEILTGLEVLKQRYIFDEDNISLNFIGLKEIRELHQK ENNLTEIKPNLDKQPVPYPKDSTGIIKSAYFGLIKLEDLDLPLLSEAVDGERILRKGIFEDNIRDYLGANEKFDVNL DMKNGLTGTNAHLFGLLNNGITIIAQDVHIISTEASLVNYQIVNGCQTSNVIFESLKDIIEKNIYIPIRLIGTEDE DTKNAIIKATNSQTALKPEQLLALRDEQKSLEEYYRAKRNQNKFLLYYERRTEQYRNEDIQKTKIINIPFQIKA TSAMFLDLPHEVSGQYGKVEQKTRGKLFTDSSLLNPYYVSGLTWYRVEAFIRNNEEGKKHRRARWHIMM VIKYLISDLKNPSKIIDKNAEKISEKVEKVMLNDAKSLEIIENALSLIKEFIINEGILDISEDRKFFERKETTTGL IEMLKNRLKTLS |
| SEQ. ID. NO. 6. | ABP10182 | MEHSNKLNIVYKSIQQMKESYGKLLKVEFHIHTPASHDYRLLPGKLFKNMKLTEVFDVALNEGLYSKEFLERI QKEDFAIFEKQVIEDINRDFHVSPSNFKEILGYQLIAHSLYKNNIHAAVISDHNTINGFKKLQAVLVDYYKSRI KGNTQRKSIKLFLGIEISCSDYYHLVGIFDEHKYTDLKNFVSKYIHSEEEGTYISCLDMVNRITENGGIPYIAHIN TSDPFLGTNLYKRSLFGFSGLKILGLTNIDSKERISNRIKKYQESSKGDPCFIHEGDSHELNQLGKKNTWIKFNN LSFKSLKKAFKNYQFCIYIDKPIYNDRFLKGIYIEPGEKGFLGDKEQPEKPFIVDFSRDLNCIIGGRGVGKSTILSI LETAFTLEVTNINQLEYISRHNLIYIVFNYKNMDYILNFPIPQITESGYSGNNYFLRKAFSETTETESGTRRLSQN WINLYRVSQVESSNGYKFQELNYNETTTIIESVYKKSYSINNIVELSNTGRISEFIRDIVLNGERLNGSKIVLSKL NKLHKNNYRKYLRENIQSVLVNIKKREENVKMAIEEFNRLNNKLIQIVYSPKLKDPTFYLKELELRYDPIFDRE KGKRVLNTYLTWDDIDEFVYEATKKFGYLEFLELILNKEHKQIENELSLNNFISGTITGEYENVSIKNMVRVYN KIEERIFRNIEKVTNSFKLLFEIIIDEFSLKFNINSKETIRTEKVVMKDIDELSLGQKVVAILTLIFNYGEHSVDSTPL VIDQPEDNLDNLYIYQNLVKSLRKIKNRQVIIATHSATIVTNADAEQVIILESDNKRGWLSKKGYPDDEVVL KHIVSILEGGRESFIHKKETYMTVLDI |
| SEQ. ID. NO. 7. | ABP10654 | MTQSPIFLTPVFKEKIWGGTALRDRFGYSIPSETTGECWAISAHPKGPSTVANGPYKGKTLIELWEEHREVF GGVEGDRPPLLTKLLDVKEDTSIKVHPDDYYAGENEEGELGKTECWYIIDCKENAEIIYGHTARSKTELVTMI NSGDWEGLLRRIKIKPGDFYYVPSGTLHALCKGALVLETQQNSDATYRVYDYDRLDSNGSPRELHFAKAVN AATVPHVDGYIDESTESRKGITIKTFVQGEYFSVYKWDINGEAEMAQDESFLICSVIEGSGLLMYEDKTCLLK KGDHFILPAQMPDFTIKGTCTLIVSHI |
| SEQ. ID. NO. 8. | ABP10655 | MKKRLIAPMLLSAASLAFFAMSGSAQAAAYTDYSLYKVEPSNTFSTESQASQAVAKLEKDTGWDASYQAS GTTTTYQISASGIHSESEAKAILSGLAKQTSITGTSSPVGSKQPYVTISSGAISGEKQANTILAKLKQETGVAGA VKAYGAAQPYMNVMTSDIADETKVKALIQSLAKQTGIKSSYQPITHTVSVTTIQSGTIVGDSRAAQIKNAFQ KESGLQASLKETVKGQAYYTFTTAAISGEANAKTLLQQLKQSTGITGSYKSINQKTTVESYNVQSAYFKGLNT VKDAISQIKKNTGVSGSYQQVGKSTSYTVNMKGITKQQLQKIDTFFKKKKWHYTSSSVKKTTTSAAYQITTA KILGEQQANKAAAFFAQKKVKATKTTAGTTAENQYQLISEETSDQSKVTKGLNILKKNQLSASAKSVKKQIA DTPKITTESLLDQTKVNQALTFFKSNHISAASQKTGQTAASSYQITTEAIISQEEIDRVLTFFKQNKIAVTTSKT GQTAYTQYKIVTAQLSSKTALNNGLTYLKSQGLTPSYTTKSNTLYKISVNEQFTGNDTAAAASSKLKQLYGW ASSIVKVKNGPQIMKTNYNLSLRDMVQKQMTVSPQTDGAAYVSLTYINTATSTVTADALNIRSTPEVSPTN VIGQFKKGDKVKIIGQTNGWAKINLGWRNASSDEVVQYVDPNNFSRDSKYYFQFLKLSQTAGLNATEVN QKVLAGKGILTGKAKAFIDAANKYGINELYLISHALLETGNGTSDLANGLTYNGKTVYNMYGIGAYDSNPNY YGAKYAYEQGWFTPEAAIIGGAKFIGSSYIHNTAYNQDTLYKMRWSATATHQYATDIGWAYKQVNRMYS LYSLLDGYTLYFDVPEFK |
| SEQ. ID. NO. 9. | ABP10656 | MYYLEIMIKMLKEIRKEPKKFDIIFVSSPPFLLLLSG |
| SEQ. ID. NO. 10. | ABP10657 | MKGVKVFHHPIIVESFRILEKLLYKKADHIVINSEGFLHYLNEHSPLVKEKVTFIPNSAREKELLISSNDAKTALK IIYVGNIGLAQNVHIIRNLAEKLHEHQIEFLIVGYGVEKKELLNYIREKNLMNVKIVNPMTRKECLELMSGCDI GIVTLKDSTVFETVLPGRIIDYITCGIPIVGSIAGYSKTIIEQEGVGLVTSNSSSEEMLANIMKIYNDPGLLKKM QKNCHKLIRENFMWETNIEKLINVIEDTR |
| SEQ. ID. NO. 11. | ABP10658 | MRKKVCMFVWNHFTNDARVLRECTALSDKYYDVDLICIHDPNNPDLDLIQKYNDHFTVYRVKRSPLLFYIQ FIYKLFKNKWSILFFLLIWICLLRMFPLLTIGFSLFAVIVLKTKLKTMLVRGSIIMRMILKGYSKKYDIYHSNDLN TLPQGFICSKFRFPKKRKLIYDSHEVQTSRTGYDSPFYSKMEAYLIRKIDIIMIVENHTRAAYNKELYGFYPKVLH NYPFLLEETKEQIDIHHMLGLPKNEKILLYQGGIQVGRGLDKLIKAMPFINEGTLLFIGDGRIKKDLENMVNN MELQHRVRFLPKVPLSELPKYTRSAYLGFQVLNNVCFNHYSASSNKLFEYIMAGVPVIGCDFPEIKKVIQGE KVGLVVDSHDHLSIAKGVNTLLENADLHYEFHKNCDKAKRKYNWETEKSQLLSLYN |

Sequence Listing

| SEQ. ID No. | SEQ. Name | Amino acids sequence (one letter code) |
|---|---|---|
| SEQ. ID. NO. 12. | ABP10659 | MQIKKNQKNQELADKYNDLKIKYHKSLEVQEDLITLCQELIREKEYIEARYNNLKESKLGRLTVWMWKRRR RNK |
| SEQ. ID. NO. 13. | ABP10660 | MKQSKDIKTLLSKQLEKVRREKEILIGLKEKEVSITGFDDFFFDTPMRILAEYNKQTLEVDAEKVYLSLFERTTN FSIPSNKEIYKLTGDRIIIDPFITLSGSVKGQIYIAFYKNNELYSTKIFEAPFDKISADVPENTTSYRFALRLEGKGY LQLNKLKIKQVFKEQIASKNIGVNRSITISKASKIQQFIDSIEAETQNYKNEKKELRIAAILDEFSYECFKHDAEIL RLSNTDWDNEILEFNPHFVFVESCWQGNQGHWQYEVANLHKNKHRTALKKLTEYCKSKNIKTVFWDKE GYENFEFFKTAASYFDYVMTADENTVKKFKETSSINNVGILPFAAQPRIHNPINKNLHHLGGIAFAGSYYNN KHESRKRDIEEIIKPALDFGIDIYDRYYNVPAAKKVNNTWPEEYQRHIVGSLNYSQMNVAYKNYNMFVNV NSVQNSKHMFARRVFELLASKTMVISGPSKGVQEYFGDLVPVACSKEETVNILKTFLYNPVYREMYEKKGH RLVLNSHTYKNRLQEICDHIGIDINLLEKPRISIISSTQRTEYMENLYNNARHQTYQNLELIIILNKNSMDAEE WKQKFSSLHFPVTILQVDENVSLGHCLNKAVQRSTGEIIAKFDDDDYYAPHYLEDMLHSMEYSGADIVGKS AHYVYLEERELLILKTVGSGAERYSDFISGATLVFKKEVFVSLGGFSDKNRGEDSDFLKRAKENGNIIYSNDS WNFCLVRRANRNSHTWNITADDLLRNSTVHSMCKDYKKPITI |
| SEQ. ID. NO. 14. | ABP10661 | MKVCVIGLGYIGLPTSVMFAKYGVDVIGVDVQPHVVDSLNNGEAHLEEPGLQEFLDEALANGNFKAQLVP EPADAFIIAVPTPNNINDNMSCDLTYVLQAVDNIIPYIRKGSTIIVESTIAPRSIEDYVQPLLEQNGFTIGEDIYL VHCPERVMPGNIFHELANNMRIVGGITPSCSEAGEKVYRTFVKSKIVKTDAKTAEMSKLMENTYRDVNIAL ANELTKICNDLHINALDVIEMANMHPRVNIHSPGPGVGGHCLAVDPYFIVAKAPETADLISRSRSINSSMPI YIVEKVREIMEMVNGRTITIGGLAYKGDIDDLRESPALEILEMLKSEKKYEVRAYDPYVNHSENAQNLTEAL GGSDLFLILTDHSLFKTINDEDTNRMSNKVIFDTRNIVRNVPEDCECINLGSIHNFLNNAVLNV |
| SEQ. ID. NO. 15. | ABP10662 | MRKYLCLFSFVILFFLTLSFYGERVLAYTDTSTYKVTIKDEFTSEDKVKGISNKINNETGWDANYKLTGNTTRA FKIITGGFYGEDKVKDVLNDFEQNTGINGSYSENGNVQTIYQITTGGFTGESKVKQVLDILQSQTGVKGTYT STGEFGKQYYYRIVSGGFQSEQRIKEVLSKFENETSIKGSYEPIGNSKITYTVLSGGFSTEDNVKKAAAETKSQTGI EASYEKIPDSESYRLVISNITESELTGIESFFGKKNWWYVKKEVKNQSYRLISEPILDDQIIDKGLSFFESNKW WASKQKTDQLGENKFRITTEKISDETKLLKALNFFESNKWWAVSQKTTIKGYRITSEVINSEAVLNKGLDFFK SKNLWATYSNLSKDTYIINLNEEFTGIENATSAVNKLSNVYGLNAEVVKIKDGPQIMNTNYNLTLSDMISKQ MNANPQTDSAAYVSLSYINTSTSTVTADYLNVRSTPEVKSDNIIGQVQKSDKVTIISKEGNWAKINMGWR KASREEVTYYINPENFSISSKYYFQFLKLSQYAGLTATEVNNKILKGKGILEGKGESFIKAAESNNINELYLIAHS LLETGNGSSELANGVMYNGKKVYNMYGIGAYDGDAVTKGAQYAYNQGWFTPEAAILGGAKFIGSSYIHN ATYHQDTLYKMRWEPTVSHQYATDIGWAYKQVNRMYSLYTLLDNYTLYYDIPKYK |
| SEQ. ID. NO. 16. | ABP10663 | MEINQLRKETIKFIDLKEYKIRIEEPYLLCVTTEDGVPFEFLINIRLNQNKLLILSSGAYDNVKLKPPIFQRYTW MTEFNHSVVYFNDPTLYINQKLSIGWGQGTKNHFYLATITNVIRELAYKIKVNTKDIFFYGSSAGGFMSLILA SFLRANAIVNNPQTDVCTFYQSHVDRLFETLYPNEDKHEVIKQFRYRLNVCAFFQKLKQVPKIFYYQNYACS FDVETQLIPFLNSIKSEKTLAHLTADKEIELHLYYDAELGHNPLNKQKTMEIIIHKAMFGS |
| SEQ. ID. NO. 17. | ABP10664 | MRYKVKLARKIKNRLFRSKKKTQKENAAVIVHPADNRVFSLFDKTKRIEEENQQVPVRKISEFSWNGSILKIA GYMYIKGLPLQKEDQVRKRLLLVNNGVLFTAVSLRDVPVDKLSIDTSNVPGAYKWAGFSQQINFSKLMND KPLPQGEYKLFLEIEAVDDQNVKHQEVHTVGNVSNFLSNDVYATKMEFHSAKKLMKFNLIVNYDEGEKTI NLSCNKLQEIDPSLLELDTGKEANFLRKLNTSLFHFAYDVFRLLPLKSNKIVFASDSRLDMTGNFEFVYEELL KREENFDFKFFLKSSIRDRKSLSELMSAYHFATSKIIFIDDFYPIIYPLKIRKNADLVQLWHAVGAFKTFGYSR IGLPGGPSPHSKNHRNYTKVIVSSENIRKHYAEGFGVDIENVIATGVPRTDFFFDEAKKAFVKERLYTEYPFLK DKKVILFAPTFRGNGQQSAHYPFEVLDFDRLYRELKDEYIFLFKIHPFVRNDANIPYQYSDFFYDFSSFREINE LLLVTDILITDYSSVCFEYALLNKPMIFFSYDVDDYIRKRDFYYDYFDFIPGPLAKTSEQMISIIKEEKYNFEQIDS FVHYFFDDLDGKASERVVDQIVFPQEEEPSEDKVLKR |
| SEQ. ID. NO. 18. | ABP10665 | MKTFLTRIVKGVFGTAYKLLSALLPVQHNKIVIASYREDHLSDNFKGVYEKLKQDPSLRITLLFRKMDKGLIGR VAYLLLHLFSSLYHLATCRVLLLDDYYFPLYVVPKRKETVAIQLWHACGAFKKFGYSIVNKPFGPSSDYLKIVPV HSNYDYAIVSAPAAVPHFAEAFQMEQKQILPLGIPRTDYFYHKEHIRTVLDEFHRVYPELKHKKKLLYAPTFR GSGEHHQEGDAIPLDLLQLKSALSHKDYVVILHLHPYMRKHAHTEEDDFVLDLTDSYSLYDLMAISDGLITDY SSVIFEYSLLKRPMYFYCPDLEDYLEERDFYYPFESFVPGPISKDVPSLVHDIESDHEADTKRIEDFSQAFITHQ DGKSSGRVADFISSFLTSGAD |
| SEQ. ID. NO. 19. | ABP10666 | MTLLLKKKYPDSKVFIFGKTPYKLDHFSFVDAAYQINDIPEDVRIDHAFECVGGRGSESAIEQIIAHVHPEAC VALLGVSEYPVEIETRMVLEKGITLGSSRSGREDFARTVDFLAQYPEVVDYLETLVGGRFPVRSIEEITNAFE ADLTSSWGKTVIEWEI |
| SEQ. ID. NO. 20. | ABP10667 | MINQTYRLVSARQFEVTYKDKVVHSDKVVVRPTHLSICAADQRYYTGSRGKEAMDKKLPMALIHEGIGKV MFDPTGTFKVGTRVVMVPNTPVEEHEVIAENYLRSSRFRSSGYDGFMQDYMFMAPDRLVELPDSINPHV AAFTELITIAVHALSRFERMAHKKRDTFGVWGTEISDLS |
| SEQ. ID. NO. 21. | ABP10668 | MIYAEILAGGKGSRMGNVNMPKQFLPLNKRPIIIHTIEKFLLNDRFDKILIVSPKEWINHTKDILKKFIGQDDR LIVVEGGSDRNESIMSGIRYIEKEFGIQDDDVIITHDSVRPFLTHRIIDENIDAVLQYGAVDTVISAIDTIIASED QEFISDIPVRDNMYGQGTPQSFRISKLVELYNKLSDEQKAVLTDACKICSLAGEKVKLVRGEVFNIKVTTPYD LKVANAILQERISQ |
| SEQ. ID. NO. 22. | ABP10669 | MTLLVSFPDNARAILKEYQMGHYSFPIHVLLTQHAKSLETEFPELTVSVINEKHPLHIYKAVFSMLSSKAVIV DNYFVLTTVLTCRPDIECIQVWHANGAFKRFGLKDINTQNRSADVRRFRKVYASFDRIVVGSEHMADIFK EFFDIKGDKFLRFGVPLTDAYYEVQENSNDLKNKYHLPADKKIILYAPTFRDHQFESFSLPFSEKQLQHDLKG EYLLAVKLHPVMKQSAELPGDSAWIKDVSDLPLADLLKMSDLLISDYSSVPFEFALLDKPILFYTYDMEAYNR TRGLIRNYSEVIPGVPCCDSRALLDQLKVMDNLQSEFERFSREWNLYSRGNASKQLLSYINEKSI |

Sequence Listing

| SEQ. ID No. | SEQ. Name | Amino acids sequence (one letter code) |
|---|---|---|
| SEQ. ID. NO. 23. | ABP10670 | MTSRFDPKQQCADDFDEQIVKKRKPGFQSVISSKRLPRIVGRHSERFMHFITYHSSFKAHYRWRD |
| SEQ. ID. NO. 24. | ABP10671 | MQTKPINQLDFVDGELTSFVSHLETSFLDQNKGAFIVTANPEIGFEAMQNPRYEAVLSSADFILPDGIGVVL<br>VSKLIGKPLQSRIAGYDLFTSLLEKADQKKKRVFFYGAAKHVIAQTIERIERDYPGIEIAGYSDGYVKNQREVA<br>DKIAATNPDMVFVALGYPNQEFFIHKYRHLFPQAVSVGLGGSFDVFSGNVKRAPSFFIRFHLEWMYRLITN<br>PARWRRMLSIPKYVTAVLKHERTSAKPQYTGQVKDQSRHL |
| SEQ. ID. NO. 25. | ABP10672 | MKKVITYGTFDLFHYGHMKLLERARCLGDYLIVGLSTDDFNLQKQKKSHHSYEHRKLILETIDFVNLVIPEKS<br>WEQKITDIKKYGVDTFVIGDDWKGKFDYLNEYCKVIYLPRTEGISSTKIKKEISDLS |
| SEQ. ID. NO. 26. | ABP10673 | MNALVRIVKEQVTSFPLILRLASYETKSQYQMNYLGVLWQFLNPLIQMLAYWFVFGMGIRNSKPVLTGAG<br>EVPFIVWMLAGLIPWFFISPTILDGSNSVFKRINMVAKMNFPISSLPSVVIASNLFSYFVMMGIYVIVLFASG<br>VYPSMHWIQYIYYLICMIAFMFSFSLFNSTISVLVRDYQFLLQAVTRLLFFLLPIFWNISEQLGKNHPNLLPVL<br>KLNPIFYLIEGFRNSFLDGKWFFQDMKYTLYFWLTFLLLLVGSILHMKFRDKFVDFL |
| SEQ. ID. NO. 27. | ABP10674 | MKLKVSFRNVSKQYHLYKKQSDKIKGLFFPAKDNGFFAVRNVSFDVYEGETIGFVGINGSGKSTMSNLLAKI<br>IPPTSGEIEMNGQPSLIAIAAGLNNQLTGRDNVRLKCLMMGLTNKEIDDMYDSIVEFAEIGDFINQPVKNY<br>SSGMKSRLGFAISVHIDPDILIIDEALSVGDQTFYQKCVDRINEFKKQGKTIFFVSHSIGQIEKMCDRVAWM<br>HYGELRMFDETKTVVKEYKAFIDWFNKLSKKEKETYKKEQTEERKKEDPEAFARFRQKKKKPKSLANAVQIA<br>ILSLTVFMAGTMFFNAPLRTIASFGAIPQNEVKNHHGNAKGKSEERLTAVNKQGFIANEKAAAYKDQGLK<br>QKADVTLPFGTEVTVAAKGKQAAKIKFDGHSYYVKKSAVAANMKHAELHAAAFTSYVSQNAASSYEYFLK<br>FLGDSRTSIQSKLNGYTEGDTADGRKTLDFDYEKISYVLENDKATELIFHNISPITPASLSLSDSDVLYDSSKKR<br>FLVNTADQVFAVDNEEHTLTLMLK |
| SEQ. ID. NO. 28. | ABP10675 | MKLKKVRKAIIPAAGLGTRFLPATKAMPKEMLPIVDKPTIQYIIEEAVEAGIEDIIIVTGKSKRAIEDHFDYSPE<br>LERNLEEKGKTELLEKVKKASNLADIHYIRQKEPKGLGHAVWCARNFIGDEPPAVLLGDDIVQAETPGLRQL<br>MDEYEKTLSSIIGVQQVPEEETHRYGIIDPLTSEGRRYQVKNFVEKPPKGTAPSNLAILGRYVFTPEIFMYLEE<br>QQVGAGGEIQLTDAIQKLNEIQRVFAYDFEGKRYDVGEKLGFITTTLEFAMQDKELRDQLVPFMEGLLNKE<br>EI |
| SEQ. ID. NO. 29. | ABP10676 | MKTVFMVVYTIDVNKGGMTTAMLNRSKMLVHNGYKSDLVTFDYNPYYENITSELRQIGKLDPDVNILNV<br>NDYYRDLNTEGNVDPSYYEDEAKTEQEGYFIQDSEYDTKQYIRYFKQGSYVKYKKWTEDGYLSHIDFFNEN<br>RQRIKREEFHKNKYKHREISFDPSNNKMNYEKYYTPDGFCYLIRWYNSETEKQQQVFLFNRNSNKVLMFK<br>NNAEFHTYWLNEIAAAENEKPIYFICDGPGSSGKVRGMKKELAHRIYMVHINHFETPYTYGSKVKQDHIDFL<br>SNIDKLDALVVLTNDQKKDIEKQFGEHGNIFIIPNSMPYTDLPDIKKDNKKVSMFVRYHKQKAIDEAIKAFV<br>RVIKKVPDARLEIFGHGAEKSRLECILIIELNLQQNVFIKGYAKNVREEMGSSLITLLTSNYEAFGLSITESFMN<br>GTPVISYDCNYGPRDVISDGIDGYIVPQKDQKALANQIIKLLNNPDLAKEMGLKGREKVLTEYTNEVVLNK<br>WLQLFNVLEKK |
| SEQ. ID. NO. 30. | ABP10677 | MYDFLNVPQPDYSWIEHPIEEAGLTYIKVPEKPVYRYYGKYVKYQRFSSSVNWLYQVILMTAQAKVQKRRV<br>RKTRTQRI |
| SEQ. ID. NO. 31. | ABP10678 | MFLTYTNGEGYEHYQYLINELSLIIFEGIFGKISIILSGGAWHFIQNNKASALSFVNHFLS |
| SEQ. ID. NO. 32. | ABP10825 | MAWFLLVIAGIEEIIAAIAMKYIDGTRKKWPIIVMTVGFGLSFYCLSQAMIVLPAGVAYAVWTGIGSIGVSA<br>VGFIWFKERFQLSQVISLCLILAGVIGLRLTSSS |
| SEQ. ID. NO. 33. | ABP10826 | MNWVLVFIAGLLEVVWASSLKHADSLLDWIIIFILIAVSFILLIRSYQKIPMAAAYTVFVGIGTVGTYLTGIVLG<br>ESFSAAQMFFLALLLAGILGMKLFTKESKSQPGGEQ |
| SEQ. ID. NO. 34. | ABP10827 | MPKQTSGKYEKILQAAIEVISEKGLDKASISDIVKKAGTAQGTFYLYFSSKNALIPAIAENLLTHTLDQIKGRLH<br>GDEDFWTVLDILIDETFLITERHKDIIVLCYSGLAIDHSMEKWETIYQPYYSWLEKIINKAIANLEVTEEINSKW<br>TARTIINLVENTAERFYIGFEQDENVEVYKKEIFSFLKRSLGTA |
| SEQ. ID. NO. 35. | ABP10828 | MSKQGNFQKSMSLFDLILIGMGAIFGSAWLFAVSNVASKAGPSGAFSWILGGAIILLIGLVYAELGAALPRT<br>GGIIRYPVYSHGHLVGYLISFVTIVAYTSLISIEVTAVRQYVAYWFPGLTIKGSDSPTISGWILQFALLCLFFLLN<br>YWSVKTFAKANFIISIFKYIVPITIIIVLIFHFQPENLSVQGFAPFGFTGIQAAISTGGVMFAYLGLHPIVSAGE<br>VQNPKRNIPIALIICIIVSTIIYTVLQVTFIGAIPTETLKHGWPAIGREFSLPFKDIAVMLGLGWLATLVILDAILS<br>PGGNGNIFMNTTSRLVYAWARNGTLFGIFSKVNKDTGTPRASLWLSFALSIFWTLPFPSWNALVNVCSVA<br>LILSYAIAPISSAALRVNAKDLNRPFYLKGMSIIGPLSFIFTAFIVYWSGWKTVSWLLGSQLVMFLIYLCFSKYT<br>PKEDVSLAQQLKSAWWLIGFYIMMLIFSYIGSFGHGLGIISNPVDLILVAIGSLAIYYWAKYTGLPKAAIDYDK |
| SEQ. ID. NO. 36. | ABP10829 | MNYIKAGKWLTVFLTFLGILLFIDLFPKEEHDQKTKSKQKPDYRAAYHFTTPDKWKNDPQKPIYFDGKYHYF<br>YLYNRDYPKGNGTEWRHAVSEDLVHWTDEGVAIPKYTNPDGDIWTGSVVVDKENTAGFGKNALVAIVT<br>QPSAKDKKQEQYLWYSTDKGKSFKFYSGNPVMPNPGTDDFRDPKVIWDDQDNKWVMVMAEGSKIGFY<br>ESDNLKDWHYTSGFFPEQAGMVECPDLYMMRASDGANKWVLGASANGKPWGKPNTYAYWTGSFDG<br>KEFKADQTEAQWLDYGFDWYGGVTFEDSKSTDPLEKRYALAWMNNWDYANNTPTMKNGPNGTDSVI<br>RELRLKEQDGTYSLVSQPIEALEQLTVSTEEIEDQDVNGSKTLSITGDTYQLDTDLSWSELKNAGVRLRESED<br>QKRHIDVGIFAEGGYSYVNRAATNQPDKSNTYVESKAPYDVSKRKVHLKILVDKTTIEVFVGDGKTIFSNEV<br>FPKPEDKGITLFSDGGTASFKNITVKHFDSIHK |

-continued

Sequence Listing

| SEQ. ID No. | SEQ. Name | Amino acids sequence (one letter code) |
|---|---|---|
| SEQ. ID. NO. 37. | ABP10830 | MNIKKFAKQATVLTFTTALLAGGATQAFAKETNQKPYKETYGISHITRHDMLQIPEQQKNEKYQVPEFDSS<br>TIKNISSAKGLDVWDSWPLQNADGTVANYHGYHIVFALAGDPKNADDTSIYMFYQKVGETSIDSWKNAG<br>RVFKDSDKFDANDSILKDQTQEWSGSATYTSDGKIRLFYTDFSGKHYGKQTLTTAQVNVSASDSSLNINGV<br>EDYKSIFDGDGKTYQNVQQFIDEGNYSSGDNHTLRDPHYVEDKGHKYLVFEANTGTEDGYQGEESLFNKA<br>YYGKSTSFFRQESQKLLQSDKKRTAELANGALGMIELNDDYTLKKVMKPLIASNTVTDEIERANVFKMNGK<br>WYLFTDSRGSKMTIDGITSNDIYMLGYVSNSLTGPYKPLNKTGLVLKMDLDPNDVTFTYSHFAVPQAKGN<br>NVVITSYMTNRGFYADKQSTFAPSFLLNIKGKKTSVVKDSILEQGQLTVNK |
| SEQ. ID. NO. 38. | ABP10831 | MKQNKRKNLQTLFETLGEKHQFNGTVLAAEGGDILYHHSFGYAEMTEKRPLKTNSLFELASLSKPFTALGIIL<br>LEEKGILGYEDKVDRWLPGFPYQGVTIRHLLNHTSGLPDYMGWFFANWDPHKIAVNQDIVDMLMNEGL<br>SGYFEPNEGWMYSNTGYVLLAVIIEKASGMSYADFMKTSIFLPAGMNETRVYNRRLSPERIDHYAYGYVY<br>DVHSETYVLPDELEETNYVVYLDGIQGDGTVNSVTSDLFRFDQALYQDDFISKASKESAFSPVRLNNGETID<br>YGFGWVLQNSPEKGRIVSHSGGWPGYSTLMIRYIDHRKTLIYLSNKEEDTEYEQAILKAAEHILFGQPYEVP<br>ERPADKKKKAIDTAIYSRYVGSYLLQDGTAAQVTAENERLYLEIAGQLRLELFPSSETRFFLRALSVEVEFTLG<br>VDAAKSFILYEDGSEEEAVRTK |
| SEQ. ID. NO. 39. | ABP10832 | MIGILAGMGPKSTSPFIDKVIDYCQKLYGASNDIDYPHMMIYSCPTPFYADRPIDHDEMKKAIIDGAVKLEK<br>TGVDFIALPCNTAHVYYEEIQQALSVPMLHIVEETIKEIPHLAKKAVVLGTEPTIQSAIYQKVLKGNGQEVIHK<br>DHWQQAVNQLIAAIKQPNHMQHTQALWQTLYEEISQHADIIISACTDLNAVLDHIQSEIPIIDSSACLAKST<br>VSTYLAYQS |
| SEQ. ID. NO. 40. | ABP10833 | MKKPVLKPFASLEIKVDPPITIGETSLGLRRFIPIRSGTITGEVKGRILPGGADSQMIRANGRTDLSARYVIETA<br>DHELIYIENNGIRQVSEPFRKQAAAGEIIEPEHVYFRTVPTFETGSEVYQWLHDRLFIGSAERTPDYVLLDIYE<br>VQ |
| SEQ. ID. NO. 41. | ABP10834 | MENFIGSHMIYTYENGWEYEIYIKNDHTIDYRIHSGMVAGRWVRDQEVNIVKLTEGVYKVSWTEPTGTDV<br>SLNFMPNEKRMHGIIFFPKWVHEHPEITVCYQNDHIDLMKESREKYETYPKYVVPEFAEITFLKNEGVDNE<br>EVISKAPYEGMTDDIRAGRL |
| SEQ. ID. NO. 42. | ABP10835 | MGKTGYIGAAIVVAACIIILSAVVCLRDTVYYQPMRWTGIILFFAGIVMVPAYSAKRKPGKEK |
| SEQ. ID. NO. 43. | ABP10836 | MTHQIVTTQYGKVKGTTENGVHKWKGIPYAKPPLGQWRFKAPEPPEVWEDVLDATAYGPICPQPSDLLS<br>LSYTELPRQSEDCLYVNVFAPDTPSQNLPVMVWIHGGAFYLGAGSEPLYDGSKLAAQGEVIVVTLNYRLGP<br>FGFLHLSSFPDEAYSDNLGLLDQAAALKWVRENISAFGGDPDNVTVFGESAGGMSIAALLAMPAAKGLFQK<br>AIMESGASRTMTKEQAASTSAAFLQVLGINEGQLDKLHTVSAEDLLKAADQLRIAEKENIFQLFFQPALDPK<br>TLPEEPEKAIAEGAASGIPLLIGTTRDEGYLFFTPDSDVHSQETLDAALEYLLGKPLAEKVADLYPRSLESQIH<br>MMTDLLFWRPAVAYASAQSHYAPVWMYRFDWHPKKPPYNKAFHALELPFVFGNLDGLERMAKAEITD<br>EVKQLSHTIQSAWITFAKTGNPSTEAVNWPAYHEETRETLILDSEITIENDPESEKRQKLFPSKGE |
| SEQ. ID. NO. 44. | ABP10837 | MIGRIIRLYRKRKGYSINQLAVESGVSKSYLSKIERGVHTNPSVQFLKKVSATLEVELTELFDAETMMYEKISG<br>GEEEWRVHLVQAVQAGMEKEELFTFTNRLKKEQPETASYRNRKLTESNIEEWKALMAEAREIGLSVHEVK<br>SFLKTMGR |
| SEQ. ID. NO. 45. | ABP10838 | MNENMSFKELYAIVRHRFVLILLITIGVTLMMGFVQFKVISPTYQASTQVLVHESDGEENSNLSDIQRNLQY<br>SSTFQSIMKSTALMEEVKAELHLSESASSLKGKVITSSENESEIINVAVQDHDPAKAAEIANTLVNKFEKEVD<br>ERMNVQGVHILSEAKASESPMIKPARLRNMVMAFGAAVMGGITLAFFLHFLDDTCKSARQLSERTGLPCL<br>GSVPDVHKGRNRGIKHFGE |
| SEQ. ID. NO. 46. | ABP10839 | MIFRKKKARRGLAQISVLHNKSVVAEQYRTIRTNIEFSSVQTNLRSILVTSSVPGEGKSFSAANLAAVFAQQ<br>QEKKVLLVDADLRKPTINQTFQVDNVTGLTNVLVGNASLSETVQKTPIDNLYVLTSGPTPPNPAELLSSKA<br>MGDLISEIYEQFSLVIFDSPPLLAVADAQILANQTDGSVLVVLSGKTKTDTVLKAKDALEQSNAKLLGALLNK<br>KKMKKSEHYSY |
| SEQ. ID. NO. 47. | ABP10840 | MIIALDTYLVLNSVIAGYQFLKDSYQFYDSGALLLTAVSLLLSYHVCAFLFNQYKQVWTYTGLGELIVLLKGIT<br>LSAAVTGIIQYAVVHTMFFRLLTACWVLQLLSIGGTRILSRVLNESIRKKRCASSRALIIGAGSGGTLMVRQLL<br>SKDEPDIIPVAFIDDDQTKHKLEIMGLPVIGGKESIMPAVQKLKINFIIIAIPSLRTHELQVLYKECVRTGVSIKI<br>MPHFDEMLLGTRTAGQIRDVKAEDLLGRKPVTLDTSEISNRIKGKTVLVTGAGGSIGSEICRQISAFQPKEIIL<br>LGHGENSIHSIYTELNGRFGKHIVFHTEIADVQDRDKMFTLMKKVEPHLNYIHVHAAAHKHVPLMEHNPEAV<br>KNNIIGTKNVAEAADMSGTETFVLISSDKAVNPANVMGATKRFAEMIIMNLGKVSRTKFVAVRFGNVLGS<br>RGSVIPIFKKQIEKGGPVTVTHPAMTRYFMTIPEASRLVIQAGALAKGRQIFVLDMGEPVKIVDLAKNLIHLS<br>GYTTEQVPIEFTGIRPGEKMYEELLNKNEVHAEQIFPKIHIGKAVDGDWPVLMRFIEDFHELSEADLRARLF<br>AAINTSDKMTAASVH |
| SEQ. ID. NO. 48. | ABP10841 | MTKKILFCATVDYHFKAFHLPYFKWFKQRGWEHVAANGQTKLPYVDEKFSIPIRRSPFDPQNLAVYRQLK<br>KVIDTYEYDIVHCHTPVGGVLARLAARQARRHGTKVLYTAHGFHFCKGAPMKNWLLYYPVEKWLSAYTD<br>CLITINEEDYKRAKGLQRPGGRTQKIHGIGVNTERFRPVSPIEQQRLREKHGFREDDFILVYPAELNLNKNQK<br>QLIEAAALLKEKIPSLRLVFAGEGAMEQTYQMLAEKLGASANVCFYGFCSDIHELIQLADVSVASSIREGLG<br>MNVLEGMAAEKPAIATDNRGHREIIRDGENGFLIKIGDSAAFARRIEQLYHKPEICRKLGQEGRKTALRFSE<br>ARTVEEMADIYSAYMDMDTKEKSV |

Sequence Listing

| SEQ. ID. No. | SEQ. Name | Amino acids sequence (one letter code) |
|---|---|---|
| SEQ. ID. NO. 49. | ABP10842 | MNSGPKVSVIMGIYNCERTLAESIESILSQSYKNWELILCDDASTDGTLRIAKQYAAHYSDRIKLIQNKTNKR LAASLNHCLSHATGDYIARQDGDDLSFPRRLEKQVAFLEKHRHYQVVGTGMLVFDEFGVRGTRILPSVPEP GIMAKGTPFCHGTIMMRASAYRTLKGYRSVRRTRRMEDIDLWLRFFEEGFRGYNLQEALYKVREDSDAFK RRSFTYSIDNAILVYQACRRLKLPLSDYIYIAKPLIRAFMPAAVMNRYHKKRVMNQKEGLVKHE |
| SEQ. ID. NO. 50. | ABP10843 | MNSSQKRVLHVLSGMNRGGAETMVMNLYRKMDKSKVQFDFLTYRNDPCAYDEEILSLGGRLFYVPSIGQ SNPLTFVRNVRNAIKENGPFSAVHAHTDFQTGFIALAARLAGVPVRVCHSHNTSWKTGFNWKDRLQLLVF RRLILANATALCACGEDAGRFLFGQSNMEREREVHLLPNGIDLELFAPNGQAADEEKAARGIAADRLIIGHV ARFHEVKNHAFLLKLAAHLKERGIRFQLVLAGDGPLRGEIEEEARQQNLLSDVLFLGTEERIHELMRTFDVF VMPSLYEGLPVVLVEAQASGLPCIISDSITEKVDAGLGLVTRLSLSEPISVWAETIARAAAAGRPKREFIKETL AQLGYDAQQNVGALLNVYNISTEKDHNR |
| SEQ. ID. NO. 51. | ABP10844 | MIVYAVNMGIVFIWSWFAKMCGGRDDSLATGYRPNKLLIWIPLASLVLVSGLRYRVGTDFQTYTLLYELAG DYQNVWQIFGFGTAKTATDPGFTALLWLMNFITEDPQIMYFTVAVVTYSFIMKTLADYGRPFELSVFLFLG TPHYYASFNGIRQYMVAAVLFWAIRYIISGNWKRYFLIVLVSSLFHSSALIMIPVYFIVRRKAWSPAIFGLSAL FLGMTFLYQKFISVFVVVLENSSYSHYEKWLMTNTNGMNVIKIAVLVLPLFLAFCYKERLRSLWPQIDIVVN LCLLGFLFGLLATKDVIFARFNIYFGLYQMILVPYFVRIFDEKSNALIYIAIVVCYFLYSYLLMPVDSSVLPYRTIF SR |
| SEQ. ID. NO. 52. | ABP10845 | METPAVSLLVAVYNTETYIRTCLESLRNQTMDNIEIIIVNDGSADASPDIAEEYAKMDNRFKVIHQENQGLG AVRNKGIEAARGEFIAFIDSDDWIEPDYCEQMLRAAGDETDLVICNYAAEFEDTGKTMDSDIAQTYQDQP KEHYIKALFEGKVRGFSWNKLYRRSMIDAHRLSFPLRGELEHVEDQFFSFRAHFFARSVSYVKTPLYHYRIHL SSIVQRYQKKLFESGLALYEANAAFLQENNKLEEYRKELDTFIVLHSSICMLNEWKTSGSRRLFEKLRNVGVI CADPVFQESLSKTGTAPFDAKRSCLLLMAKYRMIPFVAMASAVYQRVIEYKMRNRG |
| SEQ. ID. NO. 53. | ABP10846 | MSLQSLKINFAEWLLLKVKYPSQYWLGAADQPIKAAAHQKKIILTLLPSHDNLGDHAIAYASKAFLEQEYPD FDIVEVDMKDIYKSAKSLIRSRHPEDMVFIIGGGNMGDLYRYEEWTRRFIIKTFHDYRVVQLPATAHFSDTK KGRKELKRAQKIYNAHPGLLLMARDETTYQFMKQHFHEKTILKQPDMVLYLDRSKPPAEREGVYMCLRED QESVLQEDQRNRVKAALFEEFGEIKSFTTTIGRRVSRDTREQELEALWSKLQSAEAVVTDRLHGMIFCALTG TPCVVIRSFDHKVMEGYQWLKDIPFMKLIEHPEPERVTAAVNELLTKETPRAGFPRDVYFKGLRDKISGEA Q |
| SEQ. ID. NO. 54. | ABP10847 | MTPLVSIIVPMYNVEPFIEECIDSLLCQTLSDIEIIILVNDGTPDRSGEIAEDYAKRDARIRVIHQANGGLSSAR NTGIKGARGTYIGFVDGDDYVSSAMFQRLTEEAEQNQLDIVGCGFYKQSSDRRTYVPPQLEANRVLTKPE MTEQLKHAHETRFIWYVWRYLYRRELFERANLLFDEDIRFAEDSPFNLSAFCEAERVKMLDEGLYIYRENPN SLTEIPYKPAMDEHLQKQYQAKIAFYNHYGLAGACKEDLNVYICRHQLPMLLANACASQNSPKDIKKKIRQI LSYDMVRQAVRHTPIQHEKLLRGERLVLALCKWRLTFLIKLFFEQRGTMKGSAKQA |
| SEQ. ID. NO. 55. | ABP10848 | MTPFIVKTLGVEAFGFVHLTQNVINYFSIITVALSSVVVRFFSVAAHRGEREKANAYISNYLAASVLISLLLLLP LAGSAFFIDRVMNVPQALLADVRLSILIGSVLFILTFLMGFGAAPFYANRLYITSSIQAVQMLIRVLSVLLLFA CFAPKIWQIQLAALAGAVMASVLSFYFFKKLIPWFSFRMKDLSFRTSKELFQAGAWSSVNQIGVLLFLQIDL LTANLMLGASASGKYAAIIQFPLLLRSLAGTVASLFAPIMTSYYSKGDMDGLMNYANKAVRLNGVLLALPA ALLGGLAGPFLTIWLGPSFSSIAPLLFIHAGYLVVSLAFMPLFYIWTAFNQQKTPAIVTLLLGAVNVVLAVTLS GPAHLGLYGITLAGAISLILKNAIFTPLYVSRITGYKKHVFFKGIIGPLSAAVFAWTVCKAIQFIVKIDSWPSLIA AGVTVSFFYAVFAFMLVCTKEERQLVLKRFRKTKGAVNL |
| SEQ. ID. NO. 56. | ABP10849 | MILKRLFDLTAAIFLLCCTSVIILFTIAVVRLKIGSPVFFKQVRPGLHGKPFTLYKFRTMTDERDGEGNLLPDEV RLTKTGRLIRKLSIDELPQLLNVLKGDLSLVGPRPLLMDYLPLYTEKQARRHEVKPGITGWAQINGRNAISW EKKFELDVWYVDNRSFILDLKILCLTVRKVLVSEGIQQTNHVTAERFTGSGDVSS |
| SEQ. ID. NO. 57. | ABP10850 | MKNVAIVGDGGHGKVIRELINARSDTRLAAVLDDKFKTFEGGKEWYTGPPEAVTELRRLIPDVLFLIAVGN NSVRKQLAERLGLRKDDFITLIHPSAIVSRSAVIGEGTVIMAGAIIQADARIGAHCIINTGAVAEHDNQISDYV HLSPRVTLSGAVSVQEGAHVGTGASAIPQITIGAWSIVGAGSAVIRPIPDRVTAAGAPARIISSIQTSNKG |
| SEQ. ID. NO. 58. | ABP10851 | MHKKIYLSPPHMSGREQHYISEAFRSNWIAPLGPLVNSFEEQLAERVGVKAAAAVSSGTAAIHLALRLLEVK EGDSVFCQSFTFVATANPILYEKAVPVFIDSEPDTWNMSPTALERALEEAKRNGTLPKAVIAVNLYGQSAK MDEIVSLCDAYGVPVIEDAAESLGTVYKGKQSGTFGRFGIFSFNGNKIITTSGGGMLVSNDEAAIEKARFLA SQAREPAVHYQHSQIGHNYRLSNILAGVGIAQLEVLDERVEKRRTIFTRYKNVLGHIAGVRFMPEYAAGVS NRWLTTLTLDNGLSPYDVVQCLAEENIEARPLWKPLHTQQLFDPALFYSHEDTGSVCEDLFKRGICLPSGSN MTEDEQDRVIEVLLHLFQTAEVKKWTASIR |
| SEQ. ID. NO. 59. | ABP10852 | MDSKHSMISLKQKLSGLLDVIPKQSEIIYADYPLYGNVGDLFIMKGTEAFFKEHGIRVRKRWNPDNFPVGR KLDPNLIIVCQGGGNFGDLYPYYQGFREKIVQTYPNHKIVILPQSIYFQNKDNLKRTAEIFSKHANLHIMTRE KASYATAQAYFSKNHIQLLPDMAHQLFPVIPTQQPSNQKLRFIRTDHEANQALQEHTETESYDWRTVLSAS DRRTIAFLQTLNVLNKKAGNPLPIAYIWGKYSDYIVQKAIRFFSRYESVETSRLHGHILSALLQKENTVIDNSY GKNANYFHTWMEGVPGTRLIQHASKKENLPAHM |
| SEQ. ID. NO. 60. | ABP10853 | MSELFSVPYFIENLKQHIEMNQSEDKIHAMNSYYRSVVSTLVQDQLTKNAVVLKRIQHLDEAYNKVKRGES K |
| SEQ. ID. NO. 61. | ABP10854 | MLTPLSSLYMIEITPYTFMKKELPKKCLNFFPSLILLRI |

-continued

Sequence Listing

| SEQ. ID No. | SEQ. Name | Amino acids sequence (one letter code) |
|---|---|---|
| SEQ. ID NO. 62. | ABP10855 | MMDMKLQQVQVLKPQLTQELRQAITLLGYHSAELAEYIDELSLENPLIERKETDTPPLSYHKTNKNRMNA QEAGLQLSNPQKTLQDALKQQSLDMNLTNTEKKIFNYLIHSLDSNGYLEEDVEEAARRLSVSAKETEAVLAK LQSLEPAGIGARSLQECILLQLQRLPNRNEQAEMLVSAHFDAFAQKKWKALSVETGIPLHTIQDISDDIAAL HPRRGLLFARPEQDVYIEPDIFITVKNGHIAAELNTRSFPEIDLHPQYRTLLSSGSCQDTVSYLSAKYQEWRW LSRALRQRKQTITRIINELITRQKDFFLKGRSAMKPLTLREVADCLSLHESTVSRAIKGKTIQTPYGLFEMKLFF SAKAEASGEGDASNYAVKMHLEDLINQEDKTKPLSDQKLVDLLYEQHGIQISRRTVAKYRDQMKIPSSAAR KRYK |
| SEQ. ID NO. 63. | ABP10856 | MQWTQAYTPIGGNLLLSALAALVPIIFFFWALAIKRMKGYTAGLATLGIALIIAVLVYRMPAEKALMSATQG AVYGLLPIGWIIVTSVFLYKITVKTGQFDIIRSSVLSITDDRRLQALLIAFSFGAFLEGAAGFGAPVAISAALLVG LGFNPLYAAGICLIANTAPVAFGAIGIPITAVEGPTGIPAMEISQMVGRQLPFLSVFIPLYLIIIMSGFRKALEV WPAILVSGVSFAVVQYLSSNFLGPELPDVLSALVSMAALAVFLKWWKPKTTFRFAGEQESAASIETARTNP AAPAYSGGQIFKAWSPFLLLTAMISVWGIPSVKSALTGHYEGSAVFLKWLNAVGEKLTFAPGVPFLNNQIV NADGTPIEAVYKLEVLGSAGTAILIAAVLSKFITAISWKDWGTVFKETVQELKLPILTIASVVGFAYVTNSSGM STTLGMTLALTGSMFTFFSPVLGWLGVFITGSDTSANLLFGNLQKVTALSVGMDPVLSVAANSSGGVTGK MISPQSIAVACAAVGLAGKESDLFRFTIKHSLFLLLLVCIITFLQHHVFSWMIP |
| SEQ. ID NO. 64. | ABP10857 | MKYKQIKTKKIYEEVADALLDMIKNGELKPGDKLDSVQALAESFQVSRSAVREALSALKAMGLVEMKQGE GTYLKEFELNQISQPLSAALLMKKEDVKQLLEVRKLLEIGVASLAAEKRTEADLERIQDALKEMGSIEADDEL GEKADFAFHLALADASQNELLKHLMNHVSSLLLETMRETRKIWLFSKKTSVQRLYEEHERIYNAVAAGNGV QAEAAMLAHLTNVEDVLSGYFEENVQ |
| SEQ. ID NO. 65. | ABP10858 | MATIKDIAQEAGFSISTVSRVLNNDESLSVPDETREKIYEAAEKLNYRKKTVRPLVKHIAFLYWLTDKEELEDV YFKTMRLEVEKLAKAFNVDMTTYKIADGIESIPEHTEGFIAVGTFSDEELAFLRNLTENGVFIDSTPDPDHFD SVRPDLAQMTKKTVNILTEKGHKSIGFIGGTYKNPNTNQDEMDIREQTFRSYMREKAMLDERYIFCHRGFS VENGYRLMSAAIDILGDQLPTAFMIAADPIAVGCLQALNEKGIAIPNRVSIVSINNISFAKYVSPPLTTFHIDI HELCKNAVQLLLEQVQDKRRTVKTLYVGAELIVRKSMNEG |
| SEQ. ID NO. 66. | ABP10859 | MKMAKKCSVFMLCAAVSLSLAACGPKESSSAKSSSKGSELVVWEDKEKSIGIKDAVAAFEKEHDVKVKVVE KPYAKQIEDLRMDGPAGTGPDVLTMPGDQIGTAVTEGLLKELHVKKDVQSLYTDASIQSQMVDQKLYGL PKAVETTVLFYNKDLISEKELPKTLEEWYDYSKKTANGSKFGFLALFDQIYYAESVMSGYGGYIFGKAKDGSY NPSDIGINNEGAVKGAALIQKFYKDGLFPAGIIGEQGINVLESLFTEGKAAAIISGPWNVEAFSKAGINYGITK LPKLENGKNMSSFIGVKSYNVSAFSKNEELAQELAVFLANEKNSKTRYEETKEVPAVKSLANDPAIMKSGAA RAVTEQSRFSEPTPNIPEMNEIWTPADSALQTVATGKADPKQALDQAAETAKGQIKAKHSGK |
| SEQ. ID NO. 67. | ABP10860 | MQHRQVALLLSIIPGLGQFYNKQWIKGIVFLFLGASFFAVFGDLLNMGFWGIFTLGTEVPRDNSVFLLAEGI IAVIVTCFGLAVYYVNLRDAFQSGKQRDENKPLSSLKEQYQHIISEGYPYVVSGPSLFILIFAVIFPILFSFALAF TNYDLYHSPPAKLIDWVGFQTFANIFTVDIWRSTFFDVLAWTVVWTLAASTLQVSLGIFLAIIVNQKDLRFK RFFRTILILPWAVPGFVTILIFAGLFNDSFGAMNHDILAFFGIDPLPWMTDANWSRLALILMQGWLGFPYIF LVSTGVLQSIPDDLYEAATIDGASVFSKLRYITLPMVFIAMAPIIITQFTFNFNNFNIIYLFNGGGPAVTGSTA GGTDILVSWIYKLTMQSSQYSLAAALTILLSVFVISIALWQFRQTKSFKEEA |
| SEQ. ID NO. 68. | ABP10886 | MRKDKLVSTVFKNNAIEIYTIIILKNPDTLVRIKEIQLFHTKKSLAASAAKL |
| SEQ. ID NO. 69. | ABP10887 | MFPEVNDKDELQKIFLNVSGKTIHSLIRDDTNIEQNTNIIDIDRVLDHKKSDFLVRNSEEFLEHNPFFHFFSPF LSCEKIEEFIVKVRIEDAVDNEDEFVKKVIKHILDLMFEKAFRVLVLEVNIARLEGKLEGTTPEERLNHFLAVSLN DESFLKSVYKEYEVLTSLLCVTIDDYFTYVMEIIKNTKREISSLNSKFNSDNDLGAITNITTGLGDTHQKGKSVS TIYFKSGKKIIYKPRDLTLEQGFQEVLYWLDGKNIPGILNFKRVQIHTVNDSGWMEHIDYKSCFNKNEANDF YTRSGNLLCLLYLLNAVDFHHENLIAHGSFPVLVDLESLFHARLKVDQIDKKSAFVTATELVDNSVQSISLLPT KISKRVGDKDISLDIGGLGAYKEQLSPHKSLVIENAGTDTIKILRKNTFIKPQLNNPSIKTGSYLYSENYTGQIK DGFESLYSWVMLNKDEFWDKISQTFKETNSRFIFRPTYLYTQLLRISSHPDFMRDTYRRKIILHRIGIDYIQEY KDILNSEYKDLLTGDVPFFRSSIEHEHLIDSRGGKIHNILEEPPIKTVKQKIFNLSKEDLRQIDFIEMSYISNEKR LKEVTDIKFSKAANLNKIKSENWIDEATQIGEFIVENSVCGINKKQKDRMWIGPSLEGIEEDIWNANVLGFD IYNGNSGIALFLGYLGEILNRQDFKQAAIETMRPIQKFISEIKEDHPYLIGAFQGISGYFYTLNKLSNLFEDSELR KTTLENISVLSKLGKFDKVYDLIGGSLGSLAVMLSIIPNITEENNKKEILKISHIHCDHILSVAKNFEEQISWPGK FSAAYSGFSHGNSGFIAYLYKFFKLTNDEQLLEVIQRALRFERRLYSEDHNNWYTTENKDKLANGWCHGAP GILLSKLILKDNGFEDEYIEKEISTAIDSSIHNGIGNNPTYCHGDLGVLSILNYASDLTNNINLKNRCLRTYQDLF ENVLAMKWRKRDLVCTRSYSLMIGLSGIGYSMIKNYAPEIVPNFLWLE |
| SEQ. ID NO. 70. | ABP10888 | MKKDMVKNASGFIEEDELISLANGENATGGGTPVTAIITALTGTTFTVTLSAASCPTSACTNLCNK |
| SEQ. ID NO. 71. | ABP10889 | MDISYENNNFIRDAVINFSSPTNEVEKLRIKNKDYFGNFYTFFLDFYQQRLFNTLENASKENNLKLNKQKIISS ALEAFSQELIQLCIRTLIVDINDRKEKGLLEGKDSKLRYKNYNNLIFKSEYVAEILNKYPVLTYLISSRISNKILYLK EVLENLRKNRQDIYRELRIEFDEVSNIYFSSGDTHNGGKNVLIIETNQGKIVYKPHSLSPDILFNSIVDYVNNS DKILKKIYKIRTLNYKDYGYQEFIDYKECETSEKLNFYFYRVGVSLSIFHIIGCDDLHHENLIAHGEYPVVIDLETL IKNNSIYKPRNNNLIDNFHEDINYSVLGTMLLPNLQTSIFDFDLGGISNDENQTSEIWKSYIIDFEGTDEIQL TKKSVIMNSTQNRATYNGKAADPKNYIEEILKGFTDCYNFVLENISGFHDLVKKVGSSNLEVRQVLRATSIYA RFLEASTHPNYLSSFEERKKLFKKINIAEGVTDKFSKKNLYELESLMCNDVPYFSTMYNSLDICNKSTSIVNFF RESLLDVVLNKTKSISKASLKKQQYYIRMSLTTTIKDSWKKTNKHNKKYRPKLFGNNNKNYLECATEIGDLFL ETAIWNNDRSKCTWVAPIISENNKVKLGPLNFDLYEGGGVILFLALLGKENGKKEYFDLALAGMRGIEELFL SDDKMDDRLSLFTGIGSLSYIYYHLYTHTNDYKYYEKFKKYIKKINEMNISGDIALDIVGGVSSLIVFLLNLYKET KLDILNSVCCKLGNTLYQCLENDKHNYLTGLSHGYSGFTWALCYLGHITKEEKYTTLGKELLKIENKFFDLHTS |

-continued

| SEQ. ID No. | SEQ. Name | Amino acids sequence (one letter code) |
|---|---|---|
| | | NWKDLRVGEGNSDPVYWCHGAGGIALSRAFLKDLLKNKENVVDKEIDKEVDRDLSSAICKLLSDGFKKTTD HSLCHGSFGNIDILLKLSEFLNDIDLQEVAFKEAQNAINYIRDKGFIPGLQDHFDLNTFMLGLGGVGYSLLRL HNPVNPSLLAMEVRSYNE |
| SEQ. ID. NO. 72. | ABP10890 | MIVKKKKRIPIVKQLQQTECGLCCCAMLIRFYNSNETLFELRSFLEAGRDGLTIKQLKNLLVHKGFKADIYKST IPGLKKINVPFIAYWNNEHFIVVEKTKKNFYYIIDPANGRRKLTEEEFRKGFSSYILYAVPSENFTPNKRKDKN VWFGVLKNITNYKLLFSIIVFLSLISYLLTLYVPILVQKLIDTSIEHNNLNSISNIVWITFLISILYGMFVLFRGLKM ISLNIFLSKNLVVDTFAHLLKLPFKFFDLRSPGDLLFRLNSMNGFRELLSTQLISGLIDLGAVVFILAYMFFKSIP LTLITILIFAINTIFMFLTRPAVAQAIDDEVAEQSKSQAIQIESIFSIAAIKISGMENEIFSTWNNSFNDVIKRFKK RSILQNIVNTVTQVFQTIAPLVLILELLLFFDNKFTMGEVIAYHSLSVTFFGLTTSLFGTYTQFILATSYLERVKD ITETECEKNFENAVNLKLRGNVKLENVSFSYTKHSPKVLKNISLEIREGQKIAIVGSSGSGKSTLSKLIMGLYDP TEGQICFDSIPLEKLDKKQLYKQMGIVPQDITLFNSSILKNITLNNKNTSIEKVRKVAKAAQIDKEIESMPMKY NTPISEMGMNLSGGQRQRIVLARALLNDPKILILDEATSSLDLVNETLISKYLSEMGCTRVVIAHRLSTIMDS DFIIVLDKGEVVEIGKHEELIALEGVYSNLYRSQMKR |
| SEQ. ID. NO. 73. | ABP10891 | MKNYKGDGAVFLVIGFCLGLFMGVVFDILPYGLSLGILIGSLIDFYFYARYKNNKK |
| SEQ. ID. NO. 74. | ABP10892 | MSMSRKETPDDNAFIESFHSSLKSKTLYLNSIERTSTIIVERNVKDYIYYNNIPYSNETKQPITDKLSAIGCLKG VLIPVSKTG |
| SEQ. ID. NO. 75. | ABP10981 | MIDVIRVSGGYGRKDVLQDISFAVKPGEFLGILGPNGSGKTTLLKMLSGSITPRSGEVLLECRSVGSYKTKEL ARKVAALPQKTEQAFSFTVEETVQFGRYAYQSGLFRQLTGEDHDIVKRVMKQTDILRFAKKSIHELSGGEQ QRVYVAQALAQEPRYLLLDEPTSFLDLSFQKSLLDLIKQETVASKLAVIGVFHDVNIASLYCDRLLLLKDGKAE VLDRPEAALCADRIERVYHTDITALDHPERANPQFTIKAKTIPEKAEPLFLKERIEQYLPRGITFSADRPMRVL SSEEGFAWRRKLVFDSGNNSGWPHDLSTVEQEALFIQHDCKLTACHIVSESNDLCIIGMKDAKGRFIMWV VVSGCLHDGQFVKVISATAKAAAQHRVFCSDVLIAATHSGRLPDQTILLTQIQDQTAACVKALKN |
| SEQ. ID. NO. 76. | ABP10982 | MKVEGIIPAILTPITKEQDFHPGVAEKLVNHLIDSGVHGIFALGTNGEFHLFSQEEKLQIAETVVKAVNKRVP VFIGAGENSTEATISLSNQMADIGADVLSIITPYFVAPSQKELYQHFRTISENVALPVLLYNIPSRTGVSLEPET VERLAALPNIIGIKDSSGSFDNIKAYLERTKDQSFSVLAGTDSLILDTLKAGGTGAVAATANVLPQTVVSIYES YKQGNIEESEQYQKQLDPLRATFSLGSLPAPLKKATELAGIDVGPPKHPIAELSGEGLQKVKKMLEGYGIETK LVKEQ |
| SEQ. ID. NO. 77. | ABP10983 | MKTLYHFQTAARIEAGAHSLNFLGDHLDQTSGWNQIRSVFILTQPSIVSLGYADQIKEVLAEKGISSEINTDI QPEPTEQNIEEVFQLFSAGSHDAILGIGGGSVLDAAKILSVLKTNKKPISELVGTNLVEKPGVPLVLIPTTSGT GSEVTPNAIVTFPEKELKIGMVSPYLLPSLVILDPVLTIGLPKAITAATGMDAFTHALESYISNKANPFSDMFA LESMRLISSSIQEAYHHGDKLEAREKMLIGAMYGGMALTSAGTAAVHAMAYPLGGKYKMSHGVANSML LPHVTAFNADHVTDRLSDVAGVIGIEQKGSKASQAERVIQKIEEWTADLNIPQNLKAFGVSKEDVPTLAEA AADVKRLMDNNPKPMSVAEIEAVYLKLLEV |
| SEQ. ID. NO. 78. | ABP10984 | MDVLSGSVITFILAVIVVYILFTTWLTMRFRSKSSAEFNNAAKTLPAIVVGILLMSEFIGTKSTIGTAESAYTHG LAASWSIVTVSIAFFIFSYFLVGKFYKTGQYTISGIISDKFGRSTKLVVSTIMIVALLLVNLGNYLSGSAAISSILG LPLMTCAIITAIVSTFYFTFGGMKGVAWVTILHSLVKYVGVLITLGVALYLTKGWEPMTQQLPEHFFTWDG SIGWGTIGAWFIGNMGAIFATQPFIIQAITSSKSEKEAKRSTLYAALLCLPLAIAIGVIGVAARHLYPDIDAIYAF PVFMQQMNPVLSAIVATSLVASIFVGVSTVALATTTLIMDDFYVPKAKPTPEQRMKVTRYASIIIGFIPLLGV ALAPELLTLSFFTRALRTSIAVVAAMGFYLPYFNSNRGATIGLVLSGMATTVWYLLDNPFGIDNMYIAIIVPF VVLVLDRLISSPAKKESNVKEEF |
| SEQ. ID. NO. 79. | ABP10985 | MKQSEVSLLIDGRIRKNETDEARKDAFLPTDCPQNHAANLLELDNGDLLCVWFGGTQEGIADISIYMSRLA KGSSEWTQIEKLSDDPSRSEQNPVLFQEPSGRLWLMYTAQMSGNQDTAIIRYRTSDDRGHTWSGIDTLFG EAGTFIRQPLVVLDNGDWLLPVFYCITLADVKWTGNRDISAVKISSDKGKTWEEVKVPSSMGCVHMNIEK LHDGTLLALFRSRFADSIYASRSIDNGRTWSEPEPTELPNNNSSIQFTALQDGTLALVYNHMKANETTERRA SLYDEIEDEDDTRTGVDTEARPAFWGAPRAPMTLALSHDGGVTWPVKRNIEVGDGYAMTNNSKDKLNR EFSYPSIKQGKDGDLHIAFTYYRQAIKYVRVPQMWASADQE |
| SEQ. ID. NO. 80. | ABP10986 | MKIKVLGIAPYKGLGDLLTELAKEEQDIQFQLEVGDLRSGVAIAEQAVSQGIDIMMSRGGTASLIQKHVRIP VVDIPVSGYDLLRALTLIKDYQGKAAVVGFENITQGVRTISELFGIEVDLYTIKEEMEVWDLLRDIQQQGTQI VLGDVITDKAAKELGMQSMLITSGRESVKEAPHTAKQMYRLFKEASEEQRMFRDMIDQEEKGMLVIDDN SRVRFVNKMVKKWMKEGLLEPIAPAAAVNEWWDELAFAVQSIREGKLSGYFQLETGEVVWHMKGSFLS KGELLIAIEQSSSSRDDRNHPVWSFAAPVHSLHPFSSFTQQSSSMRDTVQQAQAFSQTHKPILLYGEEGTG KSDLALAIHQMSPRRQHTFMTIHCSKVKETSLLKALPAVQNEYTIFLRYVEHLPLEVQHDLALQWMKPDQQ IRWLASSSADLCEEMKAGRFDPDLYSCLQGLTLYVPSLSERVEDMEDMSRLFIAEFNSVYGTQVVGLAPEV MDAFRNRTFRENVRQFKRVLEELALTVKSGYITLAEAAPQLDRLSNEKKEESLKGYTEGTLEDIERRIIQAVL QEENMNQSKAAKRLNINRTTLWRKLKE |
| SEQ. ID. NO. 81. | ABP10987 | MTNIRCKKGANISRKILIVADDLTGANDTGVQFVKAGMSAAVLFDRSGANPGDIKEDVMILDTDTRGVSP SEAYKEVSSASHPFARLESHLFLKKIDSTLRGNIGIEIKALMDLGRFDVAVIAPAFPDARRITVDGMHYVNGL PVHETEAAVDPKTPVAESRIADLLFGQTNIQPKTIGTKQLHKPDEQIQQDLRAWKTQGHEWFVCDAETNE DLRRIVQVFMNSGQSVLWVGAAGLAGALAQHVRKALQTGKRNEPVMIVSGSASNTTNRQLAYVREQR DLLDVRINPLNVLNGCEAWEHKRAIDQVVVHQGKDVLLYTDAKPETVQRIIAFGRKQGLDRQAVGEKLSL FLGAVTSEIVKLTGLKRLVLTGGDTARAICNELGADGIQLLGEIEAGIPLGKLLNADIYAVTKAGAYGQTDSVL RAVEVLRNVEEEDRWQNQSLR |

Sequence Listing

| SEQ. ID No. | SEQ. Name | Amino acids sequence (one letter code) |
|---|---|---|
| SEQ. ID. NO. 82. | ABP10988 | MAKPIIALTMGDAAGVGPEIIIKAFEQTNLHENGTLFVIGDYSILNRAKTFIGSDVDIVKINEPEEAADVKPG VIPCLDLQLLTDELRVGEVSAEAGNAAFRYLEKAIALANENQIDGICTAPLNKEALHKAGHMYPGHTEILAEL TQTKDYAMMLAAPNLKVVHVTTHVGLLDAIHLIDAKRVYTTIQLAHDTLIRAGIPQPKIAVCGINPHAGEN GLFGHGEEEEKIVPAVERAQSEGIQAFGPLPADTLFFRAVRGDFDMVVAMYHDQGHGPIKVLGLEAGVNI TVGLPIIRTSVDHGTAFDIAGTGKADPASLEEAVRQAIMLSGTRNRHA |
| SEQ. ID. NO. 83. | ABP10989 | MEFYKKTAIITGASRGIGRAIAETLADKGANVVINGTNEELLKSMCTELNTERKCASYVAGDASLPETASLLI AEAKQQFGQIDILVNNAGINLRKTTVDTSLEEWKRVIDLNLTGIFLMCQAVIPEMTAQGGGKIVNMSSTTS KTPHHNASPAYGASKAGINYLTMHLAKELAAHRIHVNAVCPGPIETDMSKQWSEEYRAAVVERIPLKMIG SPEHVANIVAFLASDKSDFMTGETININGGTYMN |
| SEQ. ID. NO. 84. | ABP11306 | MSPPNEAPIIPLDCGSLVTFQFSSISGMNWFVCQTHSLMELAFYYLRDRIP |
| SEQ. ID. NO. 85. | ABP11307 | MKKLIENTENPRTTQSIKKDLEGLGLNKGMTVLVHSSLSSIGWVNGGAIAVIQALMDIVTEEGNIVMPSQS VDLSDPSEWHYPSVPEKWWDTIRESMPAYNAQYTPTTGMGKIVEVFRSYPEVKRSCHPNYSFIAWGKDK NKILNKQSLNFGLGEQSPLGNLYMDNSYVLLLGTDFDSNTCFHLAEYRIPFQKVVIKGAPVLINGKTVWKKY KDLEFREDLFEEIGKSFEIESDMKSGKVGSANCRLFSLKEAVDFAEKWFIEYDCKMNSRG |
| SEQ. ID. NO. 86. | ABP11308 | MSNYRDYILKGKDVAVFEIDTDPISLDPAKCDDYIGQIISQAMFEPLFIRDIETEQWVCGAAENFEVSSDGLT YIFNLRKDRFWSDGISVVAQDFVFAFQRLFHPKINSPIGQILSFIKNGEEILNGVLPVTELGVEALGPRKLKISL TECLPFLPSILGSPNTSPFPYRTEQVSWTDERLNITNGAYVLKEYKSGQFVRLERNPFYPNSSSNHVKDVLFV INRELDYSLQNYEKGNIDVTCNTYFPFEEIKRFKQRDDFYMPSGILFFLQFGNRNDLFKKKQARQALYYIVN KSQIAQTLHGGIIPWDHFASIGVSEKLFDDQSNYCYHPEKAVKLWKQEERENQALSILYADFFPNGEICHSI KSEMEKHLGITLTLEGCSFEDFVIRHEQREYDLCLALLSPLYNDPFNYFQYFLSELSEEDEDEFIDILQKALGDE KENHCTYYKKANDYLLEKLPSIPLFNGQSIFLKNPFLKGYKIFKDGSISIQNLSWGTEEKPKL |
| SEQ. ID. NO. 87. | ABP11309 | MYKLADRIQIVSLHNGRIFLIDDEITELEGSPQHTEKALKLLEKGCMEEELNRIMPLEDTQKLLEFLKEEELLRE NWENEYLDTIVEKQLYYLDDFSIDSNQLQSNLKSAKVVILGVGGVGSVLAGIENFILIDNDVVNIHN LNRQFLYTQEDFGKPKVKAAENFMRKVNPSVKVTSYQTTIDSIKSLDFLASHSIDIFINAADYPKHLDKIVDE YCFERKIPWVGSGVGRHQGFWGPLFVPGKTCCLNCFIAEEEKEMKEIEKIIRERSNSIIQASFAPTNTIVSAFL AMDVIHFLAQINQIHSYLTRCQIDFTTLKLNRFTIDEPKLCNCGGE |
| SEQ. ID. NO. 88. | ABP11310 | MLSKNYSFSLSISHLKSKSDNHQRVQEIFGVTDTQLNNRLIFKNITFLMHDVTYITGFSGSGKSTLVNLIKKDF PDAVIPTPPAKQDIPIIDLLDLELQESMKILGWVGLGEAYLYLTPYSALSEGQKTRFLLAMALSRNPSIIVDEF LSNLDRITAKVVAYSFQKICRKQEIHLIVASAHNDLIEALAPDILIDLDLNGTHRITNRPIEKPFVPDISGVQVES GTIKDYEELKRFHYFGDEDLFVDPVYIETRSALGLYMPIYLSGGYSRTELPDNKLSPLRQKLWNNLSFMGLSDVHLL RDDIYCENFVQNLSGKQKEALRYLALNVYVEMMVNNYIYFRSISKMIPLLPKEMDELKEMFLDVSDEIPVTV LLQETSLFKMQGFVVQHKQ |
| SEQ. ID. NO. 89. | ABP11311 | MPLFSTNKNVSFIYLTSCFGNGFFERGIWMLFLIEKGFSLFQIGLLQAFVNGTMFLFEIPGGMLADRYGRKV SLLIGRFMIMSYLLIIMIADSFESLALSFCLLGLGMTFISGSEESLLVDSVKEQTGENNFSRFLGRYMAIITVALS LAMMIGGFLKEISWSLVFAVSFIFQMVAFFGCFFLKETKYKKGSQRESFTLIFPKDTFNFLKTNNTSRTLIFGIA LFTGIGSIFYMFAQELFNQLGIKVYLISIFFGLESFLAAILADRAYILEKKFSSRGVMMVCVYLCGISFLLIYINFN WLILSFFIISAFYNLFTTISYSVINQDIPSKQRATLLSIISFISSLVMFISIPIFGYLSDKFGTAYLLSFTGVISMVLVA LSILSFYKNRKDSVEKHKLLKVQEK |
| SEQ. ID. NO. 90. | ABP11312 | MEKKLSHHPIDRRVDLTYDEFMKEYGLPGKPVIISNAINNWEAKKLWTLDFFREKYGHIIVPIFESGKRYELY ETTLGEYIDYILKEEQEDGIFNLADWEFSRDCPELREHYQVPNYFQSWLEDAPISLLPALRWIYINQKNTGSG LHIDYGHTASWNAVISGKKKWILLNQNESENIYNGAVDAFNPDFKKFPLYTHSQTFYGEQSEGDIMYIPSG WWHQVHNEELTIAVTENFINETNYKNCLWPLVSNIVEYQLEISKTPEKVQKV |
| SEQ. ID. NO. 91. | ABP11821 | MGGGLYGHRNIEDERLKEWIKTWKAENYIHFFCNYYGVGMNAEFNDSLAKQVELVIQESSSITVSKDRYLF DEVMKYMTPEMFYCYFRYDSSTAYCGNYYEVLIEFADELTKKKLIKGYDYVQTGGITLEKNGEVIGHIGQMS DLFWQTFYDQYIVEDYGAIEHARNNGKDITLQIWNDKVFENTEQFYKFIEQILFECNVNLGFGFKMSRFEN ESKLKGHTSNTKLCLSNIELEETPLRYFNFANYTKIPRHKYLAYYQVIEFFFTRAVRKARFPQPNELLIVKYIATN SITELEVVTWLDDIKSRGKHYTKPSEKYPALFPLEATEIVESVAKRIYLIRCSLVHSKEAPNDVNFIPNLNDEIID KEISLIKYVAEKVLYKWSNAPE |
| SEQ. ID. NO. 92. | ABP11822 | MLESTYLQITDVIGKIIPADWSKIVLYAEILDGSREVYFFFQTPENDEYIYSHDIPEQFQVSKKIYTELLIDLQEL FKQLHNEFKENNPEAWTNLTLNLESNGTFSIDYNYDDVLSSELDDLQRRDVWKC |
| SEQ. ID. NO. 93. | ABP11823 | MENELNALYRSIAETVNEMIPEPWEKFLFYAQVSETGGGTYFFYNSQNEPNHFKYSLEIPFEFDIDENEFDQ YEMELFKLSEKMRDVFKDHDQELFYSFTLSLERSGKLTVNFDYTDWFKTDYSFSDQUIWKFKYLGEEPKDP SLQKLIKKYLEEYPENPI |
| SEQ. ID. NO. 94. | ABP11824 | MKVFEAKTLLSEATDRAKEYKELRTQMVNLRKALKSVADLSDSEFSGKGASNIKAFYHDHVGVTDQWIDYI DMKIAFFNSIAGAAEDKALSDAYIEESFLEHELANANKKSKSIMSEQKKAMKDILNDIDDILPLDLFSTETFKD ELADANDKRKKTLEKLDALDEDLKTEYALSEPNEQFIKSDFQKLQEATGKGKNATPIHYNAKAYRESDIHKK KGDIETRTEAYLKIKKEEAKEREIEKLKERLKNYDADADEFYEMAKTIGYENLTAEQQRYFTQIENTRELEAG FKGVAVGLYDSGKDAVVGLWDMVTDPGGTVEAITGAMAHPIKTYEAISAAIEESYQKDMVNGDTYSRAR WVSYAVGTVVTSIVGTKGVGAVSKTGTAAKVTTKVKTAASKSATAQKAITVSKQTVDHIKQKVNTGIEVSK KHVKTKLNQIGDLTLADILPYHPRHDLVPAGVPYNAVNGVTLKEGLQKFAKVILPKPYGTSSSGRRTPAPHV |

Sequence Listing

| SEQ. ID No. | SEQ. Name | Amino acids sequence (one letter code) |
|---|---|---|
| | | PPVTVKYGEHYAKWSRKKVLKPNVEYKTKEGYTYNTDNYGRITKVEADLQLGEAKRNQYAQSNAGKPQD RLPDDDGGHLIGSQFRGSGELDNLVAQNSQINRSGGEWYKMETEWAAALKEEPPRKVSVRIRPKYLGDSL RPDSFEVIYRIEGKGLFKKFIKNQAGG |
| SEQ. ID. NO. 95. | ABP11825 | MDKDFLIIKIKDIQKGDTLTNRACGNWDMKLSRAKECKRAIVVRSGVILNVYKIVDAWESDEPAKITKTNN RVRFQLAECRDYSYLIGGTLKTKTQNPVSSLSLETLMELVK |
| SEQ. ID. NO. 96. | ABP11826 | MYLYKVNNQNQIEDIREKPFKKEKEIQDLCEANLQQMLGLGFVKSEFRISNFRIDTLAFDAETKSFVIIEYKN TKNFSVVDQGYAYLAAMLNHKADFILEYNENHDLPLKRDDVDWSQSKVIFISPVFTVYQKQSIHFKDLPIEL WEVKRYENDLIQLNQMKADGVSESIKTISQQSETIQEVSKEIKVFSEEDHLADKPFDIIELYQQLKEFIFNLDD HISIKPTKLYIAFTSNKRNFTDILLLKSGLKLWVNMKKGELHDPEERMRDVSETGHWNGNGDYEIFIKDEENIE YIMGLIKQSYEKNK |
| SEQ. ID. NO. 97. | ABP11827 | MKKRFILLGLFASVFMLAVYISFQNKNTHPVQSPVIHPEEDRIFFIYSNLFIKESVLLSTSTGERFNRRTFKVAD VPYIQMKSYKSTDLVLLAEHEPFYYTLEKDAIKEHPLSDPFAFWHEGKDVSVKAYNVDTTGNEIRINDKKMK KEYTLTLPSLVTMGASDENYIYIIQSMAIYVIDRKTEEMIETLSLASYADQFADSKEFIVASSEHELTVIEKGTW KATYIAYPEDLEYADTVYYDKESGSFYVTYEDKKGEANLLEYGKEFSFHTYSLNFPYMEAKFKGNLLYIVAQE EHKKGIGGYVGVFDIHSKKMLYQFDLPEEQVKVQDFVVVD |
| SEQ. ID. NO. 98. | ABP11828 | MGGSYLSDLCSMYQKDKFFTGFVPDELLTYACELFPLSEKETVTALLNCSMGNKAKSFVMFTSKGLYWKRF GEQEGCVTWEAFTDIQSIKSTDDYEIWFEGEEVFDVGFSSYPADLLAELLRMIQQFLSENGSDLLTEAWRD HVSVSASELKEISTLFQNSHDKMFGLTNGLLVGNEISEKREVRLRKRLHIPKDQEMISFWSTPVKQTDGITL TDKGIYFSDPFLRLFYPWHVFKETPVMLKDQELIVGKENVIQLLENLMPAEDVFAFIEQVKRRISAVTS |
| SEQ. ID. NO. 99. | ABP11889 | MLRKKGQETKDYKTQQVESWGLRLIGKNEKIEKKSNISIAILDSGIDSNHEDLKGVVKKEYNALEPSKGVIED KFGHGTAVAGIIASNDNKIGTLGIAPYADIYSVKVLDDKGRGSVESIVKGIEWSIDNNVDIVNISVGLKKSDQ KLKRVIDEANEKGVIVVAAAGNNYGLNADYPARYQNVISVGAINKKMKRAKYSARGKIDFVAPGEDILTTS PKDNYINVSGTSMATPFVSGVIANIIMQEPVKYSKTKSRFTSIYKTLKKYSTPYLSEKSDMKSLGNGLISLKKE TNNEKIN |
| SEQ. ID. NO. 100. | ABP11890 | MKKSIKFIAISLIFAIIVSIIPEKNVASAGAETPVEITNEDLQRALVENGDIVDPDSVEIVKNNEDTIKAEVDVQT DDFGIDQDLDGSDSESLIDEDLDESSSETVTAEVDKEDATAIVTSVEKDEDGKDIEKKYEVDIEEADGDDIVA TFKDLDTNQVYDVNTKEAQASFAFLVPIAVVVGGALVEHLVAASLAIVIAGVTYTVATKVRSLKLKKKKYYY YAATLNKNKTNMYIGPALSKKQAVSRLRKGDVWSVSKSKAKNVAQTAGGGRKPVGPEIHNKKDGKIKKG TYYYHYHTYNRKGGHSFY |
| SEQ. ID. NO. 101. | ABP11891 | MWESIQNGKRVNKIFESKDGNYISNFTVQGNVEKIEKELVFIRGILEKEKNN |
| SEQ. ID. NO. 102. | ABP12521 | MKLIYPYGADKIYLGNPVELFRDQDTGDYIIPKNATDIPPELNGEGMWRPMFNEEKQTWIETADQAYKKS LLEDVPSESNPTNDQLSALGKQLTEEKLARIQADQAQKALGMQLTEEVIARKEAEALSQSLGKQIAALKLDL LNLKGGMTSES |
| SEQ. ID. NO. 103. | ABP12522 | MSLNFWVYALFYKWATTSMVREAMMFHDCSVDDLKEGVSEKYVTLAQFKEITDQTYEETMKAN |
| SEQ. ID. NO. 104. | ABP12523 | MSELSEVPDMNLLEKEITEIKTEQKTLEQRVSVLERSSDRQDQQIMTLNEKLNKIEENTTWIKRTITGAIITAV STGIIGGAIAIMYSLLQH |
| SEQ. ID. NO. 105. | ABP12651 | MKLEQQEINILHSDSGPYGIAISPEGKVWFTQHKANKISCLDRTGQIQEYIVPTPDAGVMCLTVSSEGDIWF TENRANKIGKLTAKRQFIEYPLPHQHSAPYGITEGPDGDIWFTEMNGNRIGKLTSEGKIHEYELPNEGSYPS FITLGSDHSLWFTENQNNAIGKITESGELTEFPIPTPAAGPVGITKGHDDALWFVEIVGNKIGKITVSGDITEY DIPTPNARPHAIAAGVKSDLWFTEWGGIKSEG |
| SEQ. ID. NO. 106. | ABP12652 | MVYRMGGNKIGRLTSDQTIEEYTINTPHAEPHGIGCDNDGTVWFALECNKIGKLKLTK |
| SEQ. ID. NO. 107. | ABP12653 | MKVKEKRIVVNKFPSQPDEEDCRNLTLLGWGSGGFFLFLHTFR |
| SEQ. ID. NO. 108. | ABP13703 | MKQRKRIIQKDRRKLLKYFNAKFTAEERAMESLFCEKTSQSSSNVLLND |
| SEQ. ID. NO. 109. | ABP13704 | MKTKSEPKVILEPAKESDLPEFQKKLQEAFAIAVIETFGDCEDGPIPSDNDVQESFNAPGAVVYHILQDGKN VGGAVVRINSQTNHNSLDLFYVSPEYHSQGIGLSAWKAIEAQYPDTVLWETVTPYFEKRNINFYVNKCGFH IVEFYNEHHSDPHIRNGRVDDKPLPDNDDFFRFVKIMKKKD |
| SEQ. ID. NO. 110. | ABP13705 | MPLTLIWRNFEFSEKFLGTYADNVLKVLQEAQEELEDEFKIIVE |

Sequence Listing

| SEQ. ID No. | SEQ. Name | Amino acids sequence (one letter code) |
|---|---|---|
| SEQ. ID. NO. 111. | ABP13706 | MSLEEQLQSKEEELTKLVSTFAAKEGTNETSISGLEFIRSAKPLMPVHTMHEPALCIVLQGRKVISIIGEDFFY GKGEYLVVAVDLPVIGEILKASEREPYLCLRLNFNLMQIAEVSKEYQQHSTNHNAAGRGIFVDQTDGVILDA LIRLVKLLHTPEDTEILAPLIIKEILYRIMQGKHGHTVKSLVAKGSKLSEVAAALDYLRNHFSQEIKIDALAKKV NLSPSALYHHFKQVTMMTPIQYQRALRLHEARRLIFGKDMRVADAAFQVGYESPSYFNREYRKMFGKPP GKDRKENLNLYYV |
| SEQ. ID. NO. 112. | ABP13707 | MEKNNHSYGGLWVTKDRYIRHELLSNGRYVEARGNVECAYTGNYQITGDRIEYQDDAGFTADGDFINGIL YHAGMVLHRDRS |
| SEQ. ID. NO. 113. | ABP13708 | MSIKNKVVLVTGGSSGIGAATVDLLAENGATVIAAARRTDRLETLVTTLQQKGYHADYKQLDVTDFGQMQ QTVQEVTDAYGKIDVIVNNAGVMPLSKLDSLKIAEWNRMIDVNIRGVLHGIGAVLPVMKEQNSGHIVNIA SIGAYEVTPTAAVYCATKYAVRAITEGLRQEATHNIRTTLIAPGVTESELADHITDKQASEAMIEYRRQALPA SAIAHAILYAISQPIEIDVSELIVRPTLSL |
| SEQ. ID. NO. 114. | ABP13709 | MRRIDFGLTFLICTLIMLFNEIWKLLGNRPEAFKYGSIIYQVIAVFSSIITNVAIGVAGAISFYYIAQLIDKKKNRE LYTDLRKHLLFMFYNHLKLLTRLDQFREVNNRERRVADFYDIFDIPVFYDNFKKINSKEEVTRFKKNLYDYFA TQSEQQIKVFTEAFEKDIKKLKEKSNIRFFKESKDLIDTVCIIYDDDFSMISSIYLSNFEDTQNKSNYIEELVKDY YDFLNATVILYEELEEFLESMDKNRWVVFIKMLD |
| SEQ. ID. NO. 115. | ABP13710 | MENAQEIYELVKEMSKTVKEIDETTKRIENTTKRIAKGYELITEELAE |
| SEQ. ID. NO. 116. | ABP13711 | MTYRVGSMFAGIGGTCLGFIQAGAEIVWANEIDANACITYRNYFGDTYLQEGDITQIDKSTIPELDILIGGFP CQAFSIAGYRKGFEDDRGNVFFQILEVLEAQRNVYGRLPQAIMLENVKNLFTHDKGNTFRVIKEALEAYGY TVKAEVLNSMEYGNVPQNRERIYIVGFQDENQAEMFRFPEPIPLTNQLNDVVDRTRRYDERYYYDETSQY YEMLREAMVSTDTTYQLRRIYVRENRSNVCPTLTANMGTGGHNVPLVLDYENNIRKLTPEECLLLQGFPA DYHYPEGMANSHKYKQAGNSVTVPVIRRIATNIINVLNGETNANDEQEHQYAITQ |
| SEQ. ID. NO. 117. | ABP13712 | MIPFLGNRIQNAREARGLKPSQVADKVKVTRSTYSLYESENRTPSLETFIRIAETLNVSADYLLGLKEEMTSL NEEEN |
| SEQ. ID. NO. 118. | ABP13713 | MFFTNQPASNRTTYKQMLSSTGSLSNLFSESDSPYLVSRNVENAFCEALGAENLGRSDCSADASKDRVGIG IKTFLHGNGHTLQKVAEFNRDSDLYRGKSPKELINIVATLRNERIEFTKRTYGIDTMIYHCVTRKPGKILIFEEP MDLVQISSITNIKVSNNRNTITFEDGLHEYSFNVTKSTLYKRFITDEPIEEIDVEILENPYQELAKLFGFEIAPIQ VPEVSSPIENFEYVILPLFSDRGNKRHVPEKSGLNQWNAAGRPRNANEIYIPIPMWIHRKFPEFFPARDKPF QLRLPDKSLLSAKVCQDNSKALMSNPNSALGEWLLRQVMNLGERELLTYEMLERLSIDSVIVYKHSEQHYSI DFREIGSYDEFENENN |
| SEQ. ID. NO. 119. | ABP13714 | MTDTFSKEQRRKNMQAIKSRSKLEDKVTKELWNRGIRFRKNVKGLFGKPDIAIKKHKIVIFIDSCFWHACEK HGNKPKSNTEYWEKKLQRNKERDREVNKYYEEKGWNIKRIWEHELKEDFDETINRIIAFIEAVKHEQRK |
| SEQ. ID. NO. 120. | ABP13715 | MLKIKKLDFMPFFNRMICFVDVKNPDEADKKALAKDILENNKDQYQGYD |
| SEQ. ID. NO. 121. | ABP13716 | MKFIELDPALQIKVRQLEANAEEHQDKSHPDVRALWLELQKEDSICGALSEKDGSYKVCLRAPVEERNRCS LHGGKTLKGEQMTPAQKLNMMKNLRPRVVEHCWYAEESNFLASLTESEIKYMSFLEKSVKDQYHVNDGL EELLLEDILQSAIIHMRMVNRGVFEKGSRHTARPLQEVLKTIKELGWTCKEKGGKVQFVSVRNDFMASIFG NNTEEEEEDKKLN |
| SEQ. ID. NO. 122. | ABP13717 | MSLKEKLAELNKRAGKLEGSLKKASKKASSEADRLKKKRQEREYYDAYEKKFPIDKNF |
| SEQ. ID. NO. 123. | ABP13718 | MKKDWFSQRLELINKEQKLNEEFNLWKLQQITKRMKEVTKKLDELETERV |
| SEQ. ID. NO. 124. | ABP13719 | MGLFNKKSEMVKFEEELNVVQGSIREVEAELRDFDTSKKGIELELKLGADSSLTKRLKKVSEKVAETEKCLAE LRQREGEINAEKRTAYLNELADKDLASIDKGRRATVIKYELQALMRVVDERDGRWGYSKPENLLKEYGIEIG HIPAEHLRREEFDSFWKTRKNDAEKRIQNECQEAIETLKKYLGGFDK |
| SEQ. ID. NO. 125. | ABP13720 | MESKVNMLRILEFYMGETGNFKKLVVIQEIYRNNPSKMKGCELSFLKDNKFVAKGFFEAETIMVRNSFHSY NSELPELKEHHFKKMEKRDQDSHYPVSETTVLYLSGYVFAEFKFHKIANDKKIGDKVYLPIKLDDKQKPDSN EFCKLLVLEEYRDGTFELPELPKRAEMFTCWVRLELAPDSKNDSGVKVSEREFNKARMGEIKGNIA |
| SEQ. ID. NO. 126. | ABP13721 | MSEDVKKYFTTGEFSKLCRVKKQTLFHYDEIGLFSPEIKKENGYRYYSYHQFEIFQVISLFKELGVPLKEIKCLIK GKTPDKILHVLKEKSIEIDKKINELKQLQTILQTKVTLTEQALETDFSSISFEYLNEETFMLSRKTLNLPERKYVA AISELIHEVQQYELDEGYPIGGIFAREQILEKDFYNYSYFYIKVKDGAENINYHVRPKGLYAVGYEIGGKTEEA YRRIIEFIERNGMQIGENAYEEYMLDEMVVDGYENTYAKILLQVKEV |
| SEQ. ID. NO. 127. | ABP22957 | MREKKLGPVLLSGLIVGPILGSGIILLPPIIYGKTGDYAILAWFIMMIISFLFASLFGKLSVLFPNESGVAHTVEL AFGQHIKQLTSVFFIIAGSVGPVAVLMTASQYLKALFKSNGWSLETYGIILMMICLFVLLSNISSVGKVSFMF STVSTVVLLSGGISSIPFMRDKAFIKTPPHLDDPGYSILLLFWALVGWEIIGNYSLDVKNRKRTIPQAIVISSVVI TTVCIVVAAAYQWIDLHHTHTLTIILIPLLGTSFASPTMAFITTILCMSTYLLVTGGVSRLIASENKKITLISYRSK TNIPIGAISILTLVHAIVFILLFINIINVEQIVGMANAFFISNAICGILSAYKLLPGKFSKSLSLMLIISFLIILSFSSIWI LLMIALITTFYLIRHFIWIRQLKKSATNSQDKLRF |

Sequence Listing

| SEQ. ID No. | SEQ. Name | Amino acids sequence (one letter code) |
|---|---|---|
| SEQ. ID. NO. 128. | ABP22958 | MEIRHLKTFITIVEKGGFTKAAEYLGYAQSTITSHIKDIEQEIGGPLFNRFGKKMLLTEVGEYLLPYANEMIRIS EKVKQIQSNDEPMGNLVIGAPESLTVYRLPPIIHEFKKLFPKVKITLKSSTCWELKDDLRNGKVDLAFLLEYEQ EEADLYIEKLITEPMILVFPKQHKLQNTPFDDYFSSDEVILYTEHGCSYRTYFEEYMKHQGLVSENTFEFWS VEAIKQCVMCGLGISLLPLITVQKELKENKLSGLIMDETRIITQVAYHKKRWNSLAMAEFINIVKKHAELWK RTQTL |
| SEQ. ID. NO. 129. | ABP22959 | MNPLLLDVPLQLETERLILRAPHQTGDGKIVNQAIRDSFSELKAWLPFAQELPTVEETEINLRNAHINFLKRE SFRFLIFDKDSNDFIGITSLQRIDWNIPKCEIGYWVNTKYSGNGYMTEAVKKLANFGLHNIKFRRIEIRCDST NLKSRAIPEKLGFVFEGTLRNDDLSADGSKLTDTCFYSIVK |
| SEQ. ID. NO. 130. | ABP22960 | MVDQLWAYFLNLIEEAIETGKSETYFPDQPLLLKMKSISNDMLLFEIDQKQKVLLPKLDFFESLLKNAKSFFE TMNFVLEGNCDYEYELNKIDELQTKIKCM |
| SEQ. ID. NO. 131. | ABP22961 | MKVFEAKSLLSEAENRAKDYKELKNQMIKLRKAFKAVADLDDSEFSGKGANNIKAFYHDHVGVTDQWIDL IEMKIAFLTSISGVLEDASLSDAYIEESFLEHELTNAYKKSKSIMSEQKKAMKDILNDIDDILTLDLFSTETFKDE LSSAENKRKKTVDKIGDVDENLKTEYAITEPNEQFIKADFQKLQESTGKGKNATPLHYNAKAYRESDIHKKK GDIEKQSEAYLKIKKEEANKCEIKDLKKQLVKVTDPDEYLKIAKKIGYENLEPEQQVYFRQLEELQQKAEIGKG IAMGMYEAGKDTVMGLYQLARHPIESLSGTVNAALHPIDTYKIIAKDIEDTFQREMINGDSHSRAKWVSYV GSTVVLAIVGPKGIDKVSKVAKAGSKVAALKTLEVSKTGIKKGIEYVKIPSVFEQQFAMAGGSGTFPFNVLD GENYKNSALEIFKNSSTVQGLKKAKPHEVVNELKTFQSRKYTFGGQSFLIDKRGMKHILERHHPNLWDGSI KSQQSFLNKEMTVNDVADAIESIMKQNREELTKKGTKFSYQIRGSYEGQQYVVGFQKGRVGQFYPEK |
| SEQ. ID. NO. 132. | ABP22962 | MVQEVMVMKKDFGDSISNKVYEYRVLARLSQQELAKKVGVSKQTIFVMEKGNYVPTLLLAFRIAEFFKVD VNEIFTYEKGNDQK |
| SEQ. ID. NO. 133. | ABP22963 | MNNKKNIFDIVMYIIFGVLSLFLVAKTDYGTGVLVFVAILYLAVIAYKIKQVFSNSDS |
| SEQ. ID. NO. 134. | ABP22964 | MRKKRVITCVMAASLTLGSLLPAGYASAKEDSKTTPSYEELALHYKMKSEKISSNGKLVEIEYVSGNETHKV QMNGNNHTVKVDGIEQKGLNFEYDENVAKRTNYENNNLKSNEFTTQAAKPKKGYHYVGTLSGHTKAAK NALSVTMSLVGIVPGLGWGSKAATILFSYWAKEQIPDAYYKYDLYEKGAMTDSWYQYATVQFLKIKLIKRK WANLGQVLLQK |
| SEQ. ID. NO. 135. | ABP23145 | MKNFDKGTVVRTVLLLIALINQTMLMFGKSPLDITDVQVNQLADALYTAGSLIFTIGTTLAAWFKNNYVTA KGHKQKAILKQNNLTK |
| SEQ. ID. NO. 136. | ABP23146 | MTIAVKKNLVSEAKYALKCPNPMTAEYITIHNTYNDASAANEVSYMIGNTSSTSFHFAVDDKEVRQGIPTD RNAWHTGDGTNGPGNRKSIGVEICYSKSGGAKYYAAEKLAIKFVAQLLKERGWGIDRVRKHQDWSGKYC PHRILSEGRWNEVKAAIDAELKALGGKSSSKKTTSSKAVKKPSSSKKKSSFNLPSGIFKVKSPLMHSAAVEQI QTALAALHFYPDKKAKNFGIDSYYGPKTADAVRRFQLMNGLKADGIYGPATKAKLEALLK |
| SEQ. ID. NO. 137. | ABP23147 | MKRKQTFIFSMILLSVASIGLRSFWTNPFTTGVMIFVLALTIYAIIKDLRRR |
| SEQ. ID. NO. 138. | ABP23148 | MEYHLKSRQEVEDFIRHEVLTTKEAAELLGVNRQRVSQLISSGKLNPIKKLSGISLFLRTDLEEKKKELEAGRK KYRPYDE |
| SEQ. ID. NO. 139. | ABP23149 | MDEGTYNIDIVGFHGTSLESAQKIITEQNFTSGDIRNDHWLGQGAYFFREDPEQAKIWAKNKIKGSETAVI KTIVSLDNNSFLNLDTRSGLNYFNRYIKTEVKRKILEEKAEIELTTDDHSKIKHIYRCFFCNELPTNIKAIQRTFF VQSTLNEDETFKKMDVFVQGVQVCIRDLSVIDFTKTGINNVINMHTFRRRKKTKQKENYRKDVMKMRRE FNNPELIKDAENLGIKITLNSSEPGVFANVNGERYRINIDDLFSECDDDLYYHEDFKLDDFSITRDSNQHKVEI IKEEKNFYKNELVEAA |
| SEQ. ID. NO. 140. | ABP23150 | MKSFFQFDDYNIIDVNYKFNNNFEGDEAVLSPIFDFELEFEDETKDEADLILGIELGIRI |
| SEQ. ID. NO. 141. | ABP23151 | MTDFERKVYQIIVNMHLYGKNPTLDDLKRKTGKSKEDIRTAVKSLLMEGELKWDKQQKKWII |
| SEQ. ID. NO. 142. | ABP23223 | MTDSWQNGFIEKINRNGNNGGLRKPQYGALSAIRAHWTISSKPATIVLPTGTGKTETMLATILSEQIESVLII VPSNLLRDQTFEKAKSFGILPDLKMVGKNILYPNTVLYKTRIKDETEVWEWFSEANVIVSTVNAVNGLSTSIL NKLVEKVDVLMIDEAHHIAAGGWSSLREKFLNKRILQFTATPPRADGKKIDGDIIYNYSLSLAQKDGYFKPID FYPIEEFNEELGDIQIAEKAVELLNKDLEDKYMHQLLVRANSKKRAEELYNKIYSIYKKFNPVLIISGQSKKNKE NLKKLREGIAKIVVCVDMFGEGIDIPNLKIAAIHDKYKSLPITLQFIGRFARSKSGIGNARIVTNIANDDLKDAL QSLYSQDADWNQLLSMHSSDAIQTEISHRKFINQFYSNDNINIDISQIKMRISTRVFYLGGVHWNRKGWR SVLNVDKTEFFINEESSVMILIESIESQVDWSDQKIDSKYNYDVFIIYVDKKNKLIFINETNASKGNQLIKYMFS EANQISGERVFRVLDGINQLMIGTLGLKEQPSGRISFRMFAGTNIKDGINQVARASTTKSNLFATGYKDNN KISIGCSYKGKVWMRWVSVVFWRKWCQKIGSQILDSSINTDYILENSLQSEEITEYPRGIPYKIQMPVEFE LSNSELKAFYIPNEDKEIPFYLCEFNNPRLDGKQLLFELWINERKYTFSQTLKERGFVINRILGKDIKIKKSRNM ITVEEYLQDNLPQVTFFNEDGSLSIVEGNLVVNKKPLAEVLFPKEKLHIVDWKKLKVDITIESQGLTKLNNSIQ YASIKNIVPVDSLIIFDDDNSGEIADIVCISTNEEHRKITVQLYHCKYSHGTNPGARLLDLYEVCGQAERSITW NDSMVELLKRMRFRENKRINENKTSRFEKGNLSDLKTIENQIRSGFETEMKISIVQPGVSISNISQQMNQLL LATDTYLKETYGIDLNCYFSK |

Sequence Listing

| SEQ. ID No. | SEQ. Name | Amino acids sequence (one letter code) |
|---|---|---|
| SEQ. ID NO. 143. | ABP23238 | MSQAIPSSRVGVKINEWYKMIRQFSVPDAEILKAEVEQDIQQMEEDQDLLIYYSLMCFRHQLMLDYLEPG KTYGNRPTVTELLETIETPQKKLTGLLKYYSLFFRGMYEFDQKEYVEAIGYYREAEKELPFVSDDIEKAEFHFK VAEAYYHMKQTHVSMYHILQALDIYQNHPLYSIRTIQSLFVIAGNYDDFKHYDKALPHLEAALELAMDIQN DRFIAISLLNIANSYDRSGDDQMAVEHFQKAAKVSREKVPDLLPKVLFGLCWTLCKAGQTQKAFQFIEEGL DHITARSHKFYKELFLFLQAVYKETVDERKIHDLLSYFEKKNLHAYIEACARSAAAVFESSCHFEQAAAFYRKV LKAQEDILKGECLYAY |
| SEQ. ID NO. 144. | ABP23224 | MSKIPPEKYYEACITYHLVNYFEFTLEKKIYPFSISQIEEKKEGYDFGYKMSEKSFFIQYKRPYKVIPKDTYHWKI EIEQLKTINRKANNINTYYALPSFGDSMGWYEALDNTFFVNSRSLEYQIKQINRGRNIKTTFISPEKILLDKFY RISCNIVGDLHSVAVSQKNINSKIGNITNYIKGLNEDVKSSTWLYILEED |
| SEQ. ID NO. 145. | ABP23225 | MKYENVEVLGSYSVREGGSINFSMGKNLELGTEINTYIHELFHMHLTNYSSLGFLLLLFEKECNLSLEYQDEL HYNQIKELSTIIFNRTVDVQEVYANNQELLWLENNINSEFKEKSFKLKPKKYQEYCNKLNIITNDMRLNNEEK RYWIDRVCFYALNIQIFSDKFIEALSRQKLSEYLSRNHPNKRLDEALVKYSKNEKFDGVVEIRIQDILSKIKKIN IIKYFNEILSQLEPNATNFKIGDYLCENDIKKFIELNQKRMDERVKLFDFYNLDVIKVDDISNHLNFGIFAIKNY ESTINKENPYYITEALINLTPSYISEEVSYDFLNNPKIKVIGIPSQEFDIAKMKPNYIEVKDTPIVVLIDSYNTAKKI LKVLLNGELYVGDLYEQTVKNFSTILFFRERTEPKIIYIFPTLKKMSIRLVKELGIEDILVYSKDTRFKKILSIFNCE VEMLKFIKWIFSFIMKSSCIFTSIGDPATKMSFNLTRSLFDDVMKIKIPNYYIHWAALPTKKTIGEPFYSLMEF ENGENIGSFKATNQNTIIFFLNKNDAVNYRKKIFTTDSMAHKLEVVGIDRHYWNIIEKYILETGINICICTDVN NNIGKIMKLKEVDNIITQFSKV |
| SEQ. ID NO. 146. | ABP23226 | MKFKLTLCAVIALIGVSFISSSLGNEVNVASRNMTSKAANDSTNSLADKAIFDKEMTIAENGTLG |
| SEQ. ID NO. 147. | ABP23227 | MRSLGTISSPHVGMKINEWNRHIQKFNVTDAEMLKAEIERDIDIMEEDQDLLIYYQUAFRHQLMIDYVIPT EGNQMELSEYLKRIEGSNRKMEKLVEYYYYFFQGMYEFKEGNFLSAITFYQKAENTIPYISDEIERAEFYFKM AEVFYHMKQTHVSMHYSSQAYNIYKTHDLYSVRRIQCHFVIAGNYDDLESHEKALPHLEQALKGARLLESK NKRIYGQALFNIGNCYLKMGELTKAAKYMEKSIFQFKKSNFNNLTQAYHDLALIYFLQHKQEQAMDCFRK GVRFACKFDDDLFKIMFEGLQTLFIKKGEASILLNVFNKLETSQGYPYMEELALLAAKFYTEIGQMDDSVICF KKMVHARKQIQRGDCLYEI |
| SEQ. ID NO. 148. | ABP23228 | MTVREELIKRNPTPIMKNILKRYEEAKEFIQHSTKEQFEEDLSRVKNKLDTLTRAYLESANDYMNPMLREMY KTEKLLKEYDETASVVITAIQSSKVEIVLPSQNQI |
| SEQ. ID NO. 149. | ABP23229 | MDLFEECIEALKDPKEILSDELTEQYFETLNNKFPITSWARIDWDKVPQKESIETYDDLYNWLKFQGIVDTTI NLLWNPSDVPVVRTTLENALEVLDDVLAVGSDTFMYSDHGFVIEFFHDGEVTIGRSE |
| SEQ. ID NO. 150. | ABP23230 | MAQLFTAGLFLFQIGLAIMETEKGLLYKKSAEQFNNLLLLLNEIRLTYTLKF |
| SEQ. ID NO. 151. | ABP23231 | METEKMGQLYQQIAEQLNEMIPSEWTKIVLYAEILDDSSEVYFFFNTPQSEEYIYSHDIPKQFDVSKKIYVSL LIELQELFEELREEFKANNQDTWTNLTLKLENTGKFSIDYDYTDVIASDLNGTQRQVVWEYKNLGILPEDKE DKDFVINYFSL |
| SEQ. ID NO. 152. | ABP23232 | MVMKVFEAKTLLSEATDRAKEYKELRTQMVNLRKALKGVADLSDSEFSGKGASNIKAFYHDHVGVADQW IDYIDMKIAFFNSIAGAAEDKGLSDAYIEESFLEHELANANKKSKSIMSEQKKAMKDILNDIDDILPLDLFSTET FKDELADANDKRKKTLEKLDALDEDLKTEYALSEPNEQFIKSDFQKLQEATGKGKNATPIHYNAKAYRESDI HKKKGDIEKRTEAYLKIKKEEAKEREIEKLKERLKNYDYADADEFYEMAKTIGYENLTAEQQRYFTQIENTREL EAGFKGVAVGLYDSGKDAVVGLWDMVTDPGGTVEAITGAMAHPIKTYEAISAAIEESYQKDMVNGDTYS RARWVSYAVGTVVTSIVGTKGVGAVSKTGTAAKVTTKVKTAASKSATAQKAITVSKQTVDHIKQKVNTGIE VSKKHVKTKLNQIGDLTLADILPYHPRHDLVPAGVPYNAVNGVTLKEGLQKFAKVILPKPYGTSSSGRRTPA PHVPPVTVKYGEHFARWSRKKVLKPNIIYKTKEGYTYTTDNYGRITSVKADLQLGEAKRNQYAQTNAGKPQ DRKPDDDGGHLIATQFKGSGQFDNIVPMNSQINRSGGKWYEMEQEWAKALKEEPPKRVNVNIESIYKGD SLRPTKFIIEYTIGNKTKFVTIKNQAGG |
| SEQ. ID NO. 153. | ABP23233 | MDKDFLIIKIKDIQKGDTLTNRACGNWDMKLSRAKECKRAIVVRSGVILNVYKIVDAWESDEPAKITKTNN RVRFQLAECRDYSYLIGGTLKTKTQNPVSSLSLETLMELVK |
| SEQ. ID NO. 154. | ABP23234 | MYLYKVNNQNQIEDIREKPFKKEKEIQDLCEANLQQMLGLGFVKSEFRISNFRIDTLAFDAETKSFVIIEYKN TKNPFSVVDQGYAYLAAMLNHKADPILEYNENHDLPLKRDDVDWSQSKVIFISPVFTVYQKQSIHFKDLPIEL WEIKRYENDLIQLNQMKADGVSESIKTISRQSETIQEVSKEIKVFSEEDHLADKPFDIIELYQQLKEFIFNLDD HISIKPTKLYIAFTSSKRNFVDILLLKSGLKVWVNMKKGELHDPEEKMRDVSETGHWGNGDYEIFIKDDEHI EYIMGLIKQSYEKNK |
| SEQ. ID NO. 155. | ABP23235 | MKKRFILLGLFASVFMLAVYISFQNKNTHPVQSPVIHPEEDRIFFIYSNPFIKESTLLSTSTGERFNRRTFKVAD VPFIQTKSYKSTDIVLLAEHEPFYYTLKKDVIKEHPLSDPFAFWYEGKDVSVKAYNVDTTGNEIRINDKKMKK EYTLTLPSLVTMGASDENYIYIIQSMSIYVIDRKTEEMIETLSLASYADQFADSKEFIVASSEHELTVIEKETWK ATYIAYPEDLEYADTVYYDKESGSFYVTYEDKEGEANLLEYGKEFFIHIV |
| SEQ. ID NO. 156. | ABP23236 | MYIVAQEEHKQGIGGYVGVFDIHSKKMLYQFDLPEEQVKVQDFVVVD |

Sequence Listing

| SEQ. ID No. | SEQ. Name | Amino acids sequence (one letter code) |
|---|---|---|
| SEQ. ID. NO. 157. | ABP23237 | MGGLYLSDLCSMYQKDKFFTGFVPEELLTYAYELFPSSEKETVTALLNCSMGSKAKSFVMFTSKGLYWKRF GEQEGCVTWEAFTDIQSIKSTDDYEIWFDGVEVFDVGFSSYPADLLAELLRIIQQSLSENGLDLLTEPRIDHV SVSASELREISILFQNKHDKMFGLTNGLLVGNEISEKREVRLRKRLHIPKDQEMISFWSTFPVKQTDGITLTD KGIYFSDPFLRLFYPWHVFKETPVMLKDQELIVGKKNVIQLLENLMPAKDVFAFLEQVKRRISAVTSS |
| SEQ. ID. NO. 158. | ABP23502 | MFVLLLYPKQSLLIHYSSKAEKGRTLFILFLASTLNI |
| SEQ. ID. NO. 159. | ABP24563 | MFNGKHLKVKACFKSNAFLIIIKESVYIFISPLPDDAFRTP |
| SEQ. ID. NO. 160. | ABP24564 | MDQREKMDTAGGNTSCKHKKFFRKITIISTFGGLLFGYDTGVINGALPFMAQRDQLDLTPFTEGLITSSLLF GAAFGSLAGGRLADRIGRRKTILNLAFLFFIATIGCSFAPNTSVMIICRSLLGLAVGAASVTVPAFLAEMSPAE QRGKTITQNDLMIILGQLLAFTCNAVIGTSMGEYAHVWRFMLILATLPAIFLWFGMLIVPESPRWLASKGK VGEAFRVLKHVREENCAKAELTEIKASINRETEINRATLKDLSVPWIRRLVGLGIGIAVVQQITGVNSIMFYG TQILQKAGFARDAALVANIGNVGVISVIACTFGIWIVGKVGRRPLLLTGLAGTTASILLIAICSITLQGTPVLPFIV IGLTITFLAFQQSAVSVVTWLMISEIFPLRLRGLGMGISVFFLWMMNFLIGLTFPVLLDQLGMSSTFFVFVV LGASAILYVKKYLPETKGRTLEELENDFRSNQGVRKASSGKGEINM |
| SEQ. ID. NO. 161. | ABP24565 | MINGEKKVDRPIRWAMVGGGRGSQIGYIHRSAALRDHHFQLVAGAFDINPERGKDFGMNLHVTPERCYL DFQQMFEEEAKREDGIEAVSIATPNGTHYEICKAALNVGLHVVCEKPLCFTFEEAKELENLAKKKNRVVGIT YGYSGHQMIEQARQMIANGELGDIRIINMQFAHGFHSDPVEMNNPSTKWRVDPKFAGPSYVLGDLGTH PLFLSEIMIPELKINKLLCTRQSFVKSRAPLEDNAYTIMEYDNGAVGTVWSSCVNAGSMHGQKIRVIGSKAS IEWWDEQPNQLRFEIQGKPVQILERGMGYLYPEALQDDRIGGGHPEGLFEAWSNLYSRFAVAMEAADR GKELEHMWYPGIEAGVGGVRWVENCVRSADKGAVWVDYQ |
| SEQ. ID. NO. 162. | ABP24566 | MSIHIAGAPCCWGVDDPKNPYLPPWERVLQEASQAGYKGIELGPYGYIPMDIERVQAELLKNNLSIIAGTIF DDLVSESHLGNLLEQVDEICSLITKLPFSFQDKEERFRFSPPYLVLIDWGHDERDYKAGRPDQAKRLSKKEW NRMMSHIRTIAERAWKQYGVRAVIHPHAGGYIEFEDEIQQLLKDIPYDIAGLCLDTGHLYYSKMDPEQWL RDYADRVDYIHFKDIDEHVYQQVMGEHIRFFDACAKGVMCPIGQGIIDYEAIYKLLKDIHYHGYITIEQERD PRNSDTSLRDVSQSLAYLKNVGY |
| SEQ. ID. NO. 163. | ABP24567 | MEKEVFSKMKTTIYDVAEKAGVSISTVSKVINHQPVGMKSKQKVLDAMQELNYKPSVLASALTGKRTSTIG FLLPDIANPLIAEMARRVEDRAHEYGFNVVICSTDFKSEKAERERYVSLLRQKRVDGFILAGGFRNKQVIHELIS DNIPVILLSESQPYSSLTTVTVDNFLGGYELTAYLISLGHSRIAVIAEDNASSRERIRGYSQALQESDLDIHEDLI VVTDSTAESAQSLASSLLQSSNPPTAMICCNDILAIGALLAAREEHVLVPEELSITGFDNTLISKSSDPPLTTVE VPVQSMCSQAVDLLIDEIEGKASEKQKILVLPKLIVRKSTSRFH |
| SEQ. ID. NO. 164. | ABP24568 | MSLVKNGDSIKVVFVFQKNEQIEEVELNSAQLSALLHSKQV |
| SEQ. ID. NO. 165. | ABP24598 | MDINDASEHLIQLKQDLIDRSKIEMINKLKRWAFSFLKHLNFEIQTFNYGFV |
| SEQ. ID. NO. 166. | ABP24599 | MKKRLIGFLVLVPALIMSGIILIEANKKAPVEVLESAWDEFGLFSFQIGKTDPSITIGMDHTKSEAKLREYLEH NLSREAKEKYKIYIFKDDIDKLEKEHREYLKANNPNK |
| SEQ. ID. NO. 167. | ABP24600 | MRFTAGGNLSTMDSQVLDVIKKAYNLGMVNKDNMLLRNEAINAYRNSI |
| SEQ. ID. NO. 168. | ABP24601 | MLPEYRKKTPEEILEEIERLKRGRLKVYIGSAPGVGKTYRMLQEAHELKAEGLDVVIGLIETHNRKETEDLIGD LEIVPKKNIDYKGRLLEEMDTEAIIKRAPDLVLIDELAHTNVPFSQRNKRYMDVEEILKSGINVLSAVNIQHLE SLHDIVQQITGVQVRERIPDSFLHMAHEIILVDVTPEILRKRLSEGKIYHPSKIEQALNNFFTASNLGARELSL REVANDVDERVEKANEKNGKNKPSGINEKIMVCVQHGSNAERLIRRGWRIANRLKTELIILHVTNEVSMK RSTENRKKIQDWKRLAIQFNARFIIEQIKKRHIAKAITDVAKEHDVTQIILGQSARSRWEEIRKGSIVNMIMR YTTGVDIHIVSDQQPRRK |
| SEQ. ID. NO. 169. | ABP24602 | MLKIIRLALLMIICGILYPLLMTGLAQAIFPDQANGSILKNKDGQIVGSELIGQQFTKSNYFQGRISSIKYNAV GSGSNNYGPTNQEMLERTKSFIRVLEEGNPDLKTKELPIDLITNSGSGLDPDISVKAAKFQVNRVSNATGVS ESTLNKLIDNTIDGRSLGIFGEPRVNVLKLNMKVQEIISKGN |
| SEQ. ID. NO. 170. | ABP24603 | MNKSNENSEMIKEAITQSFIKLNPLSMMKNPVMFVVEGTFLVLLMLIMPSAFHSEEGYVYNLIVFLILLFTI LFANFAEALAEGRGKAQADSLKKTKKDTVARRINKNGTVTDISSADLKKGDIVLVETGDFIPGDGEIIEGLASI DESAITGESAPVIKEAGGDFSSVTGGTKVVSDSIKVRITADPGESFLDKMISLVEGAKRQKTPNEIALTILLVTL TIIFLLVVVTLLPIANYVGVHIELSTLIALLVCLIPTTIGALLSAIGIAGMDRVTQFNVLAMSGKAVEVAGDINTII LDKTGTITFGNRLAAEFIPVSSTTQEELMQAAVITSLFDETPEGRSVLELAKNNGASWEASAYESAEIIPFTAE ERMSGLIKDGHHYRKGAVDSIKAFVQEMGGPLPLDLQSKSEEVARQGGTPLAVSYNNRILGLIYLKDTVKP GMRERFDELRKMGIKTMCTGDNPLTASTIAKEAGVDDPIAEAKPEDKIRVIREEQEKGKLVAMTGDGTN DAPALAQADVGLAMNSGTIAAKEAANMVDLDSDPTKIIEVVAIGKQLLMTRGSLTTFSIANDIAKYFAIIPA MFTVAIPGMQVLNIMRLHSPTTAILSALIFNAIIIPLLIPLAMKGVKVPMSASKLLSRNILIYGLGGIVVPFIGI KLIDILVSVFMS |

-continued

Sequence Listing

| SEQ. ID. No. | SEQ. Name | Amino acids sequence (one letter code) |
|---|---|---|
| SEQ. ID. NO. 171. | ABP24604 | MKGHTRLLIPMSIILTIILVSLKVPQTLSPSIEVTTLEGVKQVISIGPVASLESIKHLGTNGGGFFGANSAHPFE NPSPLTNVIEILSMWCIPASLTYTYGRFAKKQKQGWVIFGAMFILFIAFLSLIYVSESHGNPALTALGLDPSQ GSMEGKEVRFGIAQSALFSSVTTAATTGTVNNMHDTLTPLGQITPLSLMMLNTVFGGDGVGLVNMLMY AIIGVFICGLMVGRTPEFLGRKIEPKEMKLITVALLAHPLIILAPTALAFLADIGKGSISNPGFHGVSQVLYEFA SSAANNGSGFEGLADNTPFWNISTGLVMLVGRYISIIALLAVAGSLVQKQPVPETIGTFKTDNLLFIGILVGV VLIVGALTFFPVIALGPIAEYLSIR |
| SEQ. ID. NO. 172. | ABP24605 | MGILQIIVVIMLMLFMIKPLGTYIYHVFSNEPNKTDKIFNPIEKIIYKICGMKNRLSMTWKQYAGSLLLTNMV FIAVGYVILRFQYILPLNPNGENMNSMLSFNTIISFMTNTNLQHYSGETGLSYFSQMAVIMMMMFTSAA TGIAAAIAFIRGITSKGKTIGNFLKIL |
| SEQ. ID. NO. 173. | ABP24606 | MNNNLGGITLDDVCMLAVIAVIFAVFWAFVKWCDFTIGGGEKQ |
| SEQ. ID. NO. 174. | ABP20078 | MPKQQTAELKPFFHNKTVLVTGGTGSIGSQIVKRLLMLTPKQVIVFSKDDSKQYVMSQKYAEDKRLLFVLG DVRDHRRVNQVMKGVDIVFHAAALKQVPTCEDHPFEAIQTNLIGGQNVVEAALSHRVQHVINISTDKAV FKDTDYKLIKKKGLF |
| SEQ. ID. NO. 175. | ABP20079 | MPYEEYEELKKKTIKVIQRKNYSIRIIDQKFENDNLDQLYKEVARLLFERALKSSE |
| SEQ. ID. NO. 176. | ABP20080 | MGANNQGKVFEANIEKSAADQKLFFYRIKDVNPMFLKRGAAVSKNKYDCFLHFNGYLFPFELKSTKDKSIA FREKIIKPQQIKYLKEATQYPNIIPGFLFQREPENKVYFVHIDEFLKYKNIAEKQLKHTYKNKVNKASIPIAICE EIGTEVRWMKKKVNYTYYLNKLCVELIKKEQSRDKPLHTYNTPVKTGVR |
| SEQ. ID. NO. 177. | ABP20081 | MYVLKSLLKEVYIVKKQWKPVDSRLNELMHEYSVSIEDLVERTGLPKQRINDYVSGFKSNMNIGTAMTFAD AIGCSIEELYVWNFKERRQLIK |
| SEQ. ID. NO. 178. | ABP20082 | MKTVKEAIDEKDLQRAHRNLINLADNNEELMQEIRWIKKGTTL |
| SEQ. ID. NO. 179. | ABP20083 | MNLKNIDENRYKKTYSVQPNDIFFVVRKNGNQTPYLIYKDKNKMLKLINLQSGASNYCADTIDSLVGIYIKE NQESPANKVNPIKEYFFAKSHETSIRVHNTFNYNPIK |
| SEQ. ID. NO. 180. | ABP20084 | MKTIKLYELVSEGKKPIIKFNDNVYEWIEESVDTMMMGKIIGASIEYEDSVRFLIDLNPFEAYNRSVARHDW RDDEGNCVLTWFDTSFYPKNGIEAIYLPINGRTEIAFDFTEEDSLLNEYAKVPQEISYVEWLENEVKQLISK |
| SEQ. ID. NO. 181. | ABP20085 | MIVTAWILLIMFGLFALSDLNLTEDETKHIKFFMLMKFFSVFIAAIAAGVI |
| SEQ. ID. NO. 182. | ABP20086 | MKNTEFKKTSFLEEYKRGDEMRRDFIIHEGYTAIEEIIKEVNQRGSLNEADIYYGTPKPQLSFSDVELGYMLT SMMEYATNHVGNPVDEECEFENKLAYFEYKDEIVQIFEVYGQGTESWFSKPSDDTIDKLNNTAYGVYLIQF DDFINYTKNKDSESEKLSPSSTILNDITGGYTVGRGSK |
| SEQ. ID. NO. 183. | ABP20087 | MLELDEYILKSEMDFADPEEIRSCIISFVSSLQQYIDLCKEELNEEYRV |
| SEQ. ID. NO. 184. | ABP20088 | MVELAKEENMLFFDHYPTEYGGWQTGNRDVWGIWGQRYLLKKVSDGCCEYVSR |
| SEQ. ID. NO. 185. | ABP20089 | MYGEDVEVTLDGNIKVKVFVFCLPTTCKEEKEKRALLTLKNLIDKRLKNEDLKYLDVQSDFVLIPKMIENGEF |
| SEQ. ID. NO. 186. | ABP20090 | MRVSSEALKIVIVQHLERDNDLMSEGKIIVLPCRDEKTAKEFEDFYRKKFPSTQLMSIEIVDSNIYG |
| SEQ. ID. NO. 187. | ABP20091 | METKKYVRIIRNASKYGDMTGQIFPLFGTWEDSYKIDGSDGVVYVRKKDVEVIVTENRRPKVDERVLITEVL LSSGHYKIGDIYTVLSVVDIYGTITVKEHSNCVISREYEVIVDEVKKEEADGMENVNQTVINNANTVFEKKDD KYFGYKSRFGDIVIGGAYSYRFVVQYAKTNQDVVVIPGDENTVTTPVCTTLEERLWQPEKAVKSSPRNLHY |
| SEQ. ID. NO. 188. | ABP20092 | MEVGDKIHNTNEQITALEKKKYQIETTLLEKQRDLLKLETQQNKEKLELLFELSEVLTQLQDEEWVSCMIALR IIRRNKRKYLNLFELVNEKAYINKDKFKVLHDEFFDLKQQLNEI |
| SEQ. ID. NO. 189. | ABP20093 | MIYKTFLPYADKVYLTIVDSAQREADSYFPMLDDRWKLTDKRHNKADEKNKYNYSFITFENNYRQK |
| SEQ. ID. NO. 190. | ABP20094 | MTQFDKQYNSIIKDIINNGISNEEFDVRTKWDSDGTPAHTLSVMSKQMRFDNSEVPILTTKKVAWKTAIKE LLWIWQLKSNDVNDLNKMGVHIWDQWKQEDGTIGHAYGFQLKGKKNRNLNGEKVDQVDYLLHQLKNN PSSRRHITMLWNPDELDAMALTPCVYETQWYVKHGKLHLEVRARSNDMALGNPFNVFQYNVLQRMIA QVTGYELGEYIFNIGDCHVYTRHIDNLKIQMEREQFEAPELWINPEVKDFYDFTIDDFKLINYKHGDKLFFEV AV |
| SEQ. ID. NO. 191. | ABP20095 | MFKVLDVLDGEKTKQNTYIYWLFVCGNFLFVVFYLADVFL |

| Sequence Listing | | |
|---|---|---|
| SEQ. ID. No. | SEQ. Name | Amino acids sequence (one letter code) |
| SEQ. ID. NO. 192. | ABP20096 | MLKDKNKITKSIEKINKLEEGLALFEEGDEEYLSVLVKIQGLYDEIADTALECFKEMTTKIRKTGQKRIGKGIDQ LPYTIKENIADQVNELKGSFLDESKY |
| SEQ. ID. NO. 193. | ABP20119 | MDSYPESLKKETEEIKERVRNGNIKEDRIKEIAETTVEFLKSEEKRHKYFSEVAAAMADNLSEFFKSYLKGE |
| SEQ. ID. NO. 194. | ABP20120 | MKKLRVMSLFSGIGAFEAALRNIGVEYELVGFSEIDKYAIKSYCAIHNVDEQLNYGDVSKIDKKKLPEFDLLV GGSPCQSFSVAGYRKGFEDTRGTLFFQYIDTLKEKQPRYFVFENVKGLINHDKGNTLNIMAESFSEVGYRID LELLNSKFFNVPQNRERIYIIGVREDLIENDEWVVEKGRNDVLSKGKKRLKELNIKSFNFKWSAQDIVGRRLR EILEEYVDEKYYLSEEKTSKLIEQIEKPKEKDVVFVGGINVGKRWLNNGKTYSRNFKQGNRVYDSNGIATTLT SQSVGGLGGQTSLYKVEDPIMIGHIDLKGHDAIKRVYSPDGVSPTLTTMGGGHREPKIAVEYVGNINPSGK GMNDQVYNSNGLSPTLTTNKGEGVKISVPNPEIRPVLTPEREEKRQNGRRFKEDDEPAFTVNTIDRHGVAI GEYPKYRIRKLTPLECWRLQAFDEEDFEKALSVGISNSQLYKQAGNSITVTVLESIFKELIHTYVNEESE |
| SEQ. ID. NO. 195. | ABP20121 | MDINGKDLNKIHNIDCVQFMRENMGDCSIDLTVTSPPYDDLRKYNGYSFNFEATARELYRVTKDGGVVV WVIGDKTHNGSESGTSFKQALYFKEIGFNLHDTMIYEKDSISFPDKNRYYQIFEYMFVFSKGKPKTINLISDR KNKWYNGKKHIKGHYRKMDGEKVRHNKQNLLKEFGVRFNIWRIPNGHQKSTLDKVAFEHPAIFPERLAE DHILSWSNEGDIVLDPFMGSGTTAKMAALNNRKYIGTEISKEYCDIANERLRNYIGTI |
| SEQ. ID. NO. 196. | ABP20122 | MKKVIAIDMDQVLADLLSDWVAYINTHDDPFLKEEEILCWDIKKYTNTNNNVYRHLDYDLFRNLDVIEGSQ RVVKELMKKYEVYVVTTATNHPESLKAKLEWLTEHFSFIPHSNVVLCGNKSIIKADIMIDDGIHNLESFEGM KILFDAPHNRNDNRFIRVMNWEEIERKLL |
| SEQ. ID. NO. 197. | ABP20123 | MALIILEGPDCCFKSTVAAKLSKAMKYPIIKGSSFELATSGNQKLFEHFNRLADEDSVIIDRFVYSNLVYAKKF KDYSILTEQQLRIIEDKIKLKAKVVYLHADPSVIKERLSIRGDEYIEGKDIDSILELYREVMSNAGLHTYSWDTG QWSSDEIAKDTIFLVE |
| SEQ. ID. NO. 198. | ABP20226 | MGYKLMAYGGYFLFCLFFLLMDGWRGMGICLIIAGLALLALEPYKIKAQKNIDKLKENAETLKHYESGFNPD NFFNTYKTKIAFKESDSLVKIYQLNRNEHIEEYTIPFSNIIESEITLDNQIISKVSKSGIVAGGLLAGGIGAALGGL SASSIQNEMVKSVTLKITVEDLGKPIHYIDFLPTQEVEGYNTQGYKKDSNIIQQALKNAEYWHGVMDVIIKK ASKVAQ |
| SEQ. ID. NO. 199. | ABP20227 | MSQNLKIILTPQADTSSKTVEQLNQQIKSLEKKLNSLKLNTNIDSTTLKALQEFSSAVDAYQKNLKSYNQTVR ETSTVIKNADGSVEKLTQQYKKNGEILQRETKIINNRNTALKQETQEVNKLTQATEKLGQVQKKTVQRNLQ GQPTKIVQKNRQGFDDIVYTTDPKTNSTSSKTTTNYDQQRRAIEQLKQDLEKLRQQGIVTDTTISSLGRKIN TAQSAQQIEALQNRIRMLDDKSAAVAKNNELKKTIELYQRQAQVNVQNLNTRYGSSMGSSNRQAVQDY LNAVNSLNVSTGSNNIRSQIQSLNMQFRELASSAQAANQASSFGAELTQTFKSMSTYLISGSLFYGAISGL KEMVSQAVEIDTLMTNIRRVMNNEPDYKYNELLQESIDLGDTLSNKITDILQMTGDFGRMGFDESELSTLTK TAQVLQNVSDLTPDDTVNTLTAAMLNFNIAANDSISIADKLNEVDNNYAVTTLDLANSIRKAGSTASTFGV ELNDLIGYTTAIASTTRESGNIVGNSLKTIFARIGNNQSSIKALDEIGISVKTASGEAKSASDLISEVAGKWDTL TDAQKQNTSIGVAGIYQLSRFNAMMNNFSIAQNAAKTAANSTGSAWSEQQKYADSLQARVNKLQNNFT EFAIAASDAFISDGLIEFTQAAGSLLNASTGVIKSVGFLPPLLAAVSTATLLLSKNTRTLATTLILGTRAMGQET LATAGLEAGMTRAAVASRVLKTALRGLLVSTLVGGAFAALGWALESLISSFAEAKKAKDDFEQSQQTNVEA ITTNKDSTDKLIQQYKELQKVKESRSLTSDEEQEYLQVTQQLAQTFPSLVKGYDSQGNAILKTNKELEKAIEN TKEYLALKKQETRDSAKKTFEDASKEIKKSKDELKQYKQIADYNDKGRPKWDLIADDDDYKVAADKAKQS MLKAQSDIESGNAKVKDSVLSIANAYSSIDISNTLKASISDVVNKLNLKDNLDPEELEKFSSSLGKLQEKMQK ALDSGDEKAFDNAKKDIQSLLETYSKSDSSIDVFKMSFDKAQKNIKDGDKSLSSVKSEVGDLGETLAEAGNE AEDFGKKLKEALDANSVDDIKAAIKEMSDAMQFDSVQDALNGDIFNNTKDQVAPLNDLLEKMAEGKSISA NEANTLIQKDKELAKAISIENGVVKINRDEVIKQRKVKLDAYNDMVTYSNKLMKTEVNNAIKTLNADTLRID SLRKLRKERKLDMSEAELSDLEVKSINNVADAKKELKKLEEKMLQPGGYSNSQIEAMQSVKSALESYISASEE AASTQEMNKQALVEAGTSLENWTDQQEKANEETKTSMYVVDKYKEALEKVNAEIDKYNKQVNDYPKYS QKYRDAIKKEIKALQQKKKLMQEQAKLLKDQIKSGNIAQYGIVTTTSSPGGTSTSTGGSYSGKYSSYINSAAS KYNVDPALIAAVIQQESGFNAKARSGVGAMGLMQLMPATAKSLGVNNAYDPYQNVMGGTKYLAQQLE KFGGNVEKALAAYNAGPGNVIKYGGIPPFKETQNYVKKIMANYSKSLSSATSSIASYTTNNSAFRVSSKYGQ QESGLRSSPHKGTDFAAKAGTAIKSLQSGKVQIAGYSKTAGNWVVIKQDDGTVAKYMHMLNTPSVKTGQ SVKAGQTIGKVGSTGNSTGNHLHLQIEQNGKTIDPEKYMQGIGTSISDASQAEAERQQGIAQAKSDLLSLQ GDIDSVNDQIQELQYELVQSKLDEFDKRIGFDDIRIAKDESMANRYTSDSKEFRKYTSDQKKAVAEQAKIQQ QKVNWIQKEIKTNKALNSAQRAQLQEELKQAKLDLISVQDQVRELQKQLVQSKVDETLKSIEKSSSKTQGKI KDVDNKISMTEEDEDKVKYYSKQIKLIQQQQKEAKKYIKQLEEQKKAAKGFPDIQEQITEEIENWKDKQKDF NLELYNTKKSIKDIYKSLADEVVSIYKEMYEKMRDIELEAHQKATQDKIDEIDKEDEEAKYQKELKEKNQAIQ ETKDKISKLSMDDSSEAKSQVKDLEKQLQEQQEALDEYIKDRSNTKRKEALQDQLDKDEESINNKYDDLVN DERAFKKLEDKLMDGKITDIAKQLNEFTKFINENMKSIGKSISNNLIDKLKDAASALNTVTTGNTTGKKVSSF ASGGYTGTGLGAGKLAFLHDKELILNKTDTENMLEAVKQVRQTSTDNSVKTTSKWGQPGKISDVLSKSISL VTPAMNAAVASQTSLTKGLIPTLKNFSTPTVTPSTPQGNTSNNQNSFTINVTEASNAKETASLVYKQLANG LKNTGLNFNIT |
| SEQ. ID. NO. 200. | ABP20228 | MIRQSQYFLFDNEKSIDYGVENVNTESGLVEESFLGSRSVNETYVKGRSEPYTEGVKREAKQFPLNFYVGEN YDEKKIRAIKRWLDVDDYKPLAFSENLDIVYYAMPVDTSDLVHNAARHGYVRLTMKCNSPYAYSRNTSTHS FDISSGMKTIELHNKGDVAIYPTVEILKIGDGDVKIENLSDYTDPFIFSNLKDREIVKVNGDKEIIESSLYGNERY DDFNDNYIRLDYGKNRLKVTGKCKLRLTFRFKYR |
| SEQ. ID. NO. 201. | ABP20229 | MITIRKDTEIKNIRLSLAKPDKTKIANIDEVLNPTVTLNHGSSVHELSFSIPLKATYDGVIKRNHVVDLLKPWYL IKTEFYGLAIWFIITKRTKSFSSEMDTVQVECRSLQHELSRISVLKYEETSKNLQEVVTDCLKNTSWTVGYIDT LFNVKRRQFDVSSTNKLDFLYSICEKFDAVPVFDTVKETVSFYKESDISKYKGLKLNPRQYMISMDDSDDAD |

-continued

Sequence Listing

| SEQ. ID No. | SEQ. Name | Amino acids sequence (one letter code) |
|---|---|---|
| | | ELVTRLYATGKDGISINSVNPTGQSYIDDFSYFLFPFQRDEQRNVISHSAYMPDELCHAILDYNDLVNSEGN AFNKLLTQKNEAETGLTELNNELYTLDLEVQKLLDRIEVAKKAGDDTSQLKAQLAVKQKAVALKKNQIATIE STISQISASISKLKEKLSFENNFSENQQKLLSRFISTTEWSNDSIYDENELYDDANEELESRNTPPVNVTLDIVN FFNCISEKHNWDRFSLGDIVRVQQSDLNTDIKAILSAITIDFEQSNISVTVTNGKRVQSDFEKVIKTVYRTNKI STELNKRKIEWDKVTENFNIRNDRISVQPAPPVIASDGTAITHKVNDNGSVDITIQWNYVDSNEDKYNIDG FEVYLHGSDDNEEYTFGSVQASENLQNVKYDRRTATFTGLPSNMYYTIGVQAYRRVDADIDINQILLSDIVK SNHPSENPYLPTPSIEVKGSLSGKVNGLYTISTESKPEEPETGTIWIDPKTNKQELFNGEEWIVSSAGSADSL NGFTASLTTSPNSIPVRDQSGVISGSIDGNAEMLGGRAASDYALTENIPVPPKFAKGVYTGDGTLSKQIPLA FTPDLVKITPISPEDSQLVIESQLGGYAYQVTSTGLSLIGGDLSYGALGNNLFITGSDSNCRGNKLNVKYIWE AYQQN |
| SEQ. ID NO. 202. | ABP20230 | MGSLPTKLTEVIKLADFAELYNDPILSKKRIGSVEDPYLTYSETLTVYNGRALLTEIPNREFRVEVIGDKKEWR EIEDGELEDNYFKVDYLMGVVFFNASNEGKSLTFNYSGEGASFFPASRIWIKRQGNMVIETLQGLIDDAED TIIRMNERIAECERVTKRCIEITNWCRQATSDYEYVVENTRKIYLPMVYTYQDLMDTYPNPQIGWVVTIRDT GIEYRWDGFDWINISISDQFDGYNVVSSYIEPYNIRTVWLRTNSPPSKKRVKPSKDAPDGSMVWIRKG |
| SEQ. ID NO. 203. | ABP20231 | MSDNLIPVNTMGYYDEETKQWVPIDAVALKSENYRFTADDISQKFNKIGDIDAIKATGNTLSEKIINEFNYR GINISWLGAKGDGTTDDSSVFSSIESTYQDKVFDLAGKTYVVNSFPNKNKYLNGYFIIDGNKYFSGYVSSFQ TGNSNIIIGNNAAKNFRPGDQYKGIAGHNIIAIGENALSNASEYTKNTTAIGAGALFNNKYGVYNLAIGLQS QYYVTGVQGDAFKGTRNTSVGDNSMRFNKDGYSNVAMGRNALQTNEKSLWNTALGAAAMSGYAPLN LDSKTIINNSPQTAGYQVAVGTNSLYWSNGIGNVGVGVNAGREIKNSQRNVAMGYYAMSQLDSDVSFE GKQRFFPSIQAGYTWIGQDITLTHIGHTFIVGQNLSLALDGGEKFSTTVKSITVDTFTVSTTQIAQNEISGMA QVSEYYTTTGTYVWKDNNIQVSMGNHPFQNGYKVLMSVGGREAIYFTVANSTSSGFTVSTDIIGDESGAV KITEYSDTTPMAVNYDNTAIGVKAAWKMKKGSFNTAIGGLSLENNKGDYNTALGYMALKNNTTGNQNT ALGYGALRFTTGGDEMKDISNSTGVGFNSRVSGSNQIQLGDGNSTPYSFNALQNRSDLRDKADI RDTVLG LDFINKVRPVDYKWDIRDEYVEIKEDGTVITHERDGSKKKNRYHHGVIAQEIQKVIEAEGIDFGGFQHHELS GGEDVMSIGYTEFIAPLIKAVQELSAKVEEQAKEIAALKKA |
| SEQ. ID NO. 204. | ABP20232 | MTIQARQMLVSPGKYPIKGRYAMTAEYITFHNTANDASANNEISYMRNNNETVSYHFAVDDKEVVQGLP TNRSAFHCGDGEYGTGNRKSIGVEVCYSKSGGERYRKAEEALAIKFIAQLLKERGWGVERVKKHQEWSGKY CPHRVLDEGRWNEVKAAIAAELKSLGGKSTTPTKTSTKPTTSSPSSSSAASGSLKSKVDGLRFYSKPSWEDK NVVGTVNKGIGFPTVVEKVKVGSAYQYKVKNSKGATYYITASDKYVDTGSVKASSPTPKTTSTSSSSSSIKS VGKIKIVGVSSAAIVMDKPDRNSSKNIGTVKLGSTVSISGSVKGKNNSKGYWEVIYNGKRGYISGQFGSKI |
| SEQ. ID NO. 205. | ABP20233 | MTKINWKVRLKKKTFLVAIFSATLLFVQAIASAFGYDLTVFGDNLTEKFNALLTFLTAMGIIVDPTTQGISDSE QAMDYDSPR |
| SEQ. ID NO. 206. | ABP20234 | MLEQMISSSKVGVKINEWYKYIRLFSVPDSEILKAEVEEEIRHMKEDQDLFLYYSLMCFRHQLMLDYLEPKT LNEERPKVSDLLEKIESSQTDLKGILEYYFNFFRGMYEFEQYEYLNAISFYKQAERKLSLVADEIERAEFHYKVA EIYYHMKQTHMSMHHIVQAIDSYKAHENYTVRVIQCSFVIGLNYLDMDYPEKAIPHFKDALDKAREIDMS RLIGSSLYNLGLCSFAEEAYEKASEYFKEGIRVYQDNGYEHSNRILDILLMLTKTTFKMRNHSEGISWCAHGL SLSKNLNDEIMAKMFEFIHALYVDNDNEKLNSILNYLELKSMLSDVEDLASDAAKYYNEKEDHKVAVAYYEK VLYARKQIQRGDCLYET |
| SEQ. ID NO. 207. | ABP20235 | MKLKHASVFILAIVLIGFVSTYLTNTQKDVQEARRGHTASIGFTDGHSYEIASRGHTS |

The term "comprising" whenever used in this document is intended to indicate the presence of stated features, integers, steps, components, but not to preclude the presence or addition of one or more other features, integers, steps, components or groups thereof.

The disclosure should not be seen in any way restricted to the embodiments described and a person with ordinary skill in the art will foresee many possibilities to modifications thereof.

The above described embodiments are combinable.

The following claims further set out particular embodiments of the disclosure.

REFERENCES

1. Fetissov S O. Role of the gut microbiota in host appetite control: bacterial growth to animal feeding behaviour. Nat Rev Endocrinol. 2016. doi: 10.1038/nrendo.2016.150. PubMed PMID: 27616451.
2. Baumler A J, Sperandio V. Interactions between the microbiota and pathogenic bacteria in the gut. Nature. 2016; 535. doi: 10.1038/nature18849.
3. Ganguly S, Prasad, A. Microflora in fish digestive tract plays significant role in digestion and metabolism. Reviews in Fish Biology and Fisheries. 2012; 22:11-6.
4. Ray A K, Ghosh, K., Ringo, E. Enzyme-producing bacteria isolated from fish gut: a review. Aquaculture Nutrition. 2012; 18:465-92. doi: 10.1111/j.1365-2095.2012.00943.x.
5. FAO. The state of world fisheries and aquaculture: Opportunities and challenges. Food and agriculture Organization of the United Nations. Rome, Italy. 2014. 243 p.
6. Krogdahl A, Penn, M., Thorsen, J., Refstie, S., Bakke, A. M. Important antinutrients in plant feedstuffs for aquaculture: an update on recent findings regarding responses in salmonids. Aquaculture Research. 2010; 41:333-44.
7. Sinha A K, Kumar, V., Makkar, H. P. S., De Boeck, G., Becker, K. Non-starch polysaccharides and their role in fish nutrition—A review. Food Chemistry. 2011; 127: 1409-26.
8. Joint FAO/WHO Working Group Report on Guidelines for the Evaluation of Probiotics in Food, (2002).

9. Setlow P. Spore Resistance Properties. Microbiol Spectr. 2014; 2(5). doi: 10.1128/microbiolspec.TBS-0003-2012. PubMed PM ID: 26104355.
10. Tam N K, Uyen N Q, Hong H A, Duc le H, Hoa T T, Serra C R, et al. The intestinal life cycle of *Bacillus subtilis* and close relatives. J Bacteriol. 2006; 188(7): 2692-700. doi: 10.1128/JB.188.7.2692-2700.2006. PubMed PMID: 16547057; PubMed Central PMCID: PMCPMC1428398.
11. EFSA-BIOHAZ. Scientific Opinion on the update of the list of QPS-recommended biological agents intentionally added to food and feed as notified to EFSA, European Food Safety Authority Panel on Biological Hazards (EFSA-BIOHAZ). EFSA Journal 2017; 15(3):4664. doi: 10.2903/j.efsa.2017.4664
12. Cutting S M. *Bacillus* probiotics. Food Microbiol. 2011; 28(2):214-20. doi: 10.1016/j.fm.2010.03.007. PubMed PM ID: 21315976.
13. Bader J, Albin A, Stahl U. Spore-forming bacteria and their utilisation as probiotics. Benef Microbes. 2012; 3(1):67-75. doi: 10.3920/BM2011.0039. PubMed PMID: 22348911.
14. Kunst F, Ogasawara N, Moszer I, Albertini A M, Alloni G, Azevedo V, et al. The complete genome sequence of the gram-positive bacterium *Bacillus subtilis*. Nature. 1997; 390(6657):249-56. doi: 10.1038/36786. PubMed PMID: 9384377.
15. Harwood C R, Cutting S M. Chemically defined growth media and supplements. In: Harwood C R, Cutting S M, editors. Molecular biological methods for *Bacillus*. Chichester, UK: John Wiley & Sons Ltd; 1990. p. 548.
16. EFSA-FEEDAP. Guidance on the assessment of bacterial susceptibility to antimicrobials of human and veterinary importance, European Food Safety Authority Panel on Additives and Products or Substances used in Animal Feed (EFSA-FEEDAP). EFSA Journal. 2012; 10(6):2740.
17. Serra C R, Earl A M, Barbosa T M, Kolter R, Henriques A O. Sporulation during growth in a gut isolate of *Bacillus subtilis*. J Bacteriol. 2014; 196(23):4184-96. doi: 10.1128/J6.01993-14. PubMed PMID: 25225273; PubMed Central PMCID: PMCPMC4248874.
18. Casula G, Cutting S M. *Bacillus* probiotics: spore germination in the gastrointestinal tract. Appl Environ Microbiol. 2002; 68(5):2344-52. PubMed PMID: 11976107; PubMed Central PMCID: PMCPMC127533.
19. Xue Z, Zhang W, Wang L, Hou R, Zhang M, Fei L, et al. The bamboo-eating giant panda harbors a carnivore-like gut microbiota, with excessive seasonal variations. MBio. 2015; 6(3):e00022-15. doi: 10.1128/mBio.00022-15. PubMed PMID: 25991678; PubMed Central PMCID: PMCPMC4442137.
20. Zhou Z, Zhou X, Li I, Zhong Z, Li W, Liu X, et al. Transcriptional regulation and adaptation to a high-fiber environment in *Bacillus subtilis* HH2 isolated from feces of the giant panda. PLoS One. 2015; 10(2):e0116935. doi: 10.1371/journal.pone.0116935. PubMed PMID: 25658435; PubMed Central PMCID: PMCPMC4319723.
21. EFSA-FEEDAP. Guidance for the preparation of dossiers for technological additives, European Food Safety Authority Panel on Additives and Products or Substances used in Animal Feed (EFSA-FEEDAP). EFSA Journal. 2012; 10(1).
22. EFSA-FEEDAP. Guidance on the assessment of the toxigenic potential of *Bacillus* species used in animal nutrition, European Food Safety Authority Panel on Additives and Products or Substances used in Animal Feed (EFSA-FEEDAP). EFSA Journal 2014; 12(5).
23. Cabello F C, Godfrey H P, Buschmann A H, Dolz H J. Aquaculture as yet another environmental gateway to the development and globalisation of antimicrobial resistance. Lancet Infect Dis. 2016. doi: 10.1016/S1473-3099 (16)00100-6. PubMed PMID: 27083976.

The invention claimed is:

1. A method for feeding an aquatic animal present in an aquaculture comprising the step of feeding the aquatic animal with a composition comprising a bacterial strain selected from the group consisting of: ABP1 with a deposit under the accession number CECT 9675, of 8 Jun. 2018, at Colección Espanola de Cultivos Tipo, ABP2 with a deposit under the accession number CECT 9676, of 8 Jun. 2018, at Coleccion Espanola de Cultivos Tipo, and a mixture thereof.

2. The method of claim 1, wherein the step of feeding the aquatic animal is carried out during the life span of the aquatic animal.

3. The method of claim 1, wherein the aquatic animal is selected from the group consisting of: a shellfish, fish, amberjack, arapaima, barb, bass, bluefish, bocachico, bream, bullhead, cachama, carp, catfish, catla, chanos, char, cichlid, cobia, cod, crappie, dorada, drum, eel, goby, goldfish, gourami, grouper, guapote, halibut, java, labeo, lai, loach, mackerel, milkfish, mojarra, mudfish, mullet, paco, pearlspot, pejerrey, perch, pike, pompano, roach, salmon, Atlantic salmon, sampa, sauger, sea bass, European sea bass, seabream, gilthead seabream, white seabream, shiner, sleeper, snakehead, snapper, snook, sole, spinefoot, sturgeon, sunfish, sweetfish, tench, terror, tilapia, trout, tuna, turbot, vendace, walleye, halibut, whitefish, and shrimp.

* * * * *